United States Patent
Kajimura et al.

(10) Patent No.: US 11,690,362 B2
(45) Date of Patent: Jul. 4, 2023

(54) NUCLEASE-MEDIATED REPEAT EXPANSION

(71) Applicant: Regeneran Pharmaceuticals, Inc., Tarrytown, NY (US)

(72) Inventors: Daisuke Kajimura, New York, NY (US); Aarti Sharma-Kanning, New York, NY (US); Brittany Dubose, New York, NY (US); Gustavo Droguett, New City, NY (US); Chia-Jen Siao, New York, NY (US); Junko Kuno, Holmes, NY (US); David Frendewey, New York, NY (US); Brian Zambrowicz, Sleepy Hollow, NY (US)

(73) Assignee: Regeneran Pharmaceuticals, Inc., Tarrytown, NY (US)

( * ) Notice: Subject to any disclaimer, the term of this patent is extended or adjusted under 35 U.S.C. 154(b) by 577 days.

(21) Appl. No.: 16/713,834

(22) Filed: Dec. 13, 2019

(65) Prior Publication Data

US 2020/0196581 A1 Jun. 25, 2020

Related U.S. Application Data

(60) Provisional application No. 62/829,995, filed on Apr. 5, 2019, provisional application No. 62/782,461, filed on Dec. 20, 2018.

(51) Int. Cl.
| | |
|---|---|
| *C07H 21/02* | (2006.01) |
| *A01K 67/027* | (2006.01) |
| *C12N 9/22* | (2006.01) |
| *C12N 15/85* | (2006.01) |
| *C12N 15/90* | (2006.01) |

(52) U.S. Cl.
CPC ............ *A01K 67/0276* (2013.01); *C12N 9/22* (2013.01); *C12N 15/85* (2013.01); *C12N 15/90* (2013.01); *A01K 2217/075* (2013.01); *A01K 2227/105* (2013.01)

(58) Field of Classification Search
CPC ............... C12N 2310/20; C12N 9/22
See application file for complete search history.

(56) References Cited

U.S. PATENT DOCUMENTS

| | | | |
|---|---|---|---|
| 5,670,356 A | 9/1997 | Sherf et al. | |
| 5,874,304 A | 2/1999 | Zolotukhin et al. | |
| 5,942,435 A | 8/1999 | Wheeler | |
| 6,586,251 B2 | 7/2003 | Economides et al. | |
| 6,596,541 B2 | 7/2003 | Murphy et al. | |
| 7,105,348 B2 | 9/2006 | Murphy et al. | |
| 7,294,754 B2 | 11/2007 | Poueymirou et al. | |
| 7,576,259 B2 | 8/2009 | Poueymirou et al. | |
| 7,612,250 B2 | 11/2009 | Overstrom et al. | |
| 7,659,442 B2 | 2/2010 | Poueymirou et al. | |
| 8,354,389 B2 | 1/2013 | Frendewey et al. | |
| 8,518,392 B2 | 8/2013 | Frendewey et al. | |
| 8,697,359 B1 | 4/2014 | Zhang | |
| 8,697,851 B2 | 4/2014 | Frendewey et al. | |
| 10,285,388 B2 | 5/2019 | Atanasio et al. | |
| 10,329,582 B2 | 6/2019 | Lee et al. | |
| 10,385,359 B2 | 8/2019 | Lee et al. | |
| 10,508,289 B2 | 12/2019 | Duchateau et al. | |
| 2004/0018626 A1 | 1/2004 | Murphy et al. | |
| 2004/0177390 A1 | 9/2004 | Lewis et al. | |
| 2005/0144655 A1 | 6/2005 | Economides et al. | |
| 2006/0085866 A1 | 4/2006 | Poueymirou et al. | |
| 2008/0028479 A1 | 1/2008 | Poueymirou et al. | |
| 2008/0078000 A1 | 3/2008 | Poueymirou et al. | |
| 2008/0078001 A1 | 3/2008 | Poueymirou et al. | |
| 2008/0092249 A1 | 4/2008 | Lewis et al. | |
| 2009/0324559 A1 | 12/2009 | Sakurada et al. | |
| 2010/0028931 A1 | 2/2010 | Eggan et al. | |
| 2010/0035768 A1 | 2/2010 | Gibson et al. | |
| 2013/0309670 A1 | 11/2013 | Frendewey et al. | |
| 2014/0178879 A1 | 6/2014 | Economides et al. | |
| 2014/0235933 A1 | 8/2014 | Lee et al. | |
| 2014/0309487 A1 | 10/2014 | Lee et al. | |
| 2014/0310828 A1 | 10/2014 | Lee et al. | |
| 2014/0331340 A1 | 11/2014 | Poueymirou et al. | |
| 2015/0267197 A1 | 9/2015 | Bennett et al. | |

(Continued)

FOREIGN PATENT DOCUMENTS

| | | |
|---|---|---|
| EP | 3289081 B1 | 3/2019 |
| WO | WO 1999/005266 A2 | 2/1999 |

(Continued)

OTHER PUBLICATIONS

Miyazaki (Nucleic Acids Research, 2002, 30, 24, e139).*
Abramycheva et al., "C9RF72 hexanucieotide repeat expansion in ALS patients from the Central European Russia population," Neurobiol. Aging, 36(10):2908:e5-e9, (2015).
Adams et al., "A genome-wide, end-sequenced 129Sv BAC library resource for targeting vector construction," Genomics, 86(6):753-758, (2005).

(Continued)

*Primary Examiner* — Amy H Bowman
(74) *Attorney, Agent, or Firm* — Alston & Bird LLP

(57) ABSTRACT

Nuclease-mediated methods for expanding repeats already present at a genomic locus are provided. Non-human animal genomes, non-human animal cells, and non-human animals comprising a heterologous hexanucleotide repeat expansion sequence inserted at an endogenous C9orf72 locus and methods of making such non-human animal cells and non-human animals through nuclease-mediated repeat expansion are also provided. Methods of using the non-human animal cells or non-human animals to identify therapeutic candidates that may be used to prevent, delay or treat one or more neurodegenerative disorders associated with repeat expansion at the C9orf72 locus are also provided.

47 Claims, 30 Drawing Sheets

Specification includes a Sequence Listing.

(56) References Cited

U.S. PATENT DOCUMENTS

| | | |
|---|---|---|
| 2015/0376628 A1 | 12/2015 | Schoenherr et al. |
| 2015/0376651 A1 | 12/2015 | Frendewey et al. |
| 2016/0115486 A1 | 4/2016 | Schoenherr et al. |
| 2016/0145646 A1 | 5/2016 | Frendewey et al. |
| 2016/0177339 A1 | 6/2016 | Voronina et al. |
| 2016/0273002 A1 | 9/2016 | Duchateau et al. |
| 2016/0355796 A1 | 12/2016 | Davidson et al. |
| 2018/0023077 A1 | 1/2018 | Rigo |
| 2018/0094267 A1 | 4/2018 | Heslin et al. |
| 2018/0100144 A1 | 4/2018 | Buj Bello et al. |
| 2018/0344817 A1 | 12/2018 | Smith et al. |
| 2019/0167814 A1 | 6/2019 | Dion et al. |
| 2019/0167815 A1 | 6/2019 | Holmes et al. |
| 2019/0216062 A1 | 7/2019 | Atanasio et al. |
| 2019/0249230 A1 | 8/2019 | Pederson et al. |
| 2019/0270980 A1 | 9/2019 | Ikeda et al. |
| 2020/0339638 A1 | 10/2020 | Nabhan et al. |
| 2020/0370054 A1 | 11/2020 | Heslin et al. |

FOREIGN PATENT DOCUMENTS

| | | | |
|---|---|---|---|
| WO | WO 2002/036789 A2 | 5/2002 | |
| WO | WO 2006/044962 A1 | 4/2006 | |
| WO | WO 2008/017234 A1 | 2/2008 | |
| WO | WO 2011/020014 A1 | 2/2011 | |
| WO | WO 2011/020120 A2 | 2/2011 | |
| WO | WO 2013/030588 A1 | 3/2013 | |
| WO | WO 2013/041577 A1 | 3/2013 | |
| WO | WO 2013/163394 A1 | 10/2013 | |
| WO | WO 2014/062736 A1 | 4/2014 | |
| WO | WO 2014/130706 A1 | 8/2014 | |
| WO | WO 2014/172489 A2 | 10/2014 | |
| WO | WO 2015/059265 A1 | 4/2015 | |
| WO | WO 2015/143078 A1 | 9/2015 | |
| WO | WO 2015/153760 A2 | 10/2015 | |
| WO | WO 2015/200334 A1 | 12/2015 | |
| WO | WO 2015/200805 A2 | 12/2015 | |
| WO | WO 2016/081923 A2 | 5/2016 | |
| WO | WO 2016/089692 A1 | 6/2016 | |
| WO | WO 2016/100819 A1 | 6/2016 | |
| WO | WO 2016/174056 A1 | 11/2016 | |
| WO | WO 2016/179112 A1 | 11/2016 | |
| WO | WO 2017/109757 A1 | 6/2017 | |
| WO | WO 2017/178590 A1 | 10/2017 | |
| WO | WO 2018/064600 A1 | 4/2018 | |
| WO | WO 2018/078131 A1 * | 5/2018 | ............... C12N 9/22 |
| WO | WO 2018/078134 A1 | 5/2018 | |
| WO | WO 2018/165541 A1 | 9/2018 | |
| WO | WO 2018/208972 A1 | 11/2018 | |
| WO | WO 2019/084140 A1 | 5/2019 | |
| WO | WO 2020/131632 A1 | 6/2020 | |

OTHER PUBLICATIONS

Altschul et al., "Basic local alignment search tool," J. Mol. Biol., 215(3):403-410, (1990).

Altschul et al., "Gapped BLAST and PSI-BLAST: a new generation of protein database search programs," Nucleic Acids Res., 25(17):3389-3402, (1997).

Altschul et al., "Local alignment statistics," Methods Enzymol., 266:460-480, (1996).

Angrand et al., "Simplified generation of targeting constructs using ET recombination," Nucleic Acids Res., 27(17):e16, (1999).

Auerbach et al., "Establishment and chimera analysis of 129/SvEv- and C57BL/6-derived mouse embryonic stem cell lines," Biotechniques, 29(5):1024-1032, (2000).

Bacchetti et al., "Transfer of the gene for thymidine kinase to thymidine kinase-deficient human cells by purified herpes simplex viral DNA," Proc. Natl. Acad. Sci. U.S.A., 74(4):1590-1594, (1977).

Beck et al., "Nucleotide sequence and exact localization of the neomycin phosphotransferase gene from transposon Tn5," Gene, 19(3):327-336, (1982).

Bertram, "MATra—Magnet Assisted Transfection: combining nano-technology and magnetic forces to improve intracellular delivery of nucleic acids," Curr. Pharm. Biotechnol., 7(4):277-285, (2006).

Dechiara et al., "Producing fully ES cell-derived mice from eight-cell stage embryo injections," Methods Enzymol., 476:285-294, (2010).

Festing et al., "Revised nomenclature for strain 129 mice," Mamm. Genome, 10(8):836, (1999).

GenBank Accession No. NM 001007702.1, "Rattus norvegicus similar to Riken cDNA 3110043O21 (RGD1359108, mRNA," (3 pages), Aug. 10, 2014.

GenBank Accession No. NM 001081343.1, "Mus muscuius Riken cDNA 3110043O21 gene (3110043O21Rik), mRNA," (4 pages), Dec. 12, 2015.

GenBank Accession No. NM_001256054.2, "*Homo sapiens* chromosome 9 open reading frame 72 (C9orf72), transcript variant 3, mRNA," (5 pages), Jul. 9, 2016.

GenBank Accession No. NM_018325.4, "*Homo sapiens* chromosome 9 open reading frame 72 (C9orf72), transcript variant 2, mRNA," (5 pages), Jul. 9, 2016.

GenBank Accession No. NM_145005.6, "*Homo sapiens* chromosome 9 open reading frame 72 (C9orf72), transcript variant 1, mRNA," (5 pages), Jul. 9, 2016.

GenBank Accession No. NP_001007703.1, "protein C9orf72 homolog [Rattus norvegicus]," (2 pages), Aug. 10, 2014.

GenBank Accession No. NP_001074812.1, "protein C9orf72 homolog [Mus muscuius]," (2 pages), Dec. 12, 2015.

GenBank Accession No. NP_001242983.1, "protein C9orf72 isoform a [*Homo sapiens*]," (3 pages), Jul. 9, 2016.

GenBank Accession No. NP_060795.1, "protein C9orf72 isoform a [*Homo sapiens*]," (3 pages), Jul. 9, 2016.

GenBank Accession No. NP_659442.2, "protein C9orf72 isoform b [*Homo sapiens*]," (3 pages), Jul. 9, 2016.

Gibson et al., "Enzymatic assembly of DNA molecules up to several hundred kilobases," Nat. Methods, 6(5):343-345, (2009).

Gill et al., "No Benefit from Chronic Lithium Dosing in a Sibling-Matched, Gender Balanced, Investigator-Blinded Trial Using a Standard Mouse Model of Familial ALS," PLoS One, 4(8):e6489, 8 pages, (2009).

Graham et al., "A new technique for the assay of infectivity of human adenovirus 5 DNA," Virology, 52(2):456-467, (1973).

Grigg et al., "G-Quadruplex Structures Formed by Expanded Hexanucleotide Repeat RNA and DNA from the Neurodegenerative Disease-Linked C9orf72 Gene Efficiently Sequester and Activate Heme," PLoS One, vol. 9, Issue 9, e106449, (Sep. 2014).

Hu et al., "Recognition of c9orf72 Mutant RNA by Single-Stranded Silencing RNAs," Nucleic Acid Ther., 27(2):87-94, (2017).

Lakso et al., "Targeted oncogene activation by site-specific recombination in transgenic mice," Proc. Natl. Acad. Sci. U.S.A., 89(14):6232-6236, (1992).

Meyer et al., "Gene targeting by homologous recombination in mouse zygotes mediated by zinc-finger nucleases," Proc. Natl. Acad. Sci. U.S.A., 107(34):15022-15026, (2010).

Meyer et al., "Modeling disease mutations by gene targeting in one-cell mouse embryos," Proc. Natl. Acad. Sci. U.S.A., 109(24):9354-9359, (2012).

Muller, "Ten years of gene targeting: targeted mouse mutants, from vector design to phenotype analysis," Mech. Dev., 82(1-2):3-21, (1999).

Muyrers et al., "Rapid modification of bacterial artificial chromosomes by ET-recombination," Nucleic Acids Res., 27(6):1555-1557, (1999).

Narayanan et al., "Efficient and precise engineering of a 200 kb beta-globin human/bacterial artificial chromosome in *E. coli* DH10B using an inducible homologous recombination system," Gene Ther., 6(3):442-447, (1999).

O'Gorman et al., "Recombinase-mediated gene activation and site-specific integration in mammalian cells," Science, 251(4999):1351-1355, (1991).

Panda et al., "Highly efficient targeted mutagenesis in mice using TALENs," Genetics, 195(3):703-713 plus Supporting Information, (2013).

(56) References Cited

OTHER PUBLICATIONS

Santerre et al., "Expression of prokaryotic genes for hygromycin B and G418 resistance as dominant-selection markers in mouse L cells," Gene, 30(1-3):147-156, (1984).
Skarnes et al., "A conditional knockout resource for the genome-wide study of mouse gene function," Nature, 474(7351):337-342, (2011).
Suda et al., "Mouse embryonic stem cells exhibit indefinite proliferative potential," J. Cell. Physiol., 133(1):197-201, (1987).
Tong et al., "Production of p53 gene knockout rats by homologous recombination in embryonic stem cells," Nature, 467(7312):211-213, (2010).
WIPO Application No. PCT/US2016/034304, PCT International Search Report and Written Opinion of the International Searching Authority dated Aug. 22, 2016.
Yang et al., "Homologous recombination based modification in *Escherichia coli* and germline transmission in transgenic mice of a bacterial artificial chromosome," Nat. Biotechnol., 15(9):859-865, (1999).
Yu et al., "An efficient recombination system for chromosome engineering in *Escherichia coli*," Proc. Natl. Acad. Sci. U.S.A., 97(11):5978-5983, (2000).
Zaias et al., "Reference values for serum proteins of common laboratory rodent strains," J. Am. Assoc. Lab. Anim. Sci., 48(4):387-390, (2009).
Zhang et al., "A new logic for DNA engineering using recombination in *Escherichia coli*," Nat. Genet., 20(2):123-128, (1998).
Zhu et al., "Humanising the mouse genome piece by piece," Nat. Commun. 10(1):1845, (Apr. 23, 2019).
WIPO Application No. PCT/US2017/054551, PCT International Search Report and Written Opinion of the International Searching Authority dated Dec. 11, 2017.
WIPO Application No. PCT/US2019/066317, PCT International Search Report and Written Opinion of the International Searching Authority dated Mar. 11, 2020.
Abugable et al., "DNA repair and neurological disease: From molecular understanding to the development of diagnostics and model organisms," DNA Repair (Amst.), 81:102669, 13 pages, (2019).
Almeida et al., "Modeling key pathological features of frontotemporal dementia with C9ORF72 repeat expansion in iPSC-derived human neurons," Acta. Neuropathol., 126(3):385-399, (2013).
Arogundade et al., "Antisense RNA foci are associated with nucleoli and TDP-43 mislocalization in C9orf72-ALS/FTD: a quantitative study," Acta Neuropathologica, 137(3):527-530, (2019).
Atanasio et al., "C9orf72 ablation causes immune dysregulation characterized by leukocyte expansion, autoantibody production, and glomerulonephropathy in mice," Sci. Rep., 6:23204 plus Supplementary Materials, (2016).
Atkinson et al., "C9ORF72 expression and cellular localization over mouse development," Acta. Neuropathol. Commun., 3:59, (2015).
Balendra et al., "C9orf72-mediated ALS and FTD: multiple pathways to disease," Nat. Rev. Neurol., 14(9):544-558, (2018).
Barthold, "Genetically altered mice: phenotypes, no phenotypes, and Faux phenotypes," Genetica, 122(1):75-88, (2004).
Bieniek et al., "Expanded C9ORF72 hexanucieotide repeat in depressive pseudodementia," JAMA Neurol., 71(6):775-781, (2014).
Birling, et al., "Modeling human disease in rodents by CRISPR/Cas9 genome editing," Mamm. Genome, 28(7-8):291-301, (2017).
Brevini, et al., "Porcine embryonic stem cells: Facts, challenges and hopes," Theriogenology, 68 Suppl. 1:S206-S213, (2007).
Brevini, et al., "No shortcuts to pig embryonic stem cells," Theriogenology, 74(4):544-550, (2010).
Brown et al., "Amyotrophic Lateral Sclerosis," The New England Journal of Medicine, 377(2):162-172, (2017).
Buchman et al., "Simultaneous and independent detection of C9ORF72 alleles with low and high number of GGGGCC repeats using an optimised protocol of Southern blot hybridisation," Mol. Neurodegener., 8:12, (2013).

Burberry et al., "Loss-of-function mutations in the C9ORF72 mouse ortholog cause fatal autoimmune disease," Sci. Transl. Med., 8(347):347ra93, (2016).
Cao, et al., "Isolation and Culture of Primary Bovine Embryonic Stem Cell Colonies by a Novel Method," J. Exp. Zool. A. Ecol. Genet. Physiol., 311(5):368-376, (2009).
Chan, "RNA-mediated pathogenic mechanisms in polyglutamine diseases and amyotrophic lateral sclerosis," Front. Cell. Neurosci., 8:431, (2014).
Chang et al., "Non-homologous DNA end joining and alternative pathways to double-strand break repair," Nat. Rev. Mol. Cell Biol.,18(8):495-506, (2017).
Chew et al., "C9ORF72 repeat expansions in mice cause TDP-43 pathology, neuronal loss, and behavioral deficits," Science, 348(6239):1151-1154, (2015).
Cinesi et al., "Contracting CAG/CTG repeats using the CRISPR-Cas9 nickase," Nat. Comm., 7:13272, 10 pages, (2016).
Ciura et al., "Loss of function of C9orf72 causes motor deficits in a zebrafish model of amyotrophic lateral sclerosis," Ann. Neurol., 74(2):180-187, (2013).
Clark, et al., "A future for transgenic livestock," Nat. Rev. Genet., 4(10):825-833, (2003).
Cleary et al., "Improved PCR based methods for detecting C9orf72 hexanucieotide repeat expansions," Mol. Cell. Probes, 30(4):218-224, (2016).
Conlon et al., "The C9ORF72 GGGGCC expansion forms RNA G-quadruplex inclusions and sequesters hnRNP H to disrupt splicing in ALS brains," eLife, 5:e17820, 28 pages, (2016).
Dechiara, T.M., et al., "VeiociMouse: Fully ES Cell-Derived FO-Generation Mice Obtained from the Injection of ES Cells into Eight-Cell-Stage Embryos," Methods in Molecular Biology, 530(16): 311-324, (2009).
Dejesus-Hernandez et al., "Expanded GGGGCC Hexanucieotide Repeat in Noncoding Region of C9ORF72 Causes Chromosome 9p-Linked FTD and ALS," Neuron, 72:245-256, (2011).
Dennis, "Welfare Issues of Genetically Modified Animals," ILAR J., 43(2):100-109, (2002).
Egawa et al., "Drug screening for ALS using patient-specific induced pluripotent stem cells," Sci. Transl. Med., 4(145):145ra104, (2012).
Engle, Sandra J., "Utilizing iPSC for Target Discovery in CNS," Biogen, Predict 3D, Sep. 5-6, 2019, Boston, MA, 22 pages.
Farg et al., "C9ORF72, implicated in amytrophic lateral sclerosis and frontotemporal dementia, regulates endosomal trafficking," Hum. Mol. Genet., 23(13):3579-3595, (2014).
Frendewey, et al., "The Loss-of-Allele Assay for ES Cell Screening and Mouse Genotyping," Methods Enzymol., 476:295-307, (2010).
Genoway, "Humanized Mouse Model," retrieved from https://www.genoway.com/services/customized-mouse/knockin-models/humanisation.htm on May 12, 2018.
Gomez, et al., "Derivation of cat embryonic stem-like cells from in vitro-produced blastocysts on homologous and heterologous feeder cells," Theriogenology, 74(4): 498-515, (2010).
Graham, et al., "Resources for the design of CRISPR gene editing experiments," Genome Biol., 16:260, (2015).
Harari, et al., "Bridging the Species Divide: Transgenic Mice Humanized for Type-I Interferon Response," PLoS One, 9(1): e84259, (2014).
Heutink et al., "C9orf72; abnormal RNA expression is the key," Exp. Neurol., 262 Pt B:102-110, (2014).
Houdebine, "Methods to Generate Transgenic Animals," pp. 31-48 in "Genetic Engineering in Livestock: New Applications and Interdisciplinary Perspectives," Ed. Engelhard et al., (2009).
Hukema et al., "A new inducible transgenic mouse model for C9orf72-associated GGGGCC repeat expansion supports a gain-of-function mechanism in C9orf72-associated ALS and FTD," Acta Neuropathologica Communications, 2:166, pp. 1-4, (2014).
Hukema et al., "Retraction Note to: A new inducible transgenic mouse model for C9orf72-associated GGGGCC repeat expansion supports a gain-of-function mechanism in C9orf72-associated ALS and FTD," Acta Neuropathologica Communications, 4(1):129, (2016).
Iyer et al., "A comparative bioinformatic analysis of C9orf72," PeerJ, 6:e4391, 28 pages, (2018).

(56) References Cited

OTHER PUBLICATIONS

Jean, et al., "Pluripotent genes in avian stem cells," Dev. Growth Differ., 55(1): 41-51, (2013).
Jiang et al., "Gain of Toxicity from ALS/FTD-Linked Repeat Expansions in C9ORF72 Is Alleviated by Antisense Oligonucleotides Targeting GGGGCC-Containing RNAs," Neuron, 90(3):535-550, (2016).
Kawamata, et al., "Generation of genetically modified rats from embryonic stem cells," Proc. Natl. Acad. Sci. U.S.A., 7(32):14223-14228, (2010).
Koppers et al., "C9orf72 ablation in mice does not cause motor neuron degeneration or motor deficits," Ann. Neurol., 78(3):426-438, (2015).
Kumar, et al., "Transgenic Mouse Technology: Principles and Methods," Methods Mol. Biol., 590:335-362, (2009).
La Spada et al., "Repeat expansion disease: Progress and puzzles in disease pathogenesis," Nat Rev Genet., 11(4):247-258, (2010).
Lagier-Tourenne et al., "Targeted degradation of sense and antisense C9orf72 RNA foci as therapy for ALS and frontotemporal degeneration," Proc. Natl. Acad. Sci. U.S.A., 110(47):E4530-E4539 plus supplemental materials, (2013).
Liu et al., "C9orf72 BAC Mouse Model with Motor Deficits and Neurodegenerative Features of ALS/FTD," Neuron, 90(3):521-534, (2016).
Liu et al., "c9orf72 Disease-Related Foci Are Each Composed of One Mutant Expanded Repeat RNA," Cell Chem. Biol., 24(2):141-148, (2017).
Majounie et al., "Frequency of the C9orf72 hexanucieotide repeat expansion in patients with amyotrophic lateral sclerosis and frontotemporal dementia: a cross-sectional study," Lancet Neurol., 11(4):323-330, (2012).
McMurray, "Mechanisms of trinucleotide repeat instability during human development," Nat. Rev. Genet., 11(11):786-799, (2010).
Menalled, "Knock-in mouse models of Huntington's disease," NeuroRx, 2(3):465-470, (2005).
Mori et al., "The C9orf72 GGGGCC repeat is translated into aggregating dipeptide-repeat proteins in FTLD/ALS," Science, 339(6125):1335-1338, (2013).
Mullins, et al., "Transgenesis in the rat and larger mammals," J. Clin. Invest. 97(7):1557-1560, (1996).
Munoz, et al., "Conventional pluripotency markers are unspecific for bovine embryonic-derived cell-lines," Theriogenology, 69(9): 1159-1164, (2008).
Niemann, "Transgenic farm animals get off the ground. Transgenic Animals in Agriculture, Conference Tahoe City, California, USA. Aug. 24-27, 1997." Transgenic Res., 7(1): 73-75, (1998).
O'Rourke et al., "C9orf72 BAC Transgenic Mice Display Typical Pathologic Features of ALS/FTD," Neuron, 88(5):892-901, (2015).
O'Rourke et al., "C9orf72 is required for proper macrophage and microglial function in mice," Science, 351(6279):1324-1329 plus Supplementary Materials, (2016).
Paris, et al., "Equine embryos and embryonic stem cells: defining reliable markers of pluripotency," Theriogenology, 74(4): 516-524, (2010).
Paulson, "Chapter 9: Repeat expansion diseases," Handbook of Clinical Neurology, 147:105-123, (2018).
Peters et al., "Human C9ORF72 Hexanucieotide Expansion Reproduces RNA Foci and Dipeptide Repeat Proteins but Not Neurodegeneration in BAC Transgenic Mice," Neuron, 88(5):902-909, (2015).
Picher-Martel et al., "From animal models to human disease: a genetic approach for personalized medicine in ALS," Acta. Neuropathol. Commun., 4(1):70, (2016).
Poueymirou, et al., "F0 generation mice fully derived from gene-targeted embryonic stem cells allowing immediate phenotypic analyses," Nat. Biotechnol., 25(1):91-99, (2007).
Pribadi et al., "CRISPR-Cas9 targeted deletion of the C9orf72 repeat expansion mutation corrects cellular phenotypes in patient-derived iPS cells," (2016), [Retrieved from the Internet on Oct. 30, 2019: <URL: https://www.biorxiv.org/content/biorxiv/early/2016/05/02/051193.full.pdf].
Renton et al., "A Hexanucieotide Repeat Expansion in C9ORF72 Is the Cause of Chromosome 9p21-Linked ALS-FTD," Neuron, 72:257-268, (2011).
Renton et al., "State of play in amyotrophic lateral sclerosis genetics," Nat. Neurosci., 17(1):17-23, (2014).
Rezza, et al., "Unexpected genomic rearrangements at targeted loci associated with CRISPR/Cas9-mediated knock-in," Sci. Rep., 9(1):3486, (2019).
Ristevski, "Making better transgenic models: conditional, temporal, and spatial approaches," Mol. Biotechnol., 29(2):153-163, (2005).
Robberecht et al., "The changing scene of amyotrophic lateral sclerosis," Nat. Rev. Neurosci., 14(4):248-264, (2013).
Roberson, "Mouse models of frontotemporal dementia," Ann. Neurol., 72(6):837-849, (2012).
Rogers, et al., "Disruption of the CFTR Gene Produces a Model of Cystic Fibrosis in Newborn Pigs," Science, 321(5897):1837-1841, (2008).
Schludi et al., "Distribution of dipeptide repeat proteins in cellular models and C9orf72 mutation cases suggests link to transcriptional silencing," Acta Neuropathol., 130(4):537-555, (2015).
Schludi et al., "Erratum to: Distribution of dipeptide repeat proteins in cellular models and C9orf72 mutation cases suggests link to transcriptional silencing," Acta Neuropathol., 130(4):557-558, (2015).
Sigmund, "Viewpoint: Are Studies in Genetically Altered Mice Out of Control?," Arterioscler. Thromb. Vasc. Biol., 20(6):1425-1429, (2000).
Stepto et al., "Modelling C9ORF72 hexanucieotide repeat expansion in amyotrophic lateral sclerosis and frontotemporal dementia," Acta. Neuropathol., 127(3):377-389, (2014).
Sudria-Lopez et al., "Full ablation of C9orf72 in mice causes immune system-related pathology and neoplastic events but no motor neuron defects," Acta. Neuropathol., 132(1):145-147, (2016).
Suzuki et al., "The mouse C9ORF72 ortholog is enriched in neurons known to degenerate in ALS and FTD," Nat. Neurosci.,16(12):1725-1727, (2013).
Thys et al., "DNA Replication Dynamics of the GGGGCC Repeat of the C9orf72 Gene," J. Biol. Chem., 290(48):28953-28962, (2015).
Traynor et al., "Special Issue on amyotrophic lateral sclerosis," Exp. Neurol., 262 Pt B:73-74, (2014).
Valenzuela, et al., "High-throughput engineering of the mouse genome coupled with high-resolution expression analysis," Nat. Biotechnol., 21(6):652-659, (2003).
Van Blitterswijk et al., "Genetic modifiers in carriers of repeat expansions in the C9ORF72 gene," Mol. Neurodegener., 9:38, (2014).
Van Der Zee, et al., "A pan-European study of the C9orf72 repeat associated with FTLD: geographic prevalence, genomic instability, and intermediate repeats," Hum. Mutat., 34(2):363-373, (2013).
Waite et al., "Reduced C9orf72 protein levels in frontal cortex of amyotrophic lateral sclerosis and frontotemporal degeneration brain with the C9ORF72 hexanucieotide repeat expansion," Neurobiol. Aging, 35(7):1779e5-1779e13, (2014). [Retrieved from the Internet Nov. 19, 2019: <URL: https://www.ncbi.nlm.nih.gov/pmc/articles/PMC3988882>].
Wakchaure, et al., "Transgenic Animals: A Review on its Various Dimensions and Applications in Animal Biotechnology," International Journal of Emerging Technology and Advanced Engineering, 5(11):210-213, (2015).
Xu et al., "Expanded GGGGCC repeat RNA associated with amyotrophic lateral sclerosis and frontotemporal dementia causes neurodegeneration," Proc. Natl. Acad. Sci. U.S.A., 110(19):7778-7783, (2013).
Zhou, et al., "Developing tTA transgenic rats for inducible and reversible gene expression," Int. J. Biol. Sci., 5(2):171-181, (2009).

* cited by examiner

FIG. 6C

WT Cas9

| | | |
|---|---|---|
| Expanded Clones | GGGCCGGGGCCGGGGCCGGGCCGGGCCGGGCCGGGCCGGGCCGGGCCGGGAGACCCTCGAGGGCCGCTAGCGCGATCGCG | (SEQ ID NO: 109) |
| | GGGCCGGGGCCGGGGCCGGGCCGGGCCGGGCCGGGCCGGGCCGGGCCGGGAGACC-TCGAGGGCCGCTAGCGCGATCGCG | (SEQ ID NO: 110) |
| | GGGCCGGGGCCGGGGCCGGGCCGGGCCGGGCCGGGCCGGGCCGGGCCGGGAGAC-----GAGGGCCGCTAGCGCGATCGCG | (SEQ ID NO: 111) |
| | GGGCCGGGGCCGGGGCCGGGCCGGGCCGGGCCGGGCCGGGCCGGGCCGGGAGACCC---GAGGGCCGCTAGCGCGATCGCG | (SEQ ID NO: 112) |
| | GGGCCGGGGCCGGGGCCGGGCCGGGCCGGGCCGGGCCGGGCCGGGCCGGGGC----G-GGGGCCGCTAGCGCGATCGCG | (SEQ ID NO: 113) |
| Ref. Seq. | GGGCCGGGGCCGGGGCCGGGCCGGGCCGGGCCGGGCCGGGCCGGGCCGGGAGACCCTCGAGGGCCGCTAGCGCGATCGCG | (SEQ ID NO: 109) |
| | ---------------GGCCGGGAGACCCTCGAGG------------------------------ | (SEQ ID NO: 114) | gRNA Target Sequence + PAM

Cas9 Nickase (D10A)

| | | |
|---|---|---|
| Expanded Clones | GCCGGGGCCGGGGCCGGGCCGGGAGACCCTCGAGGGCCGCTAGCGCGATCGCGGGGGCGTGGTTCGGGGCGGG | (SEQ ID NO: 115) |
| | GCCGGGGCCGGGGCCGGGCCGGGAGACCCTCGAGGGCCGCTAGCGCGATCGCGGGGGCGTGGTTCGGGGCGGG | (SEQ ID NO: 115) |
| | GCCGGGGCCGGGGCCGGGCCGGGAGACCCTCGAGGGCCGCTAGCGCGATCGCGGGGGCGTGGTTCGGGGCGGG | (SEQ ID NO: 115) |
| | GCCGGGGCCGGGGCCGGGCCGGGAGACCCTCGAGGGCCGCTAGCGCGATCGCGGGGGCGTGGTTCGGGGCGGG | (SEQ ID NO: 115) |
| | GCCGGGGCCGGGGCCGGGCCGGGAGACCCTCGAGGGCCGCTAGCGCGATCGCGGGGGCGTGGTTCGGGGCGGG | (SEQ ID NO: 115) |
| | GCCGGGGCCGGGGCCGGGCCGGGAGACCCTCGAGGGCCGCTAGCGCGATCGCGGGGGCGTGGTTCGGGGCGGG | (SEQ ID NO: 115) |
| | GCCGGGGCCGGGGCCGGGCCGGGAGACCCTCGAGGGCCGCTAGCGCGATCGCGGGGGCGTGGTTCGGGGCGGG | (SEQ ID NO: 115) |
| Ref. Seq. | GCCGGGGCCGGGGCCGGGCCGGGAGACCCTCGAGGGCCGCTAGCGCGATCGCGGGGGCGTGGTTCGGGGCGGG | (SEQ ID NO: 115) |
| | --------GGCCGGGAGACCCTCGAGG------------------------------------- | (SEQ ID NO: 114) | gRNA Target Sequence + PAM

*FIG. 17C*

Transcripts Containing Intron Sequence Near 1A

SEQUENCE LISTING

<160> NUMBER OF SEQ ID NOS: 121

<210> SEQ ID NO 1
<211> LENGTH: 6
<212> TYPE: DNA
<213> ORGANISM: Homo sapiens

-continued

```
<400> SEQUENCE: 1 ggggcc                                                                    6

<210> SEQ ID NO 2
<211> LENGTH: 3
<212> TYPE: DNA
<213> ORGANISM: Homo sapiens

<400> SEQUENCE: 2 cag                                                                       3

<210> SEQ ID NO 3
<211> LENGTH: 3
<212> TYPE: DNA
<213> ORGANISM: Homo sapiens

<400> SEQUENCE: 3 cgg                                                                       3

<210> SEQ ID NO 4
<211> LENGTH: 3
<212> TYPE: DNA
<213> ORGANISM: Homo sapiens

<400> SEQUENCE: 4 ctg                                                                       3

<210> SEQ ID NO 5
<211> LENGTH: 3
<212> TYPE: DNA
<213> ORGANISM: Homo sapiens

<400> SEQUENCE: 5 gaa                                                                       3

<210> SEQ ID NO 6
<211> LENGTH: 3
<212> TYPE: DNA
<213> ORGANISM: Homo sapiens

<400> SEQUENCE: 6 gcc                                                                       3

<210> SEQ ID NO 7
<211> LENGTH: 3
<212> TYPE: DNA
<213> ORGANISM: Homo sapiens

<400> SEQUENCE: 7 gcg                                                                       3

<210> SEQ ID NO 8
<211> LENGTH: 4
<212> TYPE: DNA
<213> ORGANISM: Homo sapiens

<400> SEQUENCE: 8 cctg                                                                      4

<210> SEQ ID NO 9
<211> LENGTH: 5
<212> TYPE: DNA
```

<213> ORGANISM: Homo sapiens

<400> SEQUENCE: 9 attct                                                                      5

<210> SEQ ID NO 10
<211> LENGTH: 5
<212> TYPE: DNA
<213> ORGANISM: Homo sapiens

<400> SEQUENCE: 10 tggaa                                                                      5

<210> SEQ ID NO 11
<211> LENGTH: 6
<212> TYPE: DNA
<213> ORGANISM: Homo sapiens

<400> SEQUENCE: 11 ggcctg                                                                     6

<210> SEQ ID NO 12
<211> LENGTH: 12
<212> TYPE: DNA
<213> ORGANISM: Homo sapiens

<400> SEQUENCE: 12
ccccgccccg cg                                                             12

<210> SEQ ID NO 13
<211> LENGTH: 1957
<212> TYPE: DNA
<213> ORGANISM: Homo sapiens

<400> SEQUENCE: 13
acgtaaccta cggtgtcccg ctaggaaaga gaggtgcgtc aaacagcgac aagttccgcc         60
cacgtaaaag atgacgcttg atatctccgg agcatttgga taatgtgaca gttggaatgc        120
agtgatgtcg actctttgcc caccgccatc tccagctgtt gccaagacag agattgcttt        180
aagtggcaaa tcacctttat tagcagctac ttttgcttac tgggacaata ttcttggtcc        240
tagagtaagg cacatttggg ctccaaagac agaacaggta cttctcagtg atggagaaat        300
aacttttctt gccaaccaca ctctaaatgg agaaatcctt cgaaatgcag agagtggtgc        360
tatagatgta aagttttttg tcttgtctga aaagggagtg attattgttt cattaatctt        420
tgatggaaac tggaatgggg atcgcagcac atatggacta tcaattatac ttccacagac        480
agaacttagt ttctacctcc cacttcatag agtgtgtgtt gatagattaa cacatataat        540
ccggaaagga agaatatgga tgcataagga aagacaagaa aatgtccaga agattatctt        600
agaaggcaca gagagaatgg aagatcaggg tcagagtatt attccaatgc ttactggaga        660
agtgattcct gtaatggaac tgctttcatc tatgaaatca cacagtgttc ctgaagaaat        720
agatatagct gatacagtac tcaatgatga tgatattggt gacagctgtc atgaaggctt        780
tcttctcaag taagaatttt tcttttcata aagctggat gaagcagata ccatcttatg        840
ctcacctatg acaagatttg gaagaaagaa ataacagac tgtctactta gattgttcta        900
gggacattac gtatttgaac tgttgcttaa atttgtgtta ttttcactc attatatttc        960 tatatatatt tggtgttatt ccatttgcta tttaaagaaa ccgagtttcc atcccagaca       1020
agaaatcatg gcccccttgct tgattctggt ttcttgtttt acttctcatt aaagctaaca       1080

-continued

```
gaatcctttc atattaagtt gtactgtaga tgaacttaag ttatttaggc gtagaacaaa      1140
attattcata tttatactga tcttttccca tccagcagtg gagtttagta cttaagagtt      1200
tgtgcccttt aaccagactc cctggattaa tgctgtgtac ccgtgggcaa ggtgcctgaa      1260
ttctctatac acctatttcc tcatctgtaa atggcaata atagtaatag tacctaatgt       1320
gtagggttgt tataagcatt gagtaagata ataatataa agcacttaga acagtgcctg       1380
gaacataaaa acacttaata atagctcata gctaacattt cctatttaca tttcttctag      1440
aaatagccag tatttgttga gtgcctacat gttagttcct ttactagttg ctttacatgt      1500
attatcttat attctgtttt aaagtttctt cacagttaca gattttcatg aaattttact      1560
tttaataaaa gagaagtaaa agtataaagt attcactttt atgttcacag tcttttcctt      1620
taggctcatg atggagtatc agaggcatga gtgtgtttaa cctaagagcc ttaatggctt      1680
gaatcagaag cactttagtc ctgtatctgt tcagtgtcag cctttcatac atcattttaa      1740
atcccatttg actttaagta agtcacttaa tctctctaca tgtcaatttc ttcagctata      1800
aaatgatggt atttcaataa ataaatacat taattaaatg atattatact gactaattgg      1860
gctgttttaa ggctcaataa gaaaatttct gtgaaaggtc tctagaaaat gtaggttcct      1920
atacaaataa aagataacat tgtgcttata aaaaaaa                              1957
```

<210> SEQ ID NO 14
<211> LENGTH: 222
<212> TYPE: PRT
<213> ORGANISM: Homo sapiens

<400> SEQUENCE: 14

```
Met Ser Thr Leu Cys Pro Pro Ser Pro Ala Val Ala Lys Thr Glu
1               5                   10                  15

Ile Ala Leu Ser Gly Lys Ser Pro Leu Leu Ala Ala Thr Phe Ala Tyr
                20                  25                  30

Trp Asp Asn Ile Leu Gly Pro Arg Val Arg His Ile Trp Ala Pro Lys
            35                  40                  45

Thr Glu Gln Val Leu Leu Ser Asp Gly Glu Ile Thr Phe Leu Ala Asn
        50                  55                  60

His Thr Leu Asn Gly Glu Ile Leu Arg Asn Ala Glu Ser Gly Ala Ile
65                  70                  75                  80

Asp Val Lys Phe Phe Val Leu Ser Glu Lys Gly Val Ile Val Ser
                85                  90                  95

Leu Ile Phe Asp Gly Asn Trp Asn Gly Asp Arg Ser Thr Tyr Gly Leu
            100                 105                 110

Ser Ile Ile Leu Pro Gln Thr Glu Leu Ser Phe Tyr Leu Pro Leu His
        115                 120                 125

Arg Val Cys Val Asp Arg Leu Thr His Ile Ile Arg Lys Gly Arg Ile
    130                 135                 140

Trp Met His Lys Glu Arg Gln Glu Asn Val Lys Ile Ile Leu Glu
145                 150                 155                 160

Gly Thr Glu Arg Met Glu Asp Gln Gly Gln Ser Ile Ile Pro Met Leu
                165                 170                 175

Thr Gly Glu Val Ile Pro Val Met Glu Leu Leu Ser Ser Met Lys Ser
            180                 185                 190

His Ser Val Pro Glu Glu Ile Asp Ile Ala Asp Thr Val Leu Asn Asp
        195                 200                 205

Asp Asp Ile Gly Asp Ser Cys His Glu Gly Phe Leu Leu Lys
```

<210> SEQ ID NO 15
<211> LENGTH: 3261
<212> TYPE: DNA
<213> ORGANISM: Homo sapiens

<400> SEQUENCE: 15

```
gggcggggct gcggttgcgg tgcctgcgcc cgcggcggcg gaggcgcagg cggtggcgag      60
tggatatctc cggagcattt ggataatgtg acagttggaa tgcagtgatg tcgactcttt     120
gcccaccgcc atctccagct gttgccaaga cagagattgc tttaagtggc aaatcacctt     180
tattagcagc tacttttgct tactgggaca atattcttgg tcctagagta aggcacattt     240
gggctccaaa gacagaacag gtacttctca gtgatggaga ataacttttt cttgccaacc     300
acactctaaa tggagaaatc cttcgaaatg cagagagtgg tgctatagat gtaaagtttt     360
ttgtcttgtc tgaaaaggga gtgattattg tttcattaat ctttgatgga aactggaatg     420
gggatcgcag cacatatgga ctatcaatta tacttccaca gacagaactt agtttctacc     480
tcccacttca tagagtgtgt gttgatagat aacacatat aatccggaaa ggaagaatat      540
ggatgcataa ggaaagacaa gaaaatgtcc agaagattac cttagaaggc acagagagaa     600
tggaagatca gggtcagagt attattccaa tgcttactgg agaagtgatt cctgtaatgg     660
aactgctttc atctatgaaa tcacacagtg ttcctgaaga aatagatata gctgatacag     720
tactcaatga tgatgatatt ggtgacagct gtcatgaagg cttcttctc aatgccatca      780
gctcacactt gcaaacctgt ggctgttccg ttgtagtagg tagcagtgca gagaaagtaa     840
ataagatagt cagaacatta tgcctttttc tgactccagc agagagaaaa tgctccaggt     900
tatgtgaagc agaatcatca tttaaatatg agtcagggct cttttgtacaa ggcctgctaa    960
aggattcaac tggaagcttt gtgctgcctt tccggcaagt catgtatgct ccatatccca    1020
ccacacacat agatgtggat gtcaatactg tgaagcagat gccaccctgt catgaacata    1080
tttataatca gcgtagatac atgagatccg agctgacagc cttctggaga gccacttcag    1140
aagaagacat ggctcaggat acgatcatct acactgacga aagctttact cctgatttga    1200
atattttttca agatgtctta cacagagaca ctctagtgaa agccttcctg gatcaggtct    1260
ttcagctgaa acctggctta tctctcagaa gtactttcct tgcacagttt ctacttgtcc    1320
ttcacagaaa agccttgaca ctaataaaat atatagaaga cgatacgcag aagggaaaaa    1380
agcccctttaa atctcttcgg aacctgaaga tagaccttga tttaacagca gagggcgatc    1440
ttaacataat aatggctctg gctgagaaaa ttaaaccagg cctacactct tttatctttg    1500
gaagaccttt ctacactagt gtgcaagaac gagatgttct aatgactttt taaatgtgta    1560
acttaataag cctattccat cacaatcatg atcgctggta agtagctca gtggtgtggg     1620
gaaacgttcc cctggatcat actccagaat tctgctctca gcaattgcag ttaagtaagt    1680
tacactacag ttctcacaag agcctgtgag gggatgtcag gtgcatcatt acattgggtg    1740
tctctttttcc tagatttatg cttttgggat acagacctat gtttacaata taataaatat    1800
tattgctatc ttttaaagat ataataatag gatgtaaact tgaccacaac tactgttttt    1860
ttgaaataca tgattcatgg tttacatgtg tcaaggtgaa atctgagttg gcttttacag    1920
atagttgact ttctatcttt tggcattctt tggtgtgtag aattactgta atacttctgc    1980
aatcaactga aaactagagc ctttaaatga tttcaattcc acagaaagaa agtgagcttg    2040
aacataggat gagctttaga aagaaaattg atcaagcaga tgtttaattg gaattgatta    2100
```

```
ttagatccta ctttgtggat ttagtccctg ggattcagtc tgtagaaatg tctaatagtt    2160
ctctatagtc cttgttcctg gtgaaccaca gttagggtgt tttgtttatt ttattgttct    2220
tgctattgtt gatattctat gtagttgagc tctgtaaaag gaaattgtat tttatgtttt    2280
agtaattgtt gccaactttt taaattaatt ttcattattt ttgagccaaa ttgaaatgtg    2340
cacctcctgt gcctttttc tccttagaaa atctaattac ttggaacaag ttcagatttc     2400
actggtcagt cattttcatc ttgttttctt cttgctaagt cttaccatgt acctgctttg    2460
gcaatcattg caactctgag attataaaat gccttagaga atatactaac taataagatc    2520 ttttttttcag aaacagaaaa tagttccttg agtacttcct tcttgcattt ctgcctatgt   2580
ttttgaagtt gttgctgttt gcctgcaata ggctataagg aatagcagga gaaattttac    2640
tgaagtgctg ttttcctagg tgctactttg gcagagctaa gttatctttt gttttcttaa    2700
tgcgtttgga ccattttgct ggctataaaa taactgatta atataattct aacacaatgt    2760
tgacattgta gttacacaaa cacaaataaa tattttattt aaaattctgg aagtaatata    2820
aaagggaaaa tatatttata agaaagggat aaaggtaata gagcccttct gccccccacc    2880
caccaaattt acacaacaaa atgacatgtt cgaatgtgaa aggtcataat agctttccca    2940
tcatgaatca gaaagatgtg gacagcttga tgttttagac aaccactgaa ctagatgact    3000
gttgtactgt agctcagtca tttaaaaaat atataaatac taccttgtag tgtcccatac    3060 tgtgttttt acatggtaga ttcttattta agtgctaact ggttattttc tttggctggt      3120
ttattgtact gttatacaga atgtaagttg tacagtgaaa taagttatta aagcatgtgt    3180
aaacattgtt atatatcttt tctcctaaat ggagaatttt gaataaaata tatttgaaat    3240
tttaaaaaaa aaaaaaaaa a                                               3261
```

<210> SEQ ID NO 16
<211> LENGTH: 481
<212> TYPE: PRT
<213> ORGANISM: Homo sapiens

<400> SEQUENCE: 16

```
Met Ser Thr Leu Cys Pro Pro Ser Pro Ala Val Ala Lys Thr Glu
1               5                   10                  15

Ile Ala Leu Ser Gly Lys Ser Pro Leu Leu Ala Ala Thr Phe Ala Tyr
                20                  25                  30

Trp Asp Asn Ile Leu Gly Pro Arg Val Arg His Ile Trp Ala Pro Lys
            35                  40                  45

Thr Glu Gln Val Leu Leu Ser Asp Gly Glu Ile Thr Phe Leu Ala Asn
        50                  55                  60

His Thr Leu Asn Gly Glu Ile Leu Arg Asn Ala Glu Ser Gly Ala Ile
65                  70                  75                  80

Asp Val Lys Phe Phe Val Leu Ser Glu Lys Gly Val Ile Val Ser
                85                  90                  95

Leu Ile Phe Asp Gly Asn Trp Asn Gly Asp Arg Ser Thr Tyr Gly Leu
            100                 105                 110

Ser Ile Ile Leu Pro Gln Thr Glu Leu Ser Phe Tyr Leu Pro Leu His
        115                 120                 125

Arg Val Cys Val Asp Arg Leu Thr His Ile Ile Arg Lys Gly Arg Ile
    130                 135                 140

Trp Met His Lys Glu Arg Gln Glu Asn Val Gln Lys Ile Ile Leu Glu
145                 150                 155                 160
```

-continued

Gly Thr Glu Arg Met Glu Asp Gln Gly Gln Ser Ile Ile Pro Met Leu
            165                 170                 175

Thr Gly Glu Val Ile Pro Val Met Glu Leu Leu Ser Ser Met Lys Ser
        180                 185                 190

His Ser Val Pro Glu Glu Ile Asp Ile Ala Asp Thr Val Leu Asn Asp
        195                 200                 205

Asp Asp Ile Gly Asp Ser Cys His Glu Gly Phe Leu Leu Asn Ala Ile
    210                 215                 220

Ser Ser His Leu Gln Thr Cys Gly Cys Ser Val Val Gly Ser Ser
225                 230                 235                 240

Ala Glu Lys Val Asn Lys Ile Val Arg Thr Leu Cys Leu Phe Leu Thr
                245                 250                 255

Pro Ala Glu Arg Lys Cys Ser Arg Leu Cys Glu Ala Glu Ser Ser Phe
            260                 265                 270

Lys Tyr Glu Ser Gly Leu Phe Val Gln Gly Leu Leu Lys Asp Ser Thr
        275                 280                 285

Gly Ser Phe Val Leu Pro Phe Arg Gln Val Met Tyr Ala Pro Tyr Pro
    290                 295                 300

Thr Thr His Ile Asp Val Asp Val Asn Thr Val Lys Gln Met Pro Pro
305                 310                 315                 320

Cys His Glu His Ile Tyr Asn Gln Arg Arg Tyr Met Arg Ser Glu Leu
                325                 330                 335

Thr Ala Phe Trp Arg Ala Thr Ser Glu Asp Met Ala Gln Asp Thr
            340                 345                 350

Ile Ile Tyr Thr Asp Glu Ser Phe Thr Pro Asp Leu Asn Ile Phe Gln
        355                 360                 365

Asp Val Leu His Arg Asp Thr Leu Val Lys Ala Phe Leu Asp Gln Val
    370                 375                 380

Phe Gln Leu Lys Pro Gly Leu Ser Leu Arg Ser Thr Phe Leu Ala Gln
385                 390                 395                 400

Phe Leu Leu Val Leu His Arg Lys Ala Leu Thr Leu Ile Lys Tyr Ile
                405                 410                 415

Glu Asp Asp Thr Gln Lys Gly Lys Lys Pro Phe Lys Ser Leu Arg Asn
            420                 425                 430

Leu Lys Ile Asp Leu Asp Leu Thr Ala Glu Gly Asp Leu Asn Ile Ile
        435                 440                 445

Met Ala Leu Ala Glu Lys Ile Lys Pro Gly Leu His Ser Phe Ile Phe
    450                 455                 460

Gly Arg Pro Phe Tyr Thr Ser Val Gln Glu Arg Asp Val Leu Met Thr
465                 470                 475                 480

Phe

<210> SEQ ID NO 17
<211> LENGTH: 3356
<212> TYPE: DNA
<213> ORGANISM: Homo sapiens

<400> SEQUENCE: 17
acgtaaccta cggtgtcccg ctaggaaaga gaggtgcgtc aaacagcgac aagttccgcc      60
cacgtaaaag atgacgcttg gtgtgtcagc cgtccctgct gcccggttgc ttctcttttg     120
ggggcggggt ctagcaagag caggtgtggg tttaggagat atctccggag catttggata     180
atgtgacagt tggaatgcag tgatgtcgac tctttgccca ccgccatctc cagctgttgc     240
caagacagag attgctttaa gtggcaaatc acctttatta gcagctactt ttgcttactg     300

```
ggacaatatt cttggtccta gagtaaggca catttgggct ccaaagacag aacaggtact    360
tctcagtgat ggagaaataa cttttcttgc caaccacact ctaaatggag aaatccttcg    420
aaatgcagag agtggtgcta tagatgtaaa gttttttgtc ttgtctgaaa agggagtgat    480
tattgtttca ttaatctttg atggaaactg aatggggat cgcagcacat atggactatc     540
aattatactt ccacagacag aacttagttt ctacctccca cttcatagag tgtgtgttga    600
tagattaaca catataatcc ggaaaggaag aatatggatg cataaggaaa gacaagaaaa    660
tgtccagaag attatcttag aaggcacaga gagaatggaa gatcagggtc agagtattat    720
tccaatgctt actggagaag tgattcctgt aatggaactg ctttcatcta tgaaatcaca    780
cagtgttcct gaagaaatag atatagctga tacagtactc aatgatgatg atattggtga    840
cagctgtcat gaaggctttc ttctcaatgc catcagctca cacttgcaaa cctgtggctg    900
ttccgttgta gtaggtagca gtgcagagaa agtaaataag atagtcagaa cattatgcct    960
ttttctgact ccagcagaga gaaaatgctc caggttatgt gaagcagaat catcatttaa   1020
atatgagtca gggctctttg tacaaggcct gctaaaggat tcaactggaa gctttgtgct   1080
gcctttccgg caagtcatgt atgctccata tcccaccaca cacatagatg tggatgtcaa   1140
tactgtgaag cagatgccac cctgtcatga acatatttat aatcagcgta gatacatgag   1200
atccgagctg acagccttct ggagagccac ttcagaagaa gacatggctc aggatacgat   1260
catctacact gacgaaagct ttactcctga tttgaatatt tttcaagatg tcttacacag   1320
agacactcta gtgaaagcct tcctggatca ggtctttcag ctgaaacctg gcttatctct   1380
cagaagtact ttccttgcac agtttctact tgtccttcac agaaaagcct tgacactaat   1440
aaaatatata gaagacgata cgcagaaggg aaaaaagccc tttaaatctc ttcggaacct   1500
gaagatagac cttgatttaa cagcagaggg cgatcttaac ataataatgg ctctggctga   1560
gaaaattaaa ccaggcctac actctttat ctttggaaga cctttctaca ctagtgtgca    1620
agaacgagat gttctaatga cttttaaat gtgtaactta ataagcctat tccatcacaa    1680
tcatgatcgc tggtaaagta gctcagtggt gtggggaaac gttcccctgg atcatactcc   1740
agaattctgc tctcagcaat tgcagttaag taagttacac tacagttctc acaagagcct   1800 gtgagggat gtcaggtgca tcattacatt gggtgtctct tttcctagat ttatgctttt     1860
gggatacaga cctatgttta caatataata aatattattg ctatctttta aagatataat   1920 ataggatgt aaacttgacc acaactactg ttttttttgaa atacatgatt catggtttac    1980
atgtgtcaag gtgaaatctg agttggcttt tacagatagt tgactttcta tcttttggca   2040
ttctttggtg tgtagaatta ctgtaatact tctgcaatca actgaaaact agagccttta   2100
aatgatttca attccacaga aagaaagtga gcttgaacat aggatgagct ttagaaagaa   2160
aattgatcaa gcagatgttt aattggaatt gattattaga tcctactttg tggatttagt   2220
ccctgggatt cagtctgtag aaatgtctaa tagttctcta tagtccttgt tcctggtgaa   2280
ccacagttag ggtgttttgt ttattttatt gttcttgcta ttgttgatat tctatgtagt   2340
tgagctctgt aaaaggaaat tgtattttat gttttagtaa ttgttgccaa cttttttaaat  2400 taattttcat tattttgag ccaaattgaa atgtgcacct cctgtgcctt ttttctcctt     2460
agaaaatcta attacttgga acaagttcag atttcactgg tcagtcattt tcatcttgtt   2520
ttcttcttgc taagtcttac catgtaccctg ctttggcaat cattgcaact ctgagattat   2580
aaaatgcctt agagaatata ctaactaata agatcttttt ttcagaaaca gaaaatagtt   2640
```

```
ccttgagtac ttccttcttg catttctgcc tatgttttg aagttgttgc tgtttgcctg    2700
caataggcta taaggaatag caggagaaat tttactgaag tgctgttttc ctaggtgcta    2760
ctttggcaga gctaagttat cttttgtttt cttaatgcgt ttggaccatt ttgctggcta    2820
taaaataact gattaatata attctaacac aatgttgaca ttgtagttac acaaacacaa    2880
ataaatattt tatttaaaat tctggaagta atataaaagg gaaatatat ttataagaaa     2940 gggataaagg taatagagcc cttctgcccc ccacccacca aatttacaca acaaaatgac    3000
atgttcgaat gtgaaaggtc ataatagctt tcccatcatg aatcagaaag atgtggacag    3060
cttgatgttt tagacaacca ctgaactaga tgactgttgt actgtagctc agtcatttaa    3120
aaaatatata aatactacct tgtagtgtcc catactgtgt ttttacatg gtagattctt     3180 atttaagtgc taactggtta ttttctttgg ctggtttatt gtactgttat acagaatgta    3240
agttgtacag tgaaataagt tattaaagca tgtgtaaaca ttgttatata tcttttctcc    3300
taaatggaga attttgaata aaatatattt gaatttaa aaaaaaaaaa aaaaaa         3356
```

<210> SEQ ID NO 18
<211> LENGTH: 481
<212> TYPE: PRT
<213> ORGANISM: Homo sapiens

<400> SEQUENCE: 18

```
Met Ser Thr Leu Cys Pro Pro Ser Pro Ala Val Ala Lys Thr Glu
1               5                   10                  15

Ile Ala Leu Ser Gly Lys Ser Pro Leu Leu Ala Ala Thr Phe Ala Tyr
            20                  25                  30

Trp Asp Asn Ile Leu Gly Pro Arg Val Arg His Ile Trp Ala Pro Lys
        35                  40                  45

Thr Glu Gln Val Leu Leu Ser Asp Gly Glu Ile Thr Phe Leu Ala Asn
    50                  55                  60

His Thr Leu Asn Gly Glu Ile Leu Arg Asn Ala Glu Ser Gly Ala Ile
65                  70                  75                  80

Asp Val Lys Phe Phe Val Leu Ser Glu Lys Gly Val Ile Ile Val Ser
                85                  90                  95

Leu Ile Phe Asp Gly Asn Trp Asn Gly Asp Arg Ser Thr Tyr Gly Leu
            100                 105                 110

Ser Ile Ile Leu Pro Gln Thr Glu Leu Ser Phe Tyr Leu Pro Leu His
        115                 120                 125

Arg Val Cys Val Asp Arg Leu Thr His Ile Ile Arg Lys Gly Arg Ile
    130                 135                 140

Trp Met His Lys Glu Arg Gln Glu Asn Val Gln Lys Ile Ile Leu Glu
145                 150                 155                 160

Gly Thr Glu Arg Met Glu Asp Gln Gly Gln Ser Ile Ile Pro Met Leu
                165                 170                 175

Thr Gly Glu Val Ile Pro Val Met Glu Leu Leu Ser Ser Met Lys Ser
            180                 185                 190

His Ser Val Pro Glu Glu Ile Asp Ile Ala Asp Thr Val Leu Asn Asp
        195                 200                 205

Asp Asp Ile Gly Asp Ser Cys His Glu Gly Phe Leu Leu Asn Ala Ile
    210                 215                 220

Ser Ser His Leu Gln Thr Cys Gly Cys Ser Val Val Gly Ser Ser
225                 230                 235                 240

Ala Glu Lys Val Asn Lys Ile Val Arg Thr Leu Cys Leu Phe Leu Thr
                245                 250                 255
```

-continued

```
Pro Ala Glu Arg Lys Cys Ser Arg Leu Cys Glu Ala Glu Ser Ser Phe
            260                 265                 270
Lys Tyr Glu Ser Gly Leu Phe Val Gln Gly Leu Leu Lys Asp Ser Thr
        275                 280                 285
Gly Ser Phe Val Leu Pro Phe Arg Gln Val Met Tyr Ala Pro Tyr Pro
    290                 295                 300
Thr Thr His Ile Asp Val Asp Val Asn Thr Val Lys Gln Met Pro Pro
305                 310                 315                 320
Cys His Glu His Ile Tyr Asn Gln Arg Arg Tyr Met Arg Ser Glu Leu
                325                 330                 335
Thr Ala Phe Trp Arg Ala Thr Ser Glu Glu Asp Met Ala Gln Asp Thr
            340                 345                 350
Ile Ile Tyr Thr Asp Glu Ser Phe Thr Pro Asp Leu Asn Ile Phe Gln
        355                 360                 365
Asp Val Leu His Arg Asp Thr Leu Val Lys Ala Phe Leu Asp Gln Val
    370                 375                 380
Phe Gln Leu Lys Pro Gly Leu Ser Leu Arg Ser Thr Phe Leu Ala Gln
385                 390                 395                 400
Phe Leu Leu Val Leu His Arg Lys Ala Leu Thr Leu Ile Lys Tyr Ile
                405                 410                 415
Glu Asp Asp Thr Gln Lys Gly Lys Lys Pro Phe Lys Ser Leu Arg Asn
            420                 425                 430
Leu Lys Ile Asp Leu Asp Leu Thr Ala Glu Gly Asp Leu Asn Ile Ile
        435                 440                 445
Met Ala Leu Ala Glu Lys Ile Lys Pro Gly Leu His Ser Phe Ile Phe
    450                 455                 460
Gly Arg Pro Phe Tyr Thr Ser Val Gln Glu Arg Asp Val Leu Met Thr
465                 470                 475                 480
Phe

<210> SEQ ID NO 19
<211> LENGTH: 16
<212> TYPE: RNA
<213> ORGANISM: Artificial Sequence
<220> FEATURE:
<223> OTHER INFORMATION: Synthetic

<400> SEQUENCE: 19
guuuuagagc uaugcu                                                      16

<210> SEQ ID NO 20
<211> LENGTH: 67
<212> TYPE: RNA
<213> ORGANISM: Artificial Sequence
<220> FEATURE:
<223> OTHER INFORMATION: Synthetic

<400> SEQUENCE: 20
agcauagcaa guuaaaauaa ggcuaguccg uuaucaacuu gaaaaagugg caccgagucg      60
gugcuuu                                                                67

<210> SEQ ID NO 21
<211> LENGTH: 77
<212> TYPE: RNA
<213> ORGANISM: Artificial Sequence
<220> FEATURE:
<223> OTHER INFORMATION: Synthetic
```

```
<400> SEQUENCE: 21
guuuuagagc uagaaauagc aaguuaaaau aaggcuaguc cguuaucaac uugaaaaagu    60
ggcaccgagu cggugcu                                                  77

<210> SEQ ID NO 22
<211> LENGTH: 82
<212> TYPE: RNA
<213> ORGANISM: Artificial Sequence
<220> FEATURE:
<223> OTHER INFORMATION: Synthetic

<400> SEQUENCE: 22
guuggaacca uucaaaacag cauagcaagu uaaaauaagg cuaguccguu aucaacuuga    60
aaaaguggca ccgagucggu gc                                            82

<210> SEQ ID NO 23
<211> LENGTH: 76
<212> TYPE: RNA
<213> ORGANISM: Artificial Sequence
<220> FEATURE:
<223> OTHER INFORMATION: Synthetic

<400> SEQUENCE: 23
guuuuagagc uagaaauagc aaguuaaaau aaggcuaguc cguuaucaac uugaaaaagu    60
ggcaccgagu cggugc                                                   76

<210> SEQ ID NO 24
<211> LENGTH: 86
<212> TYPE: RNA
<213> ORGANISM: Artificial Sequence
<220> FEATURE:
<223> OTHER INFORMATION: Synthetic

<400> SEQUENCE: 24
guuuaagagc uaugcuggaa acagcauagc aaguuuaaau aaggcuaguc cguuaucaac    60
uugaaaaagu ggcaccgagu cggugc                                        86

<210> SEQ ID NO 25
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: n = A, T, C, or G

<400> SEQUENCE: 25
gnnnnnnnnn nnnnnnnnnn ngg                                           23

<210> SEQ ID NO 26
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(21)
<223> OTHER INFORMATION: n = A, T, C, or G

<400> SEQUENCE: 26
nnnnnnnnnn nnnnnnnnnn ngg                                           23
```

```
<210> SEQ ID NO 27
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(23)
<223> OTHER INFORMATION: n = A, T, C, or G

<400> SEQUENCE: 27
ggnnnnnnnn nnnnnnnnnn nnngg                                         25

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
gctatgcgat cgccgtctcg                                               20

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
ccccggcccc ggccccgaga                                               20

<210> SEQ ID NO 30
<211> LENGTH: 20
<212> TYPE: DNA
<213> ORGANISM: Artificial Sequence
<220> FEATURE:
<223> OTHER INFORMATION: Synthetic

<400> SEQUENCE: 30
cgccgtctcg gggccggggc                                               20

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31
ccgtctcggg gccggggccg                                               20

<210> SEQ ID NO 32
<211> LENGTH: 20
<212> TYPE: DNA
<213> ORGANISM: Artificial Sequence
<220> FEATURE:
<223> OTHER INFORMATION: Synthetic

<400> SEQUENCE: 32
cggccggccc tcgagggtct                                               20

<210> SEQ ID NO 33
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 33
ggccggggcc gagaccctcg                                                    20

<210> SEQ ID NO 34
<211> LENGTH: 20
<212> TYPE: DNA
<213> ORGANISM: Artificial Sequence
<220> FEATURE:
<223> OTHER INFORMATION: Synthetic

<400> SEQUENCE: 34
gagggtctcg gccccggccc                                                    20

<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
ctcggccccg gccccggccc                                                    20

<210> SEQ ID NO 36
<211> LENGTH: 39
<212> TYPE: DNA
<213> ORGANISM: Artificial Sequence
<220> FEATURE:
<223> OTHER INFORMATION: Synthetic

<400> SEQUENCE: 36
tgcgcctccg ccgccgcggg cgcaggcacc gcaaccgca                               39

<210> SEQ ID NO 37
<211> LENGTH: 35
<212> TYPE: DNA
<213> ORGANISM: Artificial Sequence
<220> FEATURE:
<223> OTHER INFORMATION: Synthetic

<400> SEQUENCE: 37
cgcagcctgt agcaagctct ggaactcagg agtcg                                   35

<210> SEQ ID NO 38
<211> LENGTH: 16
<212> TYPE: DNA
<213> ORGANISM: Artificial Sequence
<220> FEATURE:
<223> OTHER INFORMATION: Synthetic

<400> SEQUENCE: 38
ccccggcccc ggcccc                                                        16

<210> SEQ ID NO 39
<211> LENGTH: 22
<212> TYPE: DNA
<213> ORGANISM: Artificial Sequence
<220> FEATURE:
<223> OTHER INFORMATION: Synthetic

<400> SEQUENCE: 39
```
ggggccgggg ccgggggggcc cc                                           22

<210> SEQ ID NO 40
<211> LENGTH: 3198
<212> TYPE: DNA
<213> ORGANISM: Mus musculus

<400> SEQUENCE: 40
gtgtccgggg cggggcggtc ccgggcgggg gcccggagcg ggctgcggtt gcggtccctg    60
cgccggcggt gaaggcgcag cagcggcgag tggctattgc aagcgttcgg ataatgtgag   120
acctggaatg cagtgagacc tgggatgcag ggatgtcgac tatctgcccc ccaccatctc   180
ctgctgttgc caagacagag attgctttaa gtggtgaatc accctgttg gcggctacct    240 ttgcttactg ggataatatt cttggtccta gagtaaggca tatttgggct ccaaagacag   300
accaagtgct tctcagtgat ggagaaataa cttttcttgc caaccacact ctaaatggag   360
aaattcttcg aaatgcagag agtggggcta tagatgtaaa attttttgtc ttatctgaaa   420 aagggtaat tattgtttca ttaatcttcg acggaaactg aatggagat cggagcactt     480 atggactatc aattatactg ccgcagacag agctgagctt ctacctccca cttcacagag   540
tgtgtgttga caggctaaca cacattattc gaaaaggaag aatatggatg cataaggaaa   600
gacaagaaaa tgtccagaaa attgtcttgg aaggcacaga gaggatggaa gatcagggtc   660
agagtatcat tcccatgctt actggggaag tcattcctgt aatggagctg cttgcatcta   720
tgaaatccca cagtgttcct gaagacattg atatagctga tacagtgctc aatgatgatg   780
acattggtga cagctgtcac gaaggctttc ttctcaatgc catcagctca cacctgcaga   840
cctgtggctg ttccgttgta gttggcagca gtgcagagaa agtaaataag atagtaagaa   900
cgctgtgcct tttctgaca ccagcagaga ggaaatgctc caggctgtgt gaagcagaat    960 cgtccttta gtacgaatcg ggactctttg tgcaaggctt gctaaaggat gcaacaggca   1020
gttttgtcct accccttccgg caagttatgt atgccccgta ccccaccacg cacattgatg   1080
tggatgtcaa cactgtcaag cagatgccac cgtgtcatga acatatttat aatcaacgca   1140
gatacatgag gtcagagctg acagccttct ggagggcaac ttcagaagag acatggcgc    1200 aggacaccat catctacaca gatgagagct tcactcctga tttgaatatt ttccaagatg   1260
tcttacacag agacactcta gtgaaagcct tcctggatcg ggtcttccat ttgaagcctg   1320
gcctgtctct caggagtact ttccttgcac agttcctcct cattcttcac agaaaagcct   1380
tgacactaat caagtacatc gaggatgata cgcagaaggg gaaaaagccc tttaagtctc   1440
ttcggaacct gaagatagat cttgatttaa cagcagaggg cgatcttaac ataataatgg   1500
ctctagctga gaaaattaag ccaggcctac actctttcat ctttgggaga cctttctaca   1560
ctagtgtaca agaacgtgat gttctaatga ccttttgacc gtgtggtttg ctgtgtctgt   1620
ctcttcacag tcacacctgc tgttacagtg tctcagcagt gtgtgggcac atccttcctc   1680
ccgagtcctg ctgcaggaca gggtacacta cacttgtcag tagaagtctg tacctgatgt   1740
caggtgcatc gttacagtga atgactcttc ctagaataga tgtactcttt tagggcctta   1800
tgtttacaat tatcctaagt actattgctg tcttttaaag atatgaatga tggaatatac   1860
acttgaccat aactgctgat tggtttttg ttttgttttg tttgttttct tggaaactta    1920
tgattcctgg tttacatgta ccacactgaa ccctcgtta gctttacaga taaagtgtga    1980
gttgacttcc tgccctctg tgttctgtgg tatgtccgat tacttctgcc acagctaaac    2040

-continued

```
attagagcat ttaaagtttg cagttcctca gaaaggaact tagtctgact acagattagt   2100
tcttgagaga agacactgat agggcagagc tgtaggtgaa atcagttgtt agcccttcct   2160
ttatagacgt agtccttcag attcggtctg tacagaaatg ccgaggggtc atgcatgggc   2220
cctgagtatc gtgacctgtg acaagttttt tgttggttta ttgtagttct gtcaaagaaa   2280
gtggcatttg ttttttataat tgttgccaac ttttaaggtt aattttcatt attttttgagc  2340 cgaattaaaa tgcgcacctc ctgtgccttt cccaatcttg gaaaatataa tttcttggca   2400
gagggtcaga tttcagggcc cagtcacttt catctgacca cccctttgcac ggctgccgtg   2460 tgcctggctt agattagaag tccttgttaa gtatgtcaga gtacattcgc tgataagatc   2520
tttgaagagc agggaagcgt cttgcctctt tcctttggtt tctgcctgta ctctggtgtt   2580
tcccgtgtca cctgcatcat aggaacagca gagaaatctg acccagtgct attttttctag  2640 gtgctactat ggcaaactca agtggtctgt ttctgttcct gtaacgttcg actatctcgc   2700
tagctgtgaa gtactgatta gtggagttct gtgcaacagc agtgtaggag tatacacaaa   2760
cacaaatatg tgtttctatt taaaactgtg gacttagcat aaaaagggag aatatattta   2820
ttttttacaa aagggataaa aatgggcccc gttcctcacc caccagattt agcgagaaaa   2880
agctttctat tctgaaaggt cacgtggct ttggcattac aaatcagaac aacacacact    2940
gaccatgatg gcttgtgaac taactgcaag gcactccgtc atggtaagcg agtaggtccc   3000
acctcctagt gtgccgctca ttgctttaca cagtagaatc ttatttgagt gctaattgtt   3060
gtctttgctg ctttactgtg ttgttataga aaatgtaagc tgtacagtga ataagttatt   3120
gaagcatgtg taaacactgt tatatatctt ttctcctaga tggggaattt tgaataaaat   3180
acctttgaaa ttctgtgt                                                 3198
```

<210> SEQ ID NO 41
<211> LENGTH: 481
<212> TYPE: PRT
<213> ORGANISM: Mus musculus

<400> SEQUENCE: 41

```
Met Ser Thr Ile Cys Pro Pro Ser Pro Ala Val Ala Lys Thr Glu
1               5                   10                  15

Ile Ala Leu Ser Gly Glu Ser Pro Leu Leu Ala Thr Phe Ala Tyr
                20                  25                  30

Trp Asp Asn Ile Leu Gly Pro Arg Val Arg His Ile Trp Ala Pro Lys
                35                  40                  45

Thr Asp Gln Val Leu Leu Ser Asp Gly Glu Ile Thr Phe Leu Ala Asn
    50                  55                  60

His Thr Leu Asn Gly Glu Ile Leu Arg Asn Ala Glu Ser Gly Ala Ile
65                  70                  75                  80

Asp Val Lys Phe Phe Val Leu Ser Glu Lys Gly Val Ile Ile Val Ser
                85                  90                  95

Leu Ile Phe Asp Gly Asn Trp Asn Gly Asp Arg Ser Thr Tyr Gly Leu
                100                 105                 110

Ser Ile Ile Leu Pro Gln Thr Glu Leu Ser Phe Tyr Leu Pro Leu His
                115                 120                 125

Arg Val Cys Val Asp Arg Leu Thr His Ile Ile Arg Lys Gly Arg Ile
                130                 135                 140

Trp Met His Lys Glu Arg Gln Glu Asn Val Gln Lys Ile Val Leu Glu
145                 150                 155                 160

Gly Thr Glu Arg Met Glu Asp Gln Gly Gln Ser Ile Ile Pro Met Leu
```

```
                  165                 170                 175
Thr Gly Glu Val Ile Pro Val Met Glu Leu Leu Ala Ser Met Lys Ser
                180                 185                 190

His Ser Val Pro Glu Asp Ile Asp Ile Ala Asp Thr Val Leu Asn Asp
            195                 200                 205

Asp Asp Ile Gly Asp Ser Cys His Glu Gly Phe Leu Leu Asn Ala Ile
210                 215                 220

Ser Ser His Leu Gln Thr Cys Gly Cys Ser Val Val Gly Ser Ser
225                 230                 235                 240

Ala Glu Lys Val Asn Lys Ile Val Arg Thr Leu Cys Leu Phe Leu Thr
                245                 250                 255

Pro Ala Glu Arg Lys Cys Ser Arg Leu Cys Glu Ala Glu Ser Ser Phe
            260                 265                 270

Lys Tyr Glu Ser Gly Leu Phe Val Gln Gly Leu Leu Lys Asp Ala Thr
        275                 280                 285

Gly Ser Phe Val Leu Pro Phe Arg Gln Val Met Tyr Ala Pro Tyr Pro
    290                 295                 300

Thr Thr His Ile Asp Val Asp Val Asn Thr Val Lys Gln Met Pro Pro
305                 310                 315                 320

Cys His Glu His Ile Tyr Asn Gln Arg Arg Tyr Met Arg Ser Glu Leu
                325                 330                 335

Thr Ala Phe Trp Arg Ala Thr Ser Glu Glu Asp Met Ala Gln Asp Thr
            340                 345                 350

Ile Ile Tyr Thr Asp Glu Ser Phe Thr Pro Asp Leu Asn Ile Phe Gln
        355                 360                 365

Asp Val Leu His Arg Asp Thr Leu Val Lys Ala Phe Leu Asp Gln Val
    370                 375                 380

Phe His Leu Lys Pro Gly Leu Ser Leu Arg Ser Thr Phe Leu Ala Gln
385                 390                 395                 400

Phe Leu Leu Ile Leu His Arg Lys Ala Leu Thr Leu Ile Lys Tyr Ile
                405                 410                 415

Glu Asp Asp Thr Gln Lys Gly Lys Lys Pro Phe Lys Ser Leu Arg Asn
            420                 425                 430

Leu Lys Ile Asp Leu Asp Leu Thr Ala Glu Gly Asp Leu Asn Ile Ile
        435                 440                 445

Met Ala Leu Ala Glu Lys Ile Lys Pro Gly Leu His Ser Phe Ile Phe
    450                 455                 460

Gly Arg Pro Phe Tyr Thr Ser Val Gln Glu Arg Asp Val Leu Met Thr
465                 470                 475                 480

Phe

<210> SEQ ID NO 42
<211> LENGTH: 3435
<212> TYPE: DNA
<213> ORGANISM: Rattus norvegicus

<400> SEQUENCE: 42
cgtttgtagt gtcagccatc ccaattgcct gttccttctc tgtgggagtg gtgtctagac      60
agtccaggca gggtatgcta ggcaggtgcg ttttggttgc ctcagatcgc aacttgactc     120
cataacggtg accaaagaca aaagaaggaa accagattaa aagaaccgg acacagaccc     180 ctgcagaatc tggagcggcc gtggttgggg gcggggctac gacggggcgg actcgggggc     240
gtgggagggc ggggccgggg cggggcccgg agccggctgc ggttgcggtc cctgcgccgg     300
```

```
cggtgaaggc gcagcggcgg cgagtggcta ttgcaagcgt ttggataatg tgagacctgg    360
gatgcaggga tgtcgactat ctgcccccca ccatctcctg ctgttgccaa gacagagatt    420
gctttaagtg gtgaatcacc cttgttggcg gctacctttg cttactggga taatattctt    480
ggtcctagag taaggcacat ttgggctcca aagacagacc aagtactcct cagtgatgga    540
gaaatcactt ttcttgccaa ccacactctg aatggagaaa ttcttcggaa tgcggagagt    600
ggggcaatag atgtaaagtt ttttgtctta tctgaaaagg gcgtcattat tgtttcatta    660
atcttcgacg ggaactggaa cggagatcgg agcacttacg gactatcaat tatactgccg    720
cagacggagc tgagtttcta cctcccactg cacagagtgt gtgttgacag gctaacgcac    780
atcattcgaa aaggaaggat atggatgcac aaggaaagac aagaaaatgt ccagaaaatt    840
gtcttggaag gcaccgagag gatggaagat cagggtcaga gtatcatccc tatgcttact    900
ggggaggtca tccctgtgat ggagctgctt gcgtctatga gatcacacag tgttcctgaa    960
gacctcgata tagctgatac agtactcaat gatgatgaca ttggtgacag ctgtcatgaa   1020
ggctttcttc tcaatgccat cagctcacat ctgcagacct gcggctgttc tgtggtggta   1080
ggcagcagtg cagagaaagt aaataagata gtaagaacac tgtgccttttt tctgacacca   1140
gcagagagga agtgctccag gctgtgtgaa gccgaatcgt cctttaaata cgaatctgga   1200
ctctttgtac aaggcttgct aaaggatgcg actggcagtt ttgtactacc tttccggcaa   1260
gttatgtatg ccccttatcc caccacacac atcgatgtgg atgtcaacac tgtcaagcag   1320
atgccaccgt gtcatgaaca tatttataat caacgcagat acatgaggtc agagctgaca   1380
gccttctgga gggcaacttc agaagaggac atggctcagg acaccatcat ctacacagat   1440
gagagcttca ctcctgattt gaatattttc caagatgtct tacacagaga cactctagtg   1500
aaagcctttc tggatcaggt cttccatttg aagcctggcc tgtctctcag gagtactttc   1560
cttgcacagt tcctcctcat tcttcacaga aaagccttga cactaatcaa gtacatagag   1620
gatgacacgc agaaggggaa aaagcccttt aagtctcttc ggaacctgaa gatagatctt   1680
gatttaacag cagagggcga ccttaacata taatggctc tagctgagaa aattaagcca   1740
ggcctacact ctttcatctt cgggagacct ttctacacta gtgtccaaga acgtgatgtt   1800
ctaatgactt tttaaacatg tggtttgctc cgtgtgtctc atgacagtca cacttgctgt   1860
tacagtgtct cagcgctttg gacacatcct tcctccaggg tcctgccgca ggacacgtta   1920
cactacactt gtcagtagag gtctgtacca gatgtcaggt acatcgttgt agtgaatgtc   1980
tcttttccta gactagatgt accctcgtag ggacttatgt ttacaaccct cctaagtact   2040
agtgctgtct tgtaaggata cgaatgaagg gatgtaaact tcaccacaac tgctggttgg   2100
ttttgttgtt tttgttttt gaaacttata attcatggtt tacatgcatc acactgaaac   2160
cctagttagc tttttacagg taagctgtga gttgactgcc tgtccctgtg ttctctggcc   2220
tgtacgatct gtggcgtgta ggatcacttt tgcaacaact aaaaactaaa gcactttgtt   2280
tgcagttcta cagaaagcaa cttagtctgt ctgcagattc gttttttgaaa gaagacatga   2340
gaaagcggag tttaggtga agtcagttgt tggatcttcc tttatagact tagtcctta    2400
gatgtggtct gtatagacat gcccaaccat catgcatggg cactgaatat cgtgaactgt   2460
ggtatgcttt ttgttggttt attgtacttc tgtcaaagaa agtggcattg ttttttataa   2520
ttgttgccaa gttttaaggt taattttcat tatttttgag ccaaattaaa atgtgcacct   2580
cctgtgcctt tcccaatctt ggaaaatata atttcttggc agaaggtcag atttcagggc   2640
ccagtcactt tcgtctgact tccctttgca cagtccgcca tgggcctggc ttagaagttc   2700
```

```
ttgtaaacta tgccagagag tacattcgct gataaaatct tctttgcaga gcaggagagc    2760
ttcttgcctc tttcctttca tttctgcctg gactttggtg ttctccacgt tccctgcatc    2820
ctaaggacag caggagaact ctgaccccag tgctatttct ctaggtgcta ttgtggcaaa    2880
ctcaagcggt ccgtctctgt ccctgtaacg ttcgtacctt gctggctgtg aagtactgac    2940
tggtaaagct ccgtgctaca gcagtgtagg gtatacacaa acacaagtaa gtgttttatt    3000
taaaactgtg gacttagcat aaaaagggag actatattta ttttttacaa aagggataaa    3060
aatggaaccc tttcctcacc caccagattt agtcagaaaa aaacattcta ttctgaaagg    3120
tcacagtggt tttgacatga cacatcagaa caacgcacac tgtccatgat ggcttatgaa    3180
ctccaagtca ctccatcatg gtaaatgggt agatccctcc ttctagtgtg ccacaccatt    3240
gcttcccaca gtagaatctt atttaagtgc taagtgttgt ctctgctggt ttactctgtt    3300
gttttagaga atgtaagttg tatagtgaat aagttattga agcatgtgta aacactgtta    3360
tacatctttt ctcctagatg gggaatttgg aataaaatac ctttaaaatt caaaaaaaaa    3420
aaaaaaaaaa aaaaa                                                    3435
```

<210> SEQ ID NO 43
<211> LENGTH: 481
<212> TYPE: PRT
<213> ORGANISM: Rattus norvegicus

<400> SEQUENCE: 43

```
Met Ser Thr Ile Cys Pro Pro Ser Pro Ala Val Ala Lys Thr Glu
1               5                   10                  15

Ile Ala Leu Ser Gly Glu Ser Pro Leu Leu Ala Ala Thr Phe Ala Tyr
            20                  25                  30

Trp Asp Asn Ile Leu Gly Pro Arg Val Arg His Ile Trp Ala Pro Lys
        35                  40                  45

Thr Asp Gln Val Leu Leu Ser Asp Gly Glu Ile Thr Phe Leu Ala Asn
    50                  55                  60

His Thr Leu Asn Gly Glu Ile Leu Arg Asn Ala Glu Ser Gly Ala Ile
65                  70                  75                  80

Asp Val Lys Phe Phe Val Leu Ser Glu Lys Gly Val Ile Ile Val Ser
                85                  90                  95

Leu Ile Phe Asp Gly Asn Trp Asn Gly Asp Arg Ser Tyr Gly Leu
            100                 105                 110

Ser Ile Ile Leu Pro Gln Thr Glu Leu Ser Phe Tyr Leu Pro Leu His
        115                 120                 125

Arg Val Cys Val Asp Arg Leu Thr His Ile Ile Arg Lys Gly Arg Ile
    130                 135                 140

Trp Met His Lys Glu Arg Gln Glu Asn Val Gln Lys Ile Val Leu Glu
145                 150                 155                 160

Gly Thr Glu Arg Met Glu Asp Gln Gly Gln Ser Ile Ile Pro Met Leu
                165                 170                 175

Thr Gly Glu Val Ile Pro Val Met Glu Leu Leu Ala Ser Met Arg Ser
            180                 185                 190

His Ser Val Pro Glu Asp Leu Asp Ile Ala Asp Thr Val Leu Asn Asp
        195                 200                 205

Asp Asp Ile Gly Asp Ser Cys His Glu Gly Phe Leu Leu Asn Ala Ile
    210                 215                 220

Ser Ser His Leu Gln Thr Cys Gly Cys Ser Val Val Gly Ser Ser
225                 230                 235                 240
```

```
Ala Glu Lys Val Asn Lys Ile Val Arg Thr Leu Cys Leu Phe Leu Thr
            245                 250                 255

Pro Ala Glu Arg Lys Cys Ser Arg Leu Cys Glu Ala Glu Ser Ser Phe
        260                 265                 270

Lys Tyr Glu Ser Gly Leu Phe Val Gln Gly Leu Leu Lys Asp Ala Thr
    275                 280                 285

Gly Ser Phe Val Leu Pro Phe Arg Gln Val Met Tyr Ala Pro Tyr Pro
290                 295                 300

Thr Thr His Ile Asp Val Asp Val Asn Thr Val Lys Gln Met Pro Pro
305                 310                 315                 320

Cys His Glu His Ile Tyr Asn Gln Arg Tyr Met Arg Ser Glu Leu
            325                 330                 335

Thr Ala Phe Trp Arg Ala Thr Ser Glu Glu Asp Met Ala Gln Asp Thr
            340                 345                 350

Ile Ile Tyr Thr Asp Glu Ser Phe Thr Pro Asp Leu Asn Ile Phe Gln
            355                 360                 365

Asp Val Leu His Arg Asp Thr Leu Val Lys Ala Phe Leu Asp Gln Val
        370                 375                 380

Phe His Leu Lys Pro Gly Leu Ser Leu Arg Ser Thr Phe Leu Ala Gln
385                 390                 395                 400

Phe Leu Leu Ile Leu His Arg Lys Ala Leu Thr Leu Ile Lys Tyr Ile
                405                 410                 415

Glu Asp Asp Thr Gln Lys Gly Lys Lys Pro Phe Lys Ser Leu Arg Asn
            420                 425                 430

Leu Lys Ile Asp Leu Asp Leu Thr Ala Glu Gly Asp Leu Asn Ile Ile
        435                 440                 445

Met Ala Leu Ala Glu Lys Ile Lys Pro Gly Leu His Ser Phe Ile Phe
    450                 455                 460

Gly Arg Pro Phe Tyr Thr Ser Val Gln Glu Arg Asp Val Leu Met Thr
465                 470                 475                 480

Phe

<210> SEQ ID NO 44
<211> LENGTH: 18
<212> TYPE: DNA
<213> ORGANISM: Artificial Sequence
<220> FEATURE:
<223> OTHER INFORMATION: Synthetic

<400> SEQUENCE: 44
ccccggcccc ggccccgg                                                18

<210> SEQ ID NO 45
<211> LENGTH: 17
<212> TYPE: DNA
<213> ORGANISM: Artificial Sequence
<220> FEATURE:
<223> OTHER INFORMATION: Synthetic

<400> SEQUENCE: 45
ggggccgggg ccggggc                                                 17

<210> SEQ ID NO 46
<211> LENGTH: 198
<212> TYPE: DNA
<213> ORGANISM: Homo sapiens

<400> SEQUENCE: 46
```
gggtctagca agagcaggtg tgggtttagg aggtgtgtgt ttttgttttt cccaccctct    60
ctccccacta cttgctctca cagtactcgc tgagggtgaa caagaaaaga cctgataaag   120
attaaccaga agaaaacaag gagggaaaca accgcagcct gtagcaagct ctggaactca   180
ggagtcgcgc gctatgcg                                                 198

<210> SEQ ID NO 47
<211> LENGTH: 118
<212> TYPE: DNA
<213> ORGANISM: Homo sapiens

<400> SEQUENCE: 47
gcgatcgcgg ggcgtggtcg gggcgggccc ggggcgggc cggggcggg gctgcggttg     60 cggtgcctgc gcccgcggcg gcggaggcgc aggcggtggc gagtgggtga gtgaggag    118

<210> SEQ ID NO 48
<211> LENGTH: 18
<212> TYPE: DNA
<213> ORGANISM: Artificial Sequence
<220> FEATURE:
<223> OTHER INFORMATION: Synthetic

<400> SEQUENCE: 48
ccccggcccc ggccccgg                                                  18

<210> SEQ ID NO 49
<211> LENGTH: 12
<212> TYPE: DNA
<213> ORGANISM: Artificial Sequence
<220> FEATURE:
<223> OTHER INFORMATION: Synthetic

<400> SEQUENCE: 49
agtcagtcag tc                                                        12

<210> SEQ ID NO 50
<211> LENGTH: 43
<212> TYPE: DNA
<213> ORGANISM: Artificial Sequence
<220> FEATURE:
<223> OTHER INFORMATION: Synthetic

<400> SEQUENCE: 50
ggggccgggg ccggggccgg ggccggggcc ggggagtcag tca                      43

<210> SEQ ID NO 51
<211> LENGTH: 9
<212> TYPE: DNA
<213> ORGANISM: Artificial Sequence
<220> FEATURE:
<223> OTHER INFORMATION: Synthetic

<400> SEQUENCE: 51 tcagtcagt                                                             9

<210> SEQ ID NO 52
<211> LENGTH: 20
<212> TYPE: DNA
<213> ORGANISM: Artificial Sequence
<220> FEATURE:
<223> OTHER INFORMATION: Synthetic

<400> SEQUENCE: 52
agagccccgg ccccggcccc                                              20

<210> SEQ ID NO 53
<211> LENGTH: 20
<212> TYPE: DNA
<213> ORGANISM: Artificial Sequence
<220> FEATURE:
<223> OTHER INFORMATION: Synthetic

<400> SEQUENCE: 53
tctgggagct cccggccggc                                              20

<210> SEQ ID NO 54
<211> LENGTH: 20
<212> TYPE: DNA
<213> ORGANISM: Artificial Sequence
<220> FEATURE:
<223> OTHER INFORMATION: Synthetic

<400> SEQUENCE: 54
cccggccccg gctctgggag                                              20

<210> SEQ ID NO 55
<211> LENGTH: 20
<212> TYPE: DNA
<213> ORGANISM: Artificial Sequence
<220> FEATURE:
<223> OTHER INFORMATION: Synthetic

<400> SEQUENCE: 55
cccggccccg gccccggctc                                              20

<210> SEQ ID NO 56
<211> LENGTH: 42
<212> TYPE: RNA
<213> ORGANISM: Artificial Sequence
<220> FEATURE:
<223> OTHER INFORMATION: Synthetic

<400> SEQUENCE: 56
gcuaugcgau cgccgucucg guuuuagagc uaugcuguuu ug                     42

<210> SEQ ID NO 57
<211> LENGTH: 42
<212> TYPE: RNA
<213> ORGANISM: Artificial Sequence
<220> FEATURE:
<223> OTHER INFORMATION: Synthetic

<400> SEQUENCE: 57
ccccggcccc ggccccgaga guuuuagagc uaugcuguuu ug                     42

<210> SEQ ID NO 58
<211> LENGTH: 43
<212> TYPE: DNA
<213> ORGANISM: Artificial Sequence
<220> FEATURE:
<223> OTHER INFORMATION: Synthetic

<400> SEQUENCE: 58
gcgcgctatg cgatcgccgt ctcggggccg gggccggggc cgg                    43

<210> SEQ ID NO 59
<211> LENGTH: 62
<212> TYPE: DNA
<213> ORGANISM: Artificial Sequence
<220> FEATURE:
<223> OTHER INFORMATION: Synthetic

<400> SEQUENCE: 59
ccggggccgg ggccggggcc gagaccctcg agggccggcc gctagcgcga tcgcggggcg    60
tg                                                                   62

<210> SEQ ID NO 60
<211> LENGTH: 36
<212> TYPE: DNA
<213> ORGANISM: Artificial Sequence
<220> FEATURE:
<223> OTHER INFORMATION: Synthetic

<400> SEQUENCE: 60
ggggccgggg ccggggccgg ggccggggcc ggggcc                              36

<210> SEQ ID NO 61
<211> LENGTH: 19
<212> TYPE: DNA
<213> ORGANISM: Artificial Sequence
<220> FEATURE:
<223> OTHER INFORMATION: Synthetic

<400> SEQUENCE: 61
catcccaatt gccctttcc                                                 19

<210> SEQ ID NO 62
<211> LENGTH: 21
<212> TYPE: DNA
<213> ORGANISM: Artificial Sequence
<220> FEATURE:
<223> OTHER INFORMATION: Synthetic

<400> SEQUENCE: 62
cccacacctg ctcttgctag a                                              21

<210> SEQ ID NO 63
<211> LENGTH: 17
<212> TYPE: DNA
<213> ORGANISM: Artificial Sequence
<220> FEATURE:
<223> OTHER INFORMATION: Synthetic

<400> SEQUENCE: 63
tctaggtgga aagtggg                                                   17

<210> SEQ ID NO 64
<211> LENGTH: 20
<212> TYPE: DNA
<213> ORGANISM: Artificial Sequence
<220> FEATURE:
<223> OTHER INFORMATION: Synthetic

<400> SEQUENCE: 64
gagcaggtgt gggtttagga                                                20

<210> SEQ ID NO 65
<211> LENGTH: 20
<212> TYPE: DNA
<213> ORGANISM: Artificial Sequence
<220> FEATURE:
<223> OTHER INFORMATION: Synthetic

<400> SEQUENCE: 65
ccaggtctca ctgcattcca          20

<210> SEQ ID NO 66
<211> LENGTH: 26
<212> TYPE: DNA
<213> ORGANISM: Artificial Sequence
<220> FEATURE:
<223> OTHER INFORMATION: Synthetic

<400> SEQUENCE: 66
attgcaagcg ttcggataat gtgaga          26

<210> SEQ ID NO 67
<211> LENGTH: 21
<212> TYPE: DNA
<213> ORGANISM: Artificial Sequence
<220> FEATURE:
<223> OTHER INFORMATION: Synthetic

<400> SEQUENCE: 67
gctgtcacga aggctttctt c          21

<210> SEQ ID NO 68
<211> LENGTH: 20
<212> TYPE: DNA
<213> ORGANISM: Artificial Sequence
<220> FEATURE:
<223> OTHER INFORMATION: Synthetic

<400> SEQUENCE: 68
gcactgctgc caactacaac          20

<210> SEQ ID NO 69
<211> LENGTH: 24
<212> TYPE: DNA
<213> ORGANISM: Artificial Sequence
<220> FEATURE:
<223> OTHER INFORMATION: Synthetic

<400> SEQUENCE: 69
tcaatgccat cagctcacac ctgc          24

<210> SEQ ID NO 70
<211> LENGTH: 17
<212> TYPE: DNA
<213> ORGANISM: Artificial Sequence
<220> FEATURE:
<223> OTHER INFORMATION: Synthetic

<400> SEQUENCE: 70
aagaggcgcg ggtagaa          17

<210> SEQ ID NO 71
<211> LENGTH: 22
<212> TYPE: DNA
<213> ORGANISM: Artificial Sequence
<220> FEATURE:
<223> OTHER INFORMATION: Synthetic

<400> SEQUENCE: 71
cagcttcggt cagagaaatg ag          22

<210> SEQ ID NO 72
<211> LENGTH: 24
<212> TYPE: DNA
<213> ORGANISM: Artificial Sequence

```
<220> FEATURE:
<223> OTHER INFORMATION: Synthetic

<400> SEQUENCE: 72
ctctcctcag agctcgacgc attt                                              24

<210> SEQ ID NO 73
<211> LENGTH: 20
<212> TYPE: DNA
<213> ORGANISM: Artificial Sequence
<220> FEATURE:
<223> OTHER INFORMATION: Synthetic

<400> SEQUENCE: 73
ctgcacaatt tcagcccaag                                                   20

<210> SEQ ID NO 74
<211> LENGTH: 20
<212> TYPE: DNA
<213> ORGANISM: Artificial Sequence
<220> FEATURE:
<223> OTHER INFORMATION: Synthetic

<400> SEQUENCE: 74
caggtcatgt cccacagaat                                                   20

<210> SEQ ID NO 75
<211> LENGTH: 24
<212> TYPE: DNA
<213> ORGANISM: Artificial Sequence
<220> FEATURE:
<223> OTHER INFORMATION: Synthetic

<400> SEQUENCE: 75
catatgaggg cagcaatgca agtc                                              24

<210> SEQ ID NO 76
<211> LENGTH: 42
<212> TYPE: RNA
<213> ORGANISM: Artificial Sequence
<220> FEATURE:
<223> OTHER INFORMATION: Synthetic

<400> SEQUENCE: 76
cgccgucucg gggccggggc guuuuagagc uaugcuguuu ug                          42

<210> SEQ ID NO 77
<211> LENGTH: 42
<212> TYPE: RNA
<213> ORGANISM: Artificial Sequence
<220> FEATURE:
<223> OTHER INFORMATION: Synthetic

<400> SEQUENCE: 77
ccgucucggg gccggggccg guuuuagagc uaugcuguuu ug                          42

<210> SEQ ID NO 78
<211> LENGTH: 42
<212> TYPE: RNA
<213> ORGANISM: Artificial Sequence
<220> FEATURE:
<223> OTHER INFORMATION: Synthetic

<400> SEQUENCE: 78
cggccggccc ucgagggucu guuuuagagc uaugcuguuu ug                          42
```

```
<210> SEQ ID NO 79
<211> LENGTH: 42
<212> TYPE: RNA
<213> ORGANISM: Artificial Sequence
<220> FEATURE:
<223> OTHER INFORMATION: Synthetic

<400> SEQUENCE: 79
ggccggggcc gagacccucg guuuuagagc uaugcuguuu ug          42

<210> SEQ ID NO 80
<211> LENGTH: 42
<212> TYPE: RNA
<213> ORGANISM: Artificial Sequence
<220> FEATURE:
<223> OTHER INFORMATION: Synthetic

<400> SEQUENCE: 80
gagggucucg gccccggccc guuuuagagc uaugcuguuu ug          42

<210> SEQ ID NO 81
<211> LENGTH: 42
<212> TYPE: RNA
<213> ORGANISM: Artificial Sequence
<220> FEATURE:
<223> OTHER INFORMATION: Synthetic

<400> SEQUENCE: 81
cucggccccg gccccggccc guuuuagagc uaugcuguuu ug          42

<210> SEQ ID NO 82
<211> LENGTH: 89
<212> TYPE: RNA
<213> ORGANISM: Artificial Sequence
<220> FEATURE:
<223> OTHER INFORMATION: Synthetic

<400> SEQUENCE: 82
guuggaacca uucaaaacag cauagcaagu uaaaauaagg cuaguccguu aucaacuuga    60
aaaaguggca ccgagucggu gcuuuuuuu                                     89

<210> SEQ ID NO 83
<211> LENGTH: 22
<212> TYPE: RNA
<213> ORGANISM: Artificial Sequence
<220> FEATURE:
<223> OTHER INFORMATION: Synthetic

<400> SEQUENCE: 83
guuuuagagc uaugcuguuu ug                                22

<210> SEQ ID NO 84
<211> LENGTH: 20
<212> TYPE: RNA
<213> ORGANISM: Artificial Sequence
<220> FEATURE:
<223> OTHER INFORMATION: Synthetic

<400> SEQUENCE: 84
gcuaugcgau cgccgucucg                                   20

<210> SEQ ID NO 85
<211> LENGTH: 20
<212> TYPE: RNA
<213> ORGANISM: Artificial Sequence
```

<220> FEATURE:
<223> OTHER INFORMATION: Synthetic

<400> SEQUENCE: 85
ccccggcccc ggccccgaga                                              20

<210> SEQ ID NO 86
<211> LENGTH: 20
<212> TYPE: RNA
<213> ORGANISM: Artificial Sequence
<220> FEATURE:
<223> OTHER INFORMATION: Synthetic

<400> SEQUENCE: 86
cgccgucucg gggccggggc                                              20

<210> SEQ ID NO 87
<211> LENGTH: 20
<212> TYPE: RNA
<213> ORGANISM: Artificial Sequence
<220> FEATURE:
<223> OTHER INFORMATION: Synthetic

<400> SEQUENCE: 87
ccgucucggg gccggggccg                                              20

<210> SEQ ID NO 88
<211> LENGTH: 20
<212> TYPE: RNA
<213> ORGANISM: Artificial Sequence
<220> FEATURE:
<223> OTHER INFORMATION: Synthetic

<400> SEQUENCE: 88
cggccggccc ucgagggucu                                              20

<210> SEQ ID NO 89
<211> LENGTH: 20
<212> TYPE: RNA
<213> ORGANISM: Artificial Sequence
<220> FEATURE:
<223> OTHER INFORMATION: Synthetic

<400> SEQUENCE: 89
ggccggggcc gagacccucg                                              20

<210> SEQ ID NO 90
<211> LENGTH: 20
<212> TYPE: RNA
<213> ORGANISM: Artificial Sequence
<220> FEATURE:
<223> OTHER INFORMATION: Synthetic

<400> SEQUENCE: 90
gagggucucg gccccggccc                                              20

<210> SEQ ID NO 91
<211> LENGTH: 20
<212> TYPE: RNA
<213> ORGANISM: Artificial Sequence
<220> FEATURE:
<223> OTHER INFORMATION: Synthetic

<400> SEQUENCE: 91
cucggccccg gccccggccc                                              20

```
<210> SEQ ID NO 92
<211> LENGTH: 21
<212> TYPE: DNA
<213> ORGANISM: Artificial Sequence
<220> FEATURE:
<223> OTHER INFORMATION: Synthetic

<400> SEQUENCE: 92
gatagtcgac atccctgcat c                                              21

<210> SEQ ID NO 93
<211> LENGTH: 18
<212> TYPE: DNA
<213> ORGANISM: Artificial Sequence
<220> FEATURE:
<223> OTHER INFORMATION: Synthetic

<400> SEQUENCE: 93
ggtggcgagt ggctattg                                                  18

<210> SEQ ID NO 94
<211> LENGTH: 26
<212> TYPE: DNA
<213> ORGANISM: Artificial Sequence
<220> FEATURE:
<223> OTHER INFORMATION: Synthetic

<400> SEQUENCE: 94
aagcgttcgg ataatgtgag acctgg                                         26

<210> SEQ ID NO 95
<211> LENGTH: 24
<212> TYPE: DNA
<213> ORGANISM: Artificial Sequence
<220> FEATURE:
<223> OTHER INFORMATION: Synthetic

<400> SEQUENCE: 95
tctcacagta ctcgctgagg gtga                                           24

<210> SEQ ID NO 96
<211> LENGTH: 20
<212> TYPE: DNA
<213> ORGANISM: Artificial Sequence
<220> FEATURE:
<223> OTHER INFORMATION: Synthetic

<400> SEQUENCE: 96
aagagcaggt gtgggtttag                                                20

<210> SEQ ID NO 97
<211> LENGTH: 19
<212> TYPE: DNA
<213> ORGANISM: Artificial Sequence
<220> FEATURE:
<223> OTHER INFORMATION: Synthetic

<400> SEQUENCE: 97
cggttgtttc cctccttgt                                                 19

<210> SEQ ID NO 98
<211> LENGTH: 20
<212> TYPE: DNA
<213> ORGANISM: Artificial Sequence
<220> FEATURE:
<223> OTHER INFORMATION: Synthetic
```

<400> SEQUENCE: 98
cccactactt gctctcacag                                               20

<210> SEQ ID NO 99
<211> LENGTH: 18
<212> TYPE: DNA
<213> ORGANISM: Artificial Sequence
<220> FEATURE:
<223> OTHER INFORMATION: Synthetic

<400> SEQUENCE: 99
tacaggctgc ggttgttt                                                 18

<210> SEQ ID NO 100
<211> LENGTH: 23
<212> TYPE: DNA
<213> ORGANISM: Artificial Sequence
<220> FEATURE:
<223> OTHER INFORMATION: Synthetic

<400> SEQUENCE: 100
actcgctgag ggtgaacaag aaa                                           23

<210> SEQ ID NO 101
<211> LENGTH: 18
<212> TYPE: DNA
<213> ORGANISM: Artificial Sequence
<220> FEATURE:
<223> OTHER INFORMATION: Synthetic

<400> SEQUENCE: 101
cgagtgggtg agtgagga                                                 18

<210> SEQ ID NO 102
<211> LENGTH: 17
<212> TYPE: DNA
<213> ORGANISM: Artificial Sequence
<220> FEATURE:
<223> OTHER INFORMATION: Synthetic

<400> SEQUENCE: 102
ttctacccgc gcctctt                                                  17

<210> SEQ ID NO 103
<211> LENGTH: 20
<212> TYPE: DNA
<213> ORGANISM: Artificial Sequence
<220> FEATURE:
<223> OTHER INFORMATION: Synthetic

<400> SEQUENCE: 103
atcctggcgg gtggctgttt                                               20

<210> SEQ ID NO 104
<211> LENGTH: 22
<212> TYPE: DNA
<213> ORGANISM: Artificial Sequence
<220> FEATURE:
<223> OTHER INFORMATION: Synthetic

<400> SEQUENCE: 104
cggataatgt gagacctgga at                                            22

<210> SEQ ID NO 105

```
<211> LENGTH: 18
<212> TYPE: DNA
<213> ORGANISM: Artificial Sequence
<220> FEATURE:
<223> OTHER INFORMATION: Synthetic

<400> SEQUENCE: 105
aaaggtagcc gccaacaa                                                   18

<210> SEQ ID NO 106
<211> LENGTH: 23
<212> TYPE: DNA
<213> ORGANISM: Artificial Sequence
<220> FEATURE:
<223> OTHER INFORMATION: Synthetic

<400> SEQUENCE: 106
accatctcct gctgttgcca aga                                             23

<210> SEQ ID NO 107
<211> LENGTH: 213
<212> TYPE: DNA
<213> ORGANISM: Artificial Sequence
<220> FEATURE:
<223> OTHER INFORMATION: Synthetic

<400> SEQUENCE: 107
ctcaggagtc gcgcgctatg cgatcgccgt ctcggggccg gggccggggc cggggccggg     60
gccggggccg gggccggggc cggggccggg gccggggccg gggccggggc cggggccggg    120
gccggggccg gggccggggc cggggccggg gccggggccg gggccggggc cggggccggg    180
gccggggccg gggccggggc cggggccggg gcc                                 213

<210> SEQ ID NO 108
<211> LENGTH: 291
<212> TYPE: DNA
<213> ORGANISM: Artificial Sequence
<220> FEATURE:
<223> OTHER INFORMATION: Synthetic

<400> SEQUENCE: 108
ctcaggagtc gcgcgctatg cgatcgccgt ctcggggccg gggccggggc cggggccggg     60
gccggggccg gggccggggc cggggccggg gccggggccg gggccggggc cggggccggg    120
gccggggccg gggccggggc cggggccggg gccggggccg gggccggggc cggggccggg    180
gccggggccg gggccggggc cggggccggg gccggggccg gggccggggc cggggccggg    240
gccggggccg gggccggggc cggggccggg gccggggccg gggccggggc c             291

<210> SEQ ID NO 109
<211> LENGTH: 70
<212> TYPE: DNA
<213> ORGANISM: Artificial Sequence
<220> FEATURE:
<223> OTHER INFORMATION: Synthetic

<400> SEQUENCE: 109
gggccggggc cggggccggg gccggggccg gggccgagac cctcgagggc cggccgctag     60
cgcgatcgcg                                                           70

<210> SEQ ID NO 110
<211> LENGTH: 69
<212> TYPE: DNA
<213> ORGANISM: Artificial Sequence
```

```
<220> FEATURE:
<223> OTHER INFORMATION: Synthetic

<400> SEQUENCE: 110
gggccggggc cggggccggg gccggggccg gggccgagac ctcgagggcc ggccgctagc    60
gcgatcgcg                                                            69

<210> SEQ ID NO 111
<211> LENGTH: 66
<212> TYPE: DNA
<213> ORGANISM: Artificial Sequence
<220> FEATURE:
<223> OTHER INFORMATION: Synthetic

<400> SEQUENCE: 111
gggccggggc cggggccggg gccggggccg gggccgagac gagggccggc cgctagcgcg    60
atcgcg                                                               66

<210> SEQ ID NO 112
<211> LENGTH: 68
<212> TYPE: DNA
<213> ORGANISM: Artificial Sequence
<220> FEATURE:
<223> OTHER INFORMATION: Synthetic

<400> SEQUENCE: 112
gggccggggc cggggccggg gccggggccg gggccgagac ccgagggccg gccgctagcg    60
cgatcgcg                                                             68

<210> SEQ ID NO 113
<211> LENGTH: 66
<212> TYPE: DNA
<213> ORGANISM: Artificial Sequence
<220> FEATURE:
<223> OTHER INFORMATION: Synthetic

<400> SEQUENCE: 113
gggccggggc cggggccggg gccggggccg gggccggggc cggggccggc cgctagcgcg    60
atcgcg                                                               66

<210> SEQ ID NO 114
<211> LENGTH: 23
<212> TYPE: DNA
<213> ORGANISM: Artificial Sequence
<220> FEATURE:
<223> OTHER INFORMATION: Synthetic

<400> SEQUENCE: 114
ggccggggcc gagaccctcg agg                                            23

<210> SEQ ID NO 115
<211> LENGTH: 74
<212> TYPE: DNA
<213> ORGANISM: Artificial Sequence
<220> FEATURE:
<223> OTHER INFORMATION: Synthetic

<400> SEQUENCE: 115
gccggggccg ggccggggc cgagaccctc gagggccggc cgctagcgcg atcgcggggc     60
gtggtcgggg cggg                                                      74

<210> SEQ ID NO 116
```

```
<211> LENGTH: 72
<212> TYPE: RNA
<213> ORGANISM: Artificial Sequence
<220> FEATURE:
<223> OTHER INFORMATION: Synthetic

<400> SEQUENCE: 116
aaacagcaua gcaaguuaaa auaaggcuag uccguuauca acuugaaaaa guggcaccga     60
gucggugcuu uu                                                        72

<210> SEQ ID NO 117
<211> LENGTH: 82
<212> TYPE: RNA
<213> ORGANISM: Artificial Sequence
<220> FEATURE:
<223> OTHER INFORMATION: Synthetic

<400> SEQUENCE: 117
guuggaacca uucaaaacag cauagcaagu uaaauaagg cuaguccguu aucaacuuga      60 aaaguggca ccgagucggu gc                                              82

<210> SEQ ID NO 118
<211> LENGTH: 83
<212> TYPE: RNA
<213> ORGANISM: Artificial Sequence
<220> FEATURE:
<223> OTHER INFORMATION: Synthetic

<400> SEQUENCE: 118
guuuuagagc uagaaauagc aaguuaaaau aaggcuaguc cguuaucaac uugaaaagu      60 ggcaccgagu cggugcuuuu uuu                                            83

<210> SEQ ID NO 119
<211> LENGTH: 80
<212> TYPE: RNA
<213> ORGANISM: Artificial Sequence
<220> FEATURE:
<223> OTHER INFORMATION: Synthetic

<400> SEQUENCE: 119
guuuuagagc uagaaauagc aaguuaaaau aaggcuaguc cguuaucaac uugaaaagu      60 ggcaccgagu cggugcuuuu                                                80

<210> SEQ ID NO 120
<211> LENGTH: 92
<212> TYPE: RNA
<213> ORGANISM: Artificial Sequence
<220> FEATURE:
<223> OTHER INFORMATION: Synthetic

<400> SEQUENCE: 120
guuuaagagc uaugcuggaa acagcauagc aaguuuaaau aaggcuaguc cguuaucaac    60 uugaaaagu ggcaccgagu cggugcuuuu uu                                   92
```

```
<210> SEQ ID NO 121
<211> LENGTH: 21
<212> TYPE: DNA
<213> ORGANISM: Artificial Sequence
<220> FEATURE:
<223> OTHER INFORMATION: Synthetic

<400> SEQUENCE: 121
cctcactcac ccactcgcca c                                             21
```

NUCLEASE-MEDIATED REPEAT EXPANSION

CROSS-REFERENCE TO RELATED APPLICATIONS

This application claims the benefit of U.S. Application No. 62/782,461, filed Dec. 20, 2018, and U.S. Application No. 62/829,995, filed Apr. 5, 2019, each of which is herein incorporated by reference in its entirety for all purposes.

REFERENCE TO A SEQUENCE LISTING SUBMITTED AS A TEXT FILE VIA EFS WEB

The Sequence Listing written in file 540526SEQLIST.txt is 60.0 kilobytes, was created on Dec. 13, 2019, and is hereby incorporated by reference.

BACKGROUND

More than forty diseases, most of which primarily affect the nervous system, are caused by expansions of simple sequence repeats dispersed throughout the human genome. Expanded trinucleotide repeat diseases were discovered first and remain the most frequent. More recently, tetra-, penta-, hexa-, and even dodeca-nucleotide repeat expansions have been identified as the cause of human disease, including some of the most common neurological genetic disorders. Repeat expansion diseases include both causes of myotonic dystrophy (DM1 and DM2), the most common genetic cause of amyotrophic lateral sclerosis (ALS)/frontotemporal dementia (FTD) (C9ORF72), Huntington disease, and eight other polyglutamine disorders, including the most common forms of dominantly inherited ataxia, the most common recessive ataxia (Friedreich ataxia), and the most common heritable mental retardation (fragile X syndrome). For example, expanded hexanucleotide repeats of GGGGCC (SEQ ID NO: 1) within a non-coding region of the C9ORF72 gene have been linked to both ALS and FTD. Currently, there is no cure for either disease.

While various laboratory animal models are extensively used in the development of most therapeutics, very few models exist that address repeat expansion diseases such as neurodegenerative and inflammatory diseases in ways that provide for elucidation of the exact molecular mechanism by which identified genetic components cause disease. Ideal animal models would contain the same genetic components and represent similar characteristics of human disease. Given the genetic differences between species, there is a high unmet need for the development of improved animal models that closely recapitulate repeat expansion diseases such as human neurodegenerative and/or inflammatory disease. Such improved animal models would provide significant value in the development of effective therapeutic and/or prophylactic agents.

SUMMARY

Methods for expanding a repeat expansion sequence comprising a plurality of copies of a repeat sequence at a target genomic locus in a cell are provided, and non-human animal genomes, non-human animal cells, and non-human animals comprising in their genome a heterologous hexanucleotide repeat expansion sequence inserted at an endogenous C9orf72 locus are provided.

In one aspect, provided are methods for expanding a repeat expansion sequence comprising a plurality of copies of a repeat sequence at a target genomic locus in a cell or methods for producing a modified cell with an increased number of copies of a repeat sequence at a target genomic locus. Some such methods comprise introducing into a population of cells comprising the repeat expansion sequence a nuclease agent that cleaves a nuclease target site near the 5' end or the 3' end of the repeat expansion sequence to produce a population of modified cells with an expanded repeat expansion sequence. Some such methods comprise introducing into a population of cells comprising the repeat expansion sequence a nuclease agent or a nucleic acid encoding the nuclease agent, wherein the nuclease agent cleaves a nuclease target site near the 5' end or the 3' end of the repeat expansion sequence to produce a population of modified cells with an expanded repeat expansion sequence. Some such methods comprise introducing into a population of cells comprising the repeat expansion sequence a nuclease agent that makes a double-strand break or a single-strand break at a nuclease target site near the 5' end or the 3' end of the repeat expansion sequence to produce a population of modified cells with an expanded repeat expansion sequence. Some such methods comprise introducing into a population of cells comprising the repeat expansion sequence a nuclease agent or a nucleic acid encoding the nuclease agent, wherein the nuclease agent makes a double-strand break or a single-strand break at a nuclease target site near the 5' end or the 3' end of the repeat expansion sequence to produce a population of modified cells with an expanded repeat expansion sequence. Some such methods comprise: (a) providing a population of cells comprising a repeat expansion sequence comprising a plurality of copies of the repeat sequence at the target genomic locus; (b) introducing into the population of cells a nuclease agent that cleaves a nuclease target site near the 5' end or the 3' end of the repeat expansion sequence to produce a population of modified cells; and (c) quantifying the number of copies of the repeat sequence in the population of modified cells and selecting a modified cell in which the number of copies of the repeat sequence has been increased. Some such methods comprise: (a) providing a population of cells comprising a repeat expansion sequence comprising a plurality of copies of the repeat sequence at the target genomic locus; (b) introducing into the population of cells a nuclease agent or a nucleic acid encoding the nuclease agent, wherein the nuclease agent cleaves a nuclease target site near the 5' end or the 3' end of the repeat expansion sequence to produce a population of modified cells; and (c) quantifying the number of copies of the repeat sequence in the population of modified cells and selecting a modified cell in which the number of copies of the repeat sequence has been increased. Some such methods comprise: (a) providing a population of cells comprising a repeat expansion sequence comprising a plurality of copies of the repeat sequence at the target genomic locus; (b) introducing into the population of cells a nuclease agent that makes a double-strand break or a single-strand break at a nuclease target site near the 5' end or the 3' end of the repeat expansion sequence to produce a population of modified cells; and (c) quantifying the number of copies of the repeat sequence in the population of modified cells and selecting a modified cell in which the number of copies of the repeat sequence has been increased. Some such methods comprise: (a) providing a population of cells comprising a repeat expansion sequence comprising a plurality of copies of the repeat sequence at the target genomic locus; (b) introducing into the population of cells a nuclease agent or a nucleic acid encoding the nuclease agent, wherein the nuclease agent makes a double-strand break or a single-strand break at a nuclease target site near the 5' end or the 3' end of the repeat expansion sequence to produce a population of modified cells; and (c) quantifying the number of copies of the repeat sequence in the population of modified cells and selecting a modified cell in which the number of copies of the repeat sequence has been increased.

In some such methods, an exogenous repair template is not introduced into the population of cells.

In some such methods, the nuclease target site is within about 1000, about 500, about 400, about 300, about 200, about 100, about 50, about 40, about 30, about 20, or about 10 nucleotides of the 5' end or the 3' end of the repeat expansion sequence or overlaps with the 5' end or the 3' end of the repeat expansion sequence. In some such methods, the nuclease target site is within about 100, about 50, about 40, about 30, about 20, or about 10 nucleotides of the 5' end or the 3' end of the repeat expansion sequence or overlaps with the 5' end or the 3' end of the repeat expansion sequence. In some such methods, the nuclease target site is within about 50, about 40, about 30, about 20, or about 10 nucleotides of the 5' end or the 3' end of the repeat expansion sequence or overlaps with the 5' end or the 3' end of the repeat expansion sequence. In some such methods, the nuclease target site is within about 25, about 24, about 23, about 22, about 21, about 20, about 19, about 18, about 17, about 16, about 15, about 14, about 13, about 12, about 11, about 10, about 9, about 8, about 7, about 6, about 5, about 4, about 3, about 2, or about 1 nucleotides of the 5' end or the 3' end of the repeat expansion sequence or overlaps with the 5' end or the 3' end of the repeat expansion sequence. In some such methods, the nuclease target site overlaps with the 5' end or the 3' end of the repeat expansion sequence In some such methods, the nuclease agent is a zinc finger nuclease (ZFN), a Transcription Activator-Like Effector Nuclease (TALEN), or a Clustered Regularly Interspaced Short Palindromic Repeats (CRISPR)-associated (Cas) protein and a guide RNA. Optionally, the nuclease agent is the Cas protein and the guide RNA. Optionally, the Cas protein is a Cas9 protein.

In some such methods, the nuclease target site is near the 5' end of the repeat expansion sequence. In some such methods, the nuclease target site is near the 3' end of the repeat expansion sequence. In some such methods, the nuclease target site is outside of the repeat expansion sequence.

In some such methods, the site at which the nuclease agent makes a double-strand break or a single-strand break is within about 1000, about 500, about 400, about 300, about 200, about 100, about 50, about 40, about 30, about 20, or about 10 nucleotides of the 5' end or the 3' end of the repeat expansion sequence. In some such methods, the site at which the nuclease agent makes a double-strand break or a single-strand break is within about 100, about 50, about 40, about 30, about 20, or about 10 nucleotides of the 5' end or the 3' end of the repeat expansion sequence or overlaps with the 5' end or the 3' end of the repeat expansion sequence. Optionally, the site at which the nuclease agent makes a double-strand break or a single-strand break is within about 50, about 40, about 30, about 20, or about 10 nucleotides of the 5' end or the 3' end of the repeat expansion sequence. In some such methods, the site at which the nuclease agent makes a double-strand break or a single-strand break is within about 25, about 24, about 23, about 22, about 21, about 20, about 19, about 18, about 17, about 16, about 15, about 14, about 13, about 12, about 11, about 10, about 9, about 8, about 7, about 6, about 5, about 4, about 3, about 2, or about 1 nucleotides of the 5' end or the 3' end of the repeat expansion sequence or overlaps with the 5' end or the 3' end of the repeat expansion sequence. In some such methods, the site at which the nuclease agent makes a double-strand break or a single-strand break is near the 5' end of the repeat expansion sequence. In some such methods, the site at which the nuclease agent makes a double-strand break or a single-strand break is near the 3' end of the repeat expansion sequence. In some such methods, the site at which the nuclease agent makes a double-strand break or a single-strand break is outside of the repeat expansion sequence. In some such methods, the nuclease target site is retained after repair of the double-strand break or the single strand-break by the cell. In some such methods, repair of the double-strand break or the single strand-break does not result in insertions or deletions outside of the repeat expansion sequence.

In some such methods, the nuclease agent makes a double-strand break near the 5' end or the 3' end of the repeat expansion sequence. In some such methods, the nuclease agent is a nickase that makes a single-strand break near the 5' end or the 3' end of the repeat expansion sequence.

In some such methods, a first nuclease agent and a second nuclease agent are introduced into the cell, wherein the first nuclease agent cleaves a first nuclease target site near the 5' end of the repeat expansion sequence, and the second nuclease agent cleaves a second nuclease target site near the 3' end of the repeat expansion sequence. In some such methods, a first nuclease agent or a nucleic acid encoding the first nuclease agent and a second nuclease agent or a nucleic acid encoding the second nuclease agent are introduced into the cell, wherein the first nuclease agent cleaves a first nuclease target site near the 5' end of the repeat expansion sequence, and the second nuclease agent cleaves a second nuclease target site near the 3' end of the repeat expansion sequence. In some such methods, a first nuclease agent and a second nuclease agent are introduced into the cell, wherein the first nuclease agent makes a double-strand break or a single-strand break at a first nuclease target site near the 5' end of the repeat expansion sequence, and the second nuclease agent makes a double-strand break or a single-strand break at a second nuclease target site near the 3' end of the repeat expansion sequence. In some such methods, a first nuclease agent or a nucleic acid encoding the first nuclease agent and a second nuclease agent or a nucleic acid encoding the second nuclease agent are introduced into the cell, wherein the first nuclease agent makes a double-strand break or a single-strand break at a first nuclease target site near the 5' end of the repeat expansion sequence, and the second nuclease agent makes a double-strand break or a single-strand break at a second nuclease target site near the 3' end of the repeat expansion sequence. In some such methods, the first nuclease agent makes a double-strand break at a first nuclease target site near the 5' end of the repeat expansion sequence, and the second nuclease agent makes a double-strand break at a second nuclease target site near the 3' end of the repeat expansion sequence. In some such methods, the first nuclease agent makes a single-strand break at a first nuclease target site near the 5' end of the repeat expansion sequence, and the second nuclease agent makes a single-strand break at a second nuclease target site near the 3' end of the repeat expansion sequence.

In some such methods, the repeat expansion sequence is a heterologous repeat expansion sequence.

In some such methods, the repeat expansion sequence comprises at least about 10, at least about 20, at least about 30, at least about 40, at least about 50, at least about 60, at least about 70, at least about 80, or at least about 90 copies of the repeat sequence.

In some such methods, the copies of the repeat sequence are contiguous in the repeat expansion sequence.

In some such methods, wherein the repeat sequence is a trinucleotide repeat, a tetranucleotide repeat, a pentanucleotide repeat, a hexanucleotide repeat, or a dodecanucleotide repeat.

In some such methods, the repeat sequence comprises any one of SEQ ID NOS: 1-12. Optionally, (i) the repeat sequence comprises SEQ ID NO: 2, and the target genomic locus is an HTT, AR, ATN1, ATXN1, ATXN2, ATXN3, CACNA1A, ATXN7, PPP2R2B, or TBP locus; (ii) the repeat sequence comprises SEQ ID NO: 3, and the target genomic locus is an FMR1 locus; (iii) the repeat sequence comprises SEQ ID NO: 4, and the target genomic locus is a DMPK, JPH3, ATXN8, or TCF4 locus; (iv) the repeat sequence comprises SEQ ID NO: 5, and the target genomic locus is an FXN locus; (v) the repeat sequence comprises SEQ ID NO: 6, and the target genomic locus is an AFF2 locus; (vi) the repeat sequence comprises SEQ ID NO: 7, and the target genomic locus is a PABPN1 locus; (vii) the repeat sequence comprises SEQ ID NO: 8, and the target genomic locus is a CNBP locus; (viii) the repeat sequence comprises SEQ ID NO: 9, and the target genomic locus is an ATXN10 locus; (ix) the repeat sequence comprises SEQ ID NO: 10, and the target genomic locus is a TK2 or BEAN1 locus; (x) the repeat sequence comprises SEQ ID NO: 11, and the target genomic locus is a NOP56 locus; (xi) the repeat sequence comprises SEQ ID NO: 1, and the target genomic locus is a C9ORF72 locus; or (xii) the repeat sequence comprises SEQ ID NO: 12, and the target genomic locus is a CSTB locus. Optionally, the repeat sequence comprises SEQ ID NO: 1, and the target genomic locus is a C9ORF72 locus. Optionally, the nuclease agent is a Cas9 protein and a guide RNA, and the nuclease target site comprises SEQ ID NO: 28 or 33.

In some such methods, the cells are non-human animal cells. In some such methods, the cells are non-human animal embryonic stem cells, embryonic stem-cell-derived motor neurons, brain cells, cortical cells, neuronal cells, muscle cells, heart cells, or germ cells. In some such methods, the cells are non-human animal one-cell stage embryos. In some such methods, the cells are rodent cells. In some such methods, the cells are mouse cells or rat cells. Optionally, the cells are mouse cells. Optionally, the cells are mouse embryonic stem cells or mouse one-cell stage embryos. In some such methods, the cells are human induced pluripotent stem cells. In some such methods, the cells are in vitro. In some such methods, the cells are in vivo.

In some such methods, the method comprises multiple rounds of steps (a)-(c), wherein the population of cells in step (a) in each round after the first round is a clonal population of cells expanded from the modified cell selected in step (c) of the previous round. Optionally, the method comprises at least 3 rounds or at least 4 rounds. Optionally, the method is performed a first time with a first nuclease agent that cleaves a first nuclease target site near the 5' end of the repeat expansion sequence to produce a first modified cell, and the method is performed a second time on the first modified cell with a second nuclease agent that cleaves a second nuclease target site near the 3' end of the repeat expansion sequence to produce a second modified cell. Optionally, the method is performed a first time with a first nuclease agent that cleaves a first nuclease target site near the 3' end of the repeat expansion sequence to produce a first modified cell, and the method is performed a second time on the first modified cell with a second nuclease agent that cleaves a second nuclease target site near the 5' end of the repeat expansion sequence to produce a second modified cell.

In some such methods, the method is performed a first time with a first nuclease agent that makes a double-strand break or a single-strand break at a first nuclease target site near the 5' end of the repeat expansion sequence to produce a first modified cell, and the method is performed a second time on the first modified cell with a second nuclease agent that makes a double-strand break or a single-strand break at a second nuclease target site near the 3' end of the repeat expansion sequence to produce a second modified cell. In some such methods, the method is performed a first time with a first nuclease agent that makes a double-strand break or a single-strand break at a first nuclease target site near the 3' end of the repeat expansion sequence to produce a first modified cell, and the method is performed a second time on the first modified cell with a second nuclease agent that makes a double-strand break or a single-strand break at a second nuclease target site near the 5' end of the repeat expansion sequence to produce a second modified cell. In some such methods, the method is performed a first time with a first nuclease agent that makes a double-strand break or a single-strand break at a first nuclease target site near the 5' end of the repeat expansion sequence to produce a first modified cell, and the method is performed a second time on the first modified cell with a second nuclease agent that makes a double-strand break or a single-strand break at a second nuclease target site near the 5' end of the repeat expansion sequence to produce a second modified cell. In some such methods, the method is performed a first time with a first nuclease agent that makes a double-strand break or a single-strand break at a first nuclease target site near the 3' end of the repeat expansion sequence to produce a first modified cell, and the method is performed a second time on the first modified cell with a second nuclease agent that makes a double-strand break or a single-strand break at a second nuclease target site near the 3' end of the repeat expansion sequence to produce a second modified cell. In some such methods, the method is performed a first time with a first nuclease agent that makes a double-strand break at a first nuclease target site near the 5' end of the repeat expansion sequence to produce a first modified cell, and the method is performed a second time on the first modified cell with a second nuclease agent that makes a double-strand break at a second nuclease target site near the 3' end of the repeat expansion sequence to produce a second modified cell. In some such methods, the method is performed a first time with a first nuclease agent that makes a double-strand break at a first nuclease target site near the 3' end of the repeat expansion sequence to produce a first modified cell, and the method is performed a second time on the first modified cell with a second nuclease agent that makes a double-strand break at a second nuclease target site near the 5' end of the repeat expansion sequence to produce a second modified cell. In some such methods, the method is performed a first time with a first nuclease agent that makes a double-strand break at a first nuclease target site near the 5' end of the repeat expansion sequence to produce a first modified cell, and the method is performed a second time on the first modified cell with a second nuclease agent that makes a double-strand break at a second nuclease target site near the 5' end of the repeat expansion sequence to produce a second modified cell. In some such methods, the method is performed a first time with a first nuclease agent that makes a double-strand break at a first nuclease target site near the 3' end of the repeat expansion sequence to produce a first modified cell, and the method is performed a second time on the first modified cell with a second nuclease agent that makes a double-strand break at a second nuclease target site near the 3' end of the repeat expansion sequence to produce a second modified cell. In some such methods, the method is performed a first time with a first nuclease agent that makes a single-strand break at a first nuclease target site near the 5' end of the repeat expansion sequence to produce a first modified cell, and the method is performed a second time on the first modified cell with a second nuclease agent that makes a single-strand break at a second nuclease target site near the 3' end of the repeat expansion sequence to produce a second modified cell. In some such methods, the method is performed a first time with a first nuclease agent that makes a single-strand break at a first nuclease target site near the 3' end of the repeat expansion sequence to produce a first modified cell, and the method is performed a second time on the first modified cell with a second nuclease agent that makes a single-strand break at a second nuclease target site near the 5' end of the repeat expansion sequence to produce a second modified cell. In some such methods, the method is performed a first time with a first nuclease agent that makes a single-strand break at a first nuclease target site near the 5' end of the repeat expansion sequence to produce a first modified cell, and the method is performed a second time on the first modified cell with a second nuclease agent that makes a single-strand break at a second nuclease target site near the 5' end of the repeat expansion sequence to produce a second modified cell. In some such methods, the method is performed a first time with a first nuclease agent that makes a single-strand break at a first nuclease target site near the 3' end of the repeat expansion sequence to produce a first modified cell, and the method is performed a second time on the first modified cell with a second nuclease agent that makes a single-strand break at a second nuclease target site near the 3' end of the repeat expansion sequence to produce a second modified cell. In some such methods, the first nuclease target site is the same as the second nuclease target site.

In some such methods, the nuclease target site is outside of the repeat expansion sequence, the nuclease target site is within about 50, about 40, about 30, about 20, or about 10 nucleotides of the 5' end or the 3' end of the repeat expansion sequence, and the nuclease agent is Cas9 protein and a guide RNA. In some such methods, the nuclease agent is a nickase that makes a single-strand break near the 5' end or the 3' end of the repeat expansion sequence, the nuclease target site is retained after repair of the single strand-break by the cell, and repair of the single strand-break does not result in insertions or deletions outside of the repeat expansion sequence.

In another aspect, provided is a non-human animal comprising in its genome, a non-human animal cell comprising in its genome, or a non-human animal genome comprising a heterologous hexanucleotide repeat expansion sequence inserted at an endogenous C9orf72 locus, wherein the heterologous hexanucleotide repeat expansion sequence comprises more than about 100 repeats of the hexanucleotide sequence set forth as SEQ ID NO: 1. In another aspect, provided is a non-human animal C9orf72 gene comprising a heterologous hexanucleotide repeat expansion sequence, wherein the heterologous hexanucleotide repeat expansion sequence comprises more than about 100 repeats of the hexanucleotide sequence set forth as SEQ ID NO: 1.

In some such non-human animals, non-human animal cells, or non-human animal genomes, the heterologous hexanucleotide repeat expansion sequence comprises at least about 300 repeats or at least 600 repeats of the hexanucleotide sequence set forth as SEQ ID NO: 1. In some such non-human animals, non-human animal cells, or non-human animal genomes, the heterologous hexanucleotide repeat expansion sequence comprises at least about 300 repeats, at least about 500 repeats, or at least 600 repeats of the hexanucleotide sequence set forth as SEQ ID NO: 1. In some such non-human animals, non-human animal cells, or non-human animal genomes, the repeats are contiguous in the heterologous repeat expansion sequence. In some such non-human animals, non-human animal cells, or non-human animal genomes, the heterologous hexanucleotide repeat expansion sequence is located between the first non-coding endogenous exon and exon 2 of the endogenous C9orf72 locus.

In some such non-human animals, non-human animal cells, or non-human animal genomes, the endogenous C9orf72 locus comprises a human C9ORF72 nucleotide sequence. Optionally, the human C9ORF72 nucleotide sequence comprises SEQ ID NO: 46 and/or SEQ ID NO: 47.

In some such non-human animals, non-human animal cells, or non-human animal genomes, the non-human animal is a rodent or the non-human animal cell is a rodent cell. Optionally, the rodent is a rat or a mouse or wherein the non-human animal cell is a rat cell or a mouse cell.

In some such non-human animals, non-human animal cells, or non-human animal genomes, the non-human animal, non-human animal cell, or non-human animal genome is homozygous for the heterologous hexanucleotide repeat expansion sequence. In some such non-human animals, non-human animal cells, or non-human animal genomes, the non-human animal, non-human animal cell, or non-human animal genome is heterozygous for the heterologous hexanucleotide repeat expansion sequence.

In some such non-human animals or cells, the non-human animal or non-human animal cell exhibits: (a) increased expression of C9orf72 transcripts that retain intron sequence compared to a control non-human animal or control non-human animal cell comprising a wild type C9orf72 locus; and/or (b) an increased number of RNA foci compared to a control non-human animal or control non-human animal cell comprising a wild type C9orf72 locus; and/or (c) an increased level of dipeptide repeat proteins compared to a control non-human animal or control non-human animal cell comprising a wild type C9orf72 locus.

In some such non-human animals, non-human animal cells, or non-human animal genomes, the non-human animal cell is an embryonic stem cell, an embryonic stem-cell-derived motor neuron, a brain cell, a cortical cell, a neuronal cell, a muscle cell, a heart cell, or a germ cell. In some such non-human animals, non-human animal cells, or non-human animal genomes, the non-human animal cell is a one-cell stage embryo. Optionally, the non-human animal cell or genome is in vitro. Optionally, the non-human animal cell is in vivo.

In some such non-human animals, non-human animal cells, or non-human animal genomes, the non-human animal comprises in its germline genome the heterologous hexanucleotide repeat expansion sequence inserted at the endogenous C9orf72 locus.

In another aspect, provided are nuclease agents for use in a method for producing a modified cell with an increased number of copies of a repeat sequence at a target genomic locus that comprises a repeat expansion sequence comprising a plurality of copies of the repeat sequence at the target genomic locus, wherein the nuclease agent is designed to make a double-strand break or a single-strand break at a nuclease target site near the 5' end or the 3' end of the repeat expansion sequence. In another aspect, provided are nucleic acids encoding nuclease agents for use in a method for producing a modified cell with an increased number of copies of a repeat sequence at a target genomic locus that comprises a repeat expansion sequence comprising a plurality of copies of the repeat sequence at the target genomic locus, wherein the nuclease agent is designed to make a double-strand break or a single-strand break at a nuclease target site near the 5' end or the 3' end of the repeat expansion sequence.

In another aspect, provided are methods assessing a therapeutic candidate for the treatment of a disease or a condition associated with a hexanucleotide repeat expansion sequence at a C9orf72 locus. Some such methods comprise (a) administering a candidate agent to any of the above non-human animals or non-human animal cells; (b) performing one or more assays to determine if the candidate agent has an effect on one or more signs or symptoms associated with the disease or condition; and (c) identifying the candidate agent that has an effect on the one or more signs or symptoms associated with the disease or condition as a therapeutic candidate.

In some such methods, the candidate agent is administered in vivo to the non-human animal, and the one or more assays are performed in vitro in cells isolated from the non-human animal after administration of the candidate agent. In some such methods, the candidate agent is administered in vitro to a non-human embryonic-stem-cell-derived motor neuron.

In some such methods, the one or more assays comprise quantitative polymerase chain reaction (qPCR) to detect intron-containing C9orf72 RNA transcripts. In some such methods, the one or more assays comprise measuring RNA foci comprising a C9orf72 sense or antisense RNA transcript, optionally wherein the RNA foci are measured by fluorescence in situ hybridization. In some such methods, the one or more assays comprise measuring the accumulation of dipeptide repeat proteins, optionally wherein the dipeptide repeat proteins are polyGA dipeptide repeat proteins or polyGP dipeptide repeat proteins, and optionally wherein the accumulation of dipeptide repeat proteins is measured by immunohistochemistry.

BRIEF DESCRIPTION OF THE FIGURES

FIG. 6C shows an alignment of sequences of the parental 30× repeat mouse ES cell clone and the expanded clone from FIG. 6A, starting just upstream of the repeat region and continuing through the end of the repeat region.

FIG. 17C shows alignments with the results of sequencing of several expanded mouse ES cell clones after either cleaving or nicking of a 92× repeat expansion sequence clone near the 3' end of the 92× repeat expansion sequence.

FIG. 21 (bottom) shows quantification of the western slot blots in the top portion of the figure.

DEFINITIONS

Figure 1:
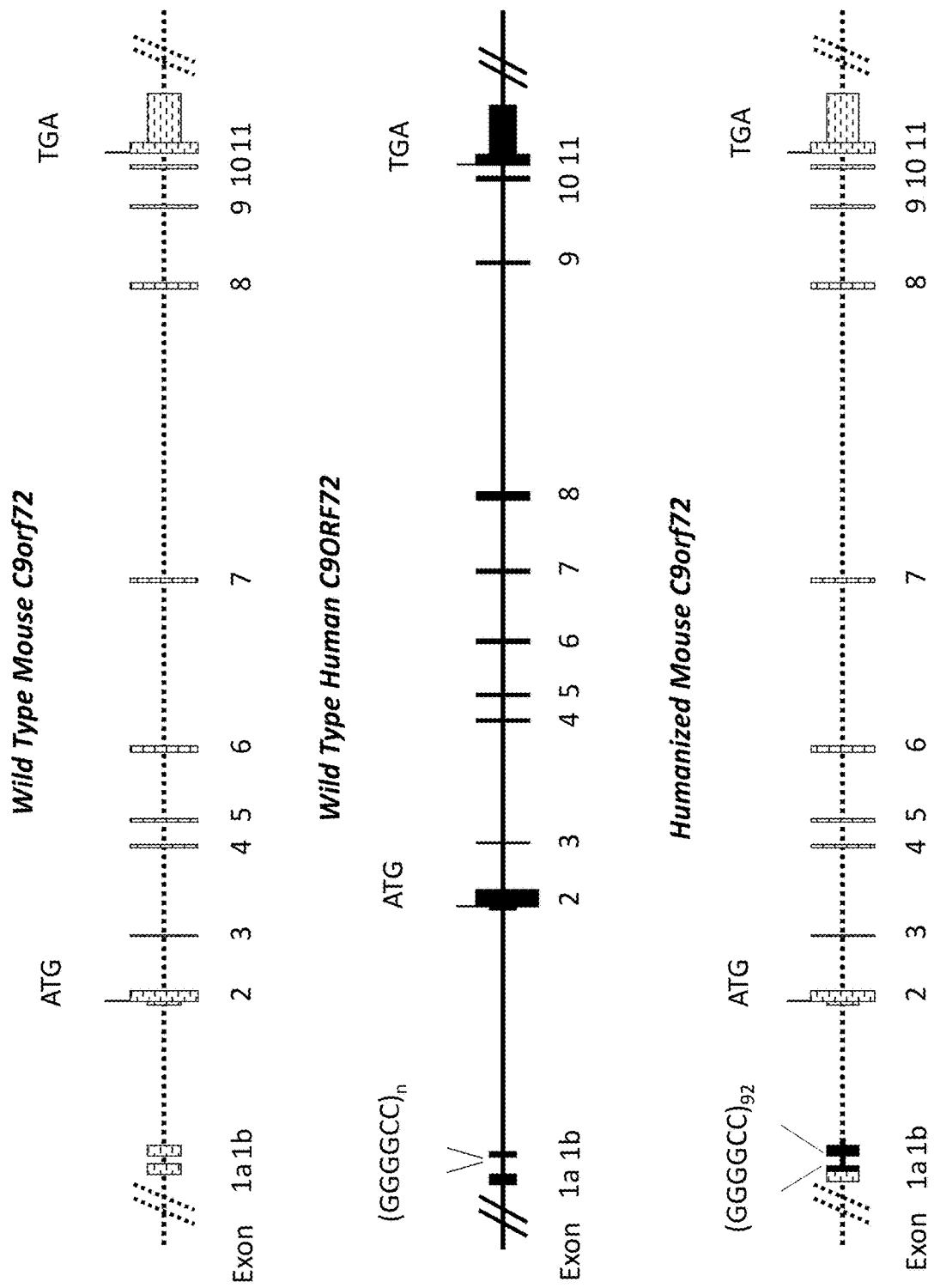
FIG. 1 (not to scale) shows schematics of the wild type mouse C9orf72 locus, the wild type human C9ORF72 locus, and a humanized mouse C9orf72 locus comprising 92 repeats of the hexanucleotide sequence set forth in SEQ ID NO: 1 (GGGGCC) (MAID8029a). Mouse sequences are indicated by dashed lines and boxes with dashes, and human sequences are indicated by solid black. The exons are represented by the boxes. The position of the hexanucleotide repeat sequence is shown.

The terms "protein," "polypeptide," and "peptide," used interchangeably herein, include polymeric forms of amino acids of any length, including coded and non-coded amino acids and chemically or biochemically modified or derivatized amino acids. The terms also include polymers that have been modified, such as polypeptides having modified peptide backbones. The term "domain" refers to any part of a protein or polypeptide having a particular function or structure.

Proteins are said to have an "N-terminus" and a "C-terminus." The term "N-terminus" relates to the start of a protein or polypeptide, terminated by an amino acid with a free amine group (—NH2). The term "C-terminus" relates to the end of an amino acid chain (protein or polypeptide), terminated by a free carboxyl group (—COOH).

The terms "nucleic acid" and "polynucleotide," used interchangeably herein, include polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

Nucleic acids are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. An end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. A nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements.

The term "genomically integrated" refers to a nucleic acid that has been introduced into a cell such that the nucleotide sequence integrates into the genome of the cell. Any protocol may be used for the stable incorporation of a nucleic acid into the genome of a cell.

The term "targeting vector" refers to a recombinant nucleic acid that can be introduced by homologous recombination, non-homologous-end-joining-mediated ligation, or any other means of recombination to a target position in the genome of a cell.

The term "viral vector" refers to a recombinant nucleic acid that includes at least one element of viral origin and includes elements sufficient for or permissive of packaging into a viral vector particle. The vector and/or particle can be utilized for the purpose of transferring DNA, RNA, or other nucleic acids into cells in vitro, ex vivo, or in vivo. Numerous forms of viral vectors are known.

The term "isolated" with respect to proteins, nucleic acids, and cells includes proteins, nucleic acids, and cells that are relatively purified with respect to other cellular or organism components that may normally be present in situ, up to and including a substantially pure preparation of the protein, nucleic acid, or cell. The term "isolated" may include proteins and nucleic acids that have no naturally occurring counterpart or proteins or nucleic acids that have been chemically synthesized and are thus substantially uncontaminated by other proteins or nucleic acids. The term "isolated" may include proteins, nucleic acids, or cells that have been separated or purified from most other cellular components or organism components with which they are naturally accompanied (e.g., but not limited to, other cellular proteins, nucleic acids, or cellular or extracellular components).

The term "wild type" includes entities having a structure and/or activity as found in a normal (as contrasted with mutant, diseased, altered, or so forth) state or context. Wild type genes and polypeptides often exist in multiple different forms (e.g., alleles).

The term "endogenous sequence" refers to a nucleic acid sequence that occurs naturally within a cell or animal. For example, an endogenous C9orf72 sequence of a non-human animal refers to a native C9orf72 sequence that naturally occurs at the C9orf72 locus in the non-human animal.

"Exogenous" molecules or sequences include molecules or sequences that are not normally present in a cell in that form. Normal presence includes presence with respect to the particular developmental stage and environmental conditions of the cell. An exogenous molecule or sequence, for example, can include a mutated version of a corresponding endogenous sequence within the cell, such as a humanized version of the endogenous sequence, or can include a sequence corresponding to an endogenous sequence within the cell but in a different form (i.e., not within a chromosome). In contrast, endogenous molecules or sequences include molecules or sequences that are normally present in that form in a particular cell at a particular developmental stage under particular environmental conditions.

The term "heterologous" when used in the context of a nucleic acid or a protein indicates that the nucleic acid or protein comprises at least two segments that do not naturally occur together in the same molecule. For example, the term "heterologous," when used with reference to segments of a nucleic acid or segments of a protein, indicates that the nucleic acid or protein comprises two or more sub-sequences that are not found in the same relationship to each other (e.g., joined together) in nature. As one example, a "heterologous" region of a nucleic acid vector is a segment of nucleic acid within or attached to another nucleic acid molecule that is not found in association with the other molecule in nature. For example, a heterologous region of a nucleic acid vector could include a coding sequence flanked by sequences not found in association with the coding sequence in nature. Likewise, a "heterologous" region of a protein is a segment of amino acids within or attached to another peptide molecule that is not found in association with the other peptide molecule in nature (e.g., a fusion protein, or a protein with a tag). Similarly, a nucleic acid or protein can comprise a heterologous label or a heterologous secretion or localization sequence.

"Codon optimization" takes advantage of the degeneracy of codons, as exhibited by the multiplicity of three-base pair codon combinations that specify an amino acid, and generally includes a process of modifying a nucleic acid sequence for enhanced expression in particular host cells by replacing at least one codon of the native sequence with a codon that is more frequently or most frequently used in the genes of the host cell while maintaining the native amino acid sequence. For example, a nucleic acid encoding a Cas9 protein can be modified to substitute codons having a higher frequency of usage in a given prokaryotic or eukaryotic cell, including a bacterial cell, a yeast cell, a human cell, a non-human cell, a mammalian cell, a rodent cell, a mouse cell, a rat cell, a hamster cell, or any other host cell, as compared to the naturally occurring nucleic acid sequence. Codon usage tables are readily available, for example, at the "Codon Usage Database." These tables can be adapted in a number of ways. See Nakamura et al. (2000) *Nucleic Acids Research* 28:292, herein incorporated by reference in its entirety for all purposes. Computer algorithms for codon optimization of a particular sequence for expression in a particular host are also available (see, e.g., Gene Forge).

The term "locus" refers to a specific location of a gene (or significant sequence), DNA sequence, polypeptide-encoding sequence, or position on a chromosome of the genome of an organism. For example, a "C9orf72 locus" may refer to the specific location of a C9orf72 gene, C9orf72 DNA sequence, C9ORF72-encoding sequence, or C9orf72 position on a chromosome of the genome of an organism that has been identified as to where such a sequence resides. A "C9orf72 locus" may comprise a regulatory element of a C9orf72 gene, including, for example, an enhancer, a promoter, 5' and/or 3' untranslated region (UTR), or a combination thereof.

The term "gene" refers to DNA sequences in a chromosome that may contain, if naturally present, at least one coding and at least one non-coding region. The DNA sequence in a chromosome that codes for a product (e.g., but not limited to, an RNA product and/or a polypeptide product) can include the coding region interrupted with non-coding introns and sequence located adjacent to the coding region on both the 5' and 3' ends such that the gene corresponds to the full-length mRNA (including the 5' and 3' untranslated sequences). Additionally, other non-coding sequences including regulatory sequences (e.g., but not limited to, promoters, enhancers, and transcription factor binding sites), polyadenylation signals, internal ribosome entry sites, silencers, insulating sequence, and matrix attachment regions may be present in a gene. These sequences may be close to the coding region of the gene (e.g., but not limited to, within 10 kb) or at distant sites, and they influence the level or rate of transcription and translation of the gene.

The term "allele" refers to a variant form of a gene. Some genes have a variety of different forms, which are located at the same position, or genetic locus, on a chromosome. A diploid organism has two alleles at each genetic locus. Each pair of alleles represents the genotype of a specific genetic locus. Genotypes are described as homozygous if there are two identical alleles at a particular locus and as heterozygous if the two alleles differ.

A "promoter" is a regulatory region of DNA usually comprising a TATA box capable of directing RNA polymerase II to initiate RNA synthesis at the appropriate transcription initiation site for a particular polynucleotide sequence. A promoter may additionally comprise other regions which influence the transcription initiation rate. The promoter sequences disclosed herein modulate transcription of an operably linked polynucleotide. A promoter can be active in one or more of the cell types disclosed herein (e.g., a eukaryotic cell, a non-human mammalian cell, a human cell, a rodent cell, a pluripotent cell, a one-cell stage embryo, a differentiated cell, or a combination thereof). A promoter can be, for example, a constitutively active promoter, a conditional promoter, an inducible promoter, a temporally restricted promoter (e.g., a developmentally regulated promoter), or a spatially restricted promoter (e.g., a cell-specific or tissue-specific promoter). Examples of promoters can be found, for example, in WO 2013/176772, herein incorporated by reference in its entirety for all purposes.

"Operable linkage" or being "operably linked" includes juxtaposition of two or more components (e.g., a promoter and another sequence element) such that both components function normally and allow the possibility that at least one of the components can mediate a function that is exerted upon at least one of the other components. For example, a promoter can be operably linked to a coding sequence if the promoter controls the level of transcription of the coding sequence in response to the presence or absence of one or more transcriptional regulatory factors. Operable linkage can include such sequences being contiguous with each other or acting in trans (e.g., a regulatory sequence can act at a distance to control transcription of the coding sequence).

The methods and compositions provided herein employ a variety of different components. Some components throughout the description can have active variants and fragments. Such components include, for example, Cas proteins, CRISPR RNAs, tracrRNAs, and guide RNAs. Biological activity for each of these components is described elsewhere herein. The term "functional" refers to the innate ability of a protein or nucleic acid (or a fragment or variant thereof) to exhibit a biological activity or function. Such biological activities or functions can include, for example, the ability of a Cas protein to bind to a guide RNA and to a target DNA sequence. The biological functions of functional fragments or variants may be the same or may in fact be changed (e.g., with respect to their specificity or selectivity or efficacy) in comparison to the original molecule, but with retention of the molecule's basic biological function.

The term "variant" refers to a nucleotide sequence differing from the sequence most prevalent in a population (e.g., by one nucleotide) or a protein sequence different from the sequence most prevalent in a population (e.g., by one amino acid).

The term "fragment," when referring to a protein, means a protein that is shorter or has fewer amino acids than the full-length protein. The term "fragment," when referring to a nucleic acid, means a nucleic acid that is shorter or has fewer nucleotides than the full-length nucleic acid. A fragment can be, for example, when referring to a protein fragment, an N-terminal fragment (i.e., removal of a portion of the C-terminal end of the protein), a C-terminal fragment (i.e., removal of a portion of the N-terminal end of the protein), or an internal fragment (i.e., removal of a portion of an internal portion of the protein).

"Sequence identity" or "identity" in the context of two polynucleotides or polypeptide sequences refers to the residues in the two sequences that are the same when aligned for maximum correspondence over a specified comparison window. When percentage of sequence identity is used in reference to proteins, residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

"Percentage of sequence identity" includes the value determined by comparing two optimally aligned sequences (greatest number of perfectly matched residues) over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. Unless otherwise specified (e.g., the shorter sequence includes a linked heterologous sequence), the comparison window is the full length of the shorter of the two sequences being compared.

Unless otherwise stated, sequence identity/similarity values include the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. "Equivalent program" includes any sequence comparison program that, for any two sequences in question, generates an alignment having identical nucleotide or amino acid residue matches and an identical percent sequence identity when compared to the corresponding alignment generated by GAP Version 10.

The term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine, or leucine for another non-polar residue. Likewise, examples of conservative substitutions include the substitution of one polar (hydrophilic) residue for another such as between arginine and lysine, between glutamine and asparagine, or between glycine and serine. Additionally, the substitution of a basic residue such as lysine, arginine, or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, or methionine for a polar (hydrophilic) residue such as cysteine, glutamine, glutamic acid or lysine and/or a polar residue for a non-polar residue. Typical amino acid categorizations are summarized in Table 1 below.

TABLE 1

Amino Acid Categorizations.

| Alanine | Ala | A | Nonpolar | Neutral | 1.8 |
|---|---|---|---|---|---|
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

A "homologous" sequence (e.g., nucleic acid sequence) includes a sequence that is either identical or substantially similar to a known reference sequence, such that it is, for example, at least 50%, at least 55%, at least 60%, at least 65%, at least 70%, at least 75%, at least 80%, at least 85%, at least 90%, at least 95%, at least 96%, at least 97%, at least 98%, at least 99%, or 100% identical to the known reference sequence. Homologous sequences can include, for example, orthologous sequence and paralogous sequences. Homologous genes, for example, typically descend from a common ancestral DNA sequence, either through a speciation event (orthologous genes) or a genetic duplication event (paralogous genes). "Orthologous" genes include genes in different species that evolved from a common ancestral gene by speciation. Orthologs typically retain the same function in the course of evolution. "Paralogous" genes include genes related by duplication within a genome. Paralogs can evolve new functions in the course of evolution.

The term "in vitro" includes artificial environments and to processes or reactions that occur within an artificial environment (e.g., a test tube or an isolated cell or cell line). The term "in vivo" includes natural environments (e.g., a cell or organism or body) and to processes or reactions that occur within a natural environment. The term "ex vivo" includes cells that have been removed from the body of an individual and processes or reactions that occur within such cells.

The term "reporter gene" refers to a nucleic acid having a sequence encoding a gene product (typically an enzyme) that is easily and quantifiably assayed when a construct comprising the reporter gene sequence operably linked to a heterologous promoter and/or enhancer element is introduced into cells containing (or which can be made to contain) the factors necessary for the activation of the promoter and/or enhancer elements. Examples of reporter genes include, but are not limited to, genes encoding beta-galactosidase (lacZ), the bacterial chloramphenicol acetyl-transferase (cat) genes, firefly luciferase genes, genes encoding beta-glucuronidase (GUS), and genes encoding fluorescent proteins. A "reporter protein" refers to a protein encoded by a reporter gene.

The term "fluorescent reporter protein" as used herein means a reporter protein that is detectable based on fluorescence wherein the fluorescence may be either from the reporter protein directly, activity of the reporter protein on a fluorogenic substrate, or a protein with affinity for binding to a fluorescent tagged compound. Examples of fluorescent proteins include green fluorescent proteins (e.g., GFP, GFP-2, tagGFP, turboGFP, eGFP, Emerald, Azami Green, Monomeric Azami Green, CopGFP, AceGFP, and ZsGreenl), yellow fluorescent proteins (e.g., YFP, eYFP, Citrine, Venus, YPet, PhiYFP, and ZsYellowl), blue fluorescent proteins (e.g., BFP, eBFP, eBFP2, Azurite, mKalamal, GFPuv, Sapphire, and T-sapphire), cyan fluorescent proteins (e.g., CFP, eCFP, Cerulean, CyPet, AmCyanl, and Midoriishi-Cyan), red fluorescent proteins (e.g., RFP, mKate, mKate2, mPlum, DsRed monomer, mCherry, mRFP1, DsRed-Express, DsRed2, DsRed-Monomer, HcRed-Tandem, HcRed1, AsRed2, eqFP611, mRaspberry, mStrawberry, and Jred), orange fluorescent proteins (e.g., mOrange, mKO, Kusabira-Orange, Monomeric Kusabira-Orange, mTangerine, and tdTomato), and any other suitable fluorescent protein whose presence in cells can be detected by flow cytometry methods.

Repair in response to double-strand breaks (DSBs) occurs principally through two conserved DNA repair pathways: homologous recombination (HR) and non-homologous end joining (NHEJ). See Kasparek & Humphrey (2011) *Seminars in Cell & Dev. Biol.* 22:886-897, herein incorporated by reference in its entirety for all purposes. Likewise, repair of a target nucleic acid mediated by an exogenous donor nucleic acid can include any process of exchange of genetic information between the two polynucleotides.

The term "recombination" includes any process of exchange of genetic information between two polynucleotides and can occur by any mechanism. Recombination can occur via homology directed repair (HDR) or homologous recombination (HR). HDR or HR includes a form of nucleic acid repair that can require nucleotide sequence homology, uses a "donor" molecule as a template for repair of a "target" molecule (i.e., the one that experienced the double-strand break), and leads to transfer of genetic information from the donor to target. Without wishing to be bound by any particular theory, such transfer can involve mismatch correction of heteroduplex DNA that forms between the broken target and the donor, and/or synthesis-dependent strand annealing, in which the donor is used to resynthesize genetic information that will become part of the target, and/or related processes. In some cases, the donor polynucleotide, a portion of the donor polynucleotide, a copy of the donor polynucleotide, or a portion of a copy of the donor polynucleotide integrates into the target DNA. See Wang et al. (2013) *Cell* 153:910-918; Mandalos et al. (2012) *PLoS One* 7:e45768:1-9; and Wang et al. (2013) *Nat. Biotechnol.* 31:530-532, each of which is herein incorporated by reference in its entirety for all purposes.

Non-homologous end joining (NHEJ) includes the repair of double-strand breaks in a nucleic acid by direct ligation of the break ends to one another or to an exogenous sequence without the need for a homologous template. Ligation of non-contiguous sequences by NHEJ can often result in deletions, insertions, or translocations near the site of the double-strand break. For example, NHEJ can also result in the targeted integration of an exogenous donor nucleic acid through direct ligation of the break ends with the ends of the exogenous donor nucleic acid (i.e., NHEJ-based capture). Such NHEJ-mediated targeted integration can be preferred for insertion of an exogenous donor nucleic acid when homology directed repair (HDR) pathways are not readily usable (e.g., in non-dividing cells, primary cells, and cells which perform homology-based DNA repair poorly). In addition, in contrast to homology-directed repair, knowledge concerning large regions of sequence identity flanking the cleavage site is not needed, which can be beneficial when attempting targeted insertion into organisms that have genomes for which there is limited knowledge of the genomic sequence. The integration can proceed via ligation of blunt ends between the exogenous donor nucleic acid and the cleaved genomic sequence, or via ligation of sticky ends (i.e., having 5' or 3' overhangs) using an exogenous donor nucleic acid that is flanked by overhangs that are compatible with those generated by a nuclease agent in the cleaved genomic sequence. See, e.g., US 2011/020722, WO 2014/033644, WO 2014/089290, and Maresca et al. (2013) *Genome Res.* 23(3):539-546, each of which is herein incorporated by reference in its entirety for all purposes. If blunt ends are ligated, target and/or donor resection may be needed to generation regions of microhomology needed for fragment joining, which may create unwanted alterations in the target sequence.

Compositions or methods "comprising" or "including" one or more recited elements may include other elements not specifically recited. For example, a composition that "comprises" or "includes" a protein may contain the protein alone or in combination with other ingredients. The transitional phrase "consisting essentially of" means that the scope of a claim is to be interpreted to encompass the specified elements recited in the claim and those that do not materially affect the basic and novel characteristic(s) of the claimed invention. Thus, the term "consisting essentially of" when used in a claim of this invention is not intended to be interpreted to be equivalent to "comprising."

"Optional" or "optionally" means that the subsequently described event or circumstance may or may not occur and that the description includes instances in which the event or circumstance occurs and instances in which the event or circumstance does not.

Designation of a range of values includes all integers within or defining the range, and all subranges defined by integers within the range.

Unless otherwise apparent from the context, the term "about" encompasses values±5 of a stated value.

The term "and/or" refers to and encompasses any and all possible combinations of one or more of the associated listed items, as well as the lack of combinations when interpreted in the alternative ("or").

The term "or" refers to any one member of a particular list and also includes any combination of members of that list.

The singular forms of the articles "a," "an," and "the" include plural references unless the context clearly dictates otherwise. For example, the term "a protein" or "at least one protein" can include a plurality of proteins, including mixtures thereof.

Statistically significant means $p \leq 0.05$.

DETAILED DESCRIPTION

I. Overview

Disclosed herein are nuclease-mediated methods for expanding repeats already present at a genomic locus. Repeat expansion diseases tend to show a striking genotype-phenotype correlation between repeat length and disease severity. The longer the repeat, the more severe the disease, and the earlier the onset of symptoms. See, e.g., Paulson (2018) Handb. Clin. Neurol., 147:105-123, (2018), herein incorporated by reference in its entirety for all purposes. However, the high GC content in repeats associated with repeat expansion diseases makes it difficult to synthesize DNA fragments with a large number of copies of a repeat and difficult to maintain such repeats in microorganisms. Therefore, preparing materials to generate targeting vectors with a large numbers of copies of a repeat and ultimately transgenic animals comprising multiple copies of the repeat is challenging. This is one of the major reasons why few useful animal models for repeat expansions diseases exist. The methods disclosed herein overcome this problem by expanding relatively shorter repeats (i.e., smaller number of repeats) that are already inserted in the right location in the genome rather than de novo targeting vector production and ES cell targeting.

Also disclosed herein are non-human animal genomes, non-human animal cells, and non-human animals comprising a heterologous hexanucleotide repeat expansion sequence inserted at an endogenous C9orf72 locus and methods of making such non-human animal cells and non-human animals through nuclease-mediated repeat expansion. Methods of using the non-human animal cells or non-human animals to identify therapeutic candidates that may be used to prevent, delay or treat one or more neurodegenerative disorders associated with repeat expansion at the C9orf72 locus are also provided.

II. Nuclease-Mediated Methods of Expanding Repeats

Various methods are provided for expanding a repeat expansion sequence comprising a plurality of copies of a repeat sequence in a cell comprising the repeat expansion sequence at a target genomic locus. Various methods are provided for obtaining a cell with an expanded repeat expansion sequence. Also provided are cells produced by such methods.

Such methods for expanding a repeat expansion sequence can comprise introducing into a cell or population of cells comprising the repeat expansion sequence a nuclease agent that cleaves a nuclease target site near the 5' end or the 3' end of the repeat expansion sequence to produce a modified cell or a population of modified cells with an expanded repeat expansion sequence. Such methods for expanding a repeat expansion sequence can comprise introducing into a cell or population of cells comprising the repeat expansion sequence a nuclease agent or a nucleic acid encoding the nuclease agent, wherein the nuclease agent cleaves a nuclease target site near the 5' end or the 3' end of the repeat expansion sequence to produce a modified cell or a population of modified cells with an expanded repeat expansion sequence. Such methods for expanding a repeat expansion sequence can comprise introducing into a cell or population of cells comprising the repeat expansion sequence a nuclease agent that makes a double-strand break or a single-strand break at a nuclease target site near the 5' end or the 3' end of the repeat expansion sequence to produce a modified cell or a population of modified cells with an expanded repeat expansion sequence. Such methods for expanding a repeat expansion sequence can comprise introducing into a cell or population of cells comprising the repeat expansion sequence a nuclease agent or a nucleic acid encoding the nuclease agent, wherein the nuclease agent makes a double-strand break or a single-strand break at a nuclease target site near the 5' end or the 3' end of the repeat expansion sequence to produce a modified cell or a population of modified cells with an expanded repeat expansion sequence. The repeat expansion sequence is all of the copies (e.g., contiguous repeats) of the repeat sequence at a particular locus. The 5' end of the repeat expansion sequence is the first nucleotide (i.e., the 5' nucleotide) of the first repeat within the repeat expansion sequence. The 3' end of the repeat expansion sequence is the last nucleotide (i.e., the 3' nucleotide) of the last repeat within the repeat expansion sequence. A nuclease target site near the 5' end of the repeat expansion sequence can be upstream of the 5' end of the repeat expansion sequence, downstream of the 5' end of the repeat expansion sequence, or overlapping with the 5' end of the repeat expansion sequence. A nuclease target site near the 3' end of the repeat expansion sequence can be upstream of the 3' end of the repeat expansion sequence, downstream of the 3' end of the repeat expansion sequence, or overlapping with the 3' end of the repeat expansion sequence. In some methods, the nuclease target site is outside of the repeat expansion sequence. In some methods, the nuclease target site overlaps the 5' end or the 3' end of the repeat expansion sequence. In some methods, the nuclease target site is inside the repeat expansion sequence.

Such methods can further comprise quantifying the number of copies of the repeat sequence in the modified cell or quantifying the number of copies of the repeat sequence in the population of modified cells and selecting a modified cell in which the number of copies of the repeat sequence has been increased. In some methods, the average percent expansion of the repeat expansion sequence (i.e., the length of the sequence of repeats added to the repeat expansion sequence divided by the starting size×100) is at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, or higher.

Some such methods comprise: (a) providing a population of cells comprising a repeat expansion sequence comprising a plurality of copies of the repeat sequence at the target genomic locus; (b) introducing into the population of cells a nuclease agent that cleaves a nuclease target site near the 5' end or the 3' end of the repeat expansion sequence to produce a population of modified cells; and (c) quantifying the number of copies of the repeat sequence in the population of modified cells and selecting a modified cell in which the number of copies of the repeat sequence has been increased. Some such methods comprise: (a) providing a population of cells comprising a repeat expansion sequence comprising a plurality of copies of the repeat sequence at the target genomic locus; (b) introducing into the population of cells a nuclease agent or a nucleic acid encoding the nuclease agent, wherein the nuclease agent cleaves a nuclease target site near the 5' end or the 3' end of the repeat expansion sequence to produce a population of modified cells; and (c) quantifying the number of copies of the repeat sequence in the population of modified cells and selecting a modified cell in which the number of copies of the repeat sequence has been increased. Some such methods comprise: (a) providing a population of cells comprising a repeat expansion sequence comprising a plurality of copies of the repeat sequence at the target genomic locus; (b) introducing into the population of cells a nuclease agent that makes a double-strand break or a single-strand break at a nuclease target site near the 5' end or the 3' end of the repeat expansion sequence to produce a population of modified cells; and (c) quantifying the number of copies of the repeat sequence in the population of modified cells and selecting a modified cell in which the number of copies of the repeat sequence has been increased. Some such methods comprise: (a) providing a population of cells comprising a repeat expansion sequence comprising a plurality of copies of the repeat sequence at the target genomic locus; (b) introducing into the population of cells a nuclease agent or a nucleic acid encoding the nuclease agent, wherein the nuclease agent makes a double-strand break or a single-strand break at a nuclease target site near the 5' end or the 3' end of the repeat expansion sequence to produce a population of modified cells; and (c) quantifying the number of copies of the repeat sequence in the population of modified cells and selecting a modified cell in which the number of copies of the repeat sequence has been increased. In some methods in which a population of cells is screened, the expansion frequency (the percentage of cell clones with repeat expansion out of the total number of screened clones) is at least about 1%, at least about 2%, at least about 3%, at least about 4%, at least about 5%, at least about 6%, at least about 7%, at least about 8%, at least about 9%, at least about 10%, or higher.

Although an understanding of mechanism is not required for practice, it is believed that cleaving the target genomic locus near repeat expansion sequence so that the exposed 5' strand contains only repetitive sequence can result in the Rad51 filament entering into a wrong location, thereby misleading the homology search by the Rad51 filament leading to expansion or contraction of the repeat. See FIG. 2. Accordingly, in some methods, the damaged chromatid utilizes the non-damaged sister chromatid as a template for its repair. Likewise, in some methods, an exogenous repair template (exogenous donor sequence) is not introduced into the cell or population of cells.

The nuclease agent cleaves (e.g., creates a double-strand break) near the repeat expansion sequence. For example, the nuclease target site can be within about 1000, about 900, about 800, about 700, about 600, about 500, about 400, about 300, about 200, about 100, about 90, about 80, about 70, about 60, about 50, about 40, about 30, about 20, or about 10 nucleotides of the 5' end or the 3' end of the repeat expansion sequence. As another example, the nuclease target site can be within about 100, about 50, about 40, about 30, about 20, or about 10 nucleotides of the 5' end or the 3' end of the repeat expansion sequence. For example, the nuclease target site can be within about 100, about 90, about 80, about 70, about 60, about 50, about 40, about 30, about 20, or about 10 nucleotides of the 5' end or the 3' end of the repeat expansion sequence. As another example, the nuclease target site can be within about 25, about 24, about 23, about 22, about 21, about 20, about 19, about 18, about 17, about 16, about 15, about 14, about 13, about 12, about 11, about 10, about 9, about 8, about 7, about 6, about 5, about 4, about 3, about 2, or about 1 nucleotides of the 5' end or the 3' end of the repeat expansion sequence. Alternatively, the nuclease target site can overlap with the 5' end or the 3' end of a repeat expansion sequence. Similarly, if the nuclease is a Cas protein, there can be a protospacer adjacent motif (PAM) sequence within about 1000, about 900, about 800, about 700, about 600, about 500, about 400, about 300, about 200, about 100, about 90, about 80, about 70, about 60, about 50, about 40, about 30, about 20, or about 10 nucleotides of the 5' end or the 3' end of the repeat expansion sequence. As another example, the PAM can be within about 100, about 50, about 40, about 30, about 20, or about 10 nucleotides of the 5' end or the 3' end of the repeat expansion sequence. For example, the PAM can be within about 100, about 90, about 80, about 70, about 60, about 50, about 40, about 30, about 20, or about 10 nucleotides of the 5' end or the 3' end of the repeat expansion sequence or overlapping with the 5' end or the 3' end of the repeat expansion sequence. As another example, the PAM can be within about 25, about 24, about 23, about 22, about 21, about 20, about 19, about 18, about 17, about 16, about 15, about 14, about 13, about 12, about 11, about 10, about 9, about 8, about 7, about 6, about 5, about 4, about 3, about 2, or about 1 nucleotides of the 5' end or the 3' end of the repeat expansion sequence or overlapping with the 5' end or the 3' end of the repeat expansion sequence.

The site at which the nuclease agent makes a double-strand break or a single-strand break is near the repeat expansion sequence. For example, the site at which the nuclease agent makes a double-strand break or a single-strand break can be within about 1000, about 900, about 800, about 700, about 600, about 500, about 400, about 300, about 200, about 100, about 90, about 80, about 70, about 60, about 50, about 40, about 30, about 20, or about 10 nucleotides of the 5' end or the 3' end of the repeat expansion sequence. As another example, the site at which the nuclease agent makes a double-strand break or a single-strand break can be within about 100, about 50, about 40, about 30, about 20, or about 10 nucleotides of the 5' end or the 3' end of the repeat expansion sequence. As one example, the site at which the nuclease agent makes a double-strand break or a single-strand break can be within about 50, about 40, about 30, about 20, or about 10 nucleotides of the 5' end or the 3' end of the repeat expansion sequence. As another example, the site at which the nuclease agent makes a double-strand break or a single-strand break can be within about 25, about 24, about 23, about 22, about 21, about 20, about 19, about 18, about 17, about 16, about 15, about 14, about 13, about 12, about 11, about 10, about 9, about 8, about 7, about 6, about 5, about 4, about 3, about 2, or about 1 nucleotides of the 5' end or the 3' end of the repeat expansion sequence (e.g., within about 20 nucleotides, within about 16 nucleotides, within about 15 nucleotides, within about 11 nucleotides, within about 10 nucleotides, within about 7 nucleotides, within about 5 nucleotides, or within about 2 nucleotides of the 5' end or the 3' end of the repeat expansion sequence). In one example, the repeat expansion sequence is a hexanucleotide repeat expansion sequence (e.g., at a C9ORF72 locus), and the site at which the nuclease agent makes a double-strand break or a single-strand break is within about 10 nucleotides, within about 7 nucleotides, within about 5 nucleotides, or within about 2 nucleotides of the 5' end or the 3' end of the repeat expansion sequence (e.g., within about 7 nucleotides of the 5' end or the 3' end of the repeat expansion sequence, within about 7 nucleotides of the 3' end of the repeat expansion sequence, or within about 2 nucleotides of the 5' end of the repeat expansion sequence3). In another example, the repeat expansion sequence is a trinucleotide repeat expansion sequence, and the site at which the nuclease agent makes a double-strand break or a single-strand break is within about 20 nucleotides, within about 16 nucleotides, within about 15 nucleotides, within about 11 nucleotides, or within about 10 nucleotides of the 5' end or the 3' end of the repeat expansion sequence (e.g., within about 16 nucleotides of the 5' end or the 3' end of the repeat expansion sequence, within about 16 nucleotides of the 5' end of the repeat expansion sequence, or within about 11 nucleotides of the 3' end of the repeat expansion sequence). In some methods, the site at which the nuclease agent makes a double-strand break or a single-strand break is near the 5' end of the repeat expansion sequence. In some methods, the site at which the nuclease agent makes a double-strand break or a single-strand break is near the 3' end of the repeat expansion sequence. In some methods, the site at which the nuclease agent makes a double-strand break or a single-strand break is inside of the repeat expansion sequence. In some methods, the site at which the nuclease agent makes a double-strand break or a single-strand break is outside of the repeat expansion sequence. The site at which the nuclease agent makes a double-strand break or a single-strand break can be destroyed or the nuclease target site can be retained after repair of the double-strand break or the single strand-break by the cell. The nuclease target site can then be reused for subsequent rounds of repeat expansion. In some methods, repair of the double-strand break or the single strand-break does not result in insertions or deletions within the nuclease target site. For example, in some methods, repair of the double-strand break or the single strand-break does not result in insertions or deletions outside of the repeat expansion sequence.

Any suitable nuclease agent can be used. For example, the nuclease agent can be a zinc finger nuclease (ZFN), a Transcription Activator-Like Effector Nuclease (TALEN), or a Clustered Regularly Interspaced Short Palindromic Repeats (CRISPR)-associated (Cas) protein and a guide RNA (e.g., a Cas9 protein and a guide RNA). Examples and descriptions of each are disclosed in more detail elsewhere herein.

In some methods, two nuclease agents can be introduced into the cell. In some methods, two nuclease agents or nucleic acids encoding two nuclease agents can be introduced into the cell. For example, the first nuclease agent can cleave a first nuclease target site is near the 5' end of the repeat expansion sequence, and the second nuclease agent can cleave a second nuclease target site is near the 3' end of the repeat expansion sequence. In one example, the first nuclease agent makes a double-strand break or a single-strand break at a first nuclease target site near the 5' end of the repeat expansion sequence, and the second nuclease agent makes a double-strand break or a single-strand break at a second nuclease target site near the 3' end of the repeat expansion sequence. Alternatively, the first nuclease agent makes a double-strand break or a single-strand break at a first nuclease target site near the 5' end of the repeat expansion sequence, and the second nuclease agent makes a double-strand break or a single-strand break at a second nuclease target site near the 5' end of the repeat expansion sequence. Alternatively, the first nuclease agent makes a double-strand break or a single-strand break at a first nuclease target site near the 3' end of the repeat expansion sequence, and the second nuclease agent makes a double-strand break or a single-strand break at a second nuclease target site near the 3' end of the repeat expansion sequence.

In another example, the first nuclease agent makes a double-strand break at a first nuclease target site near the 5' end of the repeat expansion sequence, and the second nuclease agent makes a double-strand break at a second nuclease target site near the 3' end of the repeat expansion sequence. In another example, the first nuclease agent makes a single-strand break at a first nuclease target site near the 5' end of the repeat expansion sequence, and the second nuclease agent makes a single-strand break at a second nuclease target site near the 3' end of the repeat expansion sequence. In another example, the first nuclease agent makes a single-strand break at a first nuclease target site near the 5' end of the repeat expansion sequence, and the second nuclease agent makes a double-strand break at a second nuclease target site near the 3' end of the repeat expansion sequence. In another example, the first nuclease agent makes a double-strand break at a first nuclease target site near the 5' end of the repeat expansion sequence, and the second nuclease agent makes a single-strand break at a second nuclease target site near the 3' end of the repeat expansion sequence. The first nuclease target site and the second nuclease target site can each be at the 5' end or the 3' end of the repeat expansion sequence, in any combination, and the first nuclease agent and the second nuclease agent can each make a double-strand break or a single-strand break, in any combination.

Introduction of a nuclease agent into a cell can be accomplished by any known means. Introduction of a nucleic acid encoding a nuclease agent into a cell can be accomplished by any known means. Introducing includes presenting to the cell the molecule (e.g., nucleic acid or protein) in such a manner that it gains access to the interior of the cell. The introducing can be accomplished by any means. If multiple components are introduced, they can be introduced simultaneously or sequentially in any combination. In addition, two or more of the components can be introduced into the cell by the same delivery method or different delivery methods. Similarly, if the cell is in vivo (e.g., in a non-human animal), two or more of the components can be introduced into a non-human animal by the same route of administration or different routes of administration.

Molecules introduced into the cell can be provided in compositions comprising a carrier increasing the stability of the introduced molecules (e.g., prolonging the period under given conditions of storage (e.g., −20° C., 4° C., or ambient temperature) for which degradation products remain below a threshold, such below 0.5% by weight of the starting nucleic acid or protein; or increasing the stability in vivo). Non-limiting examples of such carriers include poly(lactic acid) (PLA) microspheres, poly(D,L-lactic-coglycolic-acid) (PLGA) microspheres, liposomes, micelles, inverse micelles, lipid cochleates, and lipid microtubules.

Various methods and compositions are provided herein to allow for introduction of a nuclease agent into a cell. Various methods and compositions are provided herein to allow for introduction of a nucleic acid encoding a nuclease agent into a cell. Methods for introducing nucleic acids into various cell types are known and include, for example, stable transfection methods, transient transfection methods, and virus-mediated methods.

Transfection protocols as well as protocols for introducing nucleic acid sequences into cells may vary. Non-limiting transfection methods include chemical-based transfection methods using liposomes; nanoparticles; calcium phosphate (Graham et al. (1973) *Virology* 52 (2): 456-67, Bacchetti et al. (1977) *Proc. Natl. Acad. Sci. USA* 74 (4): 1590-4, and Kriegler, M (1991). Transfer and Expression: A Laboratory Manual. New York: W. H. Freeman and Company. pp.

96-97); dendrimers; or cationic polymers such as DEAE-dextran or polyethylenimine. Non-chemical methods include electroporation, Sono-poration, and optical transfection. Particle-based transfection includes the use of a gene gun, or magnet-assisted transfection (Bertram (2006) *Current Pharmaceutical Biotechnology* 7, 277-28). Viral methods can also be used for transfection.

Introduction of nuclease agents into a cell can also be mediated by electroporation, by intracytoplasmic injection, by viral infection, by adenovirus, by adeno-associated virus, by lentivirus, by retrovirus, by transfection, by lipid-mediated transfection, or by nucleofection. Introduction of nucleic acids encoding nuclease agents into a cell can also be mediated by electroporation, by intracytoplasmic injection, by viral infection, by adenovirus, by adeno-associated virus, by lentivirus, by retrovirus, by transfection, by lipid-mediated transfection, or by nucleofection. Nucleofection is an improved electroporation technology that enables nucleic acid substrates to be delivered not only to the cytoplasm but also through the nuclear membrane and into the nucleus. In addition, use of nucleofection in the methods disclosed herein typically requires much fewer cells than regular electroporation (e.g., only about 2 million compared with 7 million by regular electroporation). In one example, nucleofection is performed using the LONZA® NUCLEOFECTOR™ system.

Introduction of nuclease agents into a cell (e.g., a zygote) can also be accomplished by microinjection. Introduction of nucleic acids encoding nuclease agents into a cell (e.g., a zygote) can also be accomplished by microinjection. In zygotes (i.e., one-cell stage embryos), microinjection can be into the maternal and/or paternal pronucleus or into the cytoplasm. If the microinjection is into only one pronucleus, the paternal pronucleus is preferable due to its larger size. Microinjection of an mRNA is preferably into the cytoplasm (e.g., to deliver mRNA directly to the translation machinery), while microinjection of a protein or a polynucleotide encoding a protein or encoding an RNA is preferable into the nucleus/pronucleus. Alternatively, microinjection can be carried out by injection into both the nucleus/pronucleus and the cytoplasm: a needle can first be introduced into the nucleus/pronucleus and a first amount can be injected, and while removing the needle from the one-cell stage embryo a second amount can be injected into the cytoplasm. If a protein is injected into the cytoplasm and needs to be targeted to the nucleus, it can comprise a nuclear localization signal to ensure delivery to the nucleus/pronucleus. Methods for carrying out microinjection are well known. See, e.g., Nagy et al. (Nagy A, Gertsenstein M, Vintersten K, Behringer R., 2003, Manipulating the Mouse Embryo, Cold Spring Harbor, N.Y.: Cold Spring Harbor Laboratory Press); see also Meyer et al. (2010) *Proc. Natl. Acad. Sci. USA* 107:15022-15026 and Meyer et al. (2012) *Proc. Natl. Acad. Sci. USA* 109:9354-9359.

Other methods for introducing nuclease agents into a cell can include, for example, vector delivery, particle-mediated delivery, exosome-mediated delivery, lipid-nanoparticle-mediated delivery, cell-penetrating-peptide-mediated delivery, or implantable-device-mediated delivery. Other methods for introducing nucleic acids encoding nuclease agents into a cell can include, for example, vector delivery, particle-mediated delivery, exosome-mediated delivery, lipid-nanoparticle-mediated delivery, cell-penetrating-peptide-mediated delivery, or implantable-device-mediated delivery. As specific examples, a nucleic acid or protein can be introduced into a cell or non-human animal in a carrier such as a poly(lactic acid) (PLA) microsphere, a poly(D,L-lactic-coglycolic-acid) (PLGA) microsphere, a liposome, a micelle, an inverse micelle, a lipid cochleate, or a lipid microtubule. If the cell is in vivo (e.g., in a non-human animal), some specific examples of delivery to a non-human animal include hydrodynamic delivery, virus-mediated delivery (e.g., adeno-associated virus (AAV)-mediated delivery), and lipid-nanoparticle-mediated delivery.

Introduction of nuclease agents into cells can be accomplished by hydrodynamic delivery (HDD) in vivo. Introduction of nucleic acids encoding nuclease agents into cells can be accomplished by hydrodynamic delivery (HDD) in vivo. Hydrodynamic delivery has emerged as a method for intracellular DNA delivery in vivo. For gene delivery to parenchymal cells, only essential DNA sequences need to be injected via a selected blood vessel, eliminating safety concerns associated with current viral and synthetic vectors. When injected into the bloodstream, DNA is capable of reaching cells in the different tissues accessible to the blood. Hydrodynamic delivery employs the force generated by the rapid injection of a large volume of solution into the incompressible blood in the circulation to overcome the physical barriers of endothelium and cell membranes that prevent large and membrane-impermeable compounds from entering parenchymal cells. In addition to the delivery of DNA, this method is useful for the efficient intracellular delivery of RNA, proteins, and other small compounds in vivo. See, e.g., Bonamassa et al. (2011) *Pharm. Res.* 28(4): 694-701, herein incorporated by reference in its entirety for all purposes.

Introduction of nuclease agents can also be accomplished by virus-mediated delivery, such as AAV-mediated delivery or lentivirus-mediated delivery. Introduction of nucleic acids encoding nuclease agents can also be accomplished by virus-mediated delivery, such as AAV-mediated delivery or lentivirus-mediated delivery. Other exemplary viruses/viral vectors include retroviruses, adenoviruses, vaccinia viruses, poxviruses, and herpes simplex viruses. The viruses can infect dividing cells, non-dividing cells, or both dividing and non-dividing cells. The viruses can integrate into the host genome or alternatively do not integrate into the host genome. Such viruses can also be engineered to have reduced immunity. The viruses can be replication-competent or can be replication-defective (e.g., defective in one or more genes necessary for additional rounds of virion replication and/or packaging). Viruses can cause transient expression, long-lasting expression (e.g., at least 1 week, 2 weeks, 1 month, 2 months, or 3 months), or permanent expression. Exemplary viral titers (e.g., AAV titers) include $10^{12}$, $10^{13}$, $10^{14}$, $10^{15}$, and $10^{16}$ vector genomes/mL.

The ssDNA AAV genome consists of two open reading frames, Rep and Cap, flanked by two inverted terminal repeats that allow for synthesis of the complementary DNA strand. When constructing an AAV transfer plasmid, the transgene is placed between the two ITRs, and Rep and Cap can be supplied in trans. In addition to Rep and Cap, AAV can require a helper plasmid containing genes from adenovirus. These genes (E4, E2a, and VA) mediated AAV replication. For example, the transfer plasmid, Rep/Cap, and the helper plasmid can be transfected into HEK293 cells containing the adenovirus gene E1+ to produce infectious AAV particles. Alternatively, the Rep, Cap, and adenovirus helper genes may be combined into a single plasmid. Similar packaging cells and methods can be used for other viruses, such as retroviruses.

Multiple serotypes of AAV have been identified. These serotypes differ in the types of cells they infect (i.e., their tropism), allowing preferential transduction of specific cell types. Serotypes for CNS tissue include AAV1, AAV2, AAV4, AAV5, AAV8, and AAV9. Serotypes for heart tissue include AAV1, AAV8, and AAV9. Serotypes for kidney tissue include AAV2. Serotypes for lung tissue include AAV4, AAV5, AAV6, and AAV9. Serotypes for pancreas tissue include AAV8. Serotypes for photoreceptor cells include AAV2, AAV5, and AAV8. Serotypes for retinal pigment epithelium tissue include AAV1, AAV2, AAV4, AAV5, and AAV8. Serotypes for skeletal muscle tissue include AAV1, AAV6, AAV7, AAV8, and AAV9. Serotypes for liver tissue include AAV7, AAV8, and AAV9, and particularly AAV8.

Tropism can be further refined through pseudotyping, which is the mixing of a capsid and a genome from different viral serotypes. For example AAV2/5 indicates a virus containing the genome of serotype 2 packaged in the capsid from serotype 5. Use of pseudotyped viruses can improve transduction efficiency, as well as alter tropism. Hybrid capsids derived from different serotypes can also be used to alter viral tropism. For example, AAV-DJ contains a hybrid capsid from eight serotypes and displays high infectivity across a broad range of cell types in vivo. AAV-DJ8 is another example that displays the properties of AAV-DJ but with enhanced brain uptake. AAV serotypes can also be modified through mutations. Examples of mutational modifications of AAV2 include Y444F, Y500F, Y730F, and S662V. Examples of mutational modifications of AAV3 include Y705F, Y731F, and T492V. Examples of mutational modifications of AAV6 include S663V and T492V. Other pseudotyped/modified AAV variants include AAV2/1, AAV2/6, AAV2/7, AAV2/8, AAV2/9, AAV2.5, AAV8.2, and AAV/SASTG.

To accelerate transgene expression, self-complementary AAV (scAAV) variants can be used. Because AAV depends on the cell's DNA replication machinery to synthesize the complementary strand of the AAV's single-stranded DNA genome, transgene expression may be delayed. To address this delay, scAAV containing complementary sequences that are capable of spontaneously annealing upon infection can be used, eliminating the requirement for host cell DNA synthesis. However, single-stranded AAV (ssAAV) vectors can also be used.

To increase packaging capacity, longer transgenes may be split between two AAV transfer plasmids, the first with a 3' splice donor and the second with a 5' splice acceptor. Upon co-infection of a cell, these viruses form concatemers, are spliced together, and the full-length transgene can be expressed. Although this allows for longer transgene expression, expression is less efficient. Similar methods for increasing capacity utilize homologous recombination. For example, a transgene can be divided between two transfer plasmids but with substantial sequence overlap such that co-expression induces homologous recombination and expression of the full-length transgene.

Introduction of nuclease agents can also be accomplished by lipid nanoparticle (LNP)-mediated delivery. Introduction of nucleic acids encoding nuclease agents can also be accomplished by lipid nanoparticle (LNP)-mediated delivery. For example, LNP-mediated delivery can be used to deliver a combination of Cas mRNA and guide RNA or a combination of Cas protein and guide RNA. Delivery through such methods can result in transient Cas expression, and the biodegradable lipids can improve clearance, improve tolerability, and decrease immunogenicity. Lipid formulations can protect biological molecules from degradation while improving their cellular uptake. Lipid nanoparticles are particles comprising a plurality of lipid molecules physically associated with each other by intermolecular forces. These include microspheres (including unilamellar and multilamellar vesicles, e.g., liposomes), a dispersed phase in an emulsion, micelles, or an internal phase in a suspension. Such lipid nanoparticles can be used to encapsulate one or more nucleic acids or proteins for delivery. Formulations which contain cationic lipids are useful for delivering polyanions such as nucleic acids. Other lipids that can be included are neutral lipids (i.e., uncharged or zwitterionic lipids), anionic lipids, helper lipids that enhance transfection, and stealth lipids that increase the length of time for which nanoparticles can exist in vivo. Examples of suitable cationic lipids, neutral lipids, anionic lipids, helper lipids, and stealth lipids can be found in WO 2016/010840 A1, herein incorporated by reference in its entirety for all purposes. An exemplary lipid nanoparticle can comprise a cationic lipid and one or more other components. In one example, the other component can comprise a helper lipid such as cholesterol. In another example, the other components can comprise a helper lipid such as cholesterol and a neutral lipid such as DSPC. In another example, the other components can comprise a helper lipid such as cholesterol, an optional neutral lipid such as DSPC, and a stealth lipid such as S010, S024, S027, S031, or S033.

The LNP may contain one or more or all of the following: (i) a lipid for encapsulation and for endosomal escape; (ii) a neutral lipid for stabilization; (iii) a helper lipid for stabilization; and (iv) a stealth lipid. See, e.g., Finn et al. (2018) *Cell Rep.* 22(9):2227-2235 and WO 2017/173054 A1, each of which is herein incorporated by reference in its entirety for all purposes. In certain LNPs, the cargo can include a guide RNA or a nucleic acid encoding a guide RNA. In certain LNPs, the cargo can include an mRNA encoding a Cas nuclease, such as Cas9, and a guide RNA or a nucleic acid encoding a guide RNA.

The lipid for encapsulation and endosomal escape can be a cationic lipid. The lipid can also be a biodegradable lipid, such as a biodegradable ionizable lipid. One example of a suitable lipid is Lipid A or LP01, which is (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethyl amino)propoxy)carbonyl)oxy)methyl)propyl (9Z, 12Z)-octadeca-9,12-dienoate. See, e.g., Finn et al. (2018) *Cell Rep.* 22(9):2227-2235 and WO 2017/173054 A1, each of which is herein incorporated by reference in its entirety for all purposes. Another example of a suitable lipid is Lipid B, which is ((5-((dimethylamino)methyl)-1,3-phenylene)bis (oxy))bis(octane-8,1-diyl)bis(decanoate), also called ((5-((dimethylamino)methyl)-1,3-phenylene)bis(oxy))bis(octane-8,1-diyl)bis(decanoate). Another example of a suitable lipid is Lipid C, which is 2-((4-(((3-(dimethylamino)propoxy)carbonyl)oxy)hexadecanoyl)oxy)propane-1,3-diyl (9Z,9'Z, 12Z, 12'Z)-bis(octadeca-9,12-dienoate). Another example of a suitable lipid is Lipid D, which is 3-(((3-(dimethylamino)propoxy)carbonyl)oxy)-13-(octanoyloxy) tridecyl 3-octylundecanoate. Other suitable lipids include heptatriaconta-6,9,28,31-tetraen-19-yl 4-(dimethylamino) butanoate (also known as Dlin-MC3-DMA (MC3))).

Some such lipids suitable for use in the LNPs described herein are biodegradable in vivo. For example, LNPs comprising such a lipid include those where at least 75% of the lipid is cleared from the plasma within 8, 10, 12, 24, or 48 hours, or 3, 4, 5, 6, 7, or 10 days. As another example, at least 50% of the LNP is cleared from the plasma within 8, 10, 12, 24, or 48 hours, or 3, 4, 5, 6, 7, or 10 days.

Such lipids may be ionizable depending upon the pH of the medium they are in. For example, in a slightly acidic medium, the lipids may be protonated and thus bear a positive charge. Conversely, in a slightly basic medium, such as, for example, blood where pH is approximately 7.35, the lipids may not be protonated and thus bear no charge. In some embodiments, the lipids may be protonated at a pH of at least about 9, 9.5, or 10. The ability of such a lipid to bear a charge is related to its intrinsic pKa. For example, the lipid may, independently, have a pKa in the range of from about 5.8 to about 6.2.

Neutral lipids function to stabilize and improve processing of the LNPs. Examples of suitable neutral lipids include a variety of neutral, uncharged or zwitterionic lipids. Examples of neutral phospholipids suitable for use in the present disclosure include, but are not limited to, 5-heptadecylbenzene-1,3-diol (resorcinol), dipalmitoylphosphatidylcholine (DPPC), distearoylphosphatidylcholine (DSPC), phosphocholine (DOPC), dimyristoylphosphatidylcholine (DMPC), phosphatidylcholine (PLPC), 1,2-distearoyl-sn-glycero-3-phosphocholine (DAPC), phosphatidylethanolamine (PE), egg phosphatidylcholine (EPC), dilauryloylphosphatidylcholine (DLPC), dimyristoylphosphatidylcholine (DMPC), 1-myristoyl-2-palmitoyl phosphatidylcholine (MPPC), 1-palmitoyl-2-myristoyl phosphatidylcholine (PMPC), 1-palmitoyl-2-stearoyl phosphatidylcholine (PSPC), 1,2-diarachidoyl-sn-glycero-3-phosphocholine (DBPC), 1-stearoyl-2-palmitoyl phosphatidylcholine (SPPC), 1,2-dieicosenoyl-sn-glycero-3-phosphocholine (DEPC), palmitoyloleoyl phosphatidylcholine (POPC), lysophosphatidyl choline, dioleoyl phosphatidylethanolamine (DOPE), dilinoleoylphosphatidylcholine di stearoylphosphatidylethanolamine (DSPE), dimyristoyl phosphatidyl ethanolamine (DMPE), dipalmitoyl phosphatidylethanolamine (DPPE), palmitoyloleoyl phosphatidylethanolamine (POPE), lysophosphatidylethanolamine, and combinations thereof. For example, the neutral phospholipid may be selected from the group consisting of distearoylphosphatidylcholine (DSPC) and dimyristoyl phosphatidyl ethanolamine (DMPE).

Helper lipids include lipids that enhance transfection. The mechanism by which the helper lipid enhances transfection can include enhancing particle stability. In certain cases, the helper lipid can enhance membrane fusogenicity. Helper lipids include steroids, sterols, and alkyl resorcinols. Examples of suitable helper lipids suitable include cholesterol, 5-heptadecylresorcinol, and cholesterol hemisuccinate. In one example, the helper lipid may be cholesterol or cholesterol hemisuccinate.

Stealth lipids include lipids that alter the length of time the nanoparticles can exist in vivo. Stealth lipids may assist in the formulation process by, for example, reducing particle aggregation and controlling particle size. Stealth lipids may modulate pharmacokinetic properties of the LNP. Suitable stealth lipids include lipids having a hydrophilic head group linked to a lipid moiety.

The hydrophilic head group of stealth lipid can comprise, for example, a polymer moiety selected from polymers based on PEG (sometimes referred to as poly(ethylene oxide)), poly(oxazoline), poly(vinyl alcohol), poly(glycerol), poly(N-vinylpyrrolidone), polyaminoacids, and poly N-(2-hydroxypropyl)methacrylamide. The term PEG means any polyethylene glycol or other polyalkylene ether polymer. In certain LNP formulations, the PEG, is a PEG-2K, also termed PEG 2000, which has an average molecular weight of about 2,000 daltons. See, e.g., WO 2017/173054 A1, herein incorporated by reference in its entirety for all purposes.

The lipid moiety of the stealth lipid may be derived, for example, from diacylglycerol or diacylglycamide, including those comprising a dialkylglycerol or dialkylglycamide group having alkyl chain length independently comprising from about C4 to about C40 saturated or unsaturated carbon atoms, wherein the chain may comprise one or more functional groups such as, for example, an amide or ester. The dialkylglycerol or dialkylglycamide group can further comprise one or more substituted alkyl groups.

As one example, the stealth lipid may be selected from PEG-dilauroylglycerol, PEG-dimyristoylglycerol (PEG-DMG), PEG-dipalmitoylglycerol, PEG-di stearoylglycerol (PEG-DSPE), PEG-dilaurylglycamide, PEG-dimyristylglycamide, PEG-dipalmitoylglycamide, and PEG-distearoylglycamide, PEG-cholesterol (1-[8'-(Cholest-5-en-3[beta]-oxy)carboxamido-3',6'-dioxaoctanyl]carbamoyl-[omega]-methyl-poly(ethylene glycol), PEG-DMB (3,4-ditetradecoxylbenzyl-[omega]-methyl-poly(ethylene glycol)ether), 1,2-dimyristoyl-sn-glycero-3-phosphoethanolamine-N-[methoxy(polyethylene glycol)-2000] (PEG2k-DMG), 1,2-distearoyl-sn-glycero-3-phosphoethanolamine-N-[methoxy(polyethylene glycol)-2000] (PEG2k-DSPE), 1,2-distearoyl-sn-glycerol, methoxypoly ethylene glycol (PEG2k-DSG), poly(ethylene glycol)-2000-dimethacrylate (PEG2k-DMA), and 1,2-distearyloxypropyl-3-amine-N-[methoxy(polyethylene glycol)-2000] (PEG2k-DSA). In one particular example, the stealth lipid may be PEG2k-DMG.

The LNPs can comprise different respective molar ratios of the component lipids in the formulation. The mol-% of the CCD lipid may be, for example, from about 30 mol-% to about 60 mol-%, from about 35 mol-% to about 55 mol-%, from about 40 mol-% to about 50 mol-%, from about 42 mol-% to about 47 mol-%, or about 45%. The mol-% of the helper lipid may be, for example, from about 30 mol-% to about 60 mol-%, from about 35 mol-% to about 55 mol-%, from about 40 mol-% to about 50 mol-%, from about 41 mol-% to about 46 mol-%, or about 44 mol-%. The mol-% of the neutral lipid may be, for example, from about 1 mol-% to about 20 mol-%, from about 5 mol-% to about 15 mol-%, from about 7 mol-% to about 12 mol-%, or about 9 mol-%. The mol-% of the stealth lipid may be, for example, from about 1 mol-% to about 10 mol-%, from about 1 mol-% to about 5 mol-%, from about 1 mol-% to about 3 mol-%, about 2 mol-%, or about 1 mol-%.

The LNPs can have different ratios between the positively charged amine groups of the biodegradable lipid (N) and the negatively charged phosphate groups (P) of the nucleic acid to be encapsulated. This may be mathematically represented by the equation N/P. For example, the N/P ratio may be from about 0.5 to about 100, from about 1 to about 50, from about 1 to about 25, from about 1 to about 10, from about 1 to about 7, from about 3 to about 5, from about 4 to about 5, about 4, about 4.5, or about 5. The N/P ratio can also be from about 4 to about 7 or from about 4.5 to about 6. In specific examples, the N/P ratio can be 4.5 or can be 6.

In some LNPs, the cargo can comprise Cas mRNA and gRNA. The Cas mRNA and gRNAs can be in different ratios. For example, the LNP formulation can include a ratio of Cas mRNA to gRNA nucleic acid ranging from about 25:1 to about 1:25, ranging from about 10:1 to about 1:10, ranging from about 5:1 to about 1:5, or about 1:1. Alternatively, the LNP formulation can include a ratio of Cas mRNA to gRNA nucleic acid from about 1:1 to about 1:5, or about 10:1. Alternatively, the LNP formulation can include a ratio of Cas mRNA to gRNA nucleic acid of about 1:10, 25:1, 10:1, 5:1, 3:1, 1:1, 1:3, 1:5, 1:10, or 1:25. Alternatively, the LNP formulation can include a ratio of Cas mRNA to gRNA nucleic acid of from about 1:1 to about 1:2. In specific examples, the ratio of Cas mRNA to gRNA can be about 1:1 or about 1:2.

A specific example of a suitable LNP has a nitrogen-to-phosphate (N/P) ratio of 4.5 and contains biodegradable cationic lipid, cholesterol, DSPC, and PEG2k-DMG in a 45:44:9:2 molar ratio. The biodegradable cationic lipid can be (9Z,12Z)-3-((4,4-bis(octyloxy)butanoyl)oxy)-2-((((3-(diethyl amino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl)propyl (9Z, 12Z)-octadeca-9,12-dienoate. See, e.g., Finn et al. (2018) *Cell Rep.* 22(9):2227-2235, herein incorporated by reference in its entirety for all purposes. The Cas9 mRNA can be in a 1:1 ratio by weight to the guide RNA. Another specific example of a suitable LNP contains Dlin-MC3-DMA (MC3), cholesterol, DSPC, and PEG-DMG in a 50:38.5:10:1.5 molar ratio.

Another specific example of a suitable LNP has a nitrogen-to-phosphate (N/P) ratio of 6 and contains biodegradable cationic lipid, cholesterol, DSPC, and PEG2k-DMG in a 50:38:9:3 molar ratio. The biodegradable cationic lipid can be (9Z,12Z)-3-((4,4-bis(octyloxy)butanoyl)oxy)-2-((((3-(diethyl amino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl)propyl (9Z, 12Z)-octadeca-9,12-dienoate. The Cas9 mRNA can be in a 1:2 ratio by weight to the guide RNA.

The mode of delivery can be selected to decrease immunogenicity. For example, if multiple components are delivered, they may be delivered by different modes (e.g., bi-modal delivery). These different modes may confer different pharmacodynamics or pharmacokinetic properties on the subject delivered molecule. For example, the different modes can result in different tissue distribution, different half-life, or different temporal distribution. Some modes of delivery (e.g., delivery of a nucleic acid vector that persists in a cell by autonomous replication or genomic integration) result in more persistent expression and presence of the molecule, whereas other modes of delivery are transient and less persistent (e.g., delivery of an RNA or a protein). Delivery of Cas proteins in a more transient manner, for example as mRNA or protein, can ensure that the Cas/gRNA complex is only present and active for a short period of time and can reduce immunogenicity caused by peptides from the bacterially derived Cas enzyme being displayed on the surface of the cell by MHC molecules. Such transient delivery can also reduce the possibility of off-target modifications.

Administration in vivo can be by any suitable route including, for example, parenteral, intravenous, oral, subcutaneous, intra-arterial, intracranial, intrathecal, intraperitoneal, topical, intranasal, or intramuscular. Systemic modes of administration include, for example, oral and parenteral routes. Examples of parenteral routes include intravenous, intraarterial, intraosseous, intramuscular, intradermal, subcutaneous, intranasal, and intraperitoneal routes. A specific example is intravenous infusion. Nasal instillation and intravitreal injection are other specific examples. Local modes of administration include, for example, intrathecal, intracerebroventricular, intraparenchymal (e.g., localized intraparenchymal delivery to the striatum (e.g., into the caudate or into the putamen), cerebral cortex, precentral gyms, hippocampus (e.g., into the dentate gyrus or CA3 region), temporal cortex, amygdala, frontal cortex, thalamus, cerebellum, medulla, hypothalamus, tectum, tegmentum, or substantia nigra), intraocular, intraorbital, subconjuctival, intravitreal, subretinal, and transscleral routes. Significantly smaller amounts of the components (compared with systemic approaches) may exert an effect when administered locally (for example, intraparenchymal or intravitreal) compared to when administered systemically (for example, intravenously). Local modes of administration may also reduce or eliminate the incidence of potentially toxic side effects that may occur when therapeutically effective amounts of a component are administered systemically.

The repeat expansion sequence can be a heterologous repeat expansion sequence. The term heterologous when used in the context of a nucleic acid indicates that the nucleic acid comprises at least two segments that do not naturally occur together in the same molecule. For example, the term heterologous, when used with reference to segments of a nucleic acid, indicates that the nucleic acid comprises two or more sub-sequences that are not found in the same relationship to each other (e.g., joined together) in nature. As one example, a heterologous region of a nucleic acid is a segment of nucleic acid within or attached to another nucleic acid molecule that is not found in association with the other molecule in nature. For example, a heterologous region of a nucleic acid could include a C9ORF72 sequence flanked by repeat expansion sequence not found in association with the C9ORF72 sequence in nature. Alternatively, a heterologous region of nucleic acid could include a human nucleic acid sequence flanked by endogenous non-human nucleic acid sequence. For example, the repeat expansion sequence can be a human nucleic acid sequence flanked by endogenous non-human (e.g., mouse) nucleic acid sequence. In other methods, the repeat expansion sequence can be endogenous. For example, the cell can be a human cell (e.g., a human induced pluripotent stem cell), and the both the repeat expansion sequence and the flanking sequence can include human nucleic acid sequence.

The repeat expansion sequence comprises a plurality of repeats. For example, the repeat expansion sequence to be expanded can comprise at least about 10, at least about 20, at least about 30, at least about 40, at least about 50, at least about 60, at least about 70, at least about 80, or at least about 100 copies of the repeat sequence. In some repeat expansion sequences, the repeats can be contiguous (adjacent to each other without intervening sequence).

The expanded repeat expansion sequence resulting from the method can have any number of repeats. For example, the expanded repeat expansion sequence can comprise more than about 95 repeats, more than about 96 repeats, more than about 97 repeats, more than about 98 repeats, more than about 99 repeats, more than about 100 repeats, more than about 101 repeats, more than about 102 repeats, more than about 103 repeats, more than about 104 repeats, more than about 105 repeats, more than about 150 repeats, more than about 200 repeats, more than about 250 repeats, more than about 295 repeats, more than about 296 repeats, more than about 297 repeats, more than about 298 repeats, more than about 299 repeats, more than about 300 repeats, more than about 301 repeats, more than about 302 repeats, more than about 303 repeats, more than about 304 repeats, more than about 305 repeats, more than about 350 repeats, more than about 400 repeats, more than about 450 repeats, more than about 500 repeats, more than about 550 repeats, more than about 595 repeats, more than about 596 repeats, more than about 597 repeats, more than about 598 repeats, more than about 599 repeats, more than about 600 repeats, more than about 601 repeats, more than about 602 repeats, more than about 603 repeats, more than about 604 repeats, or more than about 605 repeats. Alternatively, the expanded repeat expansion sequence can comprise at least about 95 repeats, at least about 96 repeats, at least about 97 repeats, at least about 98 repeats, at least about 99 repeats, at least about 100 repeats, at least about 101 repeats, at least about 102 repeats, at least about 103 repeats, at least about 104 repeats, at least about 105 repeats, at least about 150 repeats, at least about 200 repeats, at least about 250 repeats, at least about 295 repeats, at least about 296 repeats, at least about 297 repeats, at least about 298 repeats, at least about 299 repeats, at least about 300 repeats, at least about 301 repeats, at least about 302 repeats, at least about 303 repeats, at least about 304 repeats, at least about 305 repeats, at least about 350 repeats, at least about 400 repeats, at least about 450 repeats, at least about 500 repeats, at least about 550 repeats, at least about 595 repeats, at least about 596 repeats, at least about 597 repeats, at least about 598 repeats, at least about 599 repeats, at least about 600 repeats, at least about 601 repeats, at least about 602 repeats, at least about 603 repeats, at least about 604 repeats, or at least about 605 repeats. In a specific example, the expanded repeat expansion sequence comprises more than about 100 repeats, more than about 300 repeats, more than about 600 repeats, at least about 100 repeats, at least about 300 repeats, or at least about 600 repeats.

The repeat sequence (e.g., each repeat) can comprise any number of nucleotides. As an example, the repeat sequence can be a trinucleotide repeat, a tetranucleotide repeat, a pentanucleotide repeat, a hexanucleotide repeat, or a dodecanucleotide repeat. The repeat sequence can be a repeat expansion associated with a disease such as a neurological disease. As one example, the repeat sequence can comprise, consist essentially of, or consist of any one of SEQ ID NOS: 1-12. For example, the repeat sequence can be one of the repeat sequences set forth in Table 2 and/or can be in a target genomic locus comprising one of the genes set forth in Table 2 and/or can be associated with one of the diseases set forth in Table 2.

More than 40 diseases, most of which primarily affect the nervous system, are caused by expansions of simple sequence repeats dispersed throughout the human genome. Expanded trinucleotide repeat diseases were discovered first and remain the most frequent. More recently tetra-, penta-, hexa-, and even dodecanucleotide repeat expansions have been identified as the cause of human disease, including some of the most common neurological genetic disorders. Repeat expansion diseases include both causes of myotonic dystrophy (DM1 and DM2), the most common genetic cause of amyotrophic lateral sclerosis/frontotemporal dementia (C9ORF72), Huntington disease, and eight other polyglutamine disorders, including the most common forms of dominantly inherited ataxia, the most common recessive ataxia (Friedreich ataxia), and the most common heritable mental retardation (fragile X syndrome).

Examples of repeats, the genes they occur in, and the diseases they are associated with are set forth in Table 2.

TABLE 2

Repeat Expansions Causing Neurologic Disease.

| Repeat | SEQ ID NO | Gene | Associated Neurologic Disease(s) |
|---|---|---|---|
| CAG | 2 | HTT | Huntington disease |
| | | AR | spinal and bulbar muscular atrophy |
| | | ATN1 | dentatorubral-pallidoluysian atrophy |
| | | ATXN1 | spinocerebellar ataxia type 1 |
| | | ATXN2 | spinocerebellar ataxia type 2 |
| | | ATXN3 | spinocerebellar ataxia type 3 |
| | | CACNA1A | spinocerebellar ataxia type 6 |
| | | ATXN7 | spinocerebellar ataxia type 7 |
| | | PPP2R2B | spinocerebellar ataxia type 12 |
| | | TBP | spinocerebellar ataxia type 17 |
| CGG | 3 | FMR1 (FRAX4) | fragile X, fragile X tremor ataxia syndrome |
| CTG | 4 | DMPK | myotonic dystrophy type 1 |
| | | JPH3 | Huntington disease-like 2 |
| | | ATXN8 | spinocerebellar ataxia type 8 |
| | | TCF4 | Fuchs corneal dystrophy |
| GAA | 5 | FXN (FRDA) | Friedreich ataxia |
| GCC | 6 | AFF2 (FRAXE) | FRAXE mental retardation |
| GCG | 7 | PABPN1 (PABP2) | oculopharyngeal muscular dystrophy |
| CCTG | 8 | CNBP | myotonic dystrophy type 2 |
| ATTCT | 9 | ATXN10 | spinocerebellar ataxia type 10 |
| TGGAA | 10 | TK2, BEAN1 (BEAN) | spinocerebellar ataxia type 31 |
| GGCCTG | 11 | NOP56 | spinocerebellar ataxia type 36 |
| GGGGCC | 1 | C9ORF72 | frontotemporal dementia/amyotrophic lateral sclerosis |
| CCCCGCCCCGCG | 12 | CSTB | EPM1 (myoclonic epilepsy) |

General features of repeat expansion diseases include the following: (1) repeat expansions arise from normally existing polymorphic repeats; (2) expansions are unstable (dynamic), often changing size when transmitted to the next generation; (3) longer repeats tend to cause more severe, earlier-onset disease; (4) clinical anticipation is common: earlier-onset, more severe disease in successive generations; and (5) highly variably phenotype, primarily reflecting differences in repeat size. However, the high GC content in repeats associated with repeat expansion diseases makes it difficult to synthesize DNA fragments with several copies of the repeat as well as maintain the repeat in microorganisms. Therefore, preparing materials to generate targeting vectors and ultimately transgenic animals comprising multiple copies of the repeats is challenging. This is one of the major reasons why few useful animal models for repeat expansions diseases exist. The methods disclosed herein overcome this problem by expanding relatively shorter repeats (i.e., smaller number of repeats) that are already inserted in the right location in the genome rather than de novo targeting vector production and ES cell targeting.

In a specific example, the repeat sequence can comprise, consist essentially of, or consist of GGGGCC (SEQ ID NO: 1), and the target genomic locus can be a C9ORF72 locus. In a specific example, the nuclease target site can comprise, consist essentially of, or consist of any one of SEQ ID NOS: 28-35 or can comprise, consist essentially of, or consist of SEQ ID NO: 28 or 33. As a specific example, the nuclease agent is CRISPR/Cas9 (comprising a guide RNA). The guide RNA (e.g., the DNA-targeting segment or guide sequence of the guide RNA) can comprise, consist essentially of, or consist of any one of SEQ ID NOS: 84-91 or can comprise, consist essentially of, or consist of SEQ ID NO: 84 or 89. Similarly, the guide RNA (e.g., the crRNA portion of the guide RNA) can comprise, consist essentially of, or consist of any one of SEQ ID NOS: 56, 57, and 76-81 or can comprise, consist essentially of, or consist of SEQ ID NO: 56 or 79.

The cell can be any type of cell. Optionally, the cell can be a human cell. For example, the cell can be a human induced pluripotent stem cell. Alternatively, any of the non-human animal cells disclosed in more detail elsewhere herein can be used. As some specific examples, the cells can be non-human animal one-cell stage embryos, non-human animal embryonic stem cells, embryonic stem-cell-derived motor neurons, brain cells, cortical cells, neuronal cells, muscle cells, heart cells, or germ cells. In one example, the cells can be rodent cells such as mouse cells or rat cells. For example, the cells can be mouse embryonic stem cells or mouse one-cell stage embryos. The cells can be in vitro, ex vivo, or in vivo.

Quantifying the number of copies of a repeat sequence can be accomplished by any suitable means. For example, southern blotting or polymerase chain reaction (PCR) genotyping methods can be used. As a specific example, conventional two-primer PCR can be used or prime PCR that uses three primers can be used as described in the examples. Prime PCR is a modified version of triplet repeat primed PCR developed by Warner et al. (1996) *J. Med. Genet.* 33(12):1022-1026, herein incorporated by reference in its entirety for all purposes. This method counts the number of repeats using a primer that can prime a polymerase chain reaction inside the repeat, used together with a fluorescently labeled locus-specific primer.

In some methods, the method is repeated a plurality of times (e.g., two times or three times) to achieve multiple rounds of expansion. For example, the method can comprise multiple rounds of (a) providing a population of cells comprising a repeat expansion sequence comprising a plurality of copies of the repeat sequence at the target genomic locus, (b) introducing into the population of cells a nuclease agent that cleaves a nuclease target site near the 5' end or the 3' end of the repeat expansion sequence to produce a population of modified cells, and (c) quantifying the number of copies of the repeat sequence in the population of modified cells and selecting a modified cell in which the number of copies of the repeat sequence has been increased. For example, the method can comprise multiple rounds of (a) providing a population of cells comprising a repeat expansion sequence comprising a plurality of copies of the repeat sequence at the target genomic locus, (b) introducing into the population of cells a nuclease agent or a nucleic acid encoding the nuclease agent, wherein the nuclease agent cleaves a nuclease target site near the 5' end or the 3' end of the repeat expansion sequence to produce a population of modified cells, and (c) quantifying the number of copies of the repeat sequence in the population of modified cells and selecting a modified cell in which the number of copies of the repeat sequence has been increased. For example, the method can comprise multiple rounds of (a) providing a population of cells comprising a repeat expansion sequence comprising a plurality of copies of the repeat sequence at the target genomic locus, (b) introducing into the population of cells a nuclease agent that makes a double-strand break or a single-strand break at a nuclease target site near the 5' end or the 3' end of the repeat expansion sequence to produce a population of modified cells, and (c) quantifying the number of copies of the repeat sequence in the population of modified cells and selecting a modified cell in which the number of copies of the repeat sequence has been increased. For example, the method can comprise multiple rounds of (a) providing a population of cells comprising a repeat expansion sequence comprising a plurality of copies of the repeat sequence at the target genomic locus, (b) introducing into the population of cells a nuclease agent or a nucleic acid encoding the nuclease agent, wherein the nuclease agent makes a double-strand break or a single-strand break at a nuclease target site near the 5' end or the 3' end of the repeat expansion sequence to produce a population of modified cells, and (c) quantifying the number of copies of the repeat sequence in the population of modified cells and selecting a modified cell in which the number of copies of the repeat sequence has been increased. The population of cells in step (a) in each round after the first round can be a clonal population of cells expanded from the modified cell selected in step (c) of the previous round. The method can be repeated any number of times (e.g., at least about 2 times, at least about 3 times, at least about 4 times, at least about 5 times, at least about 6 times, at least about 7 times, at least about 8 times, at least about 9 times, or at least about 10 times) so long as there remains a nuclease target site near the 5' end or the 3' end of the repeat expansion sequence for a nuclease agent to target.

For example, the method can be performed a first time with a first nuclease agent that cleaves a first nuclease target site near the 5' end of the repeat expansion sequence to produce a first modified cell, and the method can be performed a second time with a second nuclease agent that cleaves a second nuclease target site near the 3' end of the repeat expansion sequence to produce a second modified cell. Alternatively, the method can be performed a first time with a first nuclease agent that cleaves a first nuclease target site near the 3' end of the repeat expansion sequence to produce a first modified cell, and the method can be performed a second time with a second nuclease agent that cleaves a second nuclease target site near the 5' end of the repeat expansion sequence to produce a second modified cell.

As another example, the method can be performed a first time with a first nuclease agent that makes a double-strand break or a single-strand break at a first nuclease target site near the 5' end of the repeat expansion sequence to produce a first modified cell, and the method is performed a second time on the first modified cell with a second nuclease agent that makes a double-strand break or a single-strand break at a second nuclease target site near the 3' end of the repeat expansion sequence to produce a second modified cell. Alternatively, the method can be performed a first time with a first nuclease agent that makes a double-strand break or a single-strand break at a first nuclease target site near the 3' end of the repeat expansion sequence to produce a first modified cell, and the method is performed a second time on the first modified cell with a second nuclease agent that makes a double-strand break or a single-strand break at a second nuclease target site near the 5' end of the repeat expansion sequence to produce a second modified cell. Alternatively, the method can be performed a first time with a first nuclease agent that makes a double-strand break or a single-strand break at a first nuclease target site near the 5' end of the repeat expansion sequence to produce a first modified cell, and the method is performed a second time on the first modified cell with a second nuclease agent that makes a double-strand break or a single-strand break at a second nuclease target site near the 5' end of the repeat expansion sequence to produce a second modified cell. In some such methods, the first and second nuclease target sites can be the same. In other methods, they can be different. Alternatively, the method can be performed a first time with a first nuclease agent that makes a double-strand break or a single-strand break at a first nuclease target site near the 3' end of the repeat expansion sequence to produce a first modified cell, and the method is performed a second time on the first modified cell with a second nuclease agent that makes a double-strand break or a single-strand break at a second nuclease target site near the 3' end of the repeat expansion sequence to produce a second modified cell. In some such methods, the first and second nuclease target sites can be the same. In other methods, they can be different. In some such methods both the first nuclease agent and the second nuclease agent make double-strand breaks. In other methods, both the first nuclease agent and the second nuclease agent make single-strand breaks. In other methods, the first nuclease agent makes a double-strand break and the second nuclease agent makes a single-strand break, or vice versa. Any combination can be used.

In one exemplary method, the nuclease target site is outside of the repeat expansion sequence, the nuclease target site is within about 50, about 40, about 30, about 20, or about 10 nucleotides of the 5' end or the 3' end of the repeat expansion sequence, and the nuclease agent is Cas9 protein and a guide RNA. In another exemplary method, the nuclease target site is outside of the repeat expansion sequence, the nuclease target site is within about 50, about 40, about 30, about 20, or about 10 nucleotides of the 5' end or the 3' end of the repeat expansion sequence, the nuclease agent is Cas9 protein and a guide RNA, the Cas9 is a nickase that makes a single-strand break near the 5' end or the 3' end of the repeat expansion sequence, the nuclease target site is retained after repair of the single strand-break by the cell, and repair of the single strand-break does not result in insertions or deletions outside of the repeat expansion sequence.

Some methods start with a cell already comprising a repeat expansion sequence to be expanded at the target genomic locus. The preexisting repeat expansion sequence can be a repeat expansion sequence that occurred naturally in the cell or a repeat expansion sequence that was previously inserted using an exogenous repair template. Similarly, the preexisting repeat expansion sequence can be a repeat expansion sequence that was previously expanded in a first round or rounds of the nuclease-mediated methods disclosed herein. Other methods can comprise an initial step of generating the cell comprising the repeat expansion sequence to be expanded at the target genomic locus. See US 2018/0094267 and WO 2018/064600, each of which is herein incorporated by reference in its entirety for all purposes. The initial repeat expansion sequence to be expanded can be inserted into the target locus, for example, using exogenous repair templates (e.g., exogenous donor sequences such as targeting vectors) comprising the repeat expansion sequence. As one example, a targeting vector can comprise a 5' homology arm targeting a 5' target sequence at the endogenous target locus and a 3' homology arm targeting a 3' target sequence at the endogenous target locus. Exogenous repair templates can also comprise nucleic acid inserts including segments of DNA (e.g., the repeat expansion sequence) to be integrated in the target locus. Integration of a nucleic acid insert in the target locus can result in addition of a nucleic acid sequence of interest in the target locus, deletion of a nucleic acid sequence of interest in the target locus, or replacement of a nucleic acid sequence of interest in the target locus (i.e., deletion and insertion). The homology arms can flank an insert nucleic acid comprising the repeat expansion sequence to generate the initial target locus comprising the repeat expansion sequence (e.g., for use in methods of nuclease-mediated expansion of a preexisting repeat expansion sequence).

The exogenous repair templates can be for non-homologous-end-joining-mediated insertion or homologous recombination. Exogenous repair templates can comprise deoxyribonucleic acid (DNA) or ribonucleic acid (RNA), they can be single-stranded or double-stranded, and they can be in linear or circular form. For example, a repair template can be a single-stranded oligodeoxynucleotide (ssODN).

Exogenous repair templates can also comprise a heterologous sequence that is not present at an untargeted endogenous target locus. For example, an exogenous repair template can comprise a selection cassette, such as a selection cassette flanked by recombinase recognition sites.

Some exogenous repair templates comprise homology arms. If the exogenous repair template acid also comprises a nucleic acid insert, the homology arms can flank the nucleic acid insert. For ease of reference, the homology arms are referred to herein as 5' and 3' (i.e., upstream and downstream) homology arms. This terminology relates to the relative position of the homology arms to the nucleic acid insert within the exogenous repair template. The 5' and 3' homology arms correspond to regions within the target locus, which are referred to herein as "5' target sequence" and "3' target sequence," respectively.

A homology arm and a target sequence "correspond" or are "corresponding" to one another when the two regions share a sufficient level of sequence identity to one another to act as substrates for a homologous recombination reaction. The term "homology" includes DNA sequences that are either identical or share sequence identity to a corresponding sequence. The sequence identity between a given target sequence and the corresponding homology arm found in the exogenous repair template can be any degree of sequence identity that allows for homologous recombination to occur. For example, the amount of sequence identity shared by the homology arm of the exogenous repair template (or a fragment thereof) and the target sequence (or a fragment thereof) can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination. Moreover, a corresponding region of homology between the homology arm and the corresponding target sequence can be of any length that is sufficient to promote homologous recombination. In some targeting vectors, the intended mutation in the target locus is included in an insert nucleic acid flanked by the homology arms.

In cells other than one-cell stage embryos, the exogenous repair template can be a "large targeting vector" or "LTVEC," which includes targeting vectors that comprise homology arms that correspond to and are derived from nucleic acid sequences larger than those typically used by other approaches intended to perform homologous recombination in cells. LTVECs also include targeting vectors comprising nucleic acid inserts having nucleic acid sequences larger than those typically used by other approaches intended to perform homologous recombination in cells. For example, LTVECs make possible the modification of large loci that cannot be accommodated by traditional plasmid-based targeting vectors because of their size limitations. For example, the targeted locus can be (i.e., the 5' and 3' homology arms can correspond to) a locus of the cell that is not targetable using a conventional method or that can be targeted only incorrectly or only with significantly low efficiency in the absence of a nick or double-strand break induced by a nuclease agent (e.g., a Cas protein). LTVECs can be of any length and are typically at least 10 kb in length. The sum total of the 5' homology arm and the 3' homology arm in an LTVEC is typically at least 10 kb.

The screening step can comprise, for example, a quantitative assay for assessing modification of allele (MOA) of a parental chromosome. For example, the quantitative assay can be carried out via a quantitative PCR, such as a real-time PCR (qPCR). The real-time PCR can utilize a first primer set that recognizes the target locus and a second primer set that recognizes a non-targeted reference locus. The primer set can comprise a fluorescent probe that recognizes the amplified sequence.

Other examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE™ probe technology (see, e.g., US 2005/0144655, incorporated herein by reference in its entirety for all purposes).

For example, a modified cell (e.g., a modified pluripotent cell or embryonic stem (ES) cell such as a mouse ES cell or a rat ES cell) can be generated, for example, through recombination by (a) introducing into the cell one or more exogenous donor nucleic acids (e.g., targeting vectors) comprising an insert nucleic acid flanked, for example, by 5' and 3' homology arms corresponding to 5' and 3' target sites, wherein the insert nucleic acid comprises the repeat expansion sequence to generate a target locus comprising the repeat expansion sequence; and (b) identifying at least one cell comprising in its genome the insert nucleic acid integrated at the target locus (i.e., identifying at least one cell comprising the repeat expansion sequence at the target locus).

Alternatively, the modified cell can be generated by (a) introducing into the cell: (i) a nuclease agent, wherein the nuclease agent induces a nick or double-strand break at a target site within the target locus; and (ii) one or more exogenous donor nucleic acids (e.g., targeting vectors) optionally comprising an insert nucleic acid flanked by, for example, 5' and 3' homology arms corresponding to 5' and 3' target sites located in sufficient proximity to the nuclease target site, wherein the insert nucleic acid comprises the repeat expansion sequence to generate a target locus comprising the repeat expansion sequence; and (c) identifying at least one cell comprising in its genome the insert nucleic acid integrated at the endogenous target locus (i.e., identifying at least one cell comprising the repeat expansion sequence at the target locus). Alternatively, the modified cell can be generated by (a) introducing into the cell: (i) a nuclease agent or a nucleic acid encoding the nuclease agent, wherein the nuclease agent induces a nick or double-strand break at a target site within the target locus; and (ii) one or more exogenous donor nucleic acids (e.g., targeting vectors) optionally comprising an insert nucleic acid flanked by, for example, 5' and 3' homology arms corresponding to 5' and 3' target sites located in sufficient proximity to the nuclease target site, wherein the insert nucleic acid comprises the repeat expansion sequence to generate a target locus comprising the repeat expansion sequence; and (c) identifying at least one cell comprising in its genome the insert nucleic acid integrated at the endogenous target locus (i.e., identifying at least one cell comprising the repeat expansion sequence at the target locus). Any nuclease agent that induces a nick or double-strand break into a desired recognition site can be used. Examples of suitable nucleases include a Transcription Activator-Like Effector Nuclease (TALEN), a zinc-finger nuclease (ZFN), a meganuclease, and Clustered Regularly Interspersed Short Palindromic Repeats (CRISPR)/CRISPR-associated (Cas) systems (e.g., CRISPR/Cas9 systems) or components of such systems (e.g., CRISPR/Cas9). See, e.g., US 2013/0309670 and US 2015/0159175, each of which is herein incorporated by reference in its entirety for all purposes.

A. Nuclease Agents and Target Sites for Nuclease Agents

Provided herein are nuclease agents for use in a method for producing a modified cell with an increased number of copies of a repeat sequence at a target genomic locus that comprises a repeat expansion sequence comprising a plurality of copies of the repeat sequence at the target genomic locus. Also provided herein are nucleic acids encoding nuclease agents for use in a method for producing a modified cell with an increased number of copies of a repeat sequence at a target genomic locus that comprises a repeat expansion sequence comprising a plurality of copies of the repeat sequence at the target genomic locus. Such nuclease agents can be designed to make a double-strand break or a single-strand break (e.g. a nickase) at a nuclease target site near the 5' end or the 3' end of the repeat expansion sequence.

The term "target site for a nuclease agent" includes a DNA sequence at which a nick or double-strand break is induced by a nuclease agent. The target site for a nuclease agent can be endogenous (or native) to the cell or the target site can be exogenous to the cell. A target site that is exogenous to the cell is not naturally occurring in the genome of the cell. The target site can also exogenous to the polynucleotides of interest that one desires to be positioned at the target locus. In some cases, the target site is present only once in the genome of the host cell.

The length of the target site can vary, and includes, for example, target sites that are about 30-36 bp for a zinc finger nuclease (ZFN) pair (i.e., about 15-18 bp for each ZFN), about 36 bp for a Transcription Activator-Like Effector Nuclease (TALEN), or about 20 bp for a CRISPR/Cas9 guide RNA.

Any nuclease agent that induces a nick or double-strand break into a desired target site can be used in the methods and compositions disclosed herein. A naturally occurring or native nuclease agent can be employed so long as the nuclease agent induces a nick or double-strand break in a desired target site. Alternatively, a modified or engineered nuclease agent can be employed. An "engineered nuclease agent" includes a nuclease that is engineered (modified or derived) from its native form to specifically target and induce a nick or double-strand break in the desired target site. Thus, an engineered nuclease agent can be derived from a native, naturally occurring nuclease agent or it can be artificially created or synthesized. The engineered nuclease can induce a nick or double-strand break in a target site, for example, wherein the target site is not a sequence that would have been targeted by a native (non-engineered or non-modified) nuclease agent. The modification of the nuclease agent can be as little as one amino acid in a protein cleavage agent or one nucleotide in a nucleic acid cleavage agent. Producing a nick or double-strand break in a target site or other DNA can be referred to herein as "cutting" or "cleaving" the target site or other DNA.

Active variants and fragments of the exemplified target sites are also provided. Such active variants can comprise at least 65%, 70%, 75%, 80%, 85%, 90%, 91%, 92%, 93%, 94%, 95%, 96%, 97%, 98%, 99% or more sequence identity to the given target site, wherein the active variants retain biological activity and hence are capable of being targeted and cleaved by a nuclease agent in a sequence-specific manner. Assays to measure the double-strand break of a target site by a nuclease agent are known (e.g., TaqMan® qPCR assay, Frendewey (2010) *Methods in Enzymology* 476:295-307, which is incorporated by reference herein in its entirety for all purposes).

The target site of the nuclease agent can be positioned anywhere in or near the target locus. The target site can be located within a coding region of a gene, or within regulatory regions that influence the expression of the gene. A target site of the nuclease agent can be located in an intron, an exon, a promoter, an enhancer, a regulatory region, or any non-protein coding region.

One type of nuclease agent is a Transcription Activator-Like Effector Nuclease (TALEN). TAL effector nucleases are a class of sequence-specific nucleases that can be used to make double-strand breaks at specific target sequences in the genome of a prokaryotic or eukaryotic organism. TAL effector nucleases are created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA targeting specificity. Thus, the DNA-binding domains of the TAL effector nucleases can be engineered to target specific DNA target sites and thus, used to make double-strand breaks at desired target sequences. See WO 2010/079430; Morbitzer et al. (2010) *PNAS* 10.1073/pnas.1013133107; Scholze & Boch (2010) *Virulence* 1:428-432; Christian et al. (2010) *Genetics* 186:757-761; Li et al. (2010) *Nuc. Acids Res*. (2010) doi: 10.1093/nar/gkq704; and Miller et al. (2011) *Nature Biotechnology* 29:143-148, each of which is herein incorporated by reference in its entirety for all purposes.

Examples of suitable TAL nucleases, and methods for preparing suitable TAL nucleases, are disclosed, e.g., in US 2011/0239315 A1, US 2011/0269234 A1, US 2011/0145940 A1, US 2003/0232410 A1, US 2005/0208489 A1, US 2005/0026157 A1, US 2005/0064474 A1, US 2006/0188987 A1, and US 2006/0063231 A1, each of which is herein incorporated by reference in its entirety for all purposes.

In some TALENs, each monomer of the TALEN comprises 33-35 TAL repeats that recognize a single base pair via two hypervariable residues. In some TALENs, the nuclease agent is a chimeric protein comprising a TAL-repeat-based DNA binding domain operably linked to an independent nuclease such as a FokI endonuclease. For example, the nuclease agent can comprise a first TAL-repeat-based DNA binding domain and a second TAL-repeat-based DNA binding domain, wherein each of the first and the second TAL-repeat-based DNA binding domains is operably linked to a FokI nuclease, wherein the first and the second TAL-repeat-based DNA binding domain recognize two contiguous target DNA sequences in each strand of the target DNA sequence separated by a spacer sequence of varying length (12-20 bp), and wherein the FokI nuclease subunits dimerize to create an active nuclease that makes a double strand break at a target sequence.

The nuclease agent employed in the various methods and compositions disclosed herein can comprise a zinc-finger nuclease (ZFN). In some ZFNs, each monomer of the ZFN comprises 3 or more zinc finger-based DNA binding domains, wherein each zinc finger-based DNA binding domain binds to a 3 bp subsite. In other ZFNs, the ZFN is a chimeric protein comprising a zinc finger-based DNA binding domain operably linked to an independent nuclease such as a FokI endonuclease. For example, the nuclease agent can comprise a first ZFN and a second ZFN, wherein each of the first ZFN and the second ZFN is operably linked to a FokI nuclease subunit, wherein the first and the second ZFN recognize two contiguous target DNA sequences in each strand of the target DNA sequence separated by about 5-7 bp spacer, and wherein the FokI nuclease subunits dimerize to create an active nuclease that makes a double strand break. See, e.g., US20060246567; US20080182332; US20020081614; US20030021776; WO/2002/057308A2; US20130123484; US20100291048; WO/2011/017293A2; and Gaj et al. (2013) *Trends Biotechnol*. 31(7):397-405, each of which is herein incorporated by reference in its entirety for all purposes.

Another type of nuclease agent is a meganuclease. Meganucleases have been classified into four families based on conserved sequence motifs, the families are the LAGLIDADG, GIY-YIG, H-N-H, and His-Cys box families. These motifs participate in the coordination of metal ions and hydrolysis of phosphodiester bonds. Meganucleases are notable for their long target sites, and for tolerating some sequence polymorphisms in their DNA substrates. Meganuclease domains, structure and function are known, see for example, Guhan and Muniyappa (2003) *Crit. Rev. Biochem. Mol. Biol.* 38(3):199-248; Lucas et al. (2001) *Nucleic Acids Res.* 29(4):960-969; Jurica and Stoddard (1999) *Cell. Mol. Life Sci.* 55:1304-1326; Stoddard (2006) *Q. Rev. Biophys.* 38:49-95; and Moure et al. (2002) *Nat. Struct. Biol.* 9(10): 764-770. In some examples, a naturally occurring variant and/or engineered derivative meganuclease is used. Methods for modifying the kinetics, cofactor interactions, expression, optimal conditions, and/or target site specificity, and screening for activity are known. See, e.g., Epinat et al. (2003) *Nucleic Acids Res.* 31:2952-62; Chevalier et al. (2002) *Mol. Cell* 10:895-905; Gimble et al. (2003) *Mol. Biol.* 334:993-1008; Seligman et al. (2002) *Nucleic Acids Res.* 30:3870-9; Sussman et al. (2004) *J. Mol. Biol.* 342:31-41; Rosen et al. (2006) *Nucleic Acids Res.* 34:4791-800; Chames et al. (2005) *Nucleic Acids Res* 33:e178; Smith et al. (2006) *Nucleic Acids Res.* 34:e149; Gruen et al. (2002) *Nucleic Acids Res.* 30:e29; Chen and Zhao (2005) *Nucleic Acids Res.* 33:e154; WO2005105989; WO2003078619; WO2006097854; WO2006097853; WO2006097784; and WO2004031346, each of which is herein incorporated by reference in its entirety for all purposes.

Any meganuclease can be used, including, for example, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, PI-PspI, F-SceI, F-SceII, F-SuvI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp6803I, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, I-ZbiIP, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, PI-TliII, or any active variants or fragments thereof.

Meganucleases can target, for example, double-stranded DNA sequences of 12 to 40 base pairs. In some cases, the meganuclease targets one perfectly matched target sequence in the genome.

Some meganucleases are homing nucleases. One type of homing nuclease is a LAGLIDADG family of homing nucleases including, for example, I-SceI, I-CreI, and I-DmoI.

Nuclease agents can further comprise restriction endonucleases, which include Type I, Type II, Type III, and Type IV endonucleases. Type I and Type III restriction endonucleases target specific target sites, but typically cleave at a variable position from the nuclease binding site, which can be hundreds of base pairs away from the cleavage site (target site). In Type II systems the restriction activity is independent of any methylase activity, and cleavage typically occurs at specific sites within or near to the binding site. Most Type II enzymes cut palindromic sequences, however Type IIa enzymes target non-palindromic target sites and cleave outside of the target site, Type IIb enzymes cut sequences twice with both sites outside of the target site, and Type IIs enzymes target an asymmetric target site and cleave on one side and at a defined distance of about 1-20 nucleotides from the target site. Type IV restriction enzymes target methylated DNA. Restriction enzymes are further described and classified, for example, in the REBASE database (webpage at rebase.neb.com; Roberts et al. (2003) *Nucleic Acids Res.* 31(1):418-420); Roberts et al. (2003) *Nucleic Acids Res.* 31(7): 1805-1812; and Belfort et al. (2002) in *Mobile DNA II*, pp. 761-783, Eds. Craigie et al. (ASM Press, Washington, D.C.), each of which is herein incorporated by reference in its entirety.

Active variants and fragments of nuclease agents (i.e., an engineered nuclease agent) are also provided. Such active variants can comprise at least 65%, 70%, 75%, 80%, 85%, 90%, 91%, 92%, 93%, 94%, 95%, 96%, 97%, 98%, 99% or more sequence identity to the native nuclease agent, wherein the active variants retain the ability to cut at a desired target site and hence retain nick or double-strand-break-inducing activity. For example, any of the nuclease agents described herein can be modified from a native endonuclease sequence and designed to target and induce a nick or double-strand break at a target site that was not targeted by the native nuclease agent. Thus, some engineered nucleases have a specificity to induce a nick or double-strand break at a target site that is different from the corresponding native nuclease agent target site. Assays for nick or double-strand-break-inducing activity are known and generally measure the overall activity and specificity of the endonuclease on DNA substrates containing the target site.

The nuclease agent may be introduced into the cell by any means known in the art. The polypeptide encoding the nuclease agent may be directly introduced into the cell. Alternatively, a polynucleotide encoding the nuclease agent can be introduced into the cell. When a polynucleotide encoding the nuclease agent is introduced into the cell, the nuclease agent can be transiently, conditionally, or constitutively expressed within the cell. Thus, the polynucleotide encoding the nuclease agent can be contained in an expression cassette and be operably linked to a conditional promoter, an inducible promoter, a constitutive promoter, or a tissue-specific promoter. Such promoters are described in further detail elsewhere herein. Alternatively, the nuclease agent can be introduced into the cell as an mRNA encoding a nuclease agent.

A polynucleotide encoding a nuclease agent can be stably integrated in the genome of the cell and operably linked to a promoter active in the cell. Alternatively, a polynucleotide encoding a nuclease agent can be in a targeting vector (e.g., a targeting vector comprising an insert polynucleotide, or in a vector or a plasmid that is separate from a targeting vector comprising the insert polynucleotide).

When the nuclease agent is provided to the cell through the introduction of a polynucleotide encoding the nuclease agent, such a polynucleotide encoding a nuclease agent can be modified to substitute codons having a higher frequency of usage in the cell of interest, as compared to the naturally occurring polynucleotide sequence encoding the nuclease agent. For example, the polynucleotide encoding the nuclease agent can be modified to substitute codons having a higher frequency of usage in a given prokaryotic or eukaryotic cell of interest, including a bacterial cell, a yeast cell, a human cell, a non-human cell, a mammalian cell, a rodent cell, a mouse cell, a rat cell or any other host cell of interest, as compared to the naturally occurring polynucleotide sequence.

B. CRISPR/Cas Systems

The methods and compositions disclosed herein can utilize Clustered Regularly Interspersed Short Palindromic Repeats (CRISPR)/CRISPR-associated (Cas) systems or components of such systems to modify a genome within a cell. CRISPR/Cas systems include transcripts and other elements involved in the expression of, or directing the activity of, Cas genes. A CRISPR/Cas system can be, for example, a type I, a type II, a type III system, or a type V system (e.g., subtype V-A or subtype V-B). The methods and compositions disclosed herein can employ CRISPR/Cas systems by utilizing CRISPR complexes (comprising a guide RNA (gRNA) complexed with a Cas protein) for site-directed binding or cleavage of nucleic acids.

CRISPR/Cas systems used in the compositions and methods disclosed herein can be non-naturally occurring. A "non-naturally occurring" system includes anything indicating the involvement of the hand of man, such as one or more components of the system being altered or mutated from their naturally occurring state, being at least substantially free from at least one other component with which they are naturally associated in nature, or being associated with at least one other component with which they are not naturally associated. For example, some CRISPR/Cas systems employ non-naturally occurring CRISPR complexes comprising a gRNA and a Cas protein that do not naturally occur together, employ a Cas protein that does not occur naturally, or employ a gRNA that does not occur naturally.

Cas Proteins.

Cas proteins generally comprise at least one RNA recognition or binding domain that can interact with guide RNAs. Cas proteins can also comprise nuclease domains (e.g., DNase domains or RNase domains), DNA-binding domains, helicase domains, protein-protein interaction domains, dimerization domains, and other domains. Some such domains (e.g., DNase domains) can be from a native Cas protein. Other such domains can be added to make a modified Cas protein. A nuclease domain possesses catalytic activity for nucleic acid cleavage, which includes the breakage of the covalent bonds of a nucleic acid molecule. Cleavage can produce blunt ends or staggered ends, and it can be single-stranded or double-stranded. For example, a wild type Cas9 protein will typically create a blunt cleavage product. Alternatively, a wild type Cpf1 protein (e.g., FnCpf1) can result in a cleavage product with a 5-nucleotide 5' overhang, with the cleavage occurring after the 18th base pair from the PAM sequence on the non-targeted strand and after the 23rd base on the targeted strand. A Cas protein can have full cleavage activity to create a double-strand break at a target genomic locus (e.g., a double-strand break with blunt ends), or it can be a nickase that creates a single-strand break at a target genomic locus.

Examples of Cas proteins include Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof.

An exemplary Cas protein is a Cas9 protein or a protein derived from a Cas9 protein. Cas9 proteins are from a type II CRISPR/Cas system and typically share four key motifs with a conserved architecture. Motifs 1, 2, and 4 are RuvC-like motifs, and motif 3 is an HNH motif. Exemplary Cas9 proteins are from *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus, Acaryochloris marina, Neisseria meningitidis,* or *Campylobacter jejuni*. Additional examples of the Cas9 family members are described in WO 2014/131833, herein incorporated by reference in its entirety for all purposes. Cas9 from *S. pyogenes* (SpCas9) (assigned SwissProt accession number Q99ZW2) is an exemplary Cas9 protein. Cas9 from *S. aureus* (SaCas9) (assigned UniProt accession number J7RUA5) is another exemplary Cas9 protein. Cas9 from *Campylobacter jejuni* (CjCas9) (assigned UniProt accession number Q0P897) is another exemplary Cas9 protein. See, e.g., Kim et al. (2017) *Nat. Commun.* 8:14500, herein incorporated by reference in its entirety for all purposes. SaCas9 is smaller than SpCas9, and CjCas9 is smaller than both SaCas9 and SpCas9. Cas9 from *Neisseria meningitidis* (Nme2Cas9) is another exemplary Cas9 protein. See, e.g., Edraki et al. (2019) *Mol. Cell* 73(4):714-726, herein incorporated by reference in its entirety for all purposes. Cas9 proteins from *Streptococcus thermophilus* (e.g., *Streptococcus thermophilus* LMD-9 Cas9 encoded by the CRISPR1 locus (St1Cas9) or *Streptococcus thermophilus* Cas9 from the CRISPR3 locus (St3Cas9)) are other exemplary Cas9 proteins. Cas9 from *Francisella novicida* (FnCas9) or the RHA *Francisella novicida* Cas9 variant that recognizes an alternative PAM (E1369R/E1449H/R1556A substitutions) are other exemplary Cas9 proteins. These and other exemplary Cas9 proteins are reviewed, e.g., in Cebrian-Serrano and Davies (2017) *Mamm. Genome* 28(7):247-261, herein incorporated by reference in its entirety for all purposes.

Another example of a Cas protein is a Cpf1 (CRISPR from *Prevotella* and *Francisella* 1) protein. Cpf1 is a large protein (about 1300 amino acids) that contains a RuvC-like nuclease domain homologous to the corresponding domain of Cas9 along with a counterpart to the characteristic arginine-rich cluster of Cas9. However, Cpf1 lacks the HNH nuclease domain that is present in Cas9 proteins, and the RuvC-like domain is contiguous in the Cpf1 sequence, in contrast to Cas9 where it contains long inserts including the HNH domain. See, e.g., Zetsche et al. (2015) *Cell* 163(3): 759-771, herein incorporated by reference in its entirety for all purposes. Exemplary Cpf1 proteins are from *Francisella tularensis* 1, *Francisella tularensis* subsp. *novicida, Prevotella albensis, Lachnospiraceae bacterium* MC2017 1, *Butyrivibrio proteoclasticus, Peregrinibacteria bacterium* GW2011_GWA2_33_10, *Parcubacteria bacterium* GW2011_GWC2_44_17, *Smithella* sp. SCADC, *Acidaminococcus* sp. BV3L6, *Lachnospiraceae bacterium* MA2020, *Candidatus Methanoplasma termitum, Eubacterium eligens, Moraxella bovoculi* 237, *Leptospira inadai, Lachnospiraceae bacterium* ND2006, *Porphyromonas crevioricanis* 3, *Prevotella disiens,* and *Porphyromonas macacae*. Cpf1 from *Francisella novicida* U112 (FnCpf1; assigned UniProt accession number A0Q7Q2) is an exemplary Cpf1 protein.

Cas proteins can be wild type proteins (i.e., those that occur in nature), modified Cas proteins (i.e., Cas protein variants), or fragments of wild type or modified Cas proteins. Cas proteins can also be active variants or fragments with respect to catalytic activity of wild type or modified Cas proteins. Active variants or fragments with respect to catalytic activity can comprise at least 80%, 85%, 90%, 91%, 92%, 93%, 94%, 95%, 96%, 97%, 98%, 99% or more sequence identity to the wild type or modified Cas protein or a portion thereof, wherein the active variants retain the ability to cut at a desired cleavage site and hence retain nick-inducing or double-strand-break-inducing activity. Assays for nick-inducing or double-strand-break-inducing activity are known and generally measure the overall activity and specificity of the Cas protein on DNA substrates containing the cleavage site.

One example of a modified Cas protein is the modified SpCas9-HF1 protein, which is a high-fidelity variant of *Streptococcus pyogenes* Cas9 harboring alterations (N497A/ R661A/Q695A/Q926A) designed to reduce non-specific DNA contacts. See, e.g., Kleinstiver et al. (2016) *Nature* 529(7587):490-495, herein incorporated by reference in its entirety for all purposes. Another example of a modified Cas protein is the modified eSpCas9 variant (K848A/K1003A/ R1060A) designed to reduce off-target effects. See, e.g., Slaymaker et al. (2016) *Science* 351(6268):84-88, herein incorporated by reference in its entirety for all purposes. Other SpCas9 variants include K855A and K810A/K1003A/R1060A. These and other modified Cas proteins are reviewed, e.g., in Cebrian-Serrano and Davies (2017) *Mamm. Genome* 28(7):247-261, herein incorporated by reference in its entirety for all purposes. Another example of a modified Cas9 protein is xCas9, which is a SpCas9 variant that can recognize an expanded range of PAM sequences. See, e.g., Hu et al. (2018) *Nature* 556:57-63, herein incorporated by reference in its entirety for all purposes.

Cas proteins can be modified to increase or decrease one or more of nucleic acid binding affinity, nucleic acid binding specificity, and enzymatic activity. Cas proteins can also be modified to change any other activity or property of the protein, such as stability. For example, one or more nuclease domains of the Cas protein can be modified, deleted, or inactivated, or a Cas protein can be truncated to remove domains that are not essential for the function of the protein or to optimize (e.g., enhance or reduce) the activity of or a property of the Cas protein.

Cas proteins can comprise at least one nuclease domain, such as a DNase domain. For example, a wild type Cpf1 protein generally comprises a RuvC-like domain that cleaves both strands of target DNA, perhaps in a dimeric configuration. Cas proteins can also comprise at least two nuclease domains, such as DNase domains. For example, a wild type Cas9 protein generally comprises a RuvC-like nuclease domain and an HNH-like nuclease domain. The RuvC and HNH domains can each cut a different strand of double-stranded DNA to make a double-stranded break in the DNA. See, e.g., Jinek et al. (2012) *Science* 337:816-821, herein incorporated by reference in its entirety for all purposes.

One or more or all of the nuclease domains can be deleted or mutated so that they are no longer functional or have reduced nuclease activity. For example, if one of the nuclease domains is deleted or mutated in a Cas9 protein, the resulting Cas9 protein can be referred to as a nickase and can generate a single-strand break within a double-stranded target DNA but not a double-strand break (i.e., it can cleave the complementary strand or the non-complementary strand, but not both). If both of the nuclease domains are deleted or mutated, the resulting Cas protein (e.g., Cas9) will have a reduced ability to cleave both strands of a double-stranded DNA (e.g., a nuclease-null or nuclease-inactive Cas protein, or a catalytically dead Cas protein (dCas)). An example of a mutation that converts Cas9 into a nickase is a D10A (aspartate to alanine at position 10 of Cas9) mutation in the RuvC domain of Cas9 from *S. pyogenes*. Likewise, H939A (histidine to alanine at amino acid position 839), H840A (histidine to alanine at amino acid position 840), or N863A (asparagine to alanine at amino acid position N863) in the HNH domain of Cas9 from *S. pyogenes* can convert the Cas9 into a nickase. Other examples of mutations that convert Cas9 into a nickase include the corresponding mutations to Cas9 from *S. thermophilus*. See, e.g., Sapranauskas et al. (2011) *Nucleic Acids Research* 39:9275-9282 and WO 2013/141680, each of which is herein incorporated by reference in its entirety for all purposes. Such mutations can be generated using methods such as site-directed mutagenesis, PCR-mediated mutagenesis, or total gene synthesis. Examples of other mutations creating nickases can be found, for example, in WO 2013/176772 and WO 2013/142578, each of which is herein incorporated by reference in its entirety for all purposes. If all of the nuclease domains are deleted or mutated in a Cas protein (e.g., both of the nuclease domains are deleted or mutated in a Cas9 protein), the resulting Cas protein (e.g., Cas9) will have a reduced ability to cleave both strands of a double-stranded DNA (e.g., a nuclease-null or nuclease-inactive Cas protein). One specific example is a D10A/H840A *S. pyogenes* Cas9 double mutant or a corresponding double mutant in a Cas9 from another species when optimally aligned with *S. pyogenes* Cas9. Another specific example is a D10A/N863A *S. pyogenes* Cas9 double mutant or a corresponding double mutant in a Cas9 from another species when optimally aligned with *S. pyogenes* Cas9.

Examples of inactivating mutations in the catalytic domains of xCas9 are the same as those described above for SpCas9. Examples of inactivating mutations in the catalytic domains of *Staphylococcus aureus* Cas9 proteins are also known. For example, the *Staphylococcus aureus* Cas9 enzyme (SaCas9) may comprise a substitution at position N580 (e.g., N580A substitution) and a substitution at position D10 (e.g., D10A substitution) to generate a nuclease-inactive Cas protein. See, e.g., WO 2016/106236, herein incorporated by reference in its entirety for all purposes. Examples of inactivating mutations in the catalytic domains of Nme2Cas9 are also known (e.g., combination of D16A and H588A). Examples of inactivating mutations in the catalytic domains of St1Cas9 are also known (e.g., combination of D9A, D598A, H599A, and N622A). Examples of inactivating mutations in the catalytic domains of St3Cas9 are also known (e.g., combination of D10A and N870A). Examples of inactivating mutations in the catalytic domains of CjCas9 are also known (e.g., combination of D8A and H559A). Examples of inactivating mutations in the catalytic domains of FnCas9 and RHA FnCas9 are also known (e.g., N995A).

Examples of inactivating mutations in the catalytic domains of Cpf1 proteins are also known. With reference to Cpf1 proteins from *Francisella novicida* U112 (FnCpf1), *Acidaminococcus* sp. BV3L6 (AsCpf1), *Lachnospiraceae bacterium* ND2006 (LbCpf1), and *Moraxella bovoculi* 237 (MbCpf1 Cpf1), such mutations can include mutations at positions 908, 993, or 1263 of AsCpf1 or corresponding positions in Cpf1 orthologs, or positions 832, 925, 947, or 1180 of LbCpf1 or corresponding positions in Cpf1 orthologs. Such mutations can include, for example one or more of mutations D908A, E993A, and D1263A of AsCpf1 or corresponding mutations in Cpf1 orthologs, or D832A, E925A, D947A, and D1180A of LbCpf1 or corresponding mutations in Cpf1 orthologs. See, e.g., US 2016/0208243, herein incorporated by reference in its entirety for all purposes.

Cas proteins can also be operably linked to heterologous polypeptides as fusion proteins. For example, a Cas protein can be fused to a cleavage domain. See WO 2014/089290, herein incorporated by reference in its entirety for all purposes. Cas proteins can also be fused to a heterologous polypeptide providing increased or decreased stability. The fused domain or heterologous polypeptide can be located at the N-terminus, the C-terminus, or internally within the Cas protein.

As one example, a Cas protein can be fused to one or more heterologous polypeptides that provide for subcellular localization. Such heterologous polypeptides can include, for example, one or more nuclear localization signals (NLS) such as the monopartite SV40 NLS and/or a bipartite alpha-importin NLS for targeting to the nucleus, a mitochondrial localization signal for targeting to the mitochondria, an ER retention signal, and the like. See, e.g., Lange et al. (2007) *J. Biol. Chem.* 282:5101-5105, herein incorporated by reference in its entirety for all purposes. Such subcellular localization signals can be located at the N-terminus, the C-terminus, or anywhere within the Cas protein. An NLS can comprise a stretch of basic amino acids, and can be a monopartite sequence or a bipartite sequence. Optionally, a Cas protein can comprise two or more NLSs, including an NLS (e.g., an alpha-importin NLS or a monopartite NLS) at the N-terminus and an NLS (e.g., an SV40 NLS or a bipartite NLS) at the C-terminus. A Cas protein can also comprise two or more NLSs at the N-terminus and/or two or more NLSs at the C-terminus.

Cas proteins can also be operably linked to a cell-penetrating domain or protein transduction domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. See, e.g., WO 2014/089290 and WO 2013/176772, each of which is herein incorporated by reference in its entirety for all purposes. The cell-penetrating domain can be located at the N-terminus, the C-terminus, or anywhere within the Cas protein.

Cas proteins can also be operably linked to a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreenl), yellow fluorescent proteins (e.g., YFP, eYFP, Citrine, Venus, YPet, PhiYFP, ZsYellowl), blue fluorescent proteins (e.g., eBFP, eBFP2, Azurite, mKalamal, GFPuv, Sapphire, T-sapphire), cyan fluorescent proteins (e.g., eCFP, Cerulean, CyPet, AmCyanl, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRed1, AsRed2, eqFP611, mRaspberry, mStrawberry, Jred), orange fluorescent proteins (e.g., mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly(NANP), tandem affinity purification (TAP) tag, myc, AcV5, AU1, AU5, E, ECS, E2, FLAG, hemagglutinin (HA), nus, Softag 1, Softag 3, Strep, SBP, Glu-Glu, HSV, KT3, S, S1, T7, V5, VSV-G, histidine (His), biotin carboxyl carrier protein (BCCP), and calmodulin.

Cas proteins can also be tethered to labeled nucleic acids. Such tethering (i.e., physical linking) can be achieved through covalent interactions or noncovalent interactions, and the tethering can be direct (e.g., through direct fusion or chemical conjugation, which can be achieved by modification of cysteine or lysine residues on the protein or intein modification), or can be achieved through one or more intervening linkers or adapter molecules such as streptavidin or aptamers. See, e.g., Pierce et al. (2005) *Mini Rev. Med. Chem.* 5(1):41-55; Duckworth et al. (2007) *Angew. Chem. Int. Ed. Engl.* 46(46):8819-8822; Schaeffer and Dixon (2009) *Australian J. Chem.* 62(10): 1328-1332; Goodman et al. (2009) *Chembiochem.* 10(9):1551-1557; and Khatwani et al. (2012) *Bioorg. Med. Chem.* 20(14):4532-4539, each of which is herein incorporated by reference in its entirety for all purposes. Noncovalent strategies for synthesizing protein-nucleic acid conjugates include biotin-streptavidin and nickel-histidine methods. Covalent protein-nucleic acid conjugates can be synthesized by connecting appropriately functionalized nucleic acids and proteins using a wide variety of chemistries. Some of these chemistries involve direct attachment of the oligonucleotide to an amino acid residue on the protein surface (e.g., a lysine amine or a cysteine thiol), while other more complex schemes require post-translational modification of the protein or the involvement of a catalytic or reactive protein domain. Methods for covalent attachment of proteins to nucleic acids can include, for example, chemical cross-linking of oligonucleotides to protein lysine or cysteine residues, expressed protein-ligation, chemoenzymatic methods, and the use of photoaptamers. The labeled nucleic acid can be tethered to the C-terminus, the N-terminus, or to an internal region within the Cas protein. In one example, the labeled nucleic acid is tethered to the C-terminus or the N-terminus of the Cas protein. Likewise, the Cas protein can be tethered to the 5' end, the 3' end, or to an internal region within the labeled nucleic acid. That is, the labeled nucleic acid can be tethered in any orientation and polarity. For example, the Cas protein can be tethered to the 5' end or the 3' end of the labeled nucleic acid.

Cas proteins can be provided in any form. For example, a Cas protein can be provided in the form of a protein, such as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be codon optimized for efficient translation into protein in a particular cell or organism. For example, the nucleic acid encoding the Cas protein can be modified to substitute codons having a higher frequency of usage in a bacterial cell, a yeast cell, a human cell, a non-human cell, a mammalian cell, a rodent cell, a mouse cell, a rat cell, or any other host cell of interest, as compared to the naturally occurring polynucleotide sequence. When a nucleic acid encoding the Cas protein is introduced into the cell, the Cas protein can be transiently, conditionally, or constitutively expressed in the cell.

Cas proteins provided as mRNAs can be modified for improved stability and/or immunogenicity properties. The modifications may be made to one or more nucleosides within the mRNA. Examples of chemical modifications to mRNA nucleobases include pseudouridine, 1-methyl-pseudouridine, and 5-methyl-cytidine. For example, capped and polyadenylated Cas mRNA containing N1-methyl pseudouridine can be used. Likewise, Cas mRNAs can be modified by depletion of uridine using synonymous codons.

Nucleic acids encoding Cas proteins can be stably integrated in the genome of a cell and operably linked to a promoter active in the cell. Alternatively, nucleic acids encoding Cas proteins can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. For example, the nucleic acid encoding the Cas protein can be in a vector comprising a DNA encoding a gRNA. Alternatively, it can be in a vector or plasmid that is separate from the vector comprising the DNA encoding the gRNA. Promoters that can be used in an expression construct include promoters active, for example, in one or more of a eukaryotic cell, a human cell, a non-human cell, a mammalian cell, a non-human mammalian cell, a rodent cell, a mouse cell, a rat cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters. Optionally, the promoter can be a bidirectional promoter driving expression of both a Cas protein in one direction and a guide RNA in the other direction. Such bidirectional promoters can consist of (1) a complete, conventional, unidirectional Pol III promoter that contains 3 external control elements: a distal sequence element (DSE), a proximal sequence element (PSE), and a TATA box; and (2) a second basic Pol III promoter that includes a PSE and a TATA box fused to the 5' terminus of the DSE in reverse orientation. For example, in the H1 promoter, the DSE is adjacent to the PSE and the TATA box, and the promoter can be rendered bidirectional by creating a hybrid promoter in which transcription in the reverse direction is controlled by appending a PSE and TATA box derived from the U6 promoter. See, e.g., US 2016/0074535, herein incorporated by references in its entirety for all purposes. Use of a bidirectional promoter to express genes encoding a Cas protein and a guide RNA simultaneously allow for the generation of compact expression cassettes to facilitate delivery.

Guide RNAs.

A "guide RNA" or "gRNA" is an RNA molecule that binds to a Cas protein (e.g., Cas9 protein) and targets the Cas protein to a specific location within a target DNA. Guide RNAs can comprise two segments: a "DNA-targeting segment" and a "protein-binding segment." "Segment" includes a section or region of a molecule, such as a contiguous stretch of nucleotides in an RNA. Some gRNAs, such as those for Cas9, can comprise two separate RNA molecules: an "activator-RNA" (e.g., tracrRNA) and a "targeter-RNA" (e.g., CRISPR RNA or crRNA). Other gRNAs are a single RNA molecule (single RNA polynucleotide), which can also be called a "single-molecule gRNA," a "single-guide RNA," or an "sgRNA." See, e.g., WO 2013/176772, WO 2014/065596, WO 2014/089290, WO 2014/093622, WO 2014/099750, WO 2013/142578, and WO 2014/131833, each of which is herein incorporated by reference in its entirety for all purposes. For Cas9, for example, a single-guide RNA can comprise a crRNA fused to a tracrRNA (e.g., via a linker). For Cpf1, for example, only a crRNA is needed to achieve binding to a target sequence. The terms "guide RNA" and "gRNA" include both double-molecule (i.e., modular) gRNAs and single-molecule gRNAs.

An exemplary two-molecule gRNA comprises a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA") molecule. A crRNA comprises both the DNA-targeting segment (single-stranded) of the gRNA and a stretch of nucleotides that forms one half of the dsRNA duplex of the protein-binding segment of the gRNA. An example of a crRNA tail, located downstream (3') of the DNA-targeting segment, comprises, consists essentially of, or consists of GUUUUAGAGCUAUGCU (SEQ ID NO: 19). Another example of a crRNA tail, located downstream (3') of the DNA-targeting segment, comprises, consists essentially of, or consists of GUUUUAGAGCUAUGCU-GUUUUG (SEQ ID NO: 83). Any of the DNA-targeting segments (i.e., guide sequences) disclosed herein (e.g., any of SEQ ID NOS: 84-91) can be joined to the 5' end of SEQ ID NO: 19 or SEQ ID NO: 83 to form a crRNA.

A corresponding tracrRNA (activator-RNA) comprises a stretch of nucleotides that forms the other half of the dsRNA duplex of the protein-binding segment of the gRNA. A stretch of nucleotides of a crRNA are complementary to and hybridize with a stretch of nucleotides of a tracrRNA to form the dsRNA duplex of the protein-binding domain of the gRNA. As such, each crRNA can be said to have a corresponding tracrRNA. An example of a tracrRNA sequence comprises, consists essentially of, or consists of AGCAUAGCAAGUUAAAAUAAGGCUAGU-CCGUUAUCAACUUGAAAAAGUGGCACC GAGUCG-GUGCUUU (SEQ ID NO: 20). Another example of a tracrRNA sequence comprises, consists essentially of, or consists of GUUGGAACCAUUCAAAACAG-CAUAGCAAGUUAAAAUAAGGCUAGU-CCGUUAUCA ACUUGAAAAAGUGGCACCGAGUCG-GUGCUUUUUU (SEQ ID NO: 82). Other examples of tracrRNA sequences comprise, consist essentially of, or consist of AAACAGCAUAGCAAGUUAAAAUAAGGC-UAGUCCGUUAUCAACUUGAAAAAGUGG CACCGA-GUCGGUGCUUUU (SEQ ID NO: 116), or GUUGGAAC-CAUUCAAAACAGCAUAGCAAGUUAAAAUAAGGC UAGUCCGUUAUCA ACUUGAAAAAGUGGCACCGA-GUCGGUGC (SEQ ID NO: 117).

In systems in which both a crRNA and a tracrRNA are needed, the crRNA and the corresponding tracrRNA hybridize to form a gRNA. In systems in which only a crRNA is needed, the crRNA can be the gRNA. The crRNA additionally provides the single-stranded DNA-targeting segment that hybridizes to the complementary strand of a target DNA. If used for modification within a cell, the exact sequence of a given crRNA or tracrRNA molecule can be designed to be specific to the species in which the RNA molecules will be used. See, e.g., Mali et al. (2013) Science 339:823-826; Jinek et al. (2012) Science 337:816-821; Hwang et al. (2013) Nat. Biotechnol. 31:227-229; Jiang et al. (2013) Nat. Biotechnol. 31:233-239; and Cong et al. (2013) Science 339:819-823, each of which is herein incorporated by reference in its entirety for all purposes.

The DNA-targeting segment (crRNA) of a given gRNA comprises a nucleotide sequence that is complementary to a sequence on the complementary strand of the target DNA, as described in more detail below. The DNA-targeting segment of a gRNA interacts with the target DNA in a sequence-specific manner via hybridization (i.e., base pairing). As such, the nucleotide sequence of the DNA-targeting segment may vary and determines the location within the target DNA with which the gRNA and the target DNA will interact. The DNA-targeting segment of a subject gRNA can be modified to hybridize to any desired sequence within a target DNA. Naturally occurring crRNAs differ depending on the CRISPR/Cas system and organism but often contain a targeting segment of between 21 to 72 nucleotides length, flanked by two direct repeats (DR) of a length of between 21 to 46 nucleotides (see, e.g., WO 2014/131833, herein incorporated by reference in its entirety for all purposes). In the case of S. pyogenes, the DRs are 36 nucleotides long and the targeting segment is 30 nucleotides long. The 3' located DR is complementary to and hybridizes with the corresponding tracrRNA, which in turn binds to the Cas protein.

The DNA-targeting segment can have, for example, a length of at least about 12, 15, 17, 18, 19, 20, 25, 30, 35, or 40 nucleotides. Such DNA-targeting segments can have, for example, a length from about 12 to about 100, from about 12 to about 80, from about 12 to about 50, from about 12 to about 40, from about 12 to about 30, from about 12 to about 25, or from about 12 to about 20 nucleotides. For example, the DNA targeting segment can be from about 15 to about 25 nucleotides (e.g., from about 17 to about 20 nucleotides, or about 17, 18, 19, or 20 nucleotides). See, e.g., US 2016/0024523, herein incorporated by reference in its entirety for all purposes. For Cas9 from S. pyogenes, a typical DNA-targeting segment is between 16 and 20 nucleotides in length or between 17 and 20 nucleotides in length. For Cas9 from *S. aureus*, a typical DNA-targeting segment is between 21 and 23 nucleotides in length. For Cpf1, a typical DNA-targeting segment is at least 16 nucleotides in length or at least 18 nucleotides in length.

TracrRNAs can be in any form (e.g., full-length tracrRNAs or active partial tracrRNAs) and of varying lengths. They can include primary transcripts or processed forms. For example, tracrRNAs (as part of a single-guide RNA or as a separate molecule as part of a two-molecule gRNA) may comprise, consist essentially of, or consist of all or a portion of a wild type tracrRNA sequence (e.g., about or more than about 20, 26, 32, 45, 48, 54, 63, 67, 85, or more nucleotides of a wild type tracrRNA sequence). Examples of wild type tracrRNA sequences from *S. pyogenes* include 171-nucleotide, 89-nucleotide, 75-nucleotide, and 65-nucleotide versions. See, e.g., Deltcheva et al. (2011) *Nature* 471:602-607; WO 2014/093661, each of which is herein incorporated by reference in its entirety for all purposes. Examples of tracrRNAs within single-guide RNAs (sgRNAs) include the tracrRNA segments found within +48, +54, +67, and +85 versions of sgRNAs, where "+n" indicates that up to the +n nucleotide of wild type tracrRNA is included in the sgRNA. See U.S. Pat. No. 8,697,359, herein incorporated by reference in its entirety for all purposes.

The percent complementarity between the DNA-targeting segment of the guide RNA and the complementary strand of the target DNA can be at least 60% (e.g., at least 65%, at least 70%, at least 75%, at least 80%, at least 85%, at least 90%, at least 95%, at least 97%, at least 98%, at least 99%, or 100%). The percent complementarity between the DNA-targeting segment and the complementary strand of the target DNA can be at least 60% over about 20 contiguous nucleotides. As an example, the percent complementarity between the DNA-targeting segment and the complementary strand of the target DNA can be 100% over the 14 contiguous nucleotides at the 5' end of the complementary strand of the target DNA and as low as 0% over the remainder. In such a case, the DNA-targeting segment can be considered to be 14 nucleotides in length. As another example, the percent complementarity between the DNA-targeting segment and the complementary strand of the target DNA can be 100% over the seven contiguous nucleotides at the 5' end of the complementary strand of the target DNA and as low as 0% over the remainder. In such a case, the DNA-targeting segment can be considered to be 7 nucleotides in length. In some guide RNAs, at least 17 nucleotides within the DNA-targeting segment are complementary to the complementary strand of the target DNA. For example, the DNA-targeting segment can be 20 nucleotides in length and can comprise 1, 2, or 3 mismatches with the complementary strand of the target DNA. In one example, the mismatches are not adjacent to the region of the complementary strand corresponding to the protospacer adjacent motif (PAM) sequence (i.e., the reverse complement of the PAM sequence) (e.g., the mismatches are in the 5' end of the DNA-targeting segment of the guide RNA, or the mismatches are at least 2, 3, 4, 5, 6, 7, 8, 9, 10, 11, 12, 13, 14, 15, 16, 17, 18, or 19 base pairs away from the region of the complementary strand corresponding to the PAM sequence).

The protein-binding segment of a gRNA can comprise two stretches of nucleotides that are complementary to one another. The complementary nucleotides of the protein-binding segment hybridize to form a double-stranded RNA duplex (dsRNA). The protein-binding segment of a subject gRNA interacts with a Cas protein, and the gRNA directs the bound Cas protein to a specific nucleotide sequence within target DNA via the DNA-targeting segment.

Single-guide RNAs can comprise a DNA-targeting segment and a scaffold sequence (i.e., the protein-binding or Cas-binding sequence of the guide RNA). For example, such guide RNAs can have a 5' DNA-targeting segment joined to a 3' scaffold sequence. Exemplary scaffold sequences comprise, consist essentially of, or consist of: GUUUUAGAGC-UAGAAAUAGCAAGUUAAAAUAAGGCUAGU-CCGUUAUCAACUUGA AAAAGUGGCACC GAGUCGGUGCU (version 1; SEQ ID NO: 21); GUUG-GAACCAUUCAAAACAGCAUAGCAAGUUAA AAUAAGGCUAGUCCGUUAUCA ACUUGAAAAAGUGGCACCGAGUCGGUGC (version 2; SEQ ID NO: 22); GUUUUAGAGCUA-GAAAUAGCAAGUUAAAAUAAGGCUAGU-CCGUUAUCAACUUGA AAAAGUGGCACCGAGUCG-GUGC (version 3; SEQ ID NO: 23); GUUUAAGAGCUAUGCUGGAAACAG-CAUAGCAAGUUUAAAUAAGGCUAGUCCG UUAU-CAACUUGAAAAAGUGGCACCGAGUCGGUGC (version 4; SEQ ID NO: 24); GUUUUAGAGCUAGAAAUAGCAAGUUAAA AUAAGGCUAGUCCGUUAUCAACUUGA AAAAGUGGCACCGAGUCGGUGCUUUUUUU (version 5; SEQ ID NO: 118); GUUUUAGAGCUA-GAAAUAGCAAGUUAAAAUAAGGCUAGU-CCGUUAUCAACUUGA AAAAGUGGCACCG AGUCGGUGCUUUU (version 6; SEQ ID NO: 119); or GUUUAAGAGCUAUGCUGGAAACAG-CAUAGCAAGUUUAAAUAAGGCUAGUCCGUU AUCAACUUGAAAAAGUGGCACCGAGUCGGUGC-UUUUUU (version 7; SEQ ID NO: 120). Guide RNAs targeting any of the guide RNA target sequences disclosed herein can include, for example, a DNA-targeting segment on the 5' end of the guide RNA fused to any of the exemplary guide RNA scaffold sequences on the 3' end of the guide RNA. That is, any of the DNA-targeting segments disclosed herein can be joined to the 5' end of any one of the above scaffold sequences to form a single guide RNA (chimeric guide RNA).

Guide RNAs can include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth); a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like); and combinations thereof. Other examples of modifications include engineered stem loop duplex structures, engineered bulge regions, engineered hairpins 3' of the stem loop duplex structure, or any combination thereof. See, e.g., US 2015/0376586, herein incorporated by reference in its entirety for all purposes. A bulge can be an unpaired region of nucleotides within the duplex made up of the crRNA-like region and the minimum tracrRNA-like region. A bulge can comprise, on one side of the duplex, an unpaired 5'-XXXY-3' where X is any purine and Y can be a nucleotide that can form a wobble pair with a nucleotide on the opposite strand, and an unpaired nucleotide region on the other side of the duplex.

Unmodified nucleic acids can be prone to degradation. Exogenous nucleic acids can also induce an innate immune response. Modifications can help introduce stability and reduce immunogenicity. Guide RNAs can comprise modified nucleosides and modified nucleotides including, for example, one or more of the following: (1) alteration or replacement of one or both of the non-linking phosphate oxygens and/or of one or more of the linking phosphate oxygens in the phosphodiester backbone linkage; (2) alteration or replacement of a constituent of the ribose sugar such as alteration or replacement of the 2' hydroxyl on the ribose sugar; (3) replacement of the phosphate moiety with dephospho linkers; (4) modification or replacement of a naturally occurring nucleobase; (5) replacement or modification of the ribose-phosphate backbone; (6) modification of the 3' end or 5' end of the oligonucleotide (e.g., removal, modification or replacement of a terminal phosphate group or conjugation of a moiety); and (7) modification of the sugar. Other possible guide RNA modifications include modifications of or replacement of uracils or poly-uracil tracts. See, e.g., WO 2015/048577 and US 2016/0237455, each of which is herein incorporated by reference in its entirety for all purposes. Similar modifications can be made to Cas-encoding nucleic acids, such as Cas mRNAs. For example, Cas mRNAs can be modified by depletion of uridine using synonymous codons.

As one example, nucleotides at the 5' or 3' end of a guide RNA can include phosphorothioate linkages (e.g., the bases can have a modified phosphate group that is a phosphorothioate group). For example, a guide RNA can include phosphorothioate linkages between the 2, 3, or 4 terminal nucleotides at the 5' or 3' end of the guide RNA. As another example, nucleotides at the 5' and/or 3' end of a guide RNA can have 2'-O-methyl modifications. For example, a guide RNA can include 2'-O-methyl modifications at the 2, 3, or 4 terminal nucleotides at the 5' and/or 3' end of the guide RNA (e.g., the 5' end). See, e.g., WO 2017/173054 A1 and Finn et al. (2018) *Cell Rep.* 22(9):2227-2235, each of which is herein incorporated by reference in its entirety for all purposes. Other possible modifications are described in more detail elsewhere herein. In a specific example, a guide RNA includes 2'-O-methyl analogs and 3' phosphorothioate internucleotide linkages at the first three 5' and 3' terminal RNA residues. Such chemical modifications can, for example, provide greater stability and protection from exonucleases to guide RNAs, allowing them to persist within cells for longer than unmodified guide RNAs. Such chemical modifications can also, for example, protect against innate intracellular immune responses that can actively degrade RNA or trigger immune cascades that lead to cell death.

Guide RNAs can be provided in any form. For example, the gRNA can be provided in the form of RNA, either as two molecules (separate crRNA and tracrRNA) or as one molecule (sgRNA), and optionally in the form of a complex with a Cas protein. The gRNA can also be provided in the form of DNA encoding the gRNA. The DNA encoding the gRNA can encode a single RNA molecule (sgRNA) or separate RNA molecules (e.g., separate crRNA and tracrRNA). In the latter case, the DNA encoding the gRNA can be provided as one DNA molecule or as separate DNA molecules encoding the crRNA and tracrRNA, respectively.

When a gRNA is provided in the form of DNA, the gRNA can be transiently, conditionally, or constitutively expressed in the cell. DNAs encoding gRNAs can be stably integrated into the genome of the cell and operably linked to a promoter active in the cell. Alternatively, DNAs encoding gRNAs can be operably linked to a promoter in an expression construct. For example, the DNA encoding the gRNA can be in a vector comprising a heterologous nucleic acid, such as a nucleic acid encoding a Cas protein. Alternatively, it can be in a vector or a plasmid that is separate from the vector comprising the nucleic acid encoding the Cas protein. Promoters that can be used in such expression constructs include promoters active, for example, in one or more of a eukaryotic cell, a human cell, a non-human cell, a mammalian cell, a non-human mammalian cell, a rodent cell, a mouse cell, a rat cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters. Such promoters can also be, for example, bidirectional promoters. Specific examples of suitable promoters include an RNA polymerase III promoter, such as a human U6 promoter, a rat U6 polymerase III promoter, or a mouse U6 polymerase III promoter.

Alternatively, gRNAs can be prepared by various other methods. For example, gRNAs can be prepared by in vitro transcription using, for example, T7 RNA polymerase (see, e.g., WO 2014/089290 and WO 2014/065596, each of which is herein incorporated by reference in its entirety for all purposes). Guide RNAs can also be a synthetically produced molecule prepared by chemical synthesis. For example, a guide RNA can be chemically synthesized to include 2'-O-methyl analogs and 3' phosphorothioate internucleotide linkages at the first three 5' and 3' terminal RNA residues.

Guide RNAs (or nucleic acids encoding guide RNAs) can be in compositions comprising one or more guide RNAs (e.g., 1, 2, 3, 4, or more guide RNAs) and a carrier increasing the stability of the guide RNA (e.g., prolonging the period under given conditions of storage (e.g., −20° C., 4° C., or ambient temperature) for which degradation products remain below a threshold, such below 0.5% by weight of the starting nucleic acid or protein; or increasing the stability in vivo). Non-limiting examples of such carriers include poly (lactic acid) (PLA) microspheres, poly(D,L-lactic-coglycolic-acid) (PLGA) microspheres, liposomes, micelles, inverse micelles, lipid cochleates, and lipid microtubules. Such compositions can further comprise a Cas protein, such as a Cas9 protein, or a nucleic acid encoding a Cas protein.

Guide RNA Target Sequences.

Target DNAs for guide RNAs include nucleic acid sequences present in a DNA to which a DNA-targeting segment of a gRNA will bind, provided sufficient conditions for binding exist. Suitable DNA/RNA binding conditions include physiological conditions normally present in a cell. Other suitable DNA/RNA binding conditions (e.g., conditions in a cell-free system) are known in the art (see, e.g., Molecular Cloning: A Laboratory Manual, 3rd Ed. (Sambrook et al., Harbor Laboratory Press 2001), herein incorporated by reference in its entirety for all purposes). The strand of the target DNA that is complementary to and hybridizes with the gRNA can be called the "complementary strand," and the strand of the target DNA that is complementary to the "complementary strand" (and is therefore not complementary to the Cas protein or gRNA) can be called "noncomplementary strand" or "template strand."

The target DNA includes both the sequence on the complementary strand to which the guide RNA hybridizes and the corresponding sequence on the non-complementary strand (e.g., adjacent to the protospacer adjacent motif (PAM)). The term "guide RNA target sequence" as used herein refers specifically to the sequence on the non-complementary strand corresponding to (i.e., the reverse complement of) the sequence to which the guide RNA hybridizes on the complementary strand. That is, the guide RNA target sequence refers to the sequence on the non-complementary strand adjacent to the PAM (e.g., upstream or 5' of the PAM in the case of Cas9). A guide RNA target sequence is equivalent to the DNA-targeting segment of a guide RNA, but with thymines instead of uracils. As one example, a guide RNA target sequence for an SpCas9 enzyme can refer to the sequence upstream of the 5'-NGG-3' PAM on the non-complementary strand. A guide RNA is designed to have complementarity to the complementary strand of a target DNA, where hybridization between the DNA-targeting segment of the guide RNA and the complementary strand of the target DNA promotes the formation of a CRISPR complex. Full complementarity is not necessarily required, provided that there is sufficient complementarity to cause hybridization and promote formation of a CRISPR complex. If a guide RNA is referred to herein as targeting a guide RNA target sequence, what is meant is that the guide RNA hybridizes to the complementary strand sequence of the target DNA that is the reverse complement of the guide RNA target sequence on the non-complementary strand.

A target DNA or guide RNA target sequence can comprise any polynucleotide, and can be located, for example, in the nucleus or cytoplasm of a cell or within an organelle of a cell, such as a mitochondrion or chloroplast. A target DNA or guide RNA target sequence can be any nucleic acid sequence endogenous or exogenous to a cell. The guide RNA target sequence can be a sequence coding a gene product (e.g., a protein) or a non-coding sequence (e.g., a regulatory sequence) or can include both.

Site-specific binding and cleavage of a target DNA by a Cas protein can occur at locations determined by both (i) base-pairing complementarity between the guide RNA and the complementary strand of the target DNA and (ii) a short motif, called the protospacer adjacent motif (PAM), in the non-complementary strand of the target DNA. The PAM can flank the guide RNA target sequence. Optionally, the guide RNA target sequence can be flanked on the 3' end by the PAM (e.g., for Cas9). Alternatively, the guide RNA target sequence can be flanked on the 5' end by the PAM (e.g., for Cpf1). For example, the cleavage site of Cas proteins can be about 1 to about 10 or about 2 to about 5 base pairs (e.g., 3 base pairs) upstream or downstream of the PAM sequence (e.g., within the guide RNA target sequence). In the case of SpCas9, the PAM sequence (i.e., on the non-complementary strand) can be 5'-$N_1$GG-3', where $N_1$ is any DNA nucleotide, and where the PAM is immediately 3' of the guide RNA target sequence on the non-complementary strand of the target DNA. As such, the sequence corresponding to the PAM on the complementary strand (i.e., the reverse complement) would be 5'-CC$N_2$-3', where $N_2$ is any DNA nucleotide and is immediately 5' of the sequence to which the DNA-targeting segment of the guide RNA hybridizes on the complementary strand of the target DNA. In some such cases, $N_1$ and $N_2$ can be complementary and the $N_1$-$N_2$ base pair can be any base pair (e.g., $N_1$=C and $N_2$=G; $N_1$=G and $N_2$=C; $N_1$=A and $N_2$=T; or $N_1$=T, and $N_2$=A). In the case of Cas9 from S. aureus, the PAM can be NNGRRT or NNGRR, where N can A, G, C, or T, and R can be G or A. In the case of Cas9 from C. jejuni, the PAM can be, for example, NNNNACAC or NNNNRYAC, where N can be A, G, C, or T, and R can be G or A. In some cases (e.g., for FnCpf1), the PAM sequence can be upstream of the 5' end and have the sequence 5'-TTN-3'.

An example of a guide RNA target sequence is a 20-nucleotide DNA sequence immediately preceding an NGG motif recognized by an SpCas9 protein. For example, two examples of guide RNA target sequences plus PAMs are GN$_{19}$NGG (SEQ ID NO: 25) or N$_{20}$NGG (SEQ ID NO: 26). See, e.g., WO 2014/165825, herein incorporated by reference in its entirety for all purposes. The guanine at the 5' end can facilitate transcription by RNA polymerase in cells. Other examples of guide RNA target sequences plus PAMs can include two guanine nucleotides at the 5' end (e.g., GGN$_{20}$NGG; SEQ ID NO: 27) to facilitate efficient transcription by T7 polymerase in vitro. See, e.g., WO 2014/065596, herein incorporated by reference in its entirety for all purposes. Other guide RNA target sequences plus PAMs can have between 4-22 nucleotides in length of SEQ ID NOS: 25-27, including the 5' G or GG and the 3' GG or NGG. Yet other guide RNA target sequences plus PAMs can have between 14 and 20 nucleotides in length of SEQ ID NOS: 25-27.

Formation of a CRISPR complex hybridized to a target DNA can result in cleavage of one or both strands of the target DNA within or near the region corresponding to the guide RNA target sequence (i.e., the guide RNA target sequence on the non-complementary strand of the target DNA and the reverse complement on the complementary strand to which the guide RNA hybridizes). For example, the cleavage site can be within the guide RNA target sequence (e.g., at a defined location relative to the PAM sequence). The "cleavage site" includes the position of a target DNA at which a Cas protein produces a single-strand break or a double-strand break. The cleavage site can be on only one strand (e.g., when a nickase is used) or on both strands of a double-stranded DNA. Cleavage sites can be at the same position on both strands (producing blunt ends; e.g. Cas9)) or can be at different sites on each strand (producing staggered ends (i.e., overhangs); e.g., Cpf1). Staggered ends can be produced, for example, by using two Cas proteins, each of which produces a single-strand break at a different cleavage site on a different strand, thereby producing a double-strand break. For example, a first nickase can create a single-strand break on the first strand of double-stranded DNA (dsDNA), and a second nickase can create a single-strand break on the second strand of dsDNA such that overhanging sequences are created. In some cases, the guide RNA target sequence or cleavage site of the nickase on the first strand is separated from the guide RNA target sequence or cleavage site of the nickase on the second strand by at least 2, 3, 4, 5, 6, 7, 8, 9, 10, 15, 20, 25, 30, 40, 50, 75, 100, 250, 500, or 1,000 base pairs.

III. Non-Human Animals, Non-Human Animal Cells, and Non-Human Animal Genomes Comprising a Heterologous Hexanucleotide Repeat Expansion Sequence Inserted at an Endogenous C9orf72 Locus The non-human animal genomes, non-human animal cells, and non-human animals disclosed herein can comprise a heterologous hexanucleotide repeat expansion sequence inserted at an endogenous C9orf72 locus. Also disclosed are non-human animal C9orf72 genes comprising a heterologous hexanucleotide repeat expansion sequence. Also disclosed herein are genomes, cells (e.g., human induced pluripotent stem cells), and animals comprising an expanded hexanucleotide repeat expansion sequence inserted at an endogenous C9orf72 locus. Also disclosed are animal C9orf72 genes comprising an expanded hexanucleotide repeat expansion sequence. As an example, the heterologous hexanucleotide repeat expansion sequence can comprise more than 100 repeats of the hexanucleotide sequence set forth as SEQ ID NO: 1.

A. C9ORF72, Hexanucleotide Repeat Expansion Sequences, and Associated Diseases

Amyotrophic lateral sclerosis (ALS), also referred to as Lou Gehrig's disease, is the most frequent adult-onset paralytic disorder, characterized by the loss of upper and/or lower motor neurons. ALS occurs in as many as 20,000 individuals across the United States with about 5,000 new cases occurring each year. Frontotemporal dementia (FTD; also referred to as Pick's disease, frontotemporal lobar degeneration, or FTLD) is a group of disorders caused by progressive cell degeneration in the frontal or temporal lobes of the brain. FTD is reported to account for 10%-15% of all dementia cases. A hexanucleotide repeat expansion sequence between (and optionally spanning) exon 1A and 1B, two non-coding exons, of the human C9ORF72 gene have been linked to both ALS and FTD. It is estimated that the GGGGCC (SEQ ID NO: 1) hexanucleotide repeat expansion accounts for about 50% of familial and many non-familial ALS cases. It is present in about 25% of familial FTD cases and about 8% of sporadic FTD cases.

Many pathological aspects related to the hexanucleotide repeat expansion sequence in C9ORF72 have been reported such as, for example, repeat-length-dependent formation of RNA foci, sequestration of specific RNA-binding proteins, and accumulation and aggregation of dipeptide repeat proteins (e.g., poly(glycine-alanine), poly(glycine-proline), poly(glycine-arginine), poly(alanine-proline), or poly(proline-arginine) dipeptide repeat proteins) resulting from repeat-associated non-AUG (AUG) translation. Mice containing a heterologous hexanucleotide repeat expansion sequence comprising 66 repeats of the hexanucleotide sequence (GGGGCC; SEQ ID NO: 1) have been generated by somatic brain transgenesis mediated by adeno-associated virus and exhibit RNA foci and dipeptide protein aggregates resulting from repeat-associated non-AUG (AUG) translation in their neurons. See Chew et al. (2015) *Science* 348(6239):1151-1154, herein incorporated by reference in its entirety for all purposes.

Although C9ORF72 has been reported to regulate endosomal trafficking, much of the cellular function of C9ORF72 remains unknown. Indeed, C9ORF72 is a gene that encodes an uncharacterized protein with unknown function.

Mouse C9orf72 transcript variants have been reported. See, e.g., Koppers et al. (2015) *Ann. Neurol.* 78:426-438 and Atkinson et al. (2015) *Acta Neuropathologica Communications* 3:59, each of which is herein incorporated by reference in its entirety for all purposes. The genomic information for the three reported mouse C9orf72 transcript variants is also available at the Ensembl web site under designations of ENSMUST00000108127 (V1), ENSMUST00000108126 (V2), and ENSMUST00000084724 (V3). Exemplary non-human (e.g., rodent) C9orf72 mRNA and amino acid sequences are set forth in SEQ ID NOS: 40-43. The mRNA and amino acid sequences of mouse C9orf72 can be found at GenBank accession numbers NM_001081343 and NP_001074812, respectively, and are hereby incorporated by reference in their entirety for all purposes. The sequences of NM_001081343.1 and NP_001074812.1 are set forth in SEQ ID NOS: 40 and 41, respectively. The mRNA and amino acid sequences of rat C9orf72 can be found at GenBank accession numbers NM_001007702 and NP_001007703, respectively, and are hereby incorporated by reference in their entirety for all purposes. The sequences of NM_001007702.1 and NP_001007703.1 are set forth in SEQ ID NOS: 42 and 43, respectively.

Human C9ORF72 transcript variants are also known. One human C9ORF72 transcript variant lacks multiple exons in the central and 3' coding regions, and its 3' terminal exon extends beyond a splice site that is used in variant 3 (see below), which results in a novel 3' untranslated region (UTR) as compared to variant 3. This variant encodes a significantly shorter polypeptide and its C-terminal amino acid is distinct as compared to that which is encoded by two other variants. The mRNA and amino acid sequences of this variant can be found at GenBank accession numbers NM_145005.6 and NP_659442.2, respectively, and are hereby incorporated by reference in their entirety for all purposes. The sequences of NM_145005.6 and NP_659442.2 are set forth in SEQ ID NO: 13 and SEQ ID NO: 14, respectively. A second human C9ORF72 transcript variant (2) differs in the 5' untranslated region (UTR) compared to variant 3. The mRNA and amino acid sequences of this variant can be found at GenBank accession numbers NM_018325.4 and NP_060795.1, respectively, and are hereby incorporated by reference in their entirety for all purposes. The sequences of NM_018325.4 and NP_060795.1 are set forth in SEQ ID NO: 15 and SEQ ID NO: 16, respectively. A third human C9ORF72 transcript variant (3) contains the longest sequence among three reported variants and encodes the longer isoform. The mRNA and amino acid sequences of this variant can be found at GenBank accession numbers NM_001256054.2 and NP_001242983.1, respectively, and are hereby incorporated by reference in their entirety for all purposes. The sequences of NM_001256054.2 and NP_001242983.1 are set forth in SEQ ID NO: 17 and SEQ ID NO: 18, respectively. Variants 2 and 3 encode the same protein.

B. Heterologous Hexanucleotide Repeat Expansion Sequence Inserted at an Endogenous C9orf72 Locus Described herein are genomes, cells, or animals (e.g., non-human animal genomes, cells, or animals) comprising a hexanucleotide repeat expansion sequence inserted into an endogenous C9orf72 locus (e.g., an endogenous non-human animal C9orf72 locus). The cells or animals can be any type of cell or animal as described elsewhere herein. In some genomes, cells, or animals, the hexanucleotide repeat expansion sequence can be a heterologous sequence. Alternatively, it can be an endogenous sequence that is then further expanded using the methods disclosed herein. The term heterologous when used in the context of a nucleic acid indicates that the nucleic acid comprises at least two segments that do not naturally occur together in the same molecule. For example, the term heterologous, when used with reference to segments of a nucleic acid, indicates that the nucleic acid comprises two or more sub-sequences that are not found in the same relationship to each other (e.g., joined together) in nature. As one example, a heterologous region of a nucleic acid is a segment of nucleic acid within or attached to another nucleic acid molecule that is not found in association with the other molecule in nature. For example, a heterologous region of a nucleic acid could include a C9orf72 sequence flanked by repeat expansion sequence not found in association with the C9orf72 sequence in nature. Alternatively, a heterologous region of nucleic acid could include a human nucleic acid sequence flanked by endogenous non-human nucleic acid sequence.

A C9ORF72 hexanucleotide repeat expansion sequence is generally a nucleotide sequence comprising at least two instances (i.e., two repeats) of the hexanucleotide sequence GGGGCC set forth as SEQ ID NO: 1. For purposes of insertion into an endogenous non-human C9orf72 locus, a heterologous hexanucleotide repeat expansion sequence comprises a plurality of (i.e., at least two instances (repeats) of) the hexanucleotide sequence set forth as SEQ ID NO: 1.

In some heterologous hexanucleotide repeat expansion sequences, the repeats are contiguous (adjacent to each other without intervening sequence).

The heterologous hexanucleotide repeat expansion sequence can have any number of repeats. For example, the repeat expansion sequence can comprise more than about 95 repeats, more than about 96 repeats, more than about 97 repeats, more than about 98 repeats, more than about 99 repeats, more than about 100 repeats, more than about 101 repeats, more than about 102 repeats, more than about 103 repeats, more than about 104 repeats, more than about 105 repeats, more than about 150 repeats, more than about 200 repeats, more than about 250 repeats, more than about 295 repeats, more than about 296 repeats, more than about 297 repeats, more than about 298 repeats, more than about 299 repeats, more than about 300 repeats, more than about 301 repeats, more than about 302 repeats, more than about 303 repeats, more than about 304 repeats, more than about 305 repeats, more than about 350 repeats, more than about 400 repeats, more than about 450 repeats, more than about 500 repeats, more than about 550 repeats, more than about 595 repeats, more than about 596 repeats, more than about 597 repeats, more than about 598 repeats, more than about 599 repeats, more than about 600 repeats, more than about 601 repeats, more than about 602 repeats, more than about 603 repeats, more than about 604 repeats, or more than about 605 repeats. Alternatively, the repeat expansion sequence can comprise at least about 95 repeats, at least about 96 repeats, at least about 97 repeats, at least about 98 repeats, at least about 99 repeats, at least about 100 repeats, at least about 101 repeats, at least about 102 repeats, at least about 103 repeats, at least about 104 repeats, at least about 105 repeats, at least about 150 repeats, at least about 200 repeats, at least about 250 repeats, at least about 295 repeats, at least about 296 repeats, at least about 297 repeats, at least about 298 repeats, at least about 299 repeats, at least about 300 repeats, at least about 301 repeats, at least about 302 repeats, at least about 303 repeats, at least about 304 repeats, at least about 305 repeats, at least about 350 repeats, at least about 400 repeats, at least about 450 repeats, at least about 500 repeats, at least about 550 repeats, at least about 595 repeats, at least about 596 repeats, at least about 597 repeats, at least about 598 repeats, at least about 599 repeats, at least about 600 repeats, at least about 601 repeats, at least about 602 repeats, at least about 603 repeats, at least about 604 repeats, or at least about 605 repeats. In a specific example, the heterologous hexanucleotide repeat expansion sequence comprises more than about 100 repeats, more than about 300 repeats, more than about 600 repeats, at least about 100 repeats, at least about 300 repeats, or at least about 600 repeats.

The repeat expansion sequence can be located, for example, between the first non-coding endogenous exon and exon 2 of the endogenous C9orf72 locus.

In some examples, the modified endogenous non-human animal C9orf72 locus can also comprise additional orthologous C9orf72 sequence. As one example, the non-human animal C9orf72 locus can comprise a human C9ORF72 nucleotide sequence. For example, the non-human animal C9orf72 locus can comprise a replacement of 5' untranslated and/or non-coding endogenous non-human sequences of the endogenous C9orf72 locus with the hexanucleotide repeat expansion sequence and flanking orthologous human C9ORF72 sequence (i.e., heterologous (e.g., human) sequences that flank the repeats of the hexanucleotide sequence set forth as SEQ ID NO: 1). The heterologous repeat expansion sequence and/or the flanking sequence can be naturally occurring genomic sequence (e.g., naturally occurring human genomic sequence). As a specific example, the untranslated and/or non-coding sequence spanning between (and optionally encompassing at least a portion of) endogenous exon 1 (e.g., exon 1A and/or 1B) and the ATG start codon of the endogenous non-human C9orf72 locus, or a portion thereof, can be replaced with the heterologous hexanucleotide repeat expansion sequence, and optionally together with flanking orthologous human C9ORF72 sequence. For example, the sequence inserted into an endogenous C9orf72 locus can comprise from 5' to 3': a first heterologous hexanucleotide flanking sequence, a plurality of repeats of the hexanucleotide set forth in SEQ ID NO: 1, and a second heterologous hexanucleotide flanking sequence.

In one example, a heterologous human C9ORF72 sequence spanning (and optionally encompassing) all or portions of exons 1A and/or exon 1B of a human C9ORF72 gene is inserted into the endogenous C9orf72 locus. For example, the first heterologous hexanucleotide flanking sequence can comprise the sequence set forth as SEQ ID NO: 46, or a portion thereof, and/or the second heterologous hexanucleotide flanking sequence can comprise the sequence set forth as SEQ ID NO: 47, or a portion thereof. Accordingly, in some examples, the endogenous C9orf72 locus into which the heterologous hexanucleotide repeat expansion sequence is inserted can comprise a human sequence comprising the sequence set forth in SEQ ID NO: 46 and/or SEQ ID NO: 47.

In a specific example, the endogenous C9orf72 locus comprises the replacement of a part of a non-coding sequence of a mouse C9orf72 locus with a heterologous human hexanucleotide repeat expansion sequence placed in operable linkage with a mouse C9orf72 promoter and/or human regulatory elements (e.g., those that may be found in exons 1A and/or 1B of the human C9ORF72 gene). See US 2018/0094267 and WO 2018/064600, each of which is herein incorporated by reference in its entirety for all purposes. For purposes of insertion into an endogenous non-human C9orf72 locus, a heterologous hexanucleotide repeat expansion sequence can comprise a plurality of (i.e., at least two instances (repeats) of) the hexanucleotide sequence set forth as SEQ ID NO: 1 and may be identical to, or substantially identical to a genomic nucleic acid sequence spanning (and optionally including) non-coding exons 1A and 1B of a human chromosome 9 open reading frame 72 (C9ORF72), or a portion thereof.

Optionally, a C9orf72 locus comprising a hexanucleotide repeat expansion sequence can comprise other elements. Examples of such elements can include selection cassettes, reporter genes, recombinase recognition sites, or other elements. Alternatively, the locus can lack other elements (e.g., can lack a selection marker or selection cassette). Examples of suitable reporter genes and reporter proteins are disclosed elsewhere herein. Examples of suitable selection markers include neomycin phosphotransferase ($neo_r$), hygromycin B phosphotransferase ($hyg_r$), puromycin-N-acetyltransferase ($puro_r$), blasticidin S deaminase ($bsr_r$), xanthine/guanine phosphoribosyl transferase (gpt), and herpes simplex virus thymidine kinase (HSV-k). Examples of recombinases include Cre, Flp, and Dre recombinases. One example of a Cre recombinase gene is Crei, in which two exons encoding the Cre recombinase are separated by an intron to prevent its expression in a prokaryotic cell. Such recombinases can further comprise a nuclear localization signal to facilitate localization to the nucleus (e.g., NLS-Crei). Recombinase recognition sites include nucleotide sequences that are recognized by a site-specific recombinase and can serve as a substrate for a recombination event. Examples of recombinase recognition sites include FRT, FRT11, FRT71, attp, att, rox, and lox sites such as loxP, lox511, lox2272, lox66, lox71, loxM2, and lox5171.

Other elements such as reporter genes or selection cassettes can be self-deleting cassettes flanked by recombinase recognition sites. See, e.g., U.S. Pat. No. 8,697,851 and US 2013/0312129, each of which is herein incorporated by reference in its entirety for all purposes. As an example, the self-deleting cassette can comprise a Crei gene (comprises two exons encoding a Cre recombinase, which are separated by an intron) operably linked to a mouse Prm1 promoter and a neomycin resistance gene operably linked to a human ubiquitin promoter. By employing the Prm1 promoter, the self-deleting cassette can be deleted specifically in male germ cells of F0 animals. The polynucleotide encoding the selection marker can be operably linked to a promoter active in a cell being targeted. Examples of promoters are described elsewhere herein. As another specific example, a self-deleting selection cassette can comprise a hygromycin resistance gene coding sequence operably linked to one or more promoters (e.g., both human ubiquitin and EM7 promoters) followed by a polyadenylation signal, followed by a Crei coding sequence operably linked to one or more promoters (e.g., an mPrm1 promoter), followed by another polyadenylation signal, wherein the entire cassette is flanked by loxP sites.

The locus can also be a conditional allele. For example, the conditional allele can be a multifunctional allele, as described in US 2011/0104799, herein incorporated by reference in its entirety for all purposes. For example, the conditional allele can comprise: (a) an actuating sequence in sense orientation with respect to transcription of a target gene; (b) a drug selection cassette (DSC) in sense or antisense orientation; (c) a nucleotide sequence of interest (NSI) in antisense orientation; and (d) a conditional by inversion module (COIN, which utilizes an exon-splitting intron and an invertible gene-trap-like module) in reverse orientation. See, e.g., US 2011/0104799. The conditional allele can further comprise recombinable units that recombine upon exposure to a first recombinase to form a conditional allele that (i) lacks the actuating sequence and the DSC; and (ii) contains the NSI in sense orientation and the COIN in antisense orientation. See, e.g., US 2011/0104799.

C. Non-Human Animal Genomes, Non-Human Animal Cells, and Non-Human Animals Comprising a Heterologous Hexanucleotide Repeat Expansion Sequence Inserted at an Endogenous C9orf72 Locus Animal genomes, animal cells, and animals comprising a hexanucleotide repeat expansion sequence inserted at an endogenous C9orf72 locus as described elsewhere herein are provided. In some genomes, cells, or animals, the hexanucleotide repeat expansion sequence can be a heterologous sequence. Alternatively, it can be an endogenous sequence that is then further expanded using the methods disclosed herein. For example, non-human animal genomes, non-human animal cells, and non-human animals comprising a heterologous hexanucleotide repeat expansion sequence inserted at an endogenous C9orf72 locus as described elsewhere herein are provided. Alternatively, the genome or cell can be human (e.g., a human induced pluripotent stem cell). The genomes, cells, or non-human animals can be male or female. The genomes, cells, or non-human animals can be heterozygous or homozygous for the heterologous hexanucleotide repeat expansion sequence inserted at the endogenous C9orf72 locus. A diploid organism has two alleles at each genetic locus. Each pair of alleles represents the genotype of a specific genetic locus. Genotypes are described as homozygous if there are two identical alleles at a particular locus and as heterozygous if the two alleles differ. The non-human animals can comprise the heterologous hexanucleotide repeat expansion sequence inserted at the endogenous C9orf72 locus in their germline genome.

The non-human animals or non-human animal cells provided herein can exhibit, for example, one or more or all of the following characteristics: (a) increased expression of C9orf72 transcripts that retain intron sequence compared to a control non-human animal or control non-human animal cell comprising a wild type C9orf72 locus; and/or (b) an increased number of RNA foci compared to a control non-human animal or control non-human animal cell comprising a wild type C9orf72 locus; and/or (c) an increased level of dipeptide repeat proteins compared to a control non-human animal or control non-human animal cell comprising a wild type C9orf72 locus. Such dipeptide repeat proteins can be, for example, poly(glycine-alanine), poly(glycine-proline), poly(glycine-arginine), poly(alanine-proline), or poly(proline-arginine) dipeptide repeat proteins (e.g., polyGA or polyGP dipeptide repeat proteins).

The non-human animal genomes or cells provided herein can be, for example, any non-human animal genome or cell comprising a C9orf72 locus or a genomic locus homologous or orthologous to the human C9ORF72 locus. The genomes can be from or the cells can be eukaryotic cells, which include, for example, fungal cells (e.g., yeast), plant cells, animal cells, mammalian cells, non-human mammalian cells, and human cells. The term "animal" includes any member of the animal kingdom, including, for example, mammals, fishes, reptiles, amphibians, birds, and worms. A mammalian cell can be, for example, a non-human mammalian cell, a rodent cell, a rat cell, a mouse cell, or a hamster cell. Other non-human mammals include, for example, non-human primates, monkeys, apes, orangutans, cats, dogs, rabbits, horses, bulls, deer, bison, livestock (e.g., bovine species such as cows, steer, and so forth; ovine species such as sheep, goats, and so forth; and porcine species such as pigs and boars). Birds include, for example, chickens, turkeys, ostrich, geese, ducks, and so forth. Domesticated animals and agricultural animals are also included. The term "non-human" excludes humans.

The cells can also be any type of undifferentiated or differentiated state. For example, a cell can be a totipotent cell, a pluripotent cell (e.g., a human pluripotent cell or a non-human pluripotent cell such as a mouse embryonic stem (ES) cell or a rat ES cell), or a non-pluripotent cell. Totipotent cells include undifferentiated cells that can give rise to any cell type, and pluripotent cells include undifferentiated cells that possess the ability to develop into more than one differentiated cell types. Such pluripotent and/or totipotent cells can be, for example, ES cells or ES-like cells, such as an induced pluripotent stem (iPS) cells. ES cells include embryo-derived totipotent or pluripotent cells that are capable of contributing to any tissue of the developing embryo upon introduction into an embryo. ES cells can be derived from the inner cell mass of a blastocyst and are capable of differentiating into cells of any of the three vertebrate germ layers (endoderm, ectoderm, and mesoderm).

The cells provided herein can also be germ cells (e.g., sperm or oocytes). The cells can be mitotically competent cells or mitotically-inactive cells, meiotically competent cells or meiotically-inactive cells. Similarly, the cells can also be primary somatic cells or cells that are not a primary somatic cell. Somatic cells include any cell that is not a gamete, germ cell, gametocyte, or undifferentiated stem cell. For example, the cells can be neuronal cells (e.g., ES-cell-derived motor neurons), brain cells, cortical cells, or heart cells.

Suitable cells provided herein also include primary cells. Primary cells include cells or cultures of cells that have been isolated directly from an organism, organ, or tissue. Primary cells include cells that are neither transformed nor immortal. They include any cell obtained from an organism, organ, or tissue which was not previously passed in tissue culture or has been previously passed in tissue culture but is incapable of being indefinitely passed in tissue culture.

Other suitable cells provided herein include immortalized cells. Immortalized cells include cells from a multicellular organism that would normally not proliferate indefinitely but, due to mutation or alteration, have evaded normal cellular senescence and instead can keep undergoing division. Such mutations or alterations can occur naturally or be intentionally induced. Numerous types of immortalized cells are well known. Immortalized or primary cells include cells that are typically used for culturing or for expressing recombinant genes or proteins.

The cells provided herein also include one-cell stage embryos (i.e., fertilized oocytes or zygotes). Such one-cell stage embryos can be from any genetic background (e.g., BALB/c, C57BL/6, 129, or a combination thereof for mice), can be fresh or frozen, and can be derived from natural breeding or in vitro fertilization.

The cells provided herein can be normal, healthy cells, or can be diseased or mutant-bearing cells.

Non-human animals comprising a heterologous hexanucleotide repeat expansion sequence inserted at an endogenous C9orf72 locus as described herein can be made by the methods described elsewhere herein. The term "animal" includes any member of the animal kingdom, including, for example, mammals, fishes, reptiles, amphibians, birds, and worms. In a specific example, the non-human animal is a non-human mammal. Non-human mammals include, for example, non-human primates, monkeys, apes, orangutans, cats, dogs, horses, bulls, deer, bison, sheep, rabbits, rodents (e.g., mice, rats, hamsters, and guinea pigs), and livestock (e.g., bovine species such as cows and steer; ovine species such as sheep and goats; and porcine species such as pigs and boars). Birds include, for example, chickens, turkeys, ostrich, geese, and ducks. Domesticated animals and agricultural animals are also included. The term "non-human animal" excludes humans. Preferred non-human animals include, for example, rodents, such as mice and rats.

The non-human animals can be from any genetic background. For example, suitable mice can be from a 129 strain, a C57BL/6 strain, a mix of 129 and C57BL/6, a BALB/c strain, or a Swiss Webster strain. Examples of 129 strains include 129P1, 129P2, 129P3, 129X1, 129S1 (e.g., 129S1/SV, 129S1/Svlm), 129S2, 129S4, 129S5, 129S9/SvEvH, 129S6 (129/SvEvTac), 129S7, 129S8, 129T1, and 129T2. See, e.g., Festing et al. (1999) *Mammalian Genome* 10:836, herein incorporated by reference in its entirety for all purposes. Examples of C57BL strains include C57BL/A, C57BL/An, C57BL/GrFa, C57BL/Kal_wN, C57BL/6, C57BL/6J, C57BL/6ByJ, C57BL/6NJ, C57BL/10, C57BL/10ScSn, C57BL/10Cr, and C57BL/Ola. Suitable mice can also be from a mix of an aforementioned 129 strain and an aforementioned C57BL/6 strain (e.g., 50% 129 and 50% C57BL/6). Likewise, suitable mice can be from a mix of aforementioned 129 strains or a mix of aforementioned BL/6 strains (e.g., the 129S6 (129/SvEvTac) strain).

Similarly, rats can be from any rat strain, including, for example, an ACI rat strain, a Dark Agouti (DA) rat strain, a Wistar rat strain, a LEA rat strain, a Sprague Dawley (SD) rat strain, or a Fischer rat strain such as Fisher F344 or Fisher F6. Rats can also be obtained from a strain derived from a mix of two or more strains recited above. For example, a suitable rat can be from a DA strain or an ACI strain. The ACI rat strain is characterized as having black agouti, with white belly and feet and an $RT1^{av1}$ haplotype. Such strains are available from a variety of sources including Harlan Laboratories. The Dark Agouti (DA) rat strain is characterized as having an agouti coat and an $RT1^{av1}$ haplotype. Such rats are available from a variety of sources including Charles River and Harlan Laboratories. Some suitable rats can be from an inbred rat strain. See, e.g., US 2014/0235933, herein incorporated by reference in its entirety for all purposes.

IV Methods of Making Non-Human Animals or Non-Human Animal Cells Comprising in their Genome a Heterologous Hexanucleotide Repeat Expansion Sequence Inserted at an Endogenous C9orf72 Locus Various methods are provided for making an animal genome, animal cell, or animal comprising a hexanucleotide repeat expansion sequence inserted at an endogenous C9orf72 locus as disclosed elsewhere herein. Likewise, various methods are provided for making a non-human animal genome, non-human animal cell, or non-human animal comprising a heterologous hexanucleotide repeat expansion sequence inserted at an endogenous C9orf72 locus as disclosed elsewhere herein.

Any convenient method or protocol for producing a genetically modified organism is suitable for producing such a genetically modified non-human animal. See, e.g., Cho et al. (2009) *Current Protocols in Cell Biology* 42:19.11: 19.11.1-19.11.22 and Gama Sosa et al. (2010) *Brain Struct. Funct.* 214(2-3):91-109, each of which is herein incorporated by reference in its entirety for all purposes. For example, the method of producing a non-human animal comprising a heterologous hexanucleotide repeat expansion sequence inserted at an endogenous C9orf72 locus can comprise: (1) modifying the genome of a pluripotent cell to comprise the heterologous hexanucleotide repeat expansion sequence inserted at the endogenous C9orf72 locus; (2) identifying or selecting the genetically modified pluripotent cell comprising the heterologous hexanucleotide repeat expansion sequence inserted at the endogenous C9orf72 locus; (3) introducing the genetically modified pluripotent cell into a non-human animal host embryo; and (4) implanting and gestating the host embryo in a surrogate mother. For example, the method of producing a non-human animal comprising a heterologous hexanucleotide repeat expansion sequence inserted at an endogenous C9orf72 locus can comprise: (1) modifying the genome of a pluripotent cell to comprise the heterologous hexanucleotide repeat expansion sequence inserted at the endogenous C9orf72 locus; (2) identifying or selecting the genetically modified pluripotent cell comprising the heterologous hexanucleotide repeat expansion sequence inserted at the endogenous C9orf72 locus; (3) introducing the genetically modified pluripotent cell into a non-human animal host embryo; and (4) gestating the host embryo in a surrogate mother. The donor cell can be introduced into a host embryo at any stage, such as the blastocyst stage or the pre-morula stage (i.e., the 4 cell stage or the 8 cell stage). Progeny that are capable of transmitting the genetic modification though the germline can then be generated. See, e.g., U.S. Pat. No. 7,294,754, herein incorporated by reference in its entirety for all purposes. Optionally, the host embryo comprising modified pluripotent cell (e.g., a non-human ES cell) can be incubated until the blastocyst stage before being implanted into and gestated in the surrogate mother to produce an F0 non-human animal. The surrogate mother can then produce an F0 generation non-human animal comprising the heterologous hexanucleotide repeat expansion sequence inserted at the endogenous C9orf72 locus.

The methods can further comprise identifying a cell or animal having a modified target genomic C9orf72 locus. Various methods can be used to identify cells and animals having a targeted genetic modification.

Alternatively, the method of producing the non-human animals described elsewhere herein can comprise: (1) modifying the genome of a one-cell stage embryo to comprise the heterologous hexanucleotide repeat expansion sequence inserted at the endogenous C9orf72 locus using the methods described above for modifying pluripotent cells; (2) selecting the genetically modified embryo; and (3) implanting and gestating the genetically modified embryo into a surrogate mother. Alternatively, the method of producing the non-human animals described elsewhere herein can comprise: (1) modifying the genome of a one-cell stage embryo to comprise the heterologous hexanucleotide repeat expansion sequence inserted at the endogenous C9orf72 locus using the methods described above for modifying pluripotent cells; (2) selecting the genetically modified embryo; and (3) gestating the genetically modified embryo in a surrogate mother. Progeny that are capable of transmitting the genetic modification though the germline are generated.

Nuclear transfer techniques can also be used to generate the non-human mammalian animals. Briefly, methods for nuclear transfer can include the steps of: (1) enucleating an oocyte or providing an enucleated oocyte; (2) isolating or providing a donor cell or nucleus to be combined with the enucleated oocyte; (3) inserting the cell or nucleus into the enucleated oocyte to form a reconstituted cell; (4) implanting the reconstituted cell into the womb of an animal to form an embryo; and (5) allowing the embryo to develop. In such methods, oocytes are generally retrieved from deceased animals, although they may be isolated also from either oviducts and/or ovaries of live animals. Oocytes can be matured in a variety of well-known media prior to enucleation. Enucleation of the oocyte can be performed in a number of well-known manners. Insertion of the donor cell or nucleus into the enucleated oocyte to form a reconstituted cell can be by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell can be activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, can be cultured in well-known media and then transferred to the womb of an animal. See, e.g., US 2008/0092249, WO 1999/005266, US 2004/0177390, WO 2008/017234, and U.S. Pat. No. 7,612,250, each of which is herein incorporated by reference in its entirety for all purposes.

The various methods provided herein allow for the generation of a genetically modified non-human F0 animal wherein the cells of the genetically modified F0 animal comprise the heterologous hexanucleotide repeat expansion sequence inserted at the endogenous C9orf72 locus. It is recognized that depending on the method used to generate the F0 animal, the number of cells within the F0 animal that have the heterologous hexanucleotide repeat expansion sequence inserted at the endogenous C9orf72 locus will vary. The introduction of the donor ES cells into a pre-morula stage embryo from a corresponding organism (e.g., an 8-cell stage mouse embryo) via for example, the VELOCIMOUSE® method allows for a greater percentage of the cell population of the F0 animal to comprise cells having the nucleotide sequence of interest comprising the targeted genetic modification. For example, at least 50%, 60%, 65%, 70%, 75%, 85%, 86%, 87%, 87%, 88%, 89%, 90%, 91%, 92%, 93%, 94%, 95%, 96%, 97%, 98%, 99% or 100% of the cellular contribution of the non-human F0 animal can comprise a cell population having the targeted modification.

The cells of the genetically modified F0 animal can be heterozygous for the heterologous hexanucleotide repeat expansion sequence inserted at the endogenous C9orf72 locus or can be homozygous for the heterologous hexanucleotide repeat expansion sequence inserted at the endogenous C9orf72 locus.

V. Methods of Using Non-Human Animals or Non-Human Animal Cells Comprising in their Genome a Heterologous Hexanucleotide Repeat Expansion Sequence Inserted at an Endogenous C9orf72 Locus Various methods are provided for identifying or assessing therapeutic candidates for the treatment of a disease or a condition associated with a hexanucleotide repeat expansion sequence at a C9orf72 locus using the animal cells or animals comprising a hexanucleotide repeat expansion sequence inserted at an endogenous C9orf72 locus as disclosed elsewhere herein. Likewise, various methods are provided for identifying or assessing therapeutic candidates for the treatment of a disease or a condition associated with a hexanucleotide repeat expansion sequence at a C9orf72 locus using the non-human animal cells or non-human animals comprising a heterologous hexanucleotide repeat expansion sequence inserted at an endogenous C9orf72 locus as disclosed elsewhere herein.

Such methods can comprise, for example, administering a candidate agent to the non-human animal cell or non-human animal, performing one or more assays to determine if the candidate agent has an effect on one or more signs or symptoms associated with the disease or condition, and identifying the candidate agent as a therapeutic candidate if it has an effect on the one or more signs or symptoms associated with the disease or condition.

The disease or condition can be a neurodegenerative disorder associated with repeat expansion at the C9orf72 locus, such as amyotrophic lateral sclerosis (ALS) or frontotemporal dementia (FTD).

Any candidate agent can be tested. Such candidates could comprise, for example, large molecules such as siRNAs, antibodies, or CRISPR/Cas gRNAs) or small molecules. The candidate agent can be administered to the non-human animal or non-human animal cell by any means by any suitable route.

Any assay that measure a sign or symptom associated with the disease or condition can be used. As a first example, the sign or symptom can be the expression of intron-containing C9orf72 RNA transcripts. An example of an assay measuring the expression of intron-containing C9orf72 RNA transcripts is quantitative polymerase chain reaction (qPCR) using primers and probes that hybridize within the intronic region between exons 1A and 1B or exons 1B and 2 of the C9orf72 locus. Increased expression of intron-containing C9orf72 transcripts is associated with disease pathology (e.g., in ALS patients) and is observed in the cells described herein, so a candidate agent decreasing expression of intron-containing C9orf72 transcripts could be a therapeutic candidate.

As a second example, the sign or symptom can be the presence of RNA foci comprising C9orf72 sense or anti-sense RNA transcripts (e.g., nucleolar foci). Such RNA foci can be measured, for example, by fluorescence in situ hybridization. Increased cytoplasmic and/or nuclear foci (e.g., nucleolar) comprising sense or antisense C9orf72 RNA is associated with disease pathology (e.g., in ALS patients) and is observed in the cells described herein, so a candidate agent decreasing the presence of RNA foci could be a therapeutic candidate.

As yet another example, the sign or symptom can be the presence or accumulation of dipeptide repeat proteins, such as poly(glycine-alanine), poly(glycine-proline), poly(glycine-arginine), poly(alanine-proline), or poly(proline-arginine) dipeptide repeat proteins. For example, such dipeptide repeat proteins can be polyGA dipeptide repeat proteins or polyGP dipeptide repeat proteins. The presence or accumulation of dipeptide repeat proteins can be measured, for example, by immunohistochemistry, immunofluorescence, or by western slot blot. Accumulation of RAN translation products (e.g., dipeptide repeat proteins) is associated with disease pathology (e.g., in ALS patients) and is observed in the cells described herein, so a candidate agent decreasing the presence of dipeptide repeats could be a therapeutic candidate.

The candidate agent can be administered in vivo to the non-human animal, and the one or more assays can be performed in the non-human animal. Alternatively, the candidate agent can be administered in vivo to the non-human animal, and the one or more assays can be performed in vitro in cells isolated from the non-human animal after administration of the candidate agent. Alternatively, the candidate agent can be administered in vitro to cells (e.g., non-human embryonic-stem-cell-derived motor neurons), and the assays can be performed in vitro in the cells. Such cells can be, for example, an embryonic stem cell, an embryonic stem cell-derived motor neuron, a brain cell, a cortical cell, a neuronal cell, a muscle cell, or a heart cell.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

BRIEF DESCRIPTION OF THE SEQUENCES

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. When a nucleotide sequence encoding an amino acid sequence is provided, it is understood that codon degenerate variants thereof that encode the same amino acid sequence are also provided. The amino acid sequences follow the standard convention of beginning at the amino terminus of the sequence and proceeding forward (i.e., from left to right in each line) to the carboxy terminus.

TABLE 3

Description of Sequences.

| SEQ ID NO | Type | Description |
|---|---|---|
| 1 | DNA | GGGGCC C9ORF72 Hexanucleotide Repeat |
| 2 | DNA | CAG Repeat |
| 3 | DNA | CGG Repeat |
| 4 | DNA | CTG Repeat |
| 5 | DNA | GAA Repeat |
| 6 | DNA | GCC Repeat |
| 7 | DNA | GCG Repeat |
| 8 | DNA | CCTG Repeat |
| 9 | DNA | ATTCT Repeat |
| 10 | DNA | TGGAA Repeat |
| 11 | DNA | GGCCTG Repeat |
| 12 | DNA | CCCCGCCCCGCG Repeat |
| 13 | DNA | *Homo sapiens* C9ORF72 mRNA (NM_145005.6) |
| 14 | Protein | *Homo sapiens* C9ORF72 Amino Acid (NP_659442.2) |
| 15 | DNA | *Homo sapiens* C9ORF72 mRNA (NM_018325.4) |

TABLE 3-continued

Description of Sequences.

Figure 2:
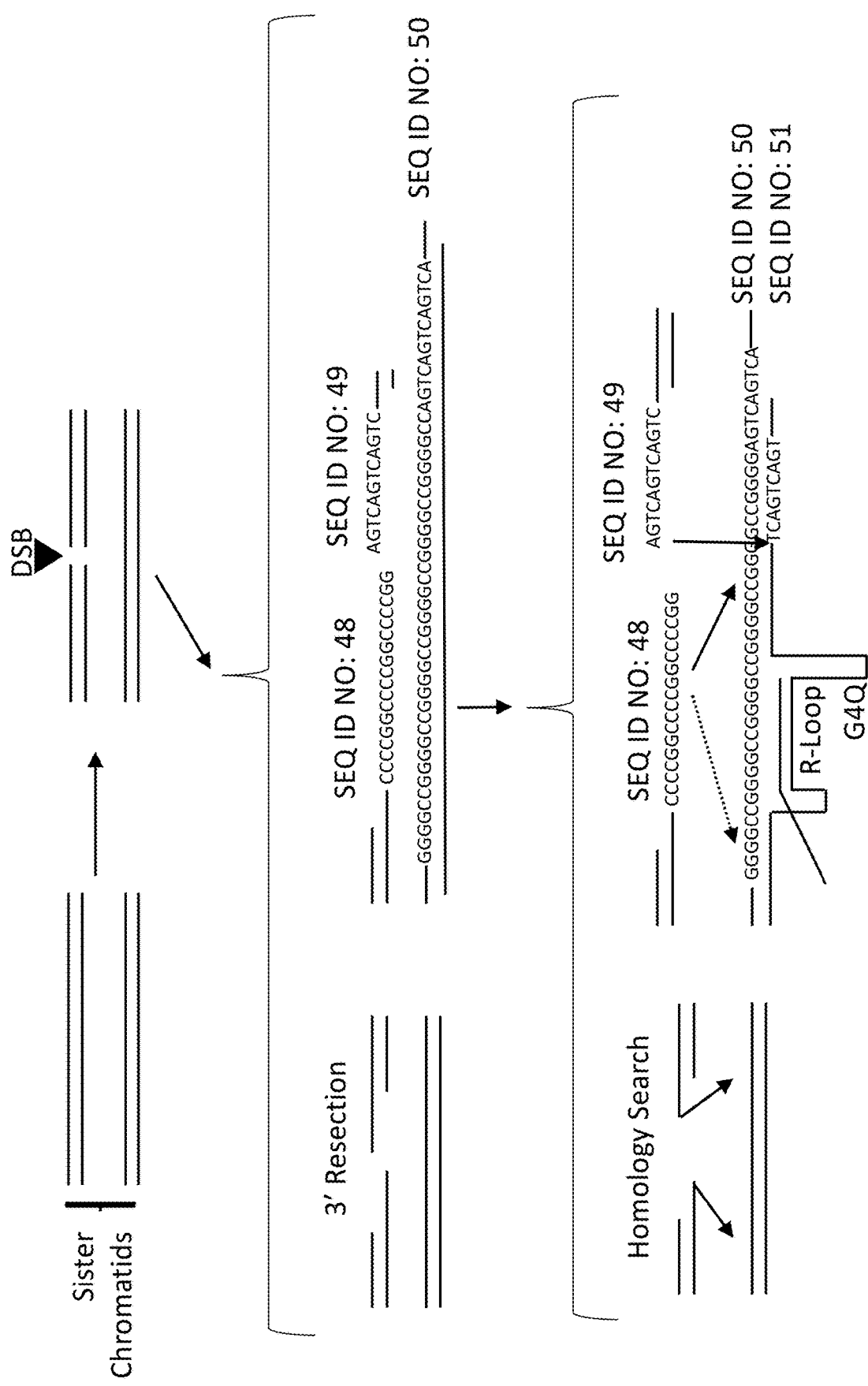
FIG. 2 (not to scale) shows a schematic of the concept of using nuclease agents to introduce a double-strand break near a repeat sequence in order to use the recombination machinery to expand the repeat sequence at a target genomic locus (such as the hexanucleotide sequence set forth in SEQ ID NO: 1 at the C9orf72 locus).
Figure 3:
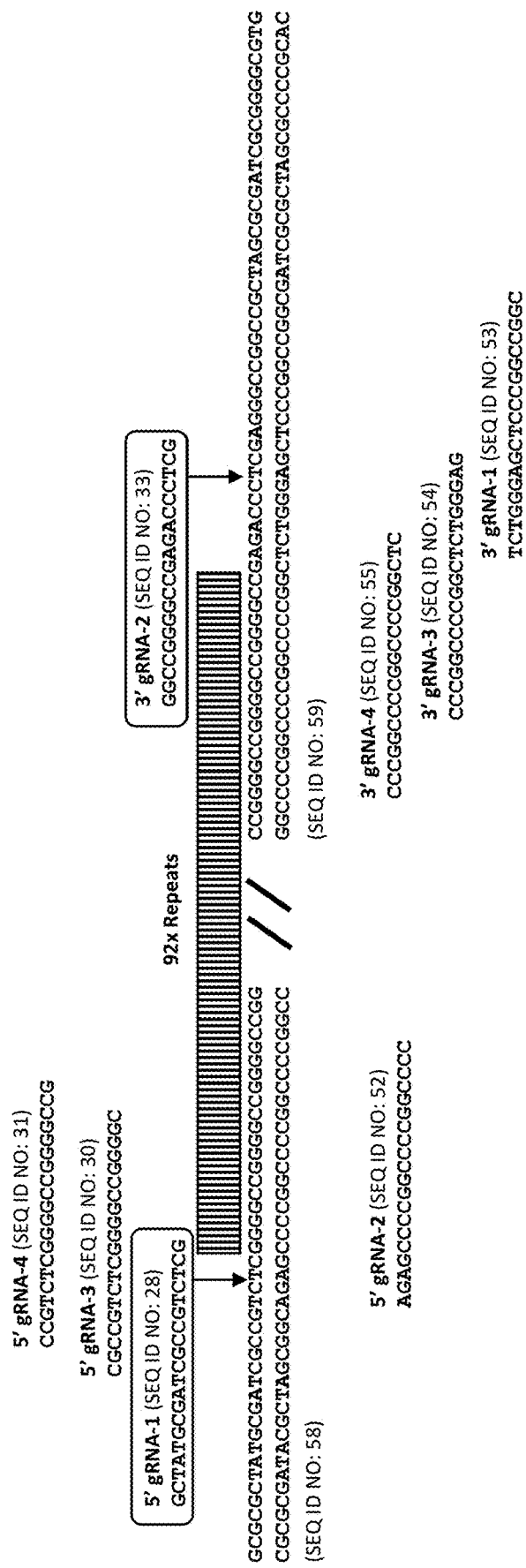
FIG. 3 (not to scale) shows a schematic with the locations of eight guide RNA target sequences located near the ends of the hexanucleotide repeat expansion sequence in C9orf72 humanized, 92×-repeat-containing ES cells (MAID8029a).
Figure 11A:
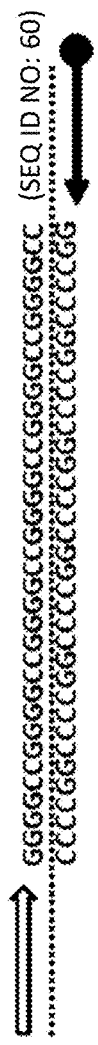
FIG. 11A (not to scale) shows a schematic of the conventional two-primer PCR used to assess the number of instances of the hexanucleotide sequence set forth in SEQ ID NO: 1 in the endogenous C9orf72 ES cell clones.
Figure 11B:
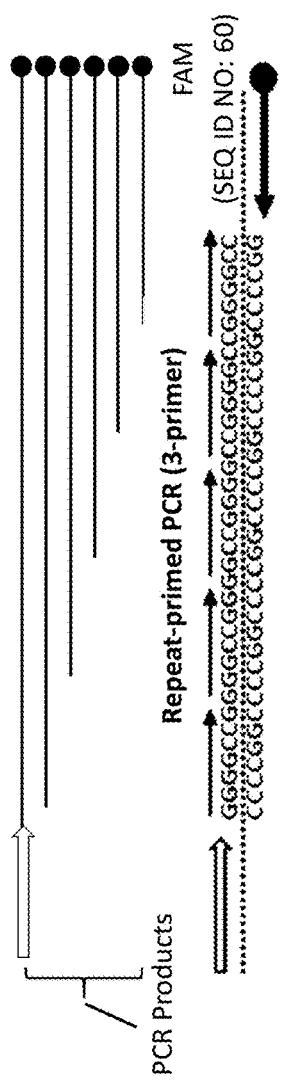
FIG. 11B (not to scale) shows a schematic of the prime PCR that uses three primers to assess the number of instances of the hexanucleotide sequence set forth in SEQ ID NO: 1 in the endogenous C9orf72 ES cell clones.
Figure 11B:
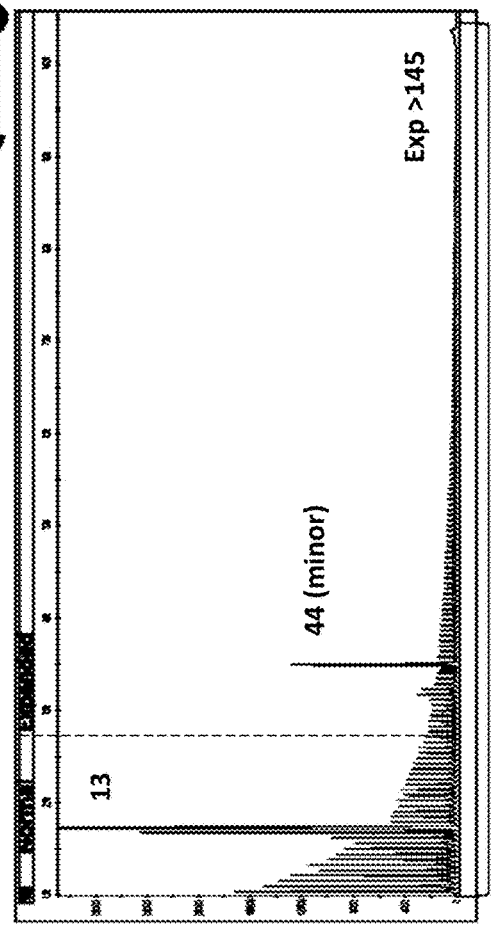

| SEQ ID NO | Type | Description |
|---|---|---|
| 16 | Protein | *Homo sapiens* C9ORF72 Amino Acid (NP_060795.1) |
| 17 | DNA | *Homo sapiens* C9ORF72 mRNA (NM_001256054.2) |
| 18 | Protein | *Homo sapiens* C9ORF72 Amino Acid (NP_001242983.1) |
| 19 | RNA | crRNA Tail |
| 20 | RNA | TracrRNA |
| 21 | RNA | gRNA Scaffold v1 |
| 22 | RNA | gRNA Scaffold v2 |
| 23 | RNA | gRNA Scaffold v3 |
| 24 | RNA | gRNA Scaffold v4 |
| 25 | DNA | Generic Guide RNA Target Sequence Plus PAM v1 |
| 26 | DNA | Generic Guide RNA Target Sequence Plus PAM v2 |
| 27 | DNA | Generic Guide RNA Target Sequence Plus PAM v3 |
| 28 | DNA | 5'gRNA-1 Target Sequence |
| 29 | DNA | 5'gRNA-2 Target Sequence |
| 30 | DNA | 5'gRNA-3 Target Sequence |
| 31 | DNA | 5'gRNA-4 Target Sequence |
| 32 | DNA | 3'gRNA-1 Target Sequence |
| 33 | DNA | 3'gRNA-2 Target Sequence |
| 34 | DNA | 3'gRNA-3 Target Sequence |
| 35 | DNA | 3'gRNA-4 Target Sequence |
| 36 | DNA | 2-Primer Fwd |
| 37 | DNA | 2-Primer Rev |
| 38 | DNA | Locked Nucleic Acid (LNA) Sense RNA Probe |
| 39 | DNA | Locked Nucleic Acid (LNA) Antisense RNA Probe |
| 40 | DNA | *Mus musculus* C9orf72 mRNA (NM_001081343.1) |
| 41 | Protein | *Mus musculus* C9ORF72 Amino Acid (NP_001074812.1) |
| 42 | DNA | *Rattus norvegicus* C9orf72 mRNA (NM_001007702.1) |
| 43 | Protein | *Rattus norvegicus* C9ORF72 Amino Acid (NP_001007703.1) |
| 44 | DNA | DNA Sense Probe |
| 45 | DNA | DNA Antisense Probe |
| 46 | DNA | Human 5' Flanking Sequence |
| 47 | DNA | Human 3' Flanking Sequence |
| 48 | DNA | Sequence 1 from FIG. 2 |
| 49 | DNA | Sequence 2 from FIG. 2 |
| 50 | DNA | Sequence 3 from FIG. 2 |
| 51 | DNA | Sequence 4 from FIG. 2 |
| 52 | DNA | gRNA_5side_repeat_2 from FIG. 3 |
| 53 | DNA | gRNA_3side_repeat_1 from FIG. 3 |
| 54 | DNA | gRNA_3side_repeat_3 from FIG. 3 |
| 55 | DNA | gRNA_3side_repeat_4 from FIG. 3 |
| 56 | RNA | 5' gRNA-1 crRNA |
| 57 | RNA | 5' gRNA-2 crRNA |
| 58 | DNA | 5' Target Locus from FIG. 3 |
| 59 | DNA | 3' Target Locus from FIG. 3 |
| 60 | DNA | Sequence from FIGS. 11A and 11B |
| 61 | DNA | Analysis A-Forward Primer |
| 62 | DNA | Analysis A-Reverse Primer |
| 63 | DNA | Analysis A-Probe |
| 64 | DNA | Analysis B-Forward Primer |
| 65 | DNA | Analysis B-Reverse Primer |
| 66 | DNA | Analysis B-Probe |
| 67 | DNA | Analysis D-Forward Primer |
| 68 | DNA | Analysis D-Reverse Primer |
| 69 | DNA | Analysis D-Probe |
| 70 | DNA | Analysis G-Forward Primer |
| 71 | DNA | Analysis G-Reverse Primer |
| 72 | DNA | Analysis G-Probe |
| 73 | DNA | Analysis H-Forward Primer |
| 74 | DNA | Analysis H-Reverse Primer |
| 75 | DNA | Analysis H-Probe |
| 76 | RNA | 5' gRNA-3 crRNA |
| 77 | RNA | 5' gRNA-4 crRNA |
| 78 | RNA | 3' gRNA-1 crRNA |
| 79 | RNA | 3' gRNA-2 crRNA |
| 80 | RNA | 3' gRNA-3 crRNA |
| 81 | RNA | 3' gRNA-4 crRNA |
| 82 | RNA | TracrRNA v2 |
| 83 | RNA | crRNA Tail v2 |
| 84 | RNA | 5'-gRNA-1 Guide Sequence |
| 85 | RNA | 5'-gRNA-2 Guide Sequence |
| 86 | RNA | 5'-gRNA-3 Guide Sequence |
| 87 | RNA | 5'-gRNA-4 Guide Sequence |
| 88 | RNA | 3'-gRNA-1 Guide Sequence |
| 89 | RNA | 3'-gRNA-2 Guide Sequence |
| 90 | RNA | 3'-gRNA-3 Guide Sequence |
| 91 | RNA | 3'-gRNA-4 Guide Sequence |

TABLE 3-continued

Description of Sequences.

| SEQ ID NO | Type | Description |
|---|---|---|
| 92 | DNA | Analysis C-Forward Primer |
| 93 | DNA | Analysis C-Reverse Primer |
| 94 | DNA | Analysis C-Probe |
| 95 | DNA | Analysis E-Forward Primer |
| 96 | DNA | Analysis E-Reverse Primer |
| 97 | DNA | Analysis E-Probe |
| 98 | DNA | Analysis F-Forward Primer |
| 99 | DNA | Analysis F-Reverse Primer |
| 100 | DNA | Analysis F-Probe |
| 101 | DNA | Analysis I-Forward Primer |
| 102 | DNA | Analysis I-Reverse Primer |
| 103 | DNA | Analysis I-Probe |
| 104 | DNA | Analysis J-Forward Primer |
| 105 | DNA | Analysis J-Reverse Primer |
| 106 | DNA | Analysis J-Probe |
| 107 | DNA | Parental Clone from FIG. 6C |
| 108 | DNA | Expanded Clone from FIG. 6C |
| 109 | DNA | Reference Sequence and WT-Cas9-Expanded Clone 1 from FIG. 17C |
| 110 | DNA | WT-Cas9-Expanded Clone 2 from FIG. 17C |
| 111 | DNA | WT-Cas9-Expanded Clone 3 from FIG. 17C |
| 112 | DNA | WT-Cas9-Expanded Clone 4 from FIG. 17C |
| 113 | DNA | WT-Cas9-Expanded Clone 5 from FIG. 17C |
| 114 | DNA | gRNA Target Sequence Plus PAM from FIG. 17C |
| 115 | DNA | Reference Sequence and Nickase-Expanded Clones from FIG. 17C |
| 116 | RNA | TracrRNA v3 |
| 117 | RNA | TracrRNA v4 |
| 118 | RNA | gRNA Scaffold v5 |
| 119 | RNA | gRNA Scaffold v6 |
| 120 | RNA | gRNA Scaffold v7 |
| 121 | DNA | Sequencing Primer |

EXAMPLES

Example 1. Hexanucleotide Repeat Expansion at the C9orf72 Gene Locus

Amyotrophic lateral sclerosis (ALS) is a progressive neurodegenerative disorder that causes motor neuron death, leading to paralysis. Five thousand people in the US are diagnosed with ALS each year. Ten percent of the disease is transmitted in families, and among this category the most common cause is GGGGCC (SEQ ID NO: 1) hexanucleotide repeat expansion at the C9ORF72 gene locus. Healthy individuals typically have less than 30 repeats, and affected patients often have more than 1000 copies of the repeat. The precise mechanism of how this long stretch of repeat causes disease has not yet been elucidated because of the lack of useful animal models. The high GC content in hexanucleotide repeat sequence makes it difficult to synthesize DNA fragments with the repeat as well as maintain the repeat in microorganisms. Therefore, preparing materials such as targeting vectors to generate transgenic animals is very challenging. This is one of the major reasons why few useful animal models for C9ORF72 repeat expansion type of ALS are available to date, and there is a strong need for better animal models in the field.

To bypass these difficult intermediate steps for targeting vector construction, we took an approach to expand a relatively shorter hexanucleotide repeat that is already inserted in the right location in the genome, rather than de novo targeting vector production and ES cell targeting. As a starting material for the repeat expansion, we used a heterozygous ES cell clone in which a part of the mouse C9orf72 gene locus was replaced with a human counterpart containing 92× repeats of the GGGGCC (SEQ ID NO: 1) hexanucleotide. See FIG. 1. We previously developed this allele. See US 2018/0094267 and WO 2018/064600, each of which is herein incorporated by reference in its entirety for all purposes.

When a DNA double-strand break (DSB) occurs in a mammalian cell chromosome, the cells recognize the DSB and repair the damage through either homologous recombination (HR) or a non-homologous recombination pathway such as non-homology end joining (NHEJ) or single-strand annealing (SSA). In HR, the damaged chromatid utilizes the non-damaged chromatid as a template for its repair. In this pathway, once a DSB occurs, the edges of the DSB are modified through many processes including 3' strand resection. The exposed 5' single strands are coated by multiple molecules of Rad51, and then the Rad51 filament begins to search for a homology sequence in the genome. The Rad51 filament is able to insert itself into double-stranded DNA where the exposed 5' single strand has homology. The invaded 5' strand initiates restoration using the very sequence where the Rad51 filament enters. The accuracy with which Rad51 filaments find a homology sequence is the key to preserving the correct DNA sequence. Our approach for expanding the repeat was based on the hypothesis that by introducing a DSB near the hexanucleotide repeat so that the exposed 5' strand contains only repetitive sequence, the Rad51 filament could enter into a wrong location, and we could mislead the homology search by the Rad51 filament leading to expansion or contraction of the repeat. See FIG. 2.

Specifically, the approach used herein was expanding an existing GGGGCC (SEQ ID NO: 1) hexanucleotide repeat at the C9orf72 intron 1 in humanized mouse embryonic stem cells by introducing a DSB near the end of the hexanucleotide repeat using a CRISPR/Cas9 nuclease. Several guide RNAs (gRNAs) were designed near the hexanucleotide repeat as close as possible to expose repetitive sequence at the 5' single strand after resection. See FIG. 3 and Table 4.

TABLE 4

C9ORF72 gRNA Target Sequences.

| Guide RNA | | SEQ ID NO |
|---|---|---|
| Target Sequence (Upstream of NGG PAM) | | |
| 5' gRNA-1 | GCTATGCGATCGCCGTCTCG | 28 |
| 5' gRNA-2 | CCCCGGCCCCGGCCCCGAGA | 29 |
| 5' gRNA-3 | CGCCGTCTCGGGGCCGGGGC | 30 |
| 5' gRNA-4 | CCGTCTCGGGGCCGGGGCCG | 31 |
| 3' gRNA-1 | CGGCCGGCCCTCGAGGGTCT | 32 |
| 3' gRNA-2 | GGCCGGGGCCGAGACCCTCG | 33 |
| 3' gRNA-3 | GAGGGTCTCGGCCCCGGCCC | 34 |
| 3' gRNA-4 | CTCGGCCCCGGCCCCGGCCC | 35 |
| Guide Sequence | | |
| 5' gRNA-1 | GCUAUGCGAUCGCCGUCUCG | 84 |
| 5' gRNA-2 | CCCCGGCCCCGGCCCCGAGA | 85 |
| 5' gRNA-3 | CGCCGUCUCGGGGCCGGGGC | 86 |
| 5' gRNA-4 | CCGUCUCGGGGCCGGGGCCG | 87 |
| 3' gRNA-1 | CGGCCGGCCCUCGAGGGUCU | 88 |
| 3' gRNA-2 | GGCCGGGGCCGAGACCCUCG | 89 |
| 3' gRNA-3 | GAGGGUCUCGGCCCCGGCCC | 90 |
| 3' gRNA-4 | CUCGGCCCCGGCCCCGGCCC | 91 |
| crRNA Sequence | | |
| 5' gRNA-1 | GCUAUGCGAUCGCCGUCUCGGUUUUAGAGCUAU GCUGUUUUG | 56 |
| 5' gRNA-2 | CCCCGGCCCCGGCCCCGAGAGUUUUAGAGCUAU GCUGUUUUG | 57 |
| 5' gRNA-3 | CGCCGUCUCGGGGCCGGGGCGUUUUAGAGCUAU GCUGUUUUG | 76 |
| 5' gRNA-4 | CCGUCUCGGGGCCGGGGCCGGUUUUAGAGCUAU GCUGUUUUG | 77 |
| 3' gRNA-1 | CGGCCGGCCCUCGAGGGUCUGUUUUAGAGCUAU GCUGUUUUG | 78 |
| 3' gRNA-2 | GGCCGGGGCCGAGACCCUCGGUUUUAGAGCUAU GCUGUUUUG | 79 |
| 3' gRNA-3 | GAGGGUCUCGGCCCCGGCCCGUUUUAGAGCUAU GCUGUUUUG | 80 |
| 3' gRNA-4 | CUCGGCCCCGGCCCCGGCCCGUUUUAGAGCUAU GCUGUUUUG | 81 |
| TracrRNA Sequence | | |
| All | GUUGGAACCAUUCAAAACAGCAUAGCAAGUUAA AAUAAGGCUAGUCCGUUAUCAACUUGAAAAAGU GGCACCGAGUCGGUGCUUUUUUU | 82 |

Figure 4:
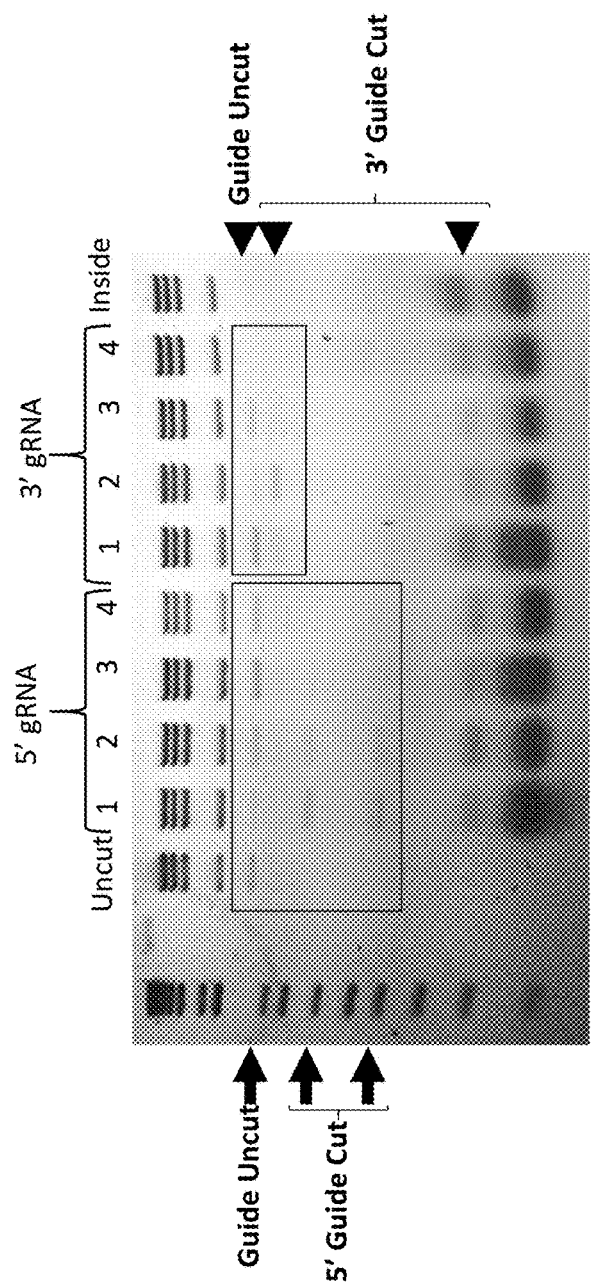
FIG. 4 shows the cleavage efficiency of the eight guide RNAs assessed in a cell-free system using a plasmid (8028 Stvec) that contains the same sequence as the humanized, 92×-repeat-containing allele (MAID8029a).

The goal was to obtain gRNAs that cleave as close as possible to the repeat and with high cleavage efficiency. DNA cleavage efficiency was tested in vitro using a plasmid (8028 Stvec) that contains the same sequence as the humanized, 92x-repeat-containing allele. The gRNAs with the highest cleavage efficiencies were chosen from both the 5' side and the 3' side of the repeat. These were 5' gRNA-1 and 3' gRNA-2. See FIG. 4.

In a first experiment, we introduced SpCas9 (*Streptococcus pyogenes* Cas9; Thermo Fisher) and gRNA into C9orf72 humanized, 30x-repeat-containing ES cells as an RNA and protein complex (RNP) by electroporation. As primer-PCR does not give us precise sequence information, and repeats more than ~90x are too long to sequence by Sanger sequencing, this experiment using the 30x-repeat allele was performed to characterize DNA sequences around the repeat region and the precise number of repeats by expanding 30x repeat.

Figure 5:
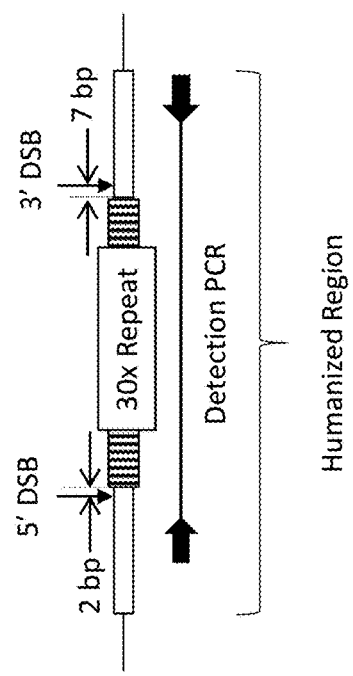
FIG. 5 (not to scale) shows a schematic of the scheme for expanding a 30× repeat in mouse embryonic stem (ES) cells by introducing a double-strand break (DSB) near the 5' end or near the 3' end of the 30× repeat expansion sequence. The humanized region is indicated by a label and the white boxes). The locations of the 5' DSB and the 3' DSB are indicated, along with the locations of the primers for detection by PCR. The distances between the 5' DSB and the 5' edge of the repeat sequence and between the 3' DSB and the 3' edge of the repeat sequence are indicated.
Figure 6A:
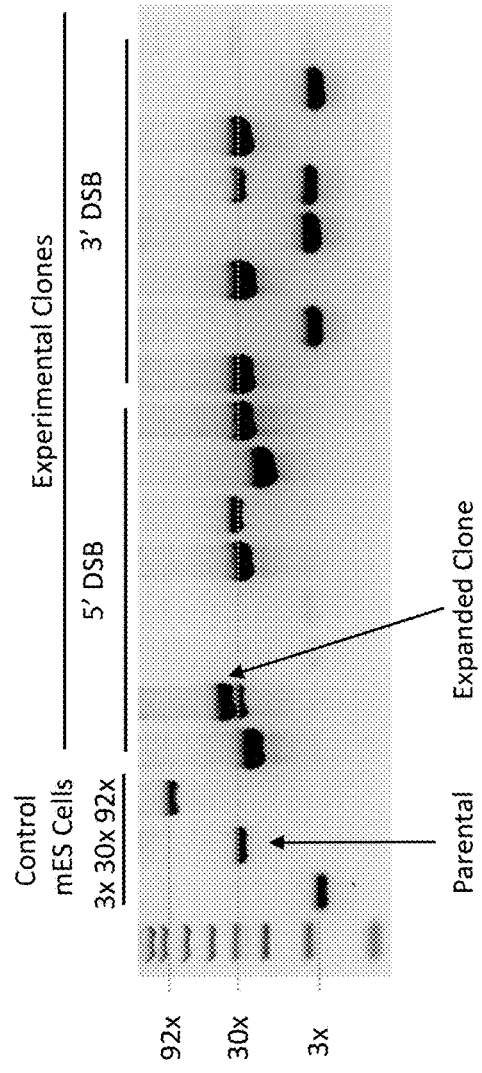
FIG. 6A shows the results of conventional PCR of the C9orf72 locus in mouse ES cells to assess the size of the repeat area following cleavage near the 5' end or near the 3' end of the 30× repeat expansion sequence. The parental clone and an expanded clone that was further analyzed are marked by arrows.
Figure 6B:
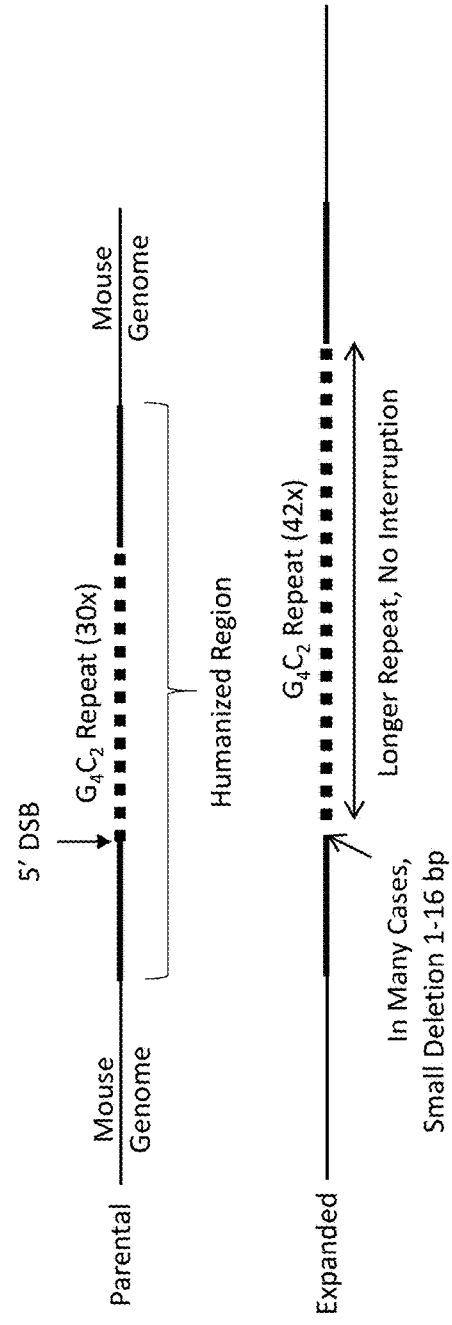
FIG. 6B (not to scale) shows a schematic comparing the parental 30× repeat clone to the expanded clone from FIG. 6A.
Figure 6C:
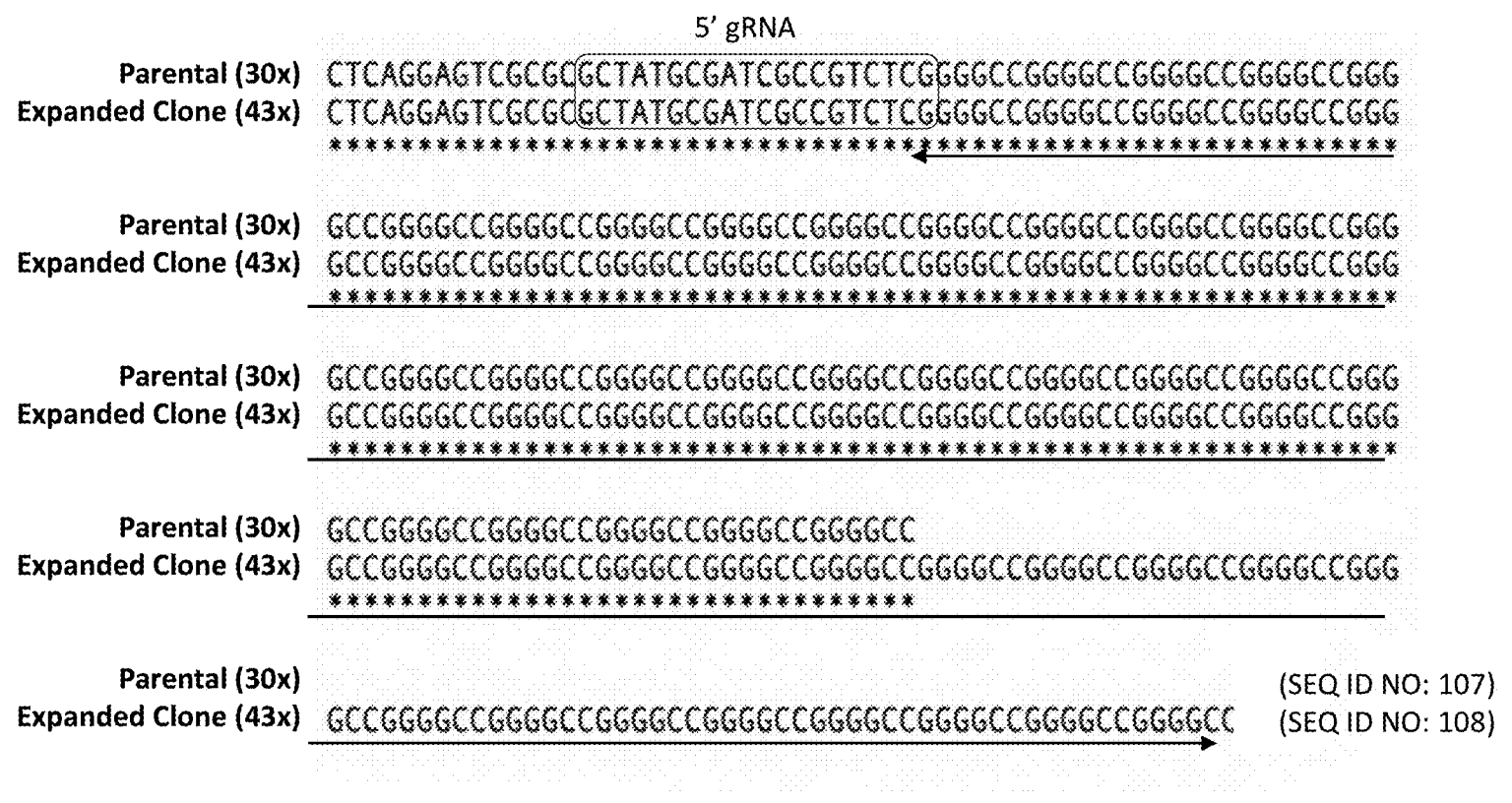

We tested introducing a single DSB at the 5' side of the repeat or a single DSB at the 3' side of the repeat using 5' gRNA-1 and 3' gRNA-2, respectively. See FIG. 5. Mouse ES cells in which C9orf72 was partially humanized and a 30xGGGGCC repeat was inserted were grown in VG ES medium. The cells received Cas9 and gRNA RNPs by electroporation. ES cell colonies were picked, the colonies were grown in a 96-well culture plate, and genomic DNA was purified for analysis. Conventional two-primer PCR of the C9orf72 locus was then performed to assess the size of the repeat area following cleavage near the 5' end of the 30x repeat expansion sequence or cleavage near the 3' end of the 30x repeat expansion sequence. The repeat size was primarily assessed using 2-primer PCR and running the amplicons on agarose gel. We picked a few clones each for expanded (>30x), retained (~30x), contracted (<30x), and collapsed (~3x), and a PCR amplicon that harbors the GGGGCC repeat region was sequenced. We confirmed that repeat number was changed as expected from agarose gel analysis. We also found that in most of the clones, even if the repeat size was same as original 30x on agarose gel, Cas9 treatment generated 1-15 bp deletions. The results are shown in FIGS. 6A-9B. As shown in FIG. 6A, the double-strand break upstream (5') of the 5' end repeat using 5' gRNA-1 triggered repeat expansion in the selected clone from 30x to 42x. See FIG. 6B. The sequence of the expanded clone compared to the sequence of the parental 30x clone is shown in FIG. 6C. This experiment showed that a double-strand break by Cas9 can expand a simple repeat sequence without interruption. This can occur with or without a small deletion at the double-strand break site, which can destroy the guide RNA target sequence. In some clones, a small deletion (e.g., 1-16 bp) was observed.

Figure 7A:
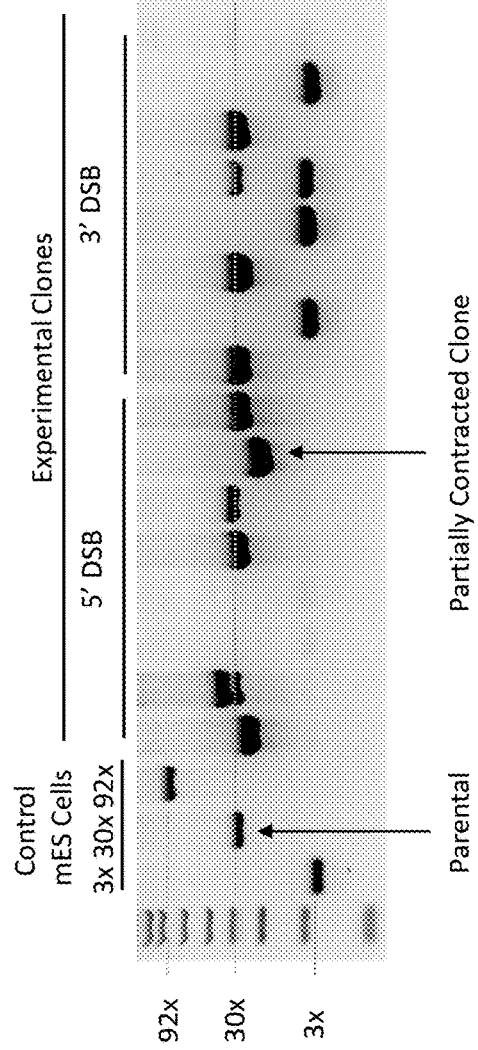
FIG. 7A shows the results of conventional PCR of the C9orf72 locus to assess the size of the repeat area following cleavage near the 5' end or near the 3' end of the 30× repeat expansion sequence in mouse ES cells. The parental clone and a partially contracted clone that was further analyzed are marked by arrows.
Figure 7B:
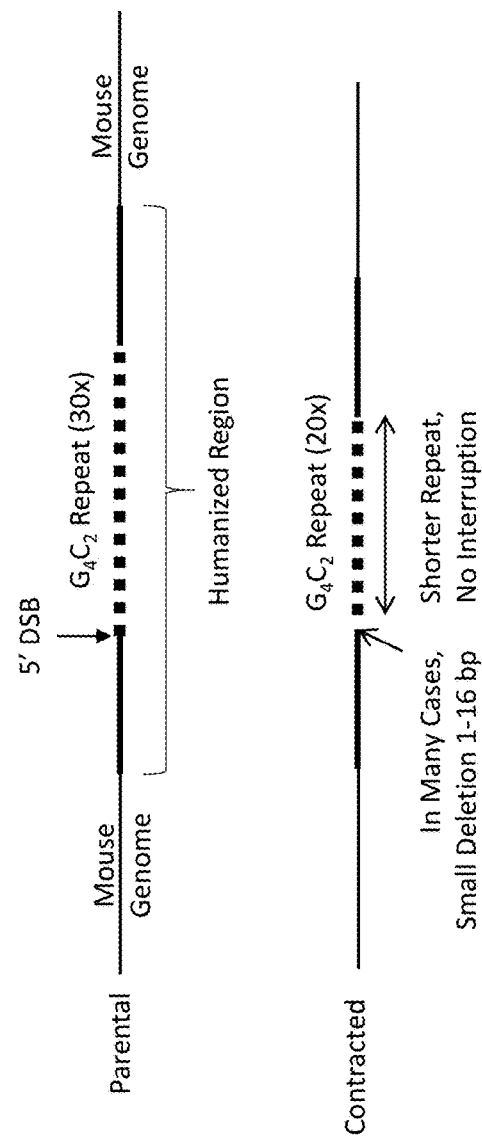
FIG. 7B (not to scale) shows a schematic comparing the parental 30× repeat clone to the partially contracted clone from FIG. 7A.

As shown in FIGS. 7A and 7B, a double-strand break upstream of the 5' end of the repeat sequence can also trigger partial repeat contraction without interruption in the repeat. Again, this can occur with or without a small deletion at the double-strand break site. The clone shown in FIGS. 7A and 7B contracted from 30 repeats to 20 repeats.

Figure 8A:
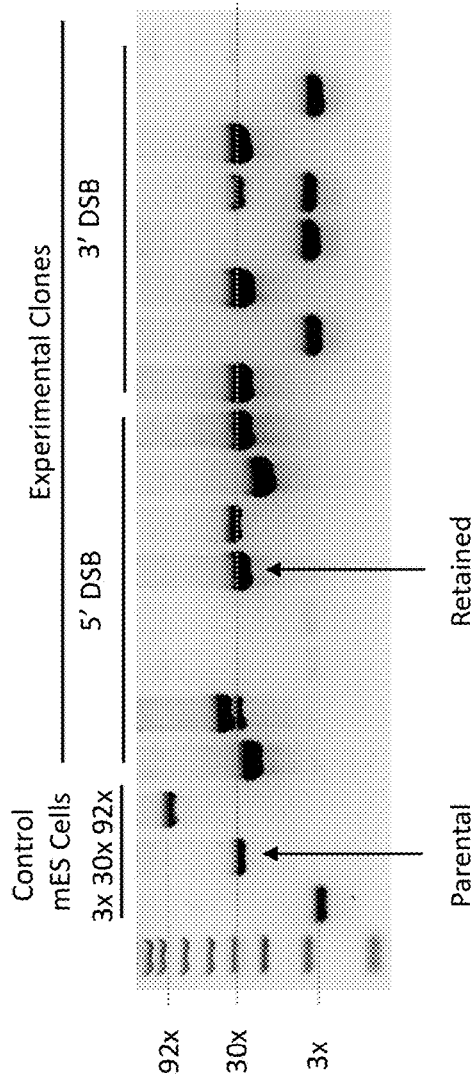
FIG. 8A shows the results of conventional PCR of the C9orf72 locus to assess the size of the repeat area following cleavage near the 5' end or near the 3' end of the 30× repeat expansion sequence in mouse ES cells. The parental clone and a clone retaining the 30× repeat sequence that was further analyzed are marked by arrows.
Figure 8B:
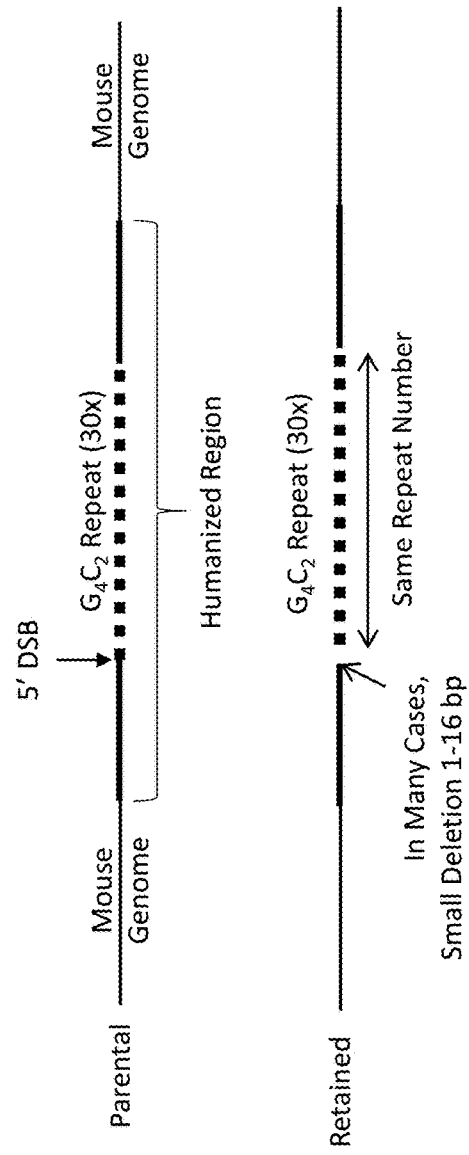
FIG. 8B (not to scale) shows a schematic comparing the parental 30× repeat clone to the clone retaining the 30× repeat sequence from FIG. 8A.

As shown in FIGS. 8A and 8B, some clones retain the same repeat number after cleavage upstream of the 5' end of the repeat sequence. Again, this can occur with or without a small deletion at the double-strand break site.

Figure 9A:
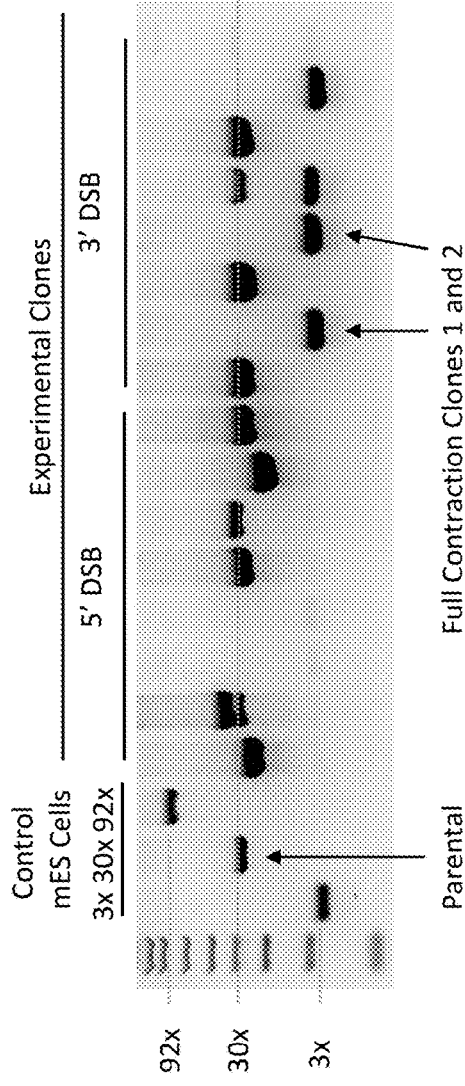
FIG. 9A shows the results of conventional PCR of the C9orf72 locus to assess the size of the repeat area following cleavage near the 5' end or near the 3' end of the 30× repeat expansion sequence in mouse ES cells. The parental clone and two contracted clones that were further analyzed are marked by arrows.
Figure 9B:
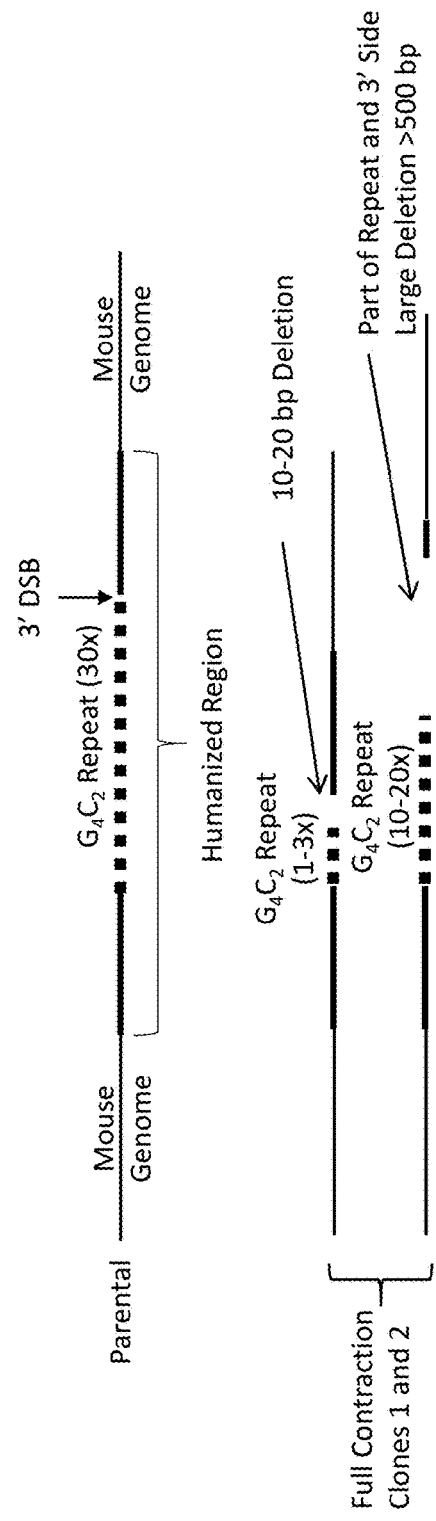
FIG. 9B (not to scale) shows a schematic comparing the parental 30× repeat clone to the contracted clones from FIG. 9A.

When introducing a double-strand break downstream (3') of the 3' end of the repeat using 3' gRNA-2, we frequently observed large deletions. Two such clones are shown in FIGS. 9A and 9B. In one clone, a 10-20 bp deletion was observed downstream of the repeat, and the repeat contracted from 30× to 1-3×. In another clone, the repeat was contracted from 30× to 10-20×, and a large deletion>500 bp was observed that included part of the repeat and sequence downstream (3' of the repeat).

Overall, we observed that the repeat expansion efficiency depends on the site of the double-strand break. Double-strand breaks upstream (5') of the 5' end of the repeat sequence induced repeat expansion more frequently than double-strand breaks downstream (3') of the 3' end of the repeat sequence. A summary of the data from the 30× parental clones is shown in Table 5.

TABLE 5

Assessment of Repeat Expansion or Contraction in 30× Repeat Parental Line.

| Rearrangement | Single 5' DSB (%) | Single 3' DSB (%) |
| --- | --- | --- |
| Expansion | 4.2 | 1.1 |
| Partial contraction | 8.3 | 2.3 |
| Retained | 50.0 | 21.6 |
| Full contraction | 0 | 61.4 |
| Not detected | 37.5 | 13.6 |
| Total | 100 | 100 |

Figure 10:
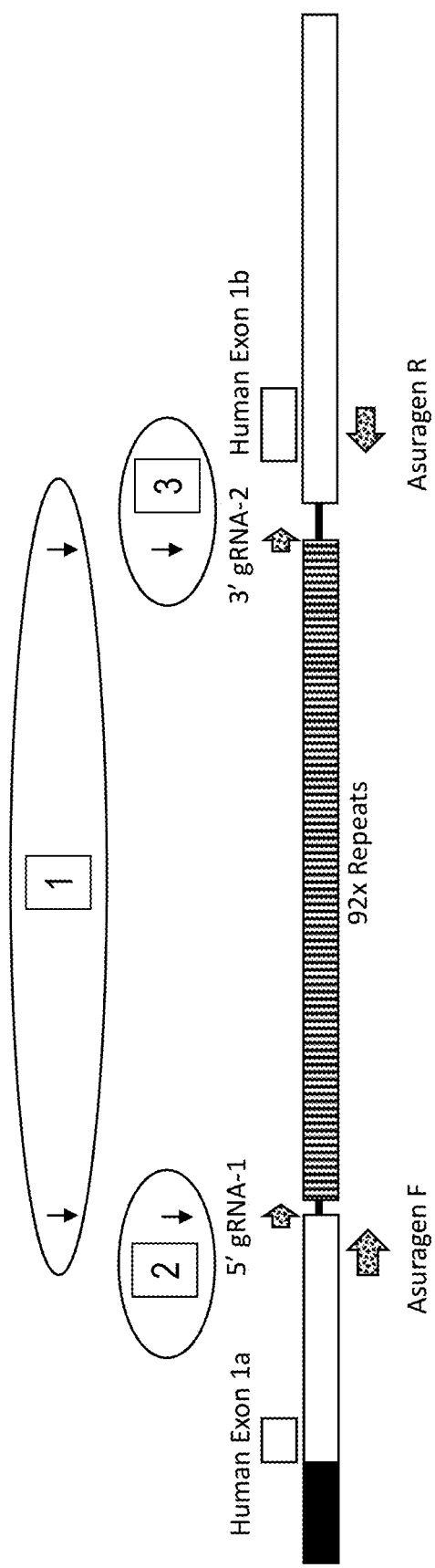
FIG. 10 (not to scale) shows a schematic of the scheme for expanding the 92× repeat by introducing a double-strand break near the 5' end (box 2), near the 3' end (box 3), or near both the 5' and 3' ends (box 1) of the 92× repeat expansion sequence in mouse ES cells. Black boxes indicate endogenous mouse sequence; white boxes indicate humanized regions.

We next tested the same thing in 92×-repeat-containing ES cells. To modify DNA in the ES cells, SpCas9 (*Streptococcus pyogenes* Cas9; Thermo Fisher) and gRNA were introduced into the C9orf72 humanized, 92×-repeat-containing ES cells (MAID8029a) as an RNA and protein complex (RNP) by electroporation. ES cell colonies were picked, the colonies were grown in a 96-well culture plate, and genomic DNA was purified for analysis. Three experiments were done: (1) introducing a single DSB at the 5' side of the repeat; (2) introducing a single DSB at the 3' side of the repeat; and (3) introducing DSBs at both the 5' and 3' sides of the repeat. See FIG. 10. The analysis was done using conventional two-primer PCR (FIG. 11A) and prime PCR that used three primers using an AmplideX PCR/CE C9orf72 kit (FIG. 11B). For prime PCR, genomic DNA from ES cells was used as the template. Three primers were used: a primer located 5' outside of the repeat, a primer located 3' outside of the repeat, and a third primer that anneals to the repetitive sequence inside the repeat as shown in FIG. 11B. This PCR reaction produces many different sizes of PCR product as shown in FIG. 11B. Because the third primer can prime the polymerase reaction in any given unit of the repeat, the number of PCR products obtained is basically the number of repeats the clone has. We ran these PCR products with capillary electrophoresis, which detects fluorescent signals (one of the primers is fluorescently labeled).

The AmplideX PCR/CE C9ORF72 Kit (Asuragen) was used according to the manufacturer's instructions to confirm the number of instances of the hexanucleotide sequence set forth as SEQ ID NO: 1 in the endogenous C9orf72 ES cell clones. Purified mESC genomic total DNA from a 3× repeat clone, a 92× repeat clone, and a 30× repeat clone was used as controls. PCR using the primers in Table 6 and a repeat-specific primer from the AmplideX PCR/CE C9ORF72 Kit was performed on an ABI 9700 thermal cycler (Thermo Fisher). Amplicons were sized by capillary electrophoresis on an ABI 3500xL GeneScan using POP-7 polymer (Thermo Fisher) and NuSieve agarose gels (Lonza). 2-log DNA ladder (New England BioLabs) molecular weight marker was loaded on agarose gels for comparison, and bands were visualized with SYBR Gold Nucleic Acid Stain (Thermo Fisher).

TABLE 6

Primers for PCR.

| Primer Name | Sequence | SEQ ID NO: |
| --- | --- | --- |
| 2-Primer Fwd | TGCGCCTCCGCCGCCGCGGGCGCAGGC ACCGCAACCGCA | 36 |
| 2-Primer Rev | CGCAGCCTGTAGCAAGCTCTGGAACTC AGGAGTCG | 37 |

Figures 12A, 12B:
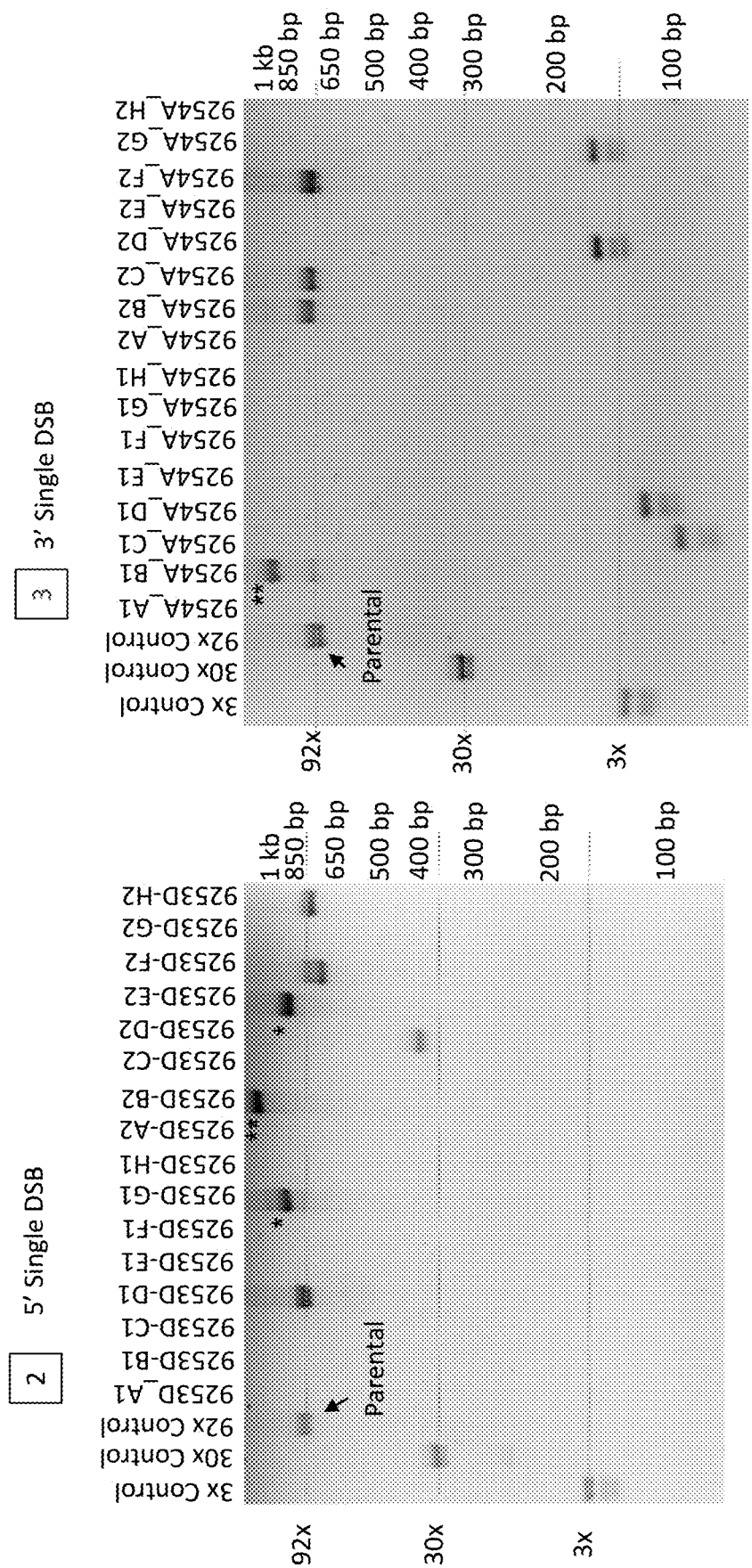
FIG. 12A shows the results of conventional PCR of the C9orf72 locus to assess the size of the repeat area following cleavage near the 5' end of the 92× repeat expansion sequence in mouse ES cells. Expanded repeats are marked by asterisks.
FIG. 12B shows the results of conventional PCR of the C9orf72 locus to assess the size of the repeat area following cleavage near the 3' end of the 92× repeat expansion sequence in mouse ES cells. Expanded repeats are marked by asterisks.
Figure 13:
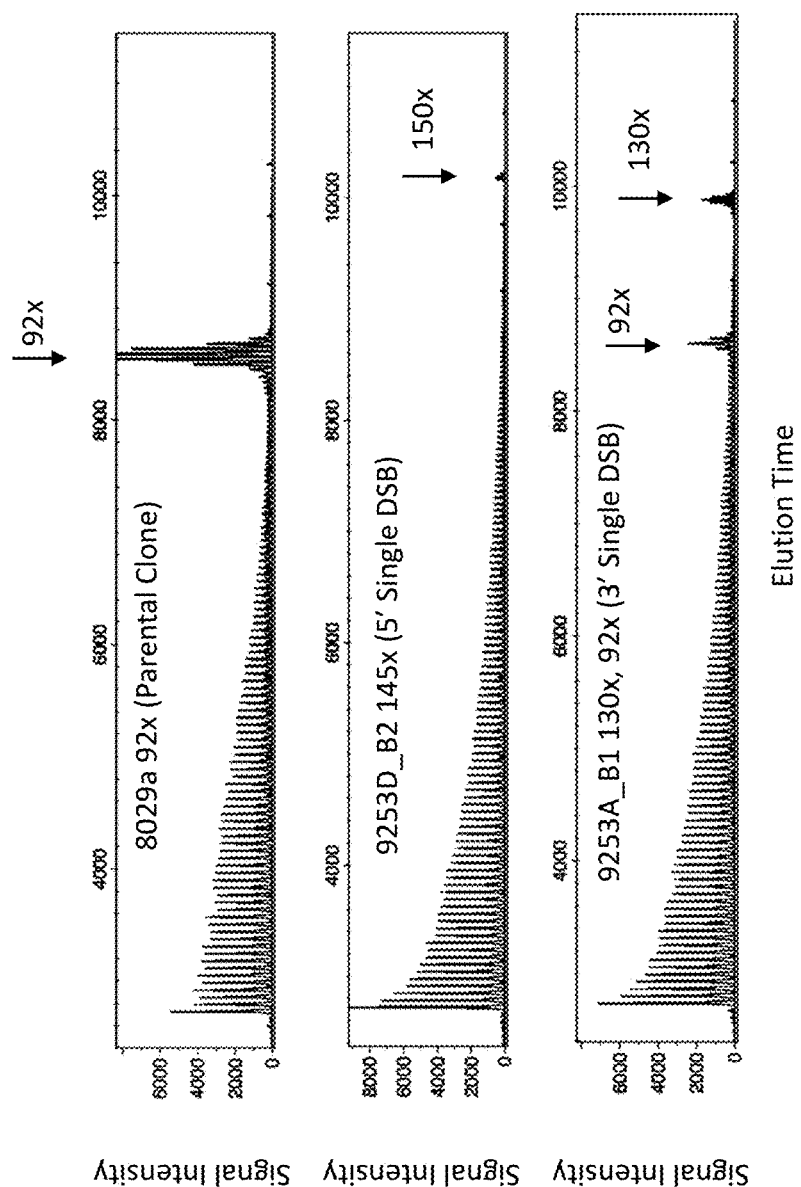
FIG. 13 shows the results of prime PCR to confirm the number of repeats in one of the clones from FIG. 12A and one of the clones from FIG. 12B. The parental 8029a (92× repeat) clone was used as a control. The figure shows results from capillary electrophoresis. Signal intensity is on the Y axis, and PCR product size is on the X axis. The readout is the number of peaks.
Figure 14:
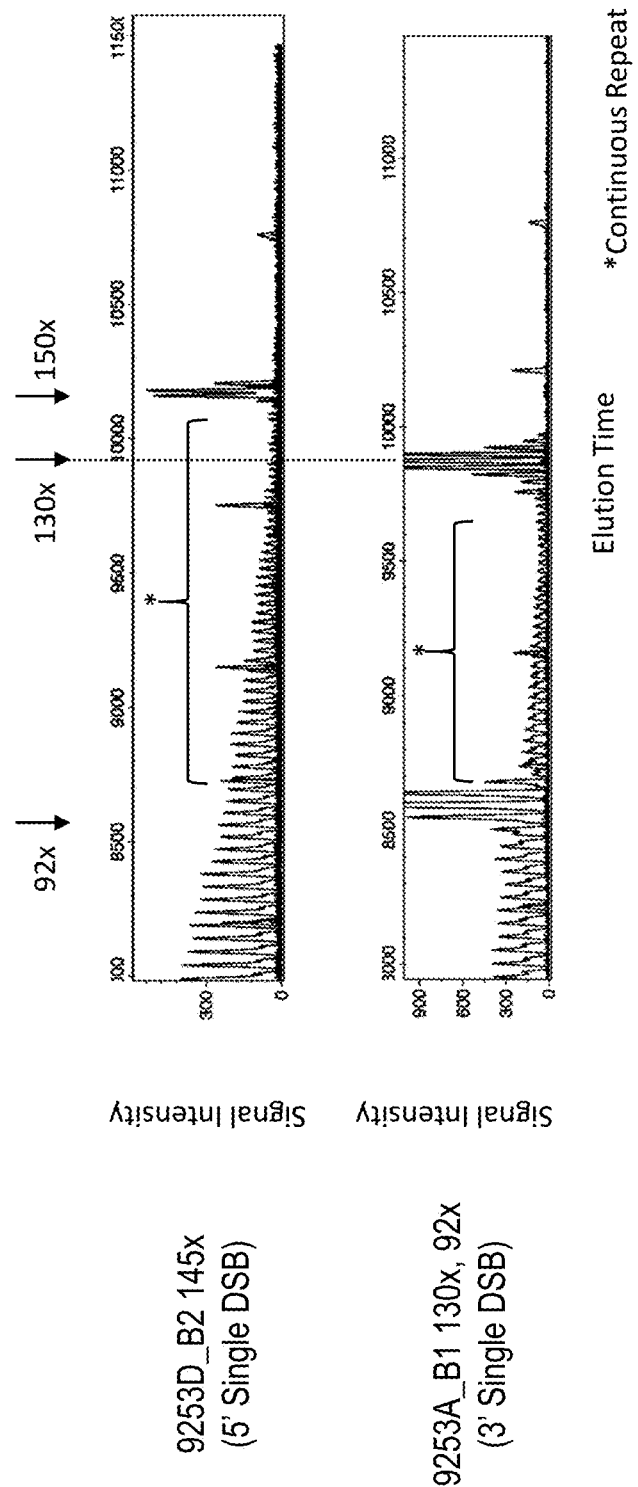
FIG. 14 shows the results of prime PCR to confirm the number of repeats in one of the clones from FIG. 12A and one of the clones from FIG. 12B.

Introducing a DSB at either side of the repeat resulted in size alteration at the repeat area as demonstrated using conventional two-primer PCR. See FIGS. 12A and 12B. Results for 16 out of 88 colonies for each condition are shown in FIGS. 12A and 12B. The 5' single DSB clone and the 3' single DSB clone with the largest expansions were chosen for further analysis using prime PCR to confirm repeat expansion. Prime PCR confirmed that clone 9253D-B2 (5' single DSB) had 145 repeat and that clone 9253A-B1 (3' single DSB) had 130 repeats and 92 repeats. See FIGS. 13 and 14. FIG. 13 shows results from capillary electrophoresis. Signal intensity is on the Y axis, and PCR product size is on the X axis. The readout is the number of peaks. The top panel is from the 92× parental clone, and there are 92 peaks. We counted 150 peaks in the middle panel and 130× peaks in the bottom panel. We observed two high peaks in the bottom panel. This is likely because the ES cell colonies we picked were not a homogenous clone.

Figure 15:
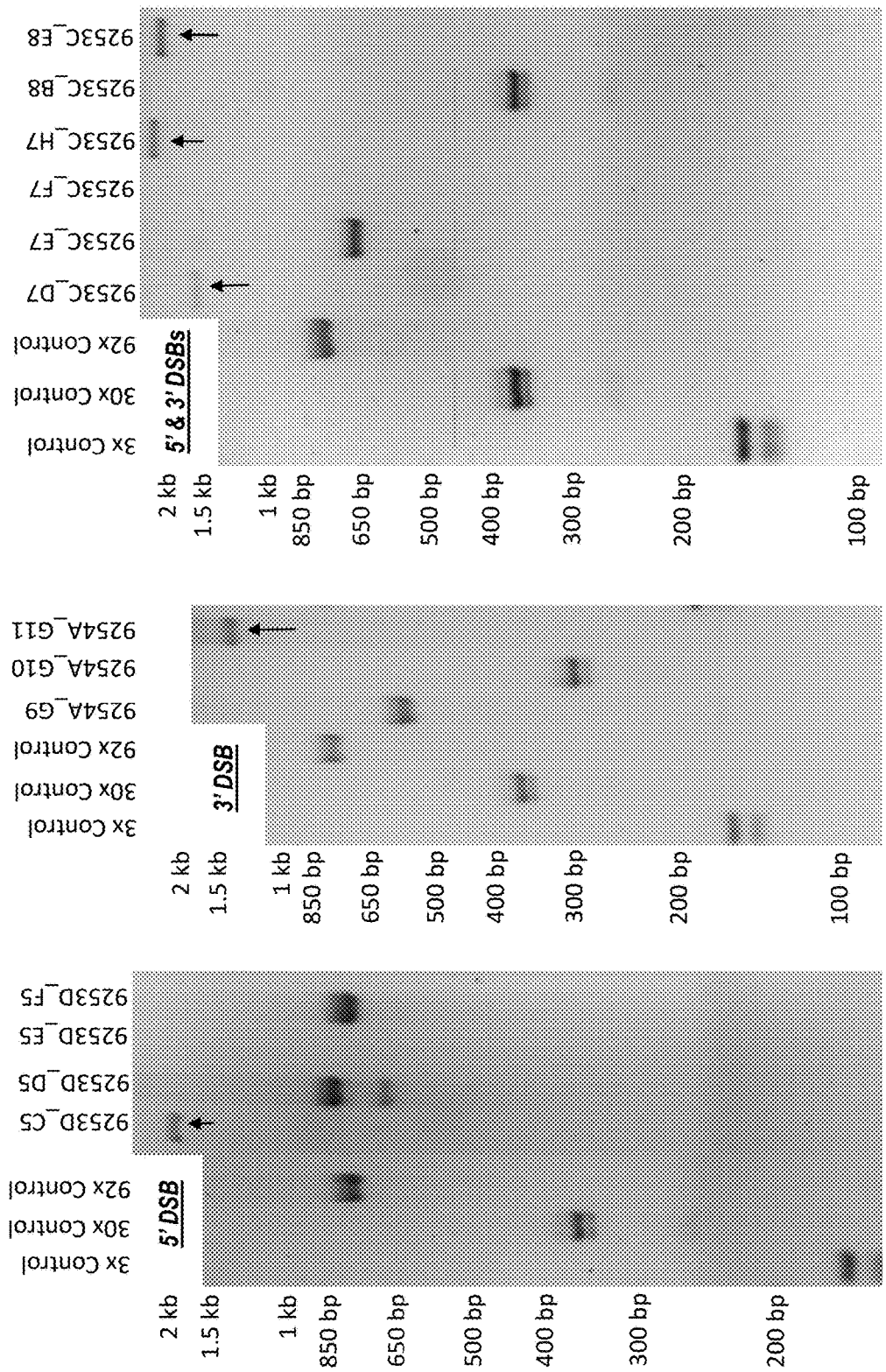
FIG. 15 shows the results of conventional PCR of the C9orf72 locus to assess the size of the repeat area following cleavage near the 5' end of the 92× repeat expansion sequence, cleavage near the 3' end of the 92× repeat expansion sequence, or cleavage near both the 5' and 3' ends of the 92× repeat expansion sequence in mouse ES cells. Expanded repeats are marked by arrows.

The same experiment was repeated again with similar results. See FIG. 15. For each condition (single 5' DSB, single 3' DSB, or both 5' and 3' DSBs), 88 clones were tested. DSBs at the repeat caused repeat instability. DSBs at either side or both sides of the repeat led to repeat expansion (from 92× up to ~300×). A complete analysis of the expansions or contractions in the different clones is provided in Table 7. Full contraction was called either by TAQMAN assay or Asuragen AmplideX PCR/CE C9ORF72 Kit. Overall, we observed that the repeat expansion efficiency depends on the starting repeat length in the parental clone. Repeat expansion was more frequently observed in parent clones having a greater starting repeat length, regardless of whether the double-strand breaks were induced upstream of the 5' side of the repeat sequence or downstream of the 3' side of the repeat sequence. See Table 6.

TABLE 7

Assessment of Repeat Expansion or Contraction after First Repeat Expansion.

|  | 92x Repeat | | | 30x Repeat | |
| --- | --- | --- | --- | --- | --- |
| Parental Line Rearrangement | 5' & 3' DSB (%) | Single 5' DSB (%) | Single 3' DSB (%) | Single 5' DSB (%) | Single 3' DSB (%) |
| Expansion (>750 bp = 92x) | 4.5 | 18.2 | 5.7 | 4.2 | 1.1 |
| Partial contraction (<750 bp, >200 bp) | 9.1 | 9.1 | 9.1 | 8.3 | 2.3 |
| Retained (750 bp) | 19.3 | 51.1 | 5.7 | 50.0 | 21.6 |
| Full contraction (<200 bp) | 46.6 | 0 | 53.4 | 0 | 61.4 |
| Not detected | 20.5 | 21.6 | 26.1 | 37.5 | 13.6 |
| Total | 100 | 100 | 100 | 100 | 100 |

Figure 16A:
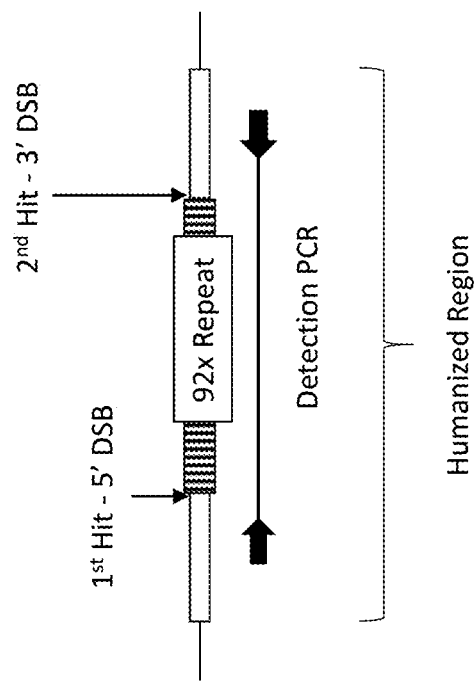
FIG. 16A (not to scale) shows a schematic of the scheme for expanding a 92× repeat in mouse ES cells by first introducing a double-strand break near the 5' end of the 92× repeat expansion sequence to generate a first expanded clone and then introducing a double-strand break near the 3' end of the repeat expansion sequence in the first expanded clone to generate a second expanded clone. The humanized region is indicated by a label and the white boxes). The locations of the 5' DSB and the 3' DSB are indicated, along with the locations of the primers for detection by PCR.
Figure 16B:
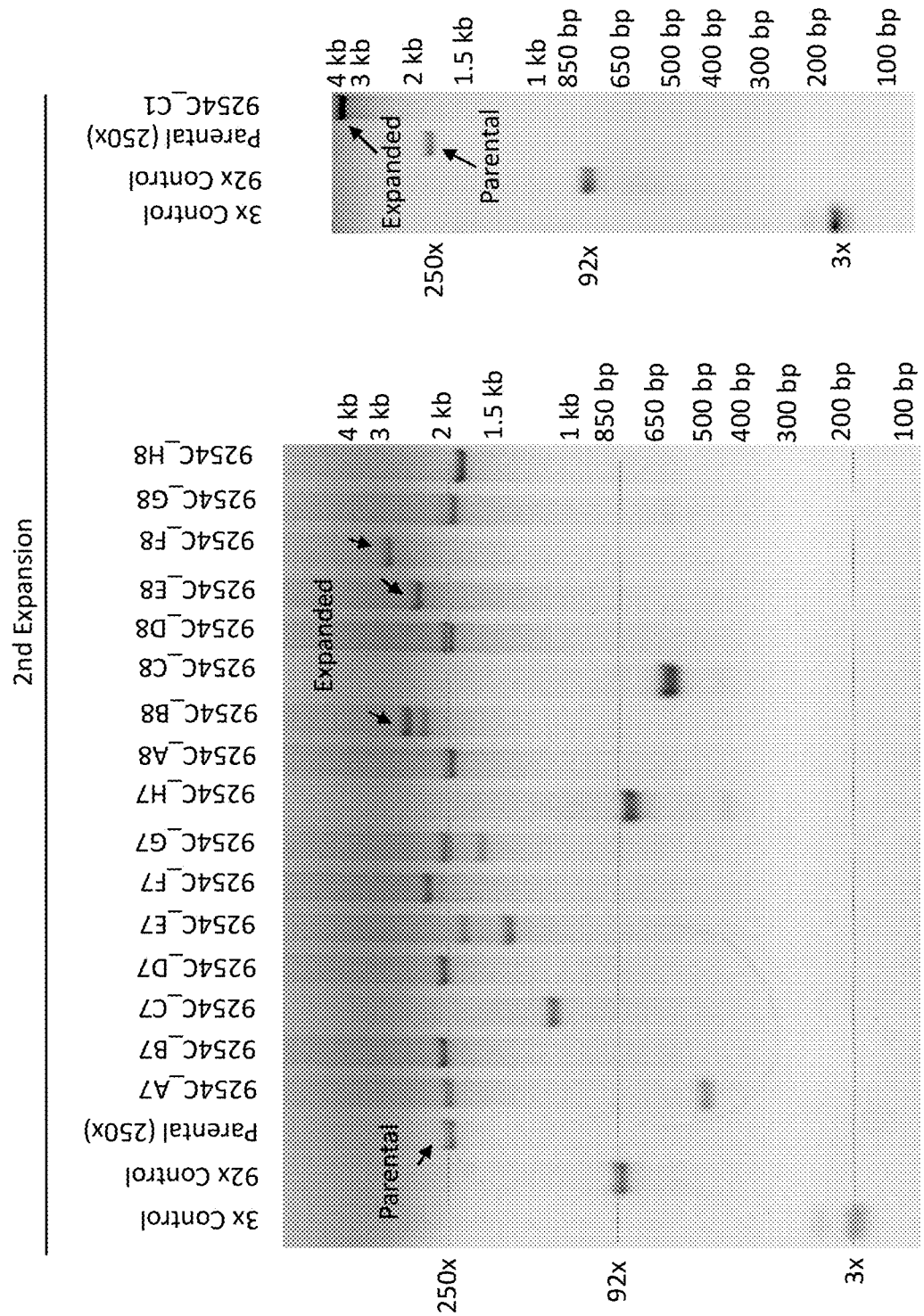
FIG. 16B shows the results of conventional PCR of the C9orf72 locus to assess the size of the repeat area following a second expansion after cleavage of a 250× repeat expansion sequence clone near the 3' end of the 250× repeat expansion sequence in mouse ES cells. Expanded repeats and parental repeats are marked by labeled arrows.

The biggest repeat was obtained by introducing both 5' and 3' DSBs together. The biggest repeat obtained by introducing a single DSB was approximately 250×, in which the 3' gRNA site was still intact and the repeat expandable. To further expand that repeat, we started with the 250× repeat clone (MAID9253D-C5) and introduced a DSB at the 3' end through introduction of the Cas9/gRNA RNP as described above. Using the 250× allele, we were able to further expand the repeat to approximately the size of ~600×. See FIGS. 16A and 16B and Table 8.

TABLE 8

Assessment of Repeat Expansion or Contraction after Second Repeat Expansion with Single 3' DSB.

| Parental clone | 8029, 92x (%) | 9253D-C5, 250x (%) |
| --- | --- | --- |
| Expansion (>parental clone) | 5.6 | 13.6 |
| Partial contraction (<parental clone, >200 bp) | 9.1 | 43.2 |
| Retained (=parental clone) | 5.6(28.4)* | 30.7(43.2)* |
| Full contraction (<200 bp) | 55.8 | 4.5 |
| Not detected | 27.3 | 2.3 |
| Total | 100 | 100 |

*Multiple bands observed

In summary, inducing double-strand breaks at the edge of the C9ORF72 hexanucleotide repeat sequence triggered repeat expansion in mouse ES cells. Repeat expansion occurred when the double-strand break was introduced either 5' side or 3' side, with different efficiency. In addition, double-strand-break-induced repeat expansion occurred more frequently when the starting repeat size was bigger. The repeat can be expanded at least twice, as long as the gRNA target sequence is intact, and we were able to expand the C9ORF72 hexanucleotide repeat sequence from 92× to approximately 600× in this manner.

Figure 17A:
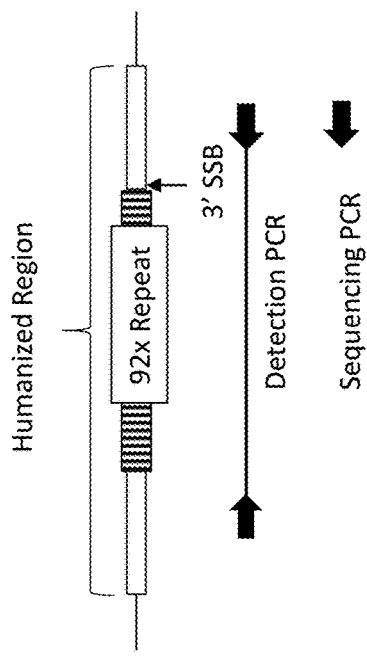
FIG. 17A (not to scale) shows a schematic of the scheme for expanding a 92× repeat by introducing a single-strand break near the 3' end of the 92× repeat expansion sequence in mouse ES cells. The humanized region is indicated by a label and the white boxes). The location of the 3' DSB is indicated, along with the locations of the primers for detection or sequencing by PCR.
Figure 17B:
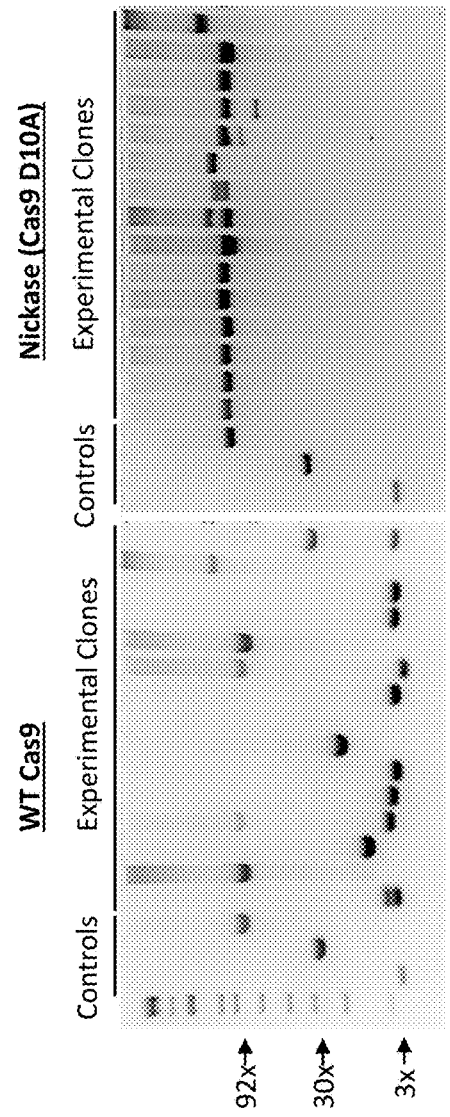
FIG. 17B shows the results of conventional PCR of the C9orf72 locus to assess the size of the repeat area following expansion after either cleaving or nicking of a 92× repeat expansion sequence clone near the 3' end of the 92× repeat expansion sequence in mouse ES cells.

We next assessed whether a single-strand break is sufficient to drive repeat expansion. To modify DNA in the ES cells, SpCas9 D10A purchased from Integrated DNA Technologies and gRNA (3' gRNA-2) were introduced into the C9orf72 humanized, 92×-repeat-containing ES cells (MAID8029a) as an RNA and protein complex (RNP) by electroporation. ES cell colonies were picked, the colonies were grown in a 96-well culture plate, and genomic DNA was purified for analysis. The analysis was done using conventional two-primer PCR as above. The experimental setup is shown in FIG. 17A, and the PCR results are shown in FIG. 17B. Like double-strand breaks, a single-strand break downstream (3') of the 3' end of the repeat region was able to trigger repeat expansion. In addition, unlike double-strand breaks, the single-strand break did not cause any large deletions (data not shown). We then performed sequencing PCR using a primer downstream (3') of the single-strand break (either the primer set forth in SEQ ID NO: 36 or the primer set forth in SEQ ID NO: 121. As shown in FIG. 17C, four out of five repeat-expanded clones generated using a Cas9 nuclease to create a double-strand break had deletions within the guide RNA target sequence and/or protospacer adjacent motif (PAM). In contrast, none of eight repeat-expanded clones generated using a Cas9 nickase to create a single-strand break had deletions in the guide RNA target sequence or PAM. Thus, the guide RNA target sequence could be reused for a second round of repeat expansion.

Figure 18A:
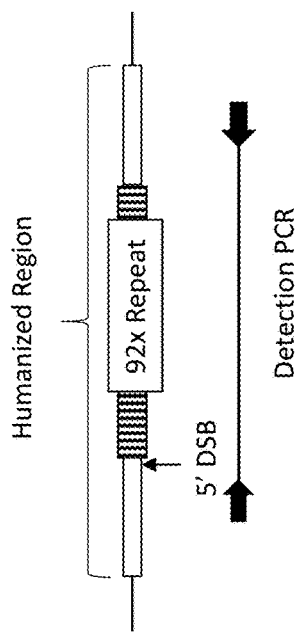
FIG. 18A (not to scale) shows a schematic of the scheme for expanding a 92× repeat in a mouse one-cell stage embryo by introducing a double-strand break (DSB) near the 5' end of the 92× repeat expansion sequence. The humanized region is indicated by a label and the white boxes). The location of the 5' DSB is indicated, along with the locations of the primers for detection by PCR.
Figure 18B:
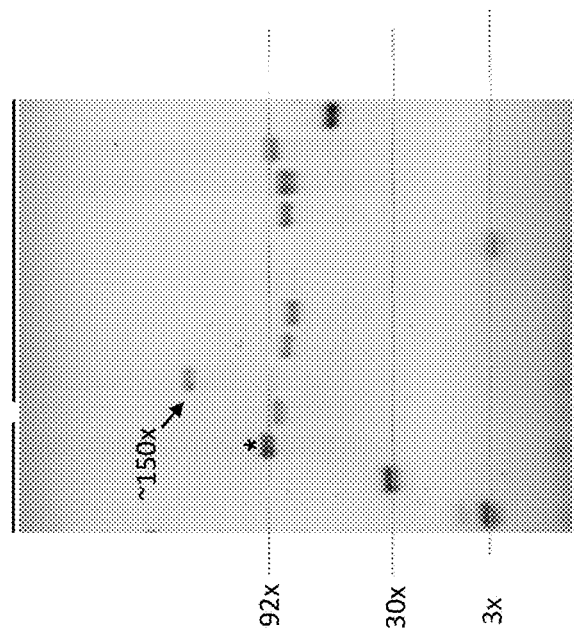
FIG. 18B shows the results of conventional PCR of the C9orf72 locus to assess the size of the repeat area following expansion in one-cell stage embryos and generation of mice after either cleaving of a 92× repeat expansion sequence in a mouse one-cell stage embryo near the 5' end of the 92× repeat expansion sequence.

We next assessed whether a double-strand break can drive repeat expansion in a mouse one-cell stage embryo. SpCas9 and gRNA (5' gRNA-1) were introduced into a C9orf72 humanized, 92×-repeat-containing mouse one-cell stage embryo as an RNA and protein complex (RNP) by pronuclear injection. Mice were generated from the one-cell stage embryos, and tail genomic DNA was collected. Analysis was done using conventional two-primer PCR as above. The experimental setup is shown in FIG. 18A, and the PCR results are shown in FIG. 18B. As with the mouse ES cells, a double-strand break upstream (5') of the 5' end of the repeat region was able to trigger repeat expansion. In one clone shown in FIG. 18B, the repeat region was expanded from 92 repeats to approximately 150 repeats.

Example 2. Trinucleotide Repeat Expansion

Hexanucleotide repeat expansion at the C9ORF72 gene locus is just one type of repeat expansion that occurs in neurologic diseases. Repeat expansions are known to occur in other genes in other neurologic diseases. These include, for example, trinucleotide repeats, tetranucleotide repeats, pentanucleotide repeats, other hexanucleotide repeats, and dodecanucleotide repeats.

Figure 19:
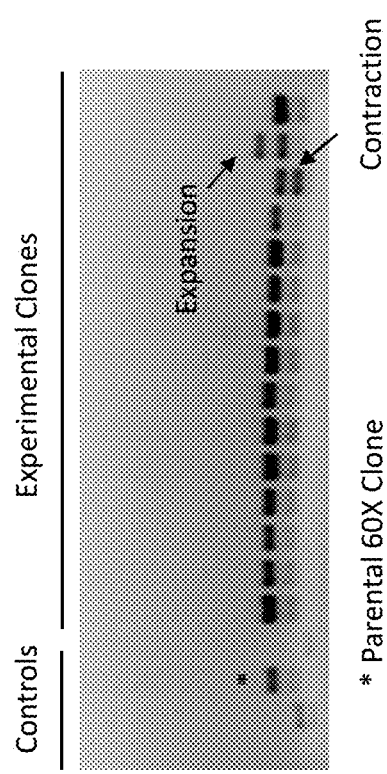
FIG. 19 shows the results of conventional PCR of a target gene locus to assess the size of the trinucleotide repeat area following expansion in mouse ES cells after either cleaving of a 60× repeat expansion sequence near the 5' end of the 60× repeat expansion sequence.

We next tested whether double-strand-break induced repeat expansion can occur at different loci with different repeat sequences. Specifically, we tested expansion of a trinucleotide repeat sequence in a second target gene that is not C9ORF72. The parental mouse ES cell clone contained 60 repeats of the trinucleotide sequence in the target gene. We designed a guide RNA to guide a Cas9 protein to cleave at a position 16 base pairs upstream (5') of the 5' end of the repeat sequence, and we designed a guide RNA to guide a Cas9 protein to cleave at a position 11 base pairs downstream (3') of the 3' end of the repeat sequence. SpCas9 and the 5' gRNA were introduced into the 60×-repeat-containing ES cells as an RNA and protein complex (RNP) by electroporation. The analysis was done using conventional two-primer PCR as above. The PCR results are shown in FIG. 19. As with the C9ORF72 hexanucleotide repeat expansion, a double-strand break upstream (5') of the 5' end of the 60× trinucleotide repeat region was able to trigger repeat expansion. In one clone shown in FIG. 19, the repeat region was expanded from 60 repeats to 85 repeats. This demonstrated that double-strand-break induced repeat expansion can occur at multiple gene loci and with multiple different types of repeats.

A summary of all the results from multiple experiments at different loci, in different cells, with different starting repeat numbers, using different Cas9 proteins (nuclease versus nickase), using different guide RNAs targeting different strands, using different Cas9 cleavage site locations, and using different cleavage site distances from the repeat is shown in Table 9.

genetically modified C9orf72 locus from Examples 1 and 2. The materials and methods are described below.

Additionally, RNA transcripts in mouse brain tissues and parental embryonic stem cells comprising a wildtype C9orf72 locus (control) or a genetically modified C9orf72 locus from Examples 1 and 2 are examined as described in US 2018/0094267 and WO 2018/064600, each of which is herein incorporated by reference in its entirety for all purposes. RNA foci and dipeptide repeat protein levels are evaluated in ESMNs derived from parental embryonic stem cells comprising a wildtype C9orf72 locus (control) or a genetically modified C9orf72 locus from Examples 1 and 2. The materials and methods are described below.

Embryonic-Stem-Cell-Derived Motor Neurons

Embryonic stem cells (ESCs) from Example 1 were cultured in embryonic stem cell medium (ESM; DMEM+ 15% fetal bovine serum+penicillin/streptomycin+glutamine+non-essential amino acids+nucleosides+β-mercapto-

TABLE 9

Repeat Expansion Frequency.

| Gene | Cells | Start Repeat # | Cas9 | gRNA | Cas9 Cleavage Site Location | Cleavage Site Distance from Repeat | Expansion Frequency* | Average Expanded Length** | Biggest Size Change |
|---|---|---|---|---|---|---|---|---|---|
| C9orf72 | ES cells | 250× | WT | Sense | 3' | 7 bp | 13% | 10% | ~600× |
| C9orf72 | ES cells | 92× | WT | Sense | 3' | 7 bp | 5-10% | 10% | ~150× |
| C9orf72 | ES cells | 92× | D10A | Sense | 3' | 7 bp | 10% | 5% | ~150× |
| C9orf72 | ES cells | 92× | WT | Sense | 5' | 2 bp | 8-20% | 10% | ~250× |
| C9orf72 | ES cells | 92× | WT | Sense | 5' | 100 bp | 0% | N/A | N/A |
| C9orf72 | ES cells | 92× | WT | Sense | 5' | 1000 bp | 0% | N/A | N/A |
| C9orf72 | ES cells | 92× | D10A | Sense | 5' | 2 bp | 10% | 5% | ~150 |
| C9orf72 | ES cells | 30× | WT | Sense | 3' | 7 bp | 0% | N/A | N/A |
| C9orf72 | ES cells | 30× | WT | Sense | 5' | 2 bp | 4-5% | 30% | 60× |
| C9orf72 | ES cells | 30× | D10A | Sense | 5' | 2 bp | 0% | N/A | N/A |
| C9orf72 | Embryo | 92× | WT | Sense | 5' | 2 bp | 1-2%*** | 50% | 150× |
| C9orf72 | Embryo | 92× | WT | Sense | 3' | 7 bp | Less than 1% | 10% | 100× |
| Tri-nucleotide repeat target gene | ES cells | 60× | WT | Sense | 5' | 16 bp | 2-3% | 33% | 85× |
| Tri-nucleotide repeat target gene | ES cells | 60× | WT | Antisense | 3' | 11 bp**** | 0% | N/A | N/A |

*How often repeat expansion observed (#expanded clone/#screened clones) × 100
**Average size change when expanded (average expanded size/starting size) × 100
***Highly mosaic
****Highly repetitive region Example 3. Analysis of Motor Neurons or Brain Tissues Comprising Hexanucleotide Repeat Expansion at the C9orf72 Gene Locus The stability of the size of the hexanucleotide repeat in the mice is confirmed using AmplideX PCR/CE C9ORF72 Kit (Asuragen) as described above.

RNA transcripts in mouse embryonic-stem-cell-derived motor neurons (ESMNs) comprising a wildtype C9orf72 locus (control) or a genetically modified C9orf72 locus from Examples 1 and 2 were examined as described in US 2018/0094267 and WO 2018/064600, each of which is herein incorporated by reference in its entirety for all purposes. RNA foci and dipeptide repeat protein levels were evaluated in ESMNs derived from parental embryonic stem cells comprising a wildtype C9orf72 locus (control) or a ethanol+sodium pyruvate+LIF) for 2 days, during which the medium was changed daily. ES medium was replaced with 7 mL of ADFNK medium (advanced DMEM/F12+neurobasal medium+10% knockout serum+penicillin/streptomycin+glutamine+β-mercaptoethanol) 1 hour before trypsinization. ADFNK medium was aspirated, and ESCs were trypsinized with 0.05% trypsin-EDTA. Pelleted cells were resuspended in 12 mL of ADFNK and grown for two days in suspension. Cells were cultured for a further 4 days in ADFNK supplemented with retinoic acid (RA), smoothened agonist, and purmorphamine to obtain limb-like motor neurons (ESMNs). Dissociated motor neurons were plated and matured in embryonic-stem-cell-derived motor neuron medium (ESMN; neurobasal medium+2% horse serum+ B27+glutamine+penicillin/streptomycin+β-mercaptoethanol+10 ng/mL GDNF, BDNF, CNTF).

Quantitative Polymerase Chain Reaction

Total RNA from each sample was extracted and reverse transcribed using primers that flank various regions and probes that detect those regions of the modified C9orf72 locus. Detectable regions include those that span the junction of mouse and human sequences, only human sequences, or only mouse sequences. qPCR of GAPDH, DROSHA, or β2-microglobulin was performed using probes and primers of readily available kits.

Specifically, RNA was isolated from embryonic-stem-cell-derived motor neurons (ESMN) comprising a wild type (WT) C9orf72 locus (control) or a genetically modified C9orf72 locus. In other experiments, RNA is also isolated from parental embryonic stem (ES) cells or total brains isolated from mice comprising a wild type (WT) C9orf72 locus (control) or a genetically modified C9orf72 locus.

Total RNA was isolated using Direct-zol RNA Miniprep plus kit according to the manufacturer's protocol (Zymo Research). Total RNA was treated with DNase using Turbo DNA-free kit according to the manufacturer's protocol (Invitrogen) and diluted to 20 ng/µL. Reverse transcription (RT) and PCR were performed in a one-step reaction with Quantitect Probe RT-PCR kit (Qiagen). The qRT-PCR reaction contained 2 µL RNA and 8 µL mixture containing RT-PCR Master mix, ROX dye, RT-mix, and 20× gene specific primer-probe mix to make a final volume of 10 µL.

Unless otherwise noted, final primer and probe concentrations were 0.5 µM and 0.25 µM, respectively. qRT-PCR was performed on a ViiA™ 7 Real-Time PCR Detection System (ThermoFisher). PCR reactions were done in quadruplicates with RT-step at 45° C. 10 min followed by 95° C. 10 min and 2-step cycling 95° C. 5 s, 60° C. 30 s for 45 cycles in an optical 384-well plate. The sequences of the primers and probes and SEQ ID NO used in each analysis (A, B, C, D, E, F, G, H, I, and J) are provided in Table 10.

TABLE 10

Primers and Probes.

Analysis A

| | | |
|---|---|---|
| Forward Primer | CATCCCAATTGCCCTTTCC | (SEQ ID NO: 61) |
| Reverse Primer | CCCACACCTGCTCTTGCTAGA | (SEQ ID NO: 62) |
| Probe | TCTAGGTGGAAAGTGGG | (SEQ ID NO: 63) |

Analysis B

| | | |
|---|---|---|
| Forward Primer | GAGCAGGTGTGGGTTTAGGA | (SEQ ID NO: 64) |
| Reverse Primer | CCAGGTCTCACTGCATTCCA | (SEQ ID NO: 65) |
| Probe | ATTGCAAGCGTTCGGATAATGTGAGA | (SEQ ID NO: 66) |

Analysis C

| | | |
|---|---|---|
| Forward Primer | GATAGTCGACATCCCTGCATC | (SEQ ID NO: 92) |
| Reverse Primer | GGTGGCGAGTGGCTATTG | (SEQ ID NO: 93) |
| Probe | AAGCGTTCGGATAATGTGAGACCTGG | (SEQ ID NO: 94) |

TABLE 10-continued

Primers and Probes.

Analysis D

| | | |
|---|---|---|
| Forward Primer | GCTGTCACGAAGGCTTTCTTC | (SEQ ID NO: 67) |
| Reverse Primer | GCACTGCTGCCAACTACAAC | (SEQ ID NO: 68) |
| Probe | TCAATGCCATCAGCTCACACCTGC | (SEQ ID NO: 69) |

Analysis E

| | | |
|---|---|---|
| Forward Primer | TCTCACAGTACTCGCTGAGGGTGA | (SEQ ID NO: 95) |
| Reverse Primer | AAGAGCAGGTGTGGGTTTAG | (SEQ ID NO: 96) |
| Probe | CGGTTGTTTCCCTCCTTGT | (SEQ ID NO: 97) |

Analysis F

| | | |
|---|---|---|
| Forward Primer | CCCACTACTTGCTCTCACAG | (SEQ ID NO: 98) |
| Reverse Primer | TACAGGCTGCGGTTGTTT | (SEQ ID NO: 99) |
| Probe | ACTCGCTGAGGGTGAACAAGAAA | (SEQ ID NO: 100) |

Analysis G

| | | |
|---|---|---|
| Forward Primer | AAGAGGCGCGGGTAGAA | (SEQ ID NO: 70) |
| Reverse Primer | CAGCTTCGGTCAGAGAAATGAG | (SEQ ID NO: 71) |
| Probe | CTCTCCTCAGAGCTCGACGCATTT | (SEQ ID NO: 72) |

Analysis H

| | | |
|---|---|---|
| Forward Primer | CTGCACAATTTCAGCCCAAG | (SEQ ID NO: 73) |
| Reverse Primer | CAGGTCATGTCCCACAGAAT | (SEQ ID NO: 74) |
| Probe | CATATGAGGGCAGCAATGCAAGTC | (SEQ ID NO: 75) |

Analysis I

| | | |
|---|---|---|
| Forward Primer | CGAGTGGGTGAGTGAGGA | (SEQ ID NO: 101) |
| Reverse Primer | TTCTACCCGCGCCTCTT | (SEQ ID NO: 102) |
| Probe | ATCCTGGCGGGTGGCTGTTT | (SEQ ID NO: 103) |

Analysis J

| | | |
|---|---|---|
| Forward Primer | CGGATAATGTGAGACCTGGAAT | (SEQ ID NO: 104) |
| Reverse Primer | AAAGGTAGCCGCCAACAA | (SEQ ID NO: 105) |
| Probe | ACCATCTCCTGCTGTTGCCAAGA | (SEQ ID NO: 106) |

Western Blot Analysis

Differentiated embryoid bodies (EBs) were collected and homogenized in SDS sample buffer (2% SDS, 10% glycerol, 5% β-mercaptoethanol, 60 mM TrisHCl, pH 6.8, bromophenol blue). Protein extracts were quantified using the RC DC protein assay (BioRad). Extracts (10 µg) were run on a 4-20% SDS-PAGE gel (ThermoFisher) and transferred onto a nitrocellulose membrane using an iBLOT transfer unit (ThermoFisher). Immunoblots were probed with primary antibodies against C9ORF72 and GAPDH (Millipore). Bound antibody was detected by incubation with secondary antibodies conjugated to horseradish peroxidase (Abcam) followed by chemiluminescence using a SuperSignal West Pico chemiluminescent substrate (Thermo Scientific). Signal was detected by autoradiography using Full Speed Blue sensitive medical X-Ray film (Ewen Parker XRay Corporation). Relative protein levels were calculated using ImageJ. Data not shown.

Fluorescent In Situ Hybridization (FISH) for Detection of Sense or Antisense RNA Transcription Products Fluorescent in situ hybridization (FISH) was used to determine the location of RNA transcribed from the hexanucleotide repeat sequence set forth as SEQ ID NO: 1 in embryonic-stem-cell-derived motor neurons (ESMNs) generated as described above. Briefly, ESMNs were grown in four-well chamber slides (Lab-Tek II chamber slide system, ThermoFisher Scientific) and fixed with 4% PFA (Electron Microscopy Sciences) in PBS. Cells were then permeabilized with diethyl pyrocarbonate (DEPC) PBS/0.2% Triton X-100 (Fisher Scientific, catalog #BP151) and washed with DEPC-PBS, blocked and stained with LNA oligonucleotides for the detection of RNA transcription products, as described below. After staining, slides were subsequently incubated with an appropriate fluorescent dye, mounted with Fluoromount G (Southern Biotech) and visualized using confocal microscopy.

Slides were pre-hybridized with buffer consisting of 50% formamide (IBI Scientific, catalog #IB72020), DEPC 2×SSC [300 mM sodium chloride, 30 mM sodium citrate (pH 7.0)], 10% (w/v) dextran sulfate (Sigma-Aldrich, catalog #D8960), and DEPC 50 mM sodium phosphate (pH 7.0) for 30 min at 66° C. for LNA probes. The hybridization buffer was then drained off, and 400 µL of 40 nM LNA probe mix in hybridization buffer was added to each of the slides and incubated in the dark for 3 hours at 66° C. (for LNA probes). Slides incubated with LNA probes were rinsed once in DEPC 2×SSC/0.1% Tween 20 (Fisher Scientific, catalog no. BP337) at room temperature and in DEPC 0.1×SSC three times at 65° C. Slides were subsequently incubated with 1 µg/mL DAPI (Molecular Probes Inc.).

In another experiment, slides are pre-hybridized with buffer consisting of 50% formamide (IBI Scientific, catalog #IB72020), DEPC 2×SSC [300 mM sodium chloride, 30 mM sodium citrate (pH 7.0)], 10% (w/v) dextran sulfate (Sigma-Aldrich, catalog #D8960), and DEPC 50 mM sodium phosphate (pH 7.0) for 30 min at 66° C. (for LNA probes) or 55° C. (for DNA probes). The hybridization buffer is then drained off, and 400 µL of 200 ng/mL of DNA probe mix in hybridization buffer is added to each of the slides and incubated in the dark for 3 hours at 55° C. Slides incubated with DNA probes are washed three times with 40% formamide in 2×SSC and briefly washed one time in PBS. Slides are subsequently incubated with 1 µg/mL DAPI (Molecular Probes Inc.).

The sequences and SEQ ID NOS of the LNA and DNA oligonucleotide probes used in this example, as well as the hybridization conditions of the probes, are provided in Table 11 below. A locked nucleic acid (LNA) is a nucleic acid analog in which the ribose moiety is modified with an extra bridge connecting the 2' oxygen and the 4' carbon.

TABLE 11

LNA and DNA Probes.

| Probe | Sequence (SEQ ID NO) | Hybridization Method |
|---|---|---|
| LNA sense $G_4C_2$ RNA | TYE563-CCCCGGCCCCGG CCCC (SEQ ID NO: 38) | 66° C. hybridization and washes in 0.1 × SSC |
| LNA antisense $G_4C_2$ RNA | TYE563-GGGGCCGGGGCC GGGGGGCCCC (SEQ ID NO: 39) | 66° C. hybridization and washes in 0.1 × SSC |
| DNA sense $G_4C_2$ RNA | CCCCGGCCCCGGCCCCGG-Cy3 (SEQ ID NO: 44) | 55° C. hybridization and washes in 2 × SSC |
| DNA antisense $G_4C_2$ RNA | GGGGCCGGGGCCGGGGC-Cy3 (SEQ ID NO: 45) | 55° C. hybridization and washes in 2 × SSC |

Detection of Dipeptide Repeat Protein Products (Immunofluorescence and Western Slot Blot)

Immunofluorescence was used to assess dipeptide repeat protein production in embryonic-stem-cell-derived motor neurons (ESMNs) generated as described above. Briefly, ESMNs were grown in four-well chamber slides (Lab-Tek II chamber slide system, ThermoFisher Scientific) and fixed with 4% PFA (Electron Microscopy Sciences) in PBS. Cells were then permeabilized with diethyl pyrocarbonate (DEPC) PBS/0.2% Triton X-100 (Fisher Scientific, catalog #BP151) and washed with DEPC-PBS, blocked and stained with anti-polyGA antibody for the detection of RAN translation products, as described below. After staining, slides were subsequently incubated with an appropriate fluorescent dye, mounted with Fluoromount G (Southern Biotech) and visualized using confocal microscopy.

After permeabilization, slides were blocked with 5% normal donkey serum diluted in Tris buffered saline (pH 7.4) with 0.2% Triton X100 (TBS-T). Slides were incubated overnight at 4° C. with primary antibodies against poly-GA (Millipore) diluted in TBS-T with 5% normal donkey. After washing 3 times with TBS-T, slides were incubated with species-specific secondary antibodies coupled to Alexa 488 or 555 (1:1000 in TBS-T, ThermoFisher) and DAPI (1 µg/mL) (Molecular Probes Inc.) for 1 hr at room temperature. After washing 3 times with TBS-T, slides were mounted with Fluoromount G (Southern Biotech) and visualized using confocal microscopy.

For slot blot assays, differentiated embryoid bodies (EBs) were collected and homogenized in SDS sample buffer (2% SDS, 10% glycerol, 5% β-mercaptoethanol, 60 mM TrisHCl, pH 6.8, bromophenol blue). Protein extracts were quantified using the RC DC protein assay (BioRad). Lysates containing 0 µg, 1.25 µg, 2.5 µg, 5 µg, 10 µg, or 20 µg were immobilized onto nitrocellulose membranes with Bio-Slot 48-well microfiltration system (BioRad) under vacuum. The membranes were washed in TBS-T and blotted with an antibody against poly(GP) (1:5,000, Novus biologicals) and poly GA (1:5000, Millipore). After the membrane was incubated with HRP conjugated secondary antibody, bands were visualized by the ECL plus Western Blotting Detection System (Pierce).

Results

Figures 20A, 20B:
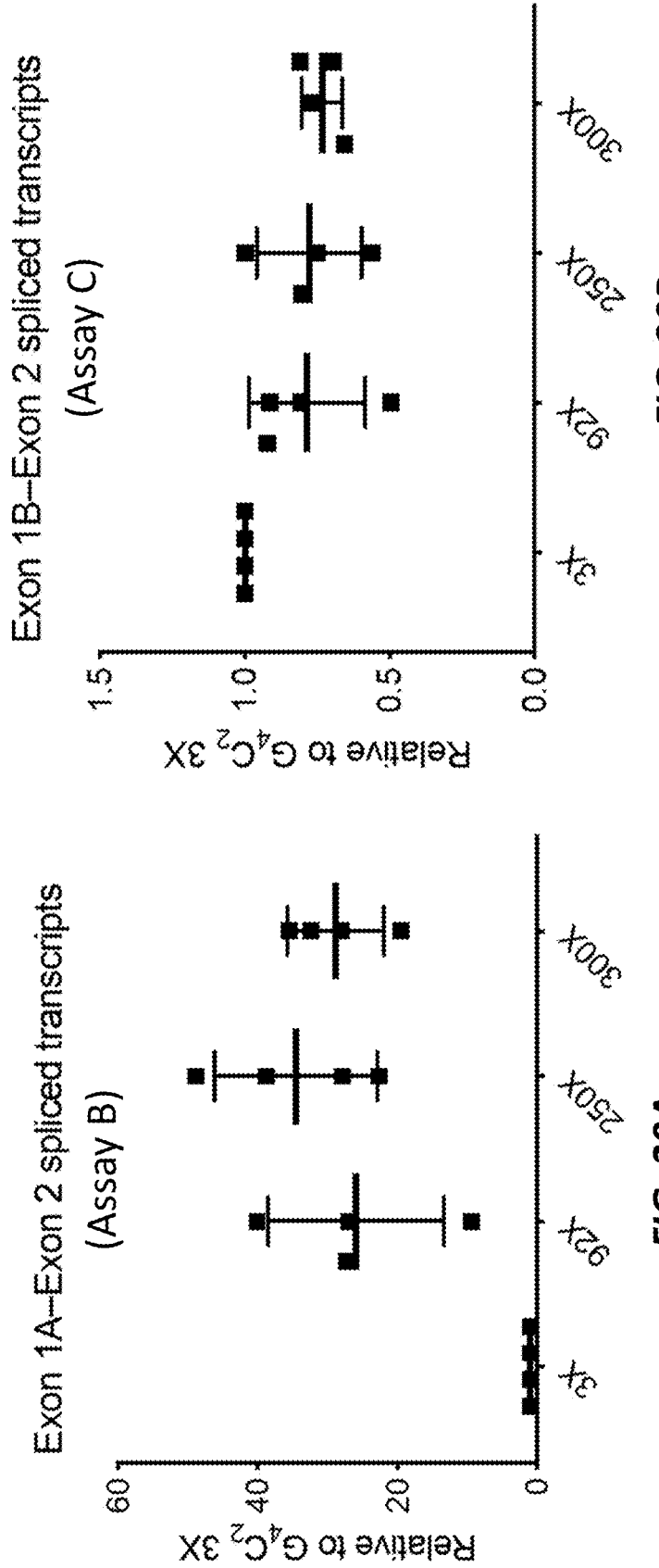
FIGS. 20A-20D show bar graphs showing expression levels (as determined by the TAQMAN® quantitative reverse transcription-coupled PCR (RT-qPCR) assays shown in the depiction of the C9orf72 locus at the top of each figure) of transcripts from the C9orf72 locus (y-axis) that are exon 1A-exon 2 spliced transcripts (FIG. 20A), that are exon 1B-exon 2 spliced transcripts (FIG. 20B), that contain intron sequence near exon 1A (FIG. 20C), and the retain intron sequence near exon 1B (FIG. 20D) in embryonic-stem-cell-derived motor neurons (ESMNs) that are heterozygous for a modified C9orf72 locus comprising 3, 92, 250, or 300 repeats of the hexanucleotide sequence set forth as SEQ ID NO: 1 relative to ESMNs comprising 3 repeats of the hexanucleotide sequence set forth as SEQ ID NO: 1.
Figure 20D:
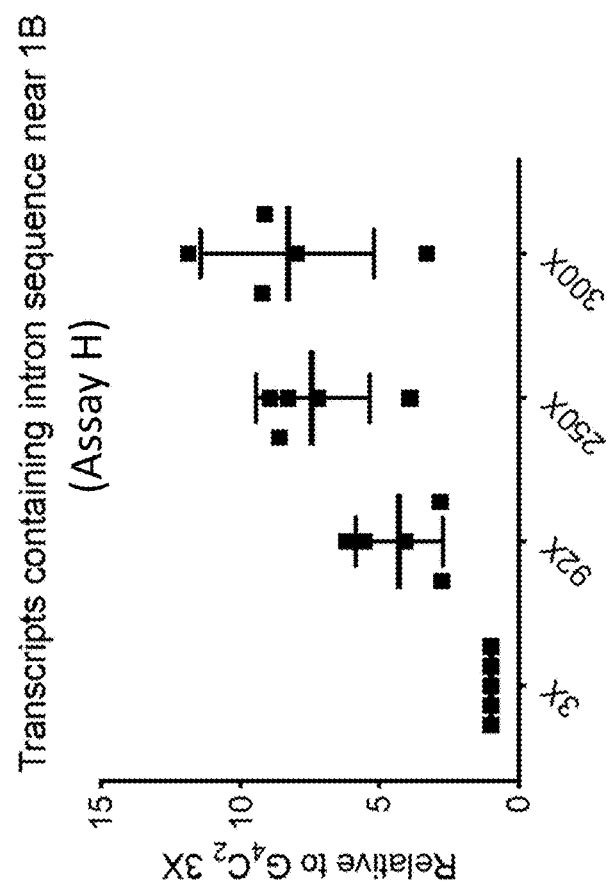
Figure 20C:
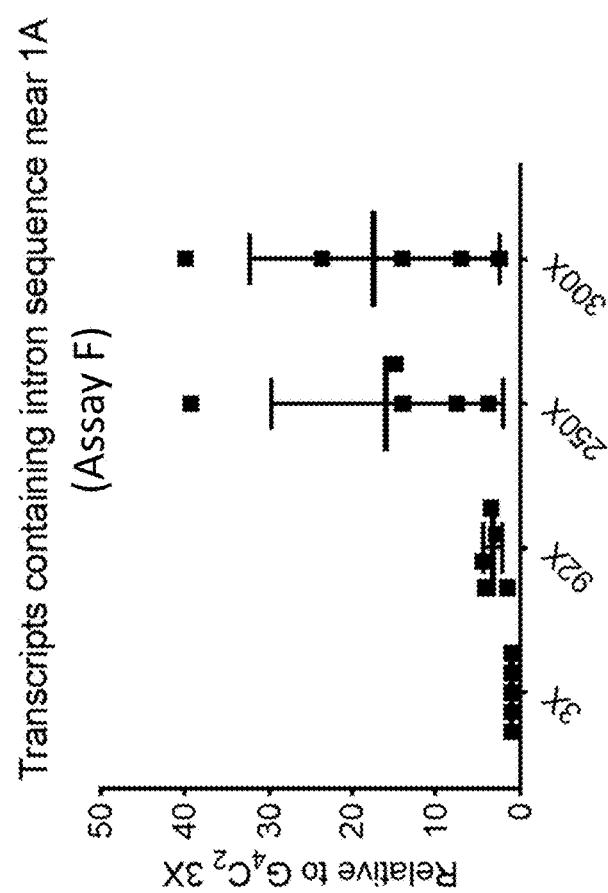
Figures 20E, 20F:
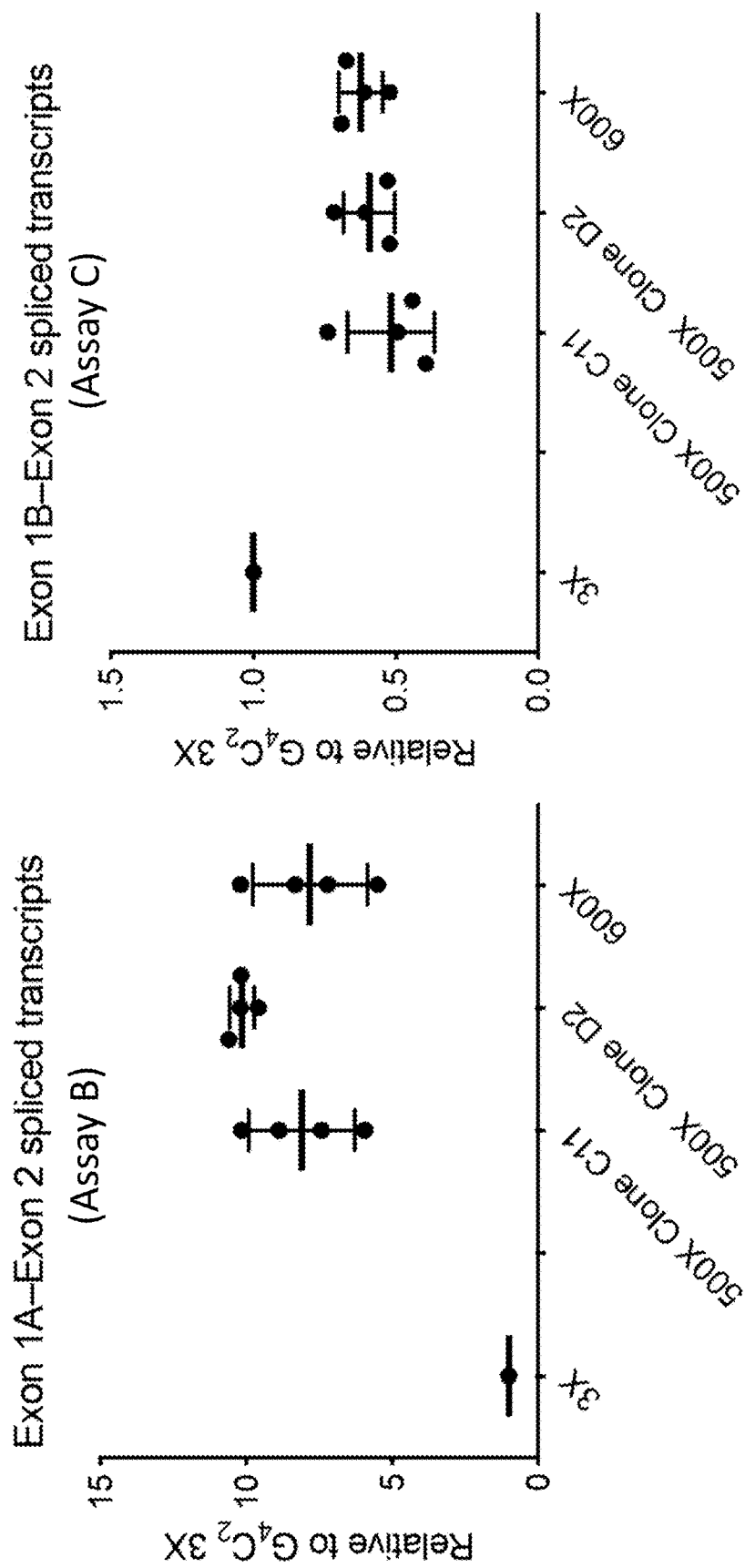
FIGS. 20E-20H show bar graphs showing expression levels (as determined by the TAQMAN® quantitative reverse transcription-coupled PCR (RT-qPCR) assays shown in the depiction of the C9orf72 locus at the top of each figure) of transcripts from the C9orf72 locus (y-axis) that are exon 1A-exon 2 spliced transcripts (FIG. 20E), that are exon 1B-exon 2 spliced transcripts (FIG. 20F), that contain intron sequence near exon 1A (FIG. 20G), and the retain intron sequence near exon 1B (FIG. 20H) in embryonic-stem-cell-derived motor neurons (ESMNs) that are heterozygous for a modified C9orf72 locus comprising 3, 500, or 600 repeats of the hexanucleotide sequence set forth as SEQ ID NO: 1 relative to ESMNs comprising 3 repeats of the hexanucleotide sequence set forth as SEQ ID NO: 1.
Figures 20G, 20H:
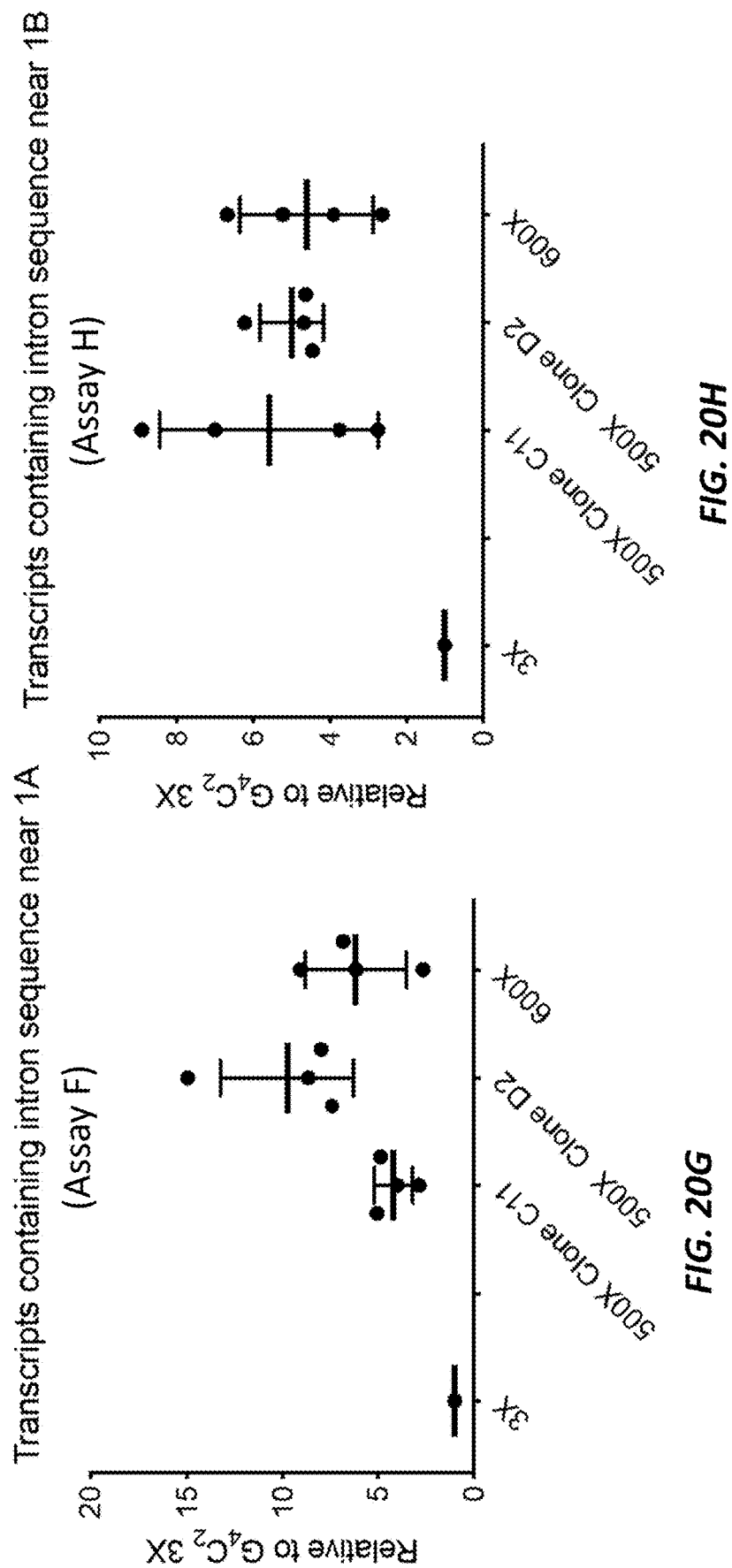
Figure 21:
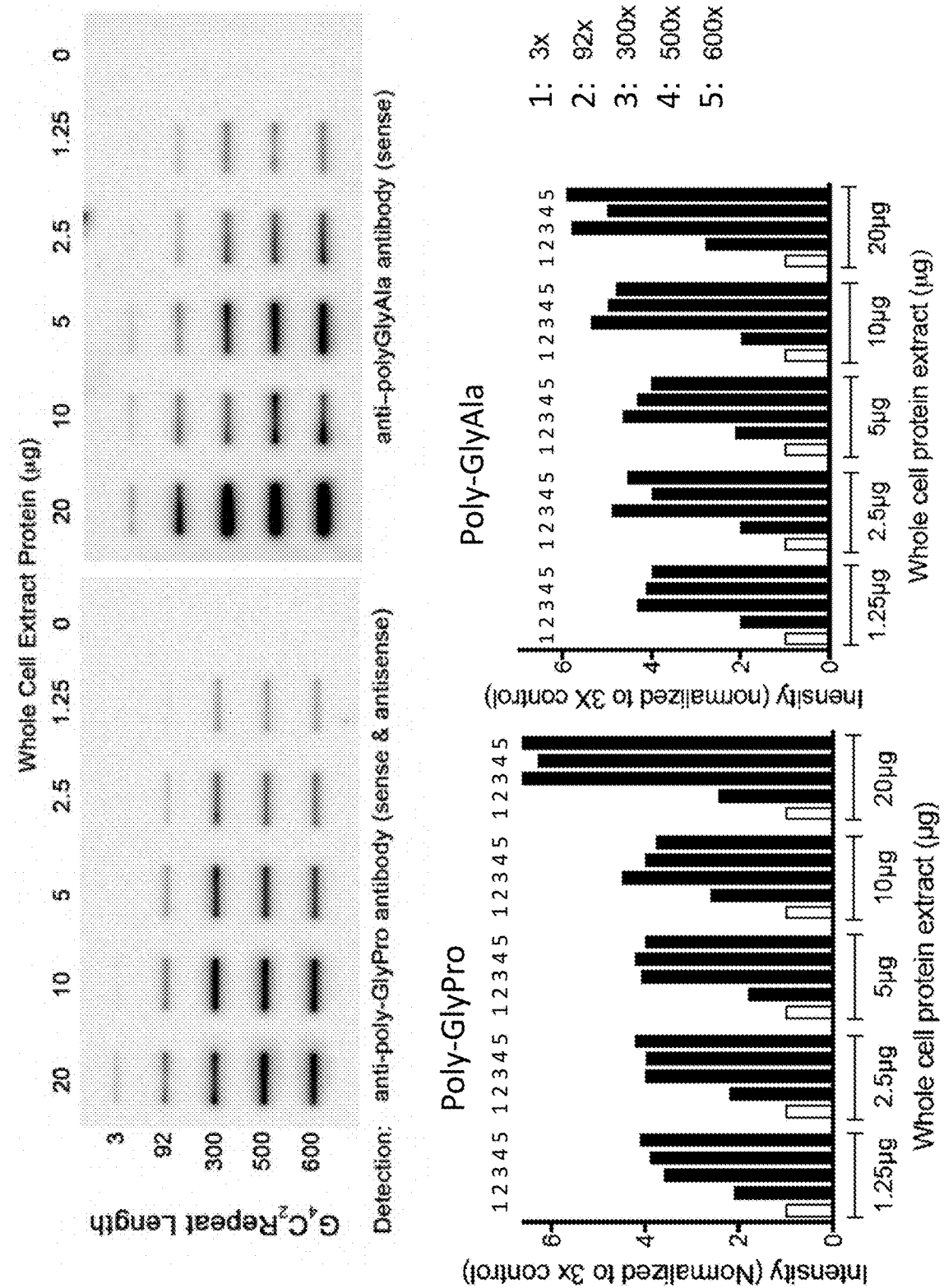
FIG. 21 (top) shows a western slot blot image of lysates of from embryonic-stem-cell-derived motor neurons (ESMNs) heterozygous for a modified C9orf72 locus comprising 3, 92, 300, 500, or 600 repeats of the hexanucleotide sequence set forth as SEQ ID NO: 1. Lysates containing 0 µg, 1.25 µg, 2.5 µg, 5 µg, 10 µg, or 20 µg total proteins were blotted with anti-poly-GlyPro antibody or anti-poly-GlyAla antibody.

Embryonic-stem-cell-derived motor neurons (ESMNs) comprising an allelic series of humanized C9orf72 allele with 3 repeats, 92 repeats, 250 repeats, 300 repeats, 500 repeats, or 600 repeats of the $G_4C_2$ hexanucleotide sequence were tested. As shown in FIG. 20C, FIG. 20D, FIG. 20G, and FIG. 20H, ESMNs comprising the hexanucleotide repeat expansion sequence at the C9orf72 locus showed increased expression of C9orf72 mRNA transcripts that retain intron 1 sequences. In addition, larger $G_4C_2$ repeat expansions had increased use of exon 1A and decreased use of exon 1B. See FIGS. 20A and 20B, respectively, and FIGS. 20E and 20F, respectively. The ESMNs containing $G_4C_2$ repeat expansions also contained nuclear and cytoplasmic sense and antisense C9orf72 RNA foci (data not shown). The sense $G_4C_2$ foci were larger and distributed to the nucleolus (data not shown). The localization of RNA foci with nucleoli in ESMNs with repeat expansions greater than 300 reproduces pathological findings in ALS-patient-derived cells. In addition, an increased number of repeats of the $G_4C2$ hexanucleotide sequence directly correlated with the presence of increased dipeptide repeat proteins (polyGA and polyGP) translated (through RAN translation, a non-AUG mechanism) from transcripts of the hexanucleotide repeat sequence. See, e.g., FIG. 21. In summary, motor neurons derived from the allelic series ES cells reproduce molecular hallmarks of ALS disease (sense and antisense repeat RNA foci, repeat RNA foci localized to nucleoli, at least two of the five forms of dipeptide repeat proteins, and increased accumulation of intron-containing transcripts, supporting the use of the non-human animals disclosed herein as a disease model for neurodegenerative disease.

The quantitative PCR reactions for assays C, B, F, H, E, and D in Table 10 were repeated in two types of ESMNs: hypaxial-like motor neurons (MNs) and limb-like motor neurons (MNs). Hypaxial-like MNs innervate hypaxial MNs in models. Examples of muscles innervated by hypaxial MNs include the intercostal muscles, diaphragm, and muscles of the abdominal wall. Limb-like MNs are those which arise from the lateral motor column and innervate distal limb muscles such as those in the forelimb and hindlimb (tibialis anterior, gastrocnemius and the gluteal muscles). Primarily hypaxial MNs are generated by the protocol that adds retinoic acid (RA) and sonic hedgehog agonist (SAG). Limb-like MNs can be generated by adding 1 µM purmorphamine on top of the RA and SAG we can generate limb-like MNs.

Figures 23A, 23B:
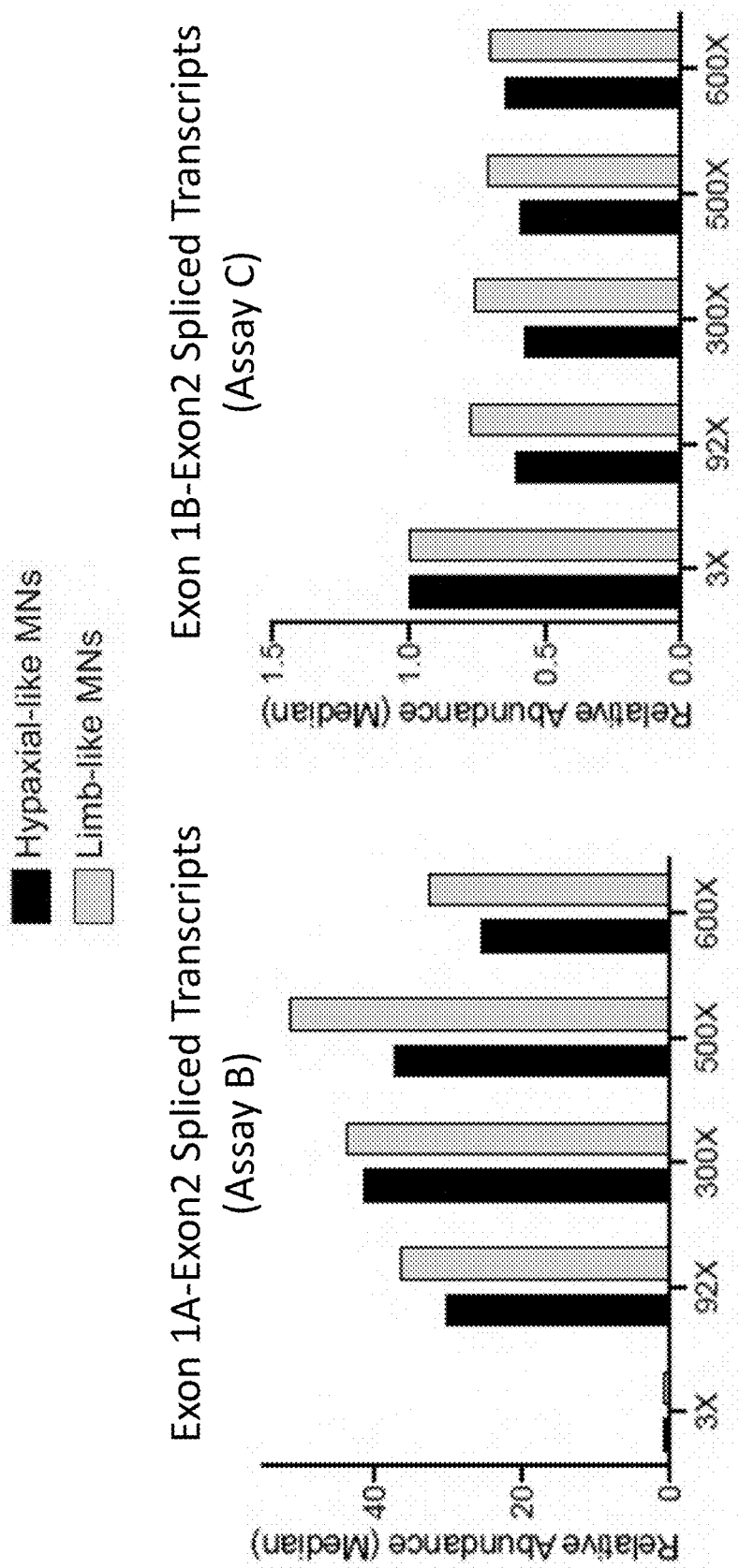
FIGS. 23A-23D show bar graphs showing expression levels (as determined by the TAQMAN® quantitative reverse transcription-coupled PCR (RT-qPCR) assays shown in the depiction of the C9orf72 locus at the top of each figure) of transcripts from the C9orf72 locus (y-axis) that are exon 1A-exon 2 spliced transcripts (FIG. 23A), that are exon 1B-exon 2 spliced transcripts (FIG. 23B), that contain intron sequence near exon 1A (FIG. 23C), and that retain intron sequence near exon 1B (FIG. 23D) in embryonic-stem-cell-derived motor neurons (ESMNs) that are hypaxial-like motor neurons or limb-like motor neurons and are heterozygous for a modified C9orf72 locus comprising 3, 92, 300, 500, or 600 repeats of the hexanucleotide sequence set forth as SEQ ID NO: 1 relative to ESMNs comprising 3 repeats of the hexanucleotide sequence set forth as SEQ ID NO: 1.
Figures 23C, 23D:
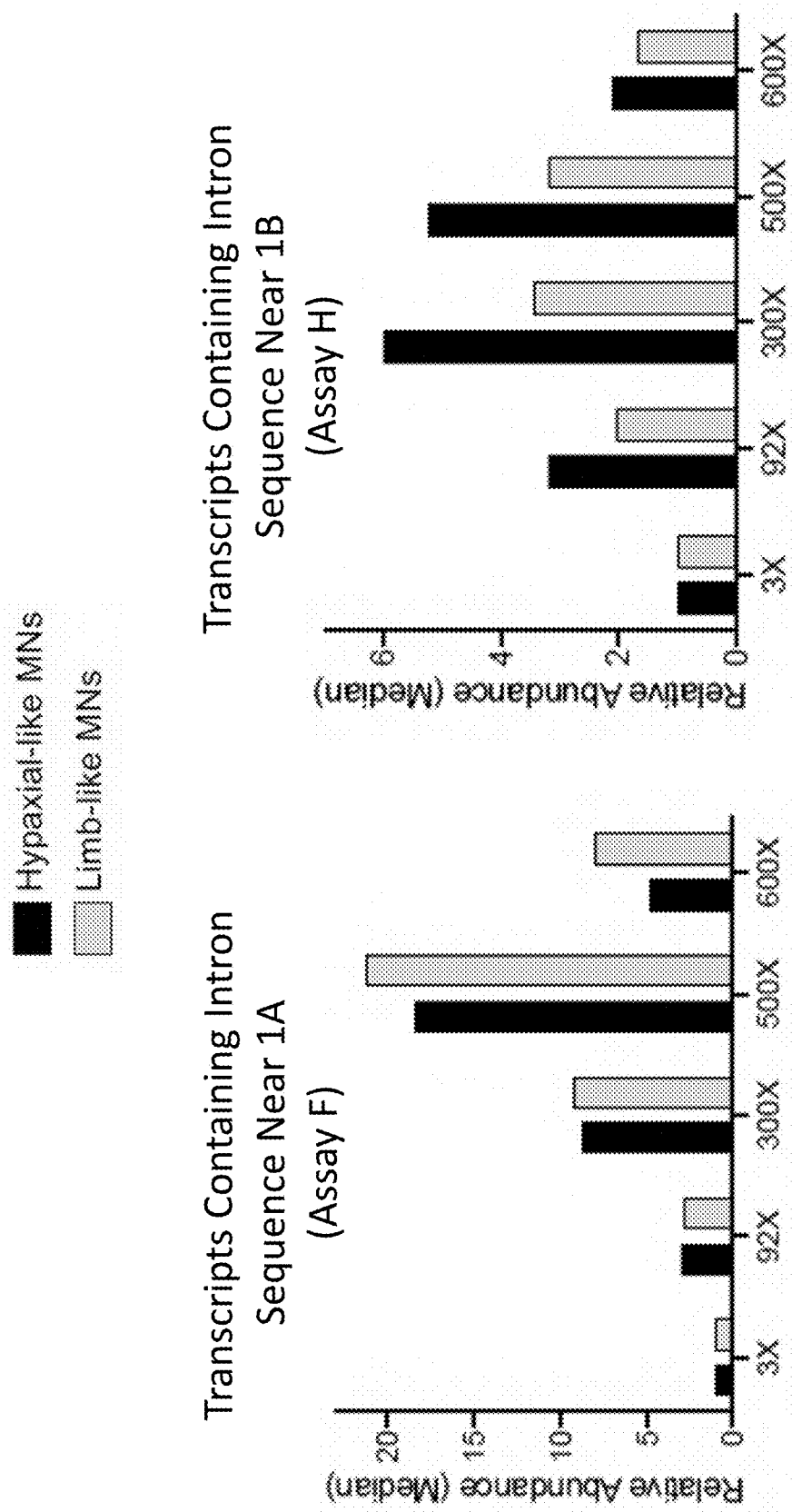
Figures 23E, 23F:
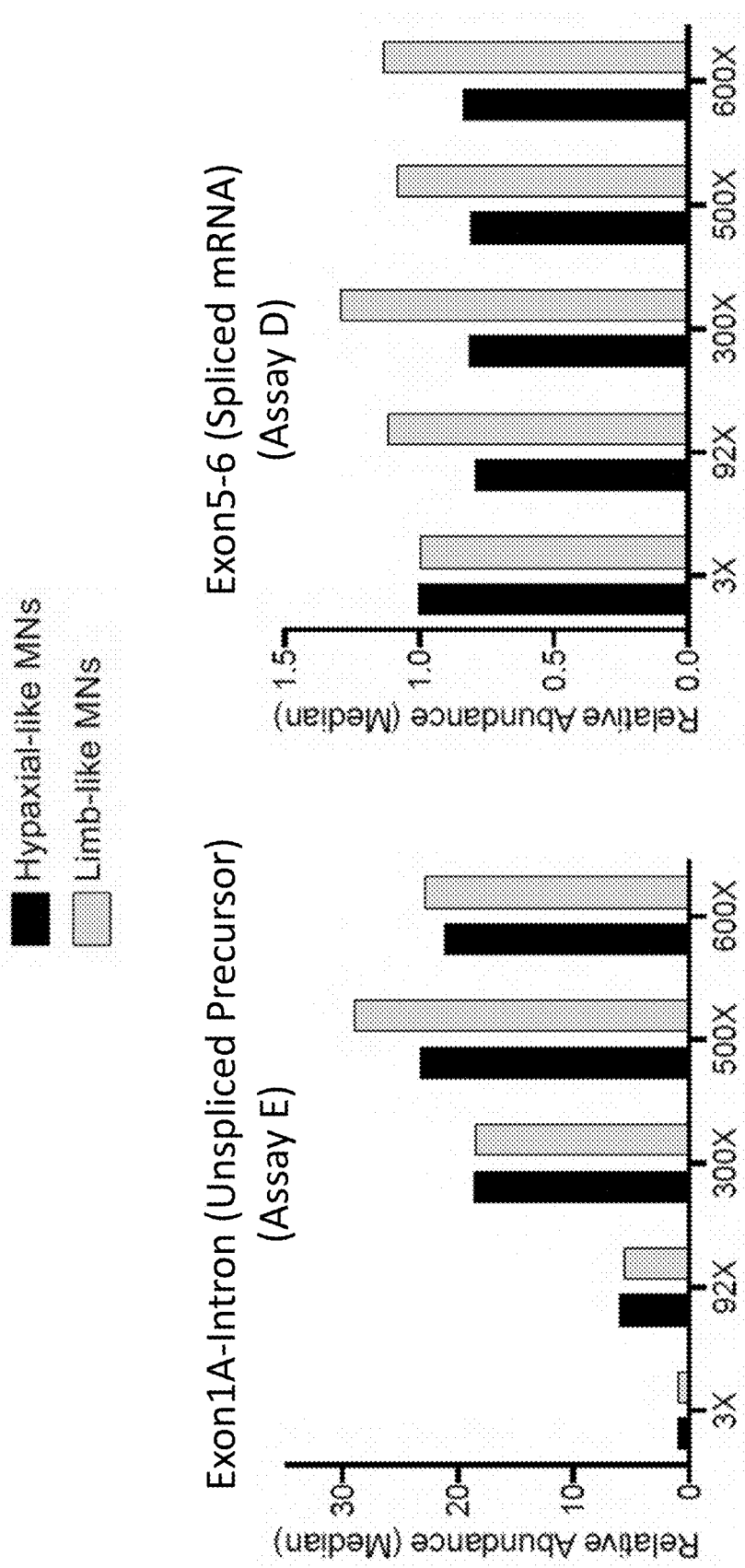
FIGS. 23E-23F show bar graphs showing expression levels (as determined by the TAQMAN® quantitative reverse transcription-coupled PCR (RT-qPCR) assays shown in the depiction of the C9orf72 locus at the top of each figure) of transcripts from the C9orf72 locus (y-axis) that are unspliced precursor transcripts (FIG. 23E) or spliced C9orf72 mRNAs (FIG. 23F) in embryonic-stem-cell-derived motor neurons (ESMNs) that are hypaxial-like motor neurons or limb-like motor neurons and are heterozygous for a modified C9orf72 locus comprising 3, 92, 300, 500, or 600 repeats of the hexanucleotide sequence set forth as SEQ ID NO: 1 relative to ESMNs comprising 3 repeats of the hexanucleotide sequence set forth as SEQ ID NO: 1.

Motor neurons comprising an allelic series of humanized C9orf72 allele with 3 repeats, 92 repeats, 300 repeats, 500 repeats, or 600 repeats of the $G_4C_2$ hexanucleotide sequence were tested. As shown in FIG. 23A and FIG. 23B, larger $G_4C_2$ repeat expansions had increased use of exon 1A and decreased use of exon 1B. As shown in FIG. 23C and FIG. 23D, ESMNs comprising the hexanucleotide repeat expansion sequence at the C9orf72 locus showed increased expression of C9orf72 mRNA transcripts that retain intron 1 sequences. As shown in FIG. 23E, larger $G_4C_2$ repeat expansions had increased expression of unspliced precursors. As shown in FIG. 23F, expression of spliced C9orf72 mRNA did not change much with repeat size.

Example 4. Generation of Mice Comprising Hexanucleotide Repeat Expansion at the C9orf72 Gene Locus F0 mice were generated using the VELOCIMOUSE® method using the 300× repeat ES cell clones described in Example 1. See, e.g., U.S. Pat. Nos. 7,576,259; 7,659,442; 7,294,754; US 2008/0078000; and Poueymirou et al. (2007) Nat. Biotechnol. 25(1):91-99, each of which is herein incorporated by reference in its entirety for all purposes. In the VELOCIMOUSE® method, targeted mouse embryonic stem (ES) cells are injected through laser-assisted injection into pre-morula stage embryos, e.g., eight-cell-stage embryos, which efficiently yields F0 generation mice that are fully ES-cell-derived.

Figure 22B:
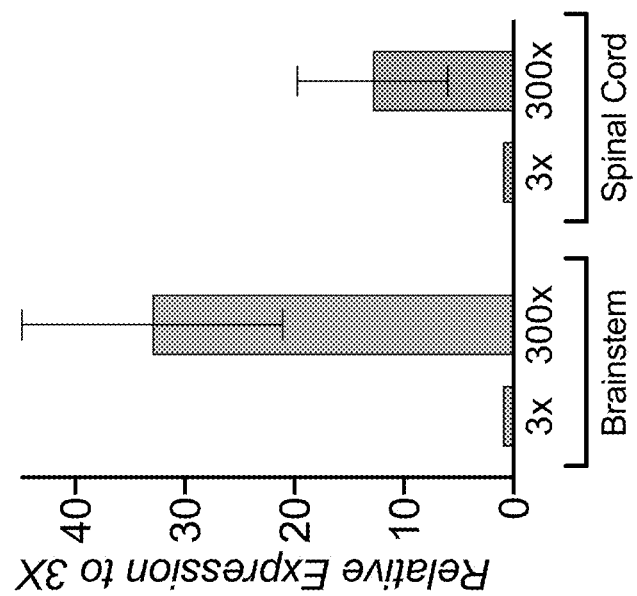
FIGS. 22A-22B show bar graphs showing expression levels (as determined by the TAQMAN® quantitative reverse transcription-coupled PCR (RT-qPCR) assays shown in the depiction of the C9orf72 locus at the top of each figure) of transcripts from the C9orf72 locus (y-axis) that contain intron sequence near exon 1A in embryonic-stem-cell-derived motor neurons (ESMNs) that are heterozygous for a modified C9orf72 locus comprising 3, 92, 300, 500, or 600 repeats of the hexanucleotide sequence set forth as SEQ ID NO: 1 relative to ESMNs comprising 3 repeats of the hexanucleotide sequence set forth as SEQ ID NO: 1 (FIG. 22A) or in brain stem and spinal cord samples from mice that are heterozygous for a modified (humanized) C9orf72 locus comprising 3 or 300 repeats of the hexanucleotide sequence set forth as SEQ ID NO: 1 relative to brain stem and spinal cord samples from mice comprising 3 repeats of the hexanucleotide sequence set forth as SEQ ID NO: 1 (FIG. 22B).

RNA transcripts from brain stem and spinal cord samples from the C9orf72 300× repeat mice (i.e., the humanized C9orf72 allele with 300 repeats of the $G_4C_2$ hexanucleotide sequence) and control C9orf72 3× repeat mice (i.e., the humanized C9orf72 allele with 3 repeats of the $G_4C_2$ hexanucleotide sequence) were tested as in Example 3. RNA foci and dipeptide repeat protein levels were evaluated in brain stem and spinal cord samples from the C9orf72 300× repeat mice as in Example 3. As shown in FIG. 22B, brain stem and spinal cord samples from the C9orf72 300× repeat mice showed increased expression of C9orf72 mRNA transcripts that retain intron 1 sequences. In addition, the spinal cord samples (i.e., L4/L5 lumbar spinal cord motor neurons) were tested for and were shown to contain nuclear and cytoplasmic sense and antisense C9orf72 RNA foci (data not shown). Similarly, these samples had an increased presence of dipeptide repeat proteins (polyGA) translated (through RAN translation, a non-AUG mechanism) from transcripts of the hexanucleotide repeat sequence (data not shown).

Figure 22A:
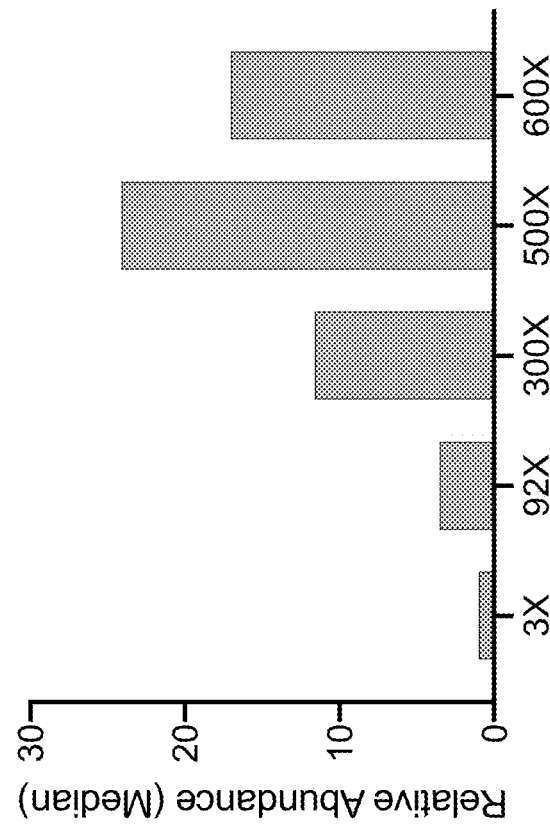

Likewise, embryonic-stem-cell-derived motor neurons (ESMNs) comprising an allelic series of humanized C9orf72 allele with 3 repeats, 92 repeats, 300 repeats, 500 repeats, or 600 repeats of the $G_4C_2$ hexanucleotide sequence were tested. As shown in FIG. 22A, ESMNs comprising the hexanucleotide repeat expansion sequence at the C9orf72 locus showed increased expression of C9orf72 mRNA transcripts that retain intron 1 sequences. The ESMNs containing $G_4C_2$ repeat expansions also contained nuclear and cytoplasmic sense and antisense C9orf72 RNA foci and an increased presence of dipeptide repeat proteins (polyGA) translated (through RAN translation, a non-AUG mechanism) from transcripts of the hexanucleotide repeat sequence (data not shown).

F0 mice were also generated having a mouse C9orf72 gene locus replaced with a human counterpart containing approximately 500 repeats or approximately 600 repeats of the GGGGCC (SEQ ID NO: 1) hexanucleotide using known methods.

We claim:

1. A method for producing a modified cell with an increased number of copies of a repeat sequence at a target genomic locus, comprising:
   (a) providing a population of cells comprising a repeat expansion sequence comprising a plurality of copies of the repeat sequence at the target genomic locus;
   (b) introducing into the population of cells a nuclease agent or a nucleic acid encoding the nuclease agent, wherein the nuclease agent is a zinc finger nuclease (ZFN), a Transcription Activator-Like Effector Nuclease (TALEN), or a Clustered Regularly Interspaced Short Palindromic Repeats (CRISPR)-associated (Cas) protein and a guide RNA, and wherein the nuclease agent makes a double-strand break or a single-strand break at a nuclease target site within about 25 nucleotides of the 5' end or the 3' end of the repeat expansion sequence to produce a population of modified cells; and
   (c) quantifying the number of copies of the repeat sequence in the population of modified cells and selecting a modified cell in which the number of copies of the repeat sequence has been increased.

2. The method of claim 1, wherein an exogenous repair template is not introduced into the population of cells.

3. The method of claim 1, wherein the nuclease target site is within about 20 nucleotides of the 5' end or the 3' end of the repeat expansion sequence or overlaps with the 5' end or the 3' end of the repeat expansion sequence.

4. The method of claim 3, wherein the nuclease target site is within about 15 nucleotides of the 5' end or the 3' end of the repeat expansion sequence or overlaps with the 5' end or the 3' end of the repeat expansion sequence.

5. The method of claim 4, wherein the nuclease target site overlaps with the 5' end or the 3' end of the repeat expansion sequence.

6. The method of claim 1, wherein the nuclease target site is within about 25 nucleotides of the 5' end of the repeat expansion sequence.

7. The method of claim 1, wherein the nuclease target site is within about 25 nucleotides of the 3' end of the repeat expansion sequence.

8. The method of claim 1, wherein the nuclease target site is outside of the repeat expansion sequence.

9. The method of claim 1, wherein the site at which the nuclease agent makes the double-strand break or the single-strand break is within about 25 nucleotides of the 5' end or the 3' end of the repeat expansion sequence.

10. The method of claim 9, wherein the site at which the nuclease agent makes the double-strand break or the single-strand break is within about 15 nucleotides of the 5' end or the 3' end of the repeat expansion sequence.

11. The method of claim 1, wherein the site at which the nuclease agent makes the double-strand break or the single-strand break is within about 25 nucleotides of the 5' end of the repeat expansion sequence.

12. The method of claim 1, wherein the site at which the nuclease agent makes the double-strand break or the single-strand break is within about 25 nucleotides of the 3' end of the repeat expansion sequence.

13. The method of claim 1, wherein the site at which the nuclease agent makes the double-strand break or the single-strand break is outside of the repeat expansion sequence.

14. The method of claim 1, wherein the nuclease target site is retained after repair of the double-strand break or the single strand-break by the cells.

15. The method of claim 1, wherein repair of the double-strand break or the single strand-break does not result in insertions or deletions outside of the repeat expansion sequence.

16. The method of claim 1, wherein the nuclease agent makes the double-strand break within about 25 nucleotides of the 5' end or the 3' end of the repeat expansion sequence.

17. The method of claim 1, wherein the nuclease agent is a nickase that makes the single-strand break within about 25 nucleotides of the 5' end or the 3' end of the repeat expansion sequence.

18. The method of claim 1, wherein a first nuclease agent or a nucleic acid encoding the first nuclease agent and a second nuclease agent or a nucleic acid encoding the second nuclease agent are introduced into the population of cells, wherein the first nuclease agent makes a double-strand break or a single-strand break at a first nuclease target site within about 25 nucleotides of the 5' end of the repeat expansion sequence, and the second nuclease agent makes a double-strand break or a single-strand break at a second nuclease target site within about 25 nucleotides of the 3' end of the repeat expansion sequence.

19. The method of claim 18, wherein the first nuclease agent makes the double-strand break at the first nuclease target site within about 25 nucleotides of the 5' end of the repeat expansion sequence, and the second nuclease agent makes the double-strand break at the second nuclease target site within about 25 nucleotides of the 3' end of the repeat expansion sequence.

20. The method of claim 18, wherein the first nuclease agent makes the single-strand break at the first nuclease target site within about 25 nucleotides of the 5' end of the repeat expansion sequence, and the second nuclease agent makes the single-strand break at the second nuclease target site within about 25 nucleotides of the 3' end of the repeat expansion sequence.

21. The method of claim 1, wherein the nuclease agent is the Cas protein and the guide RNA.

22. The method of claim 21, wherein the Cas protein is a Cas9 protein.

23. The method of claim 1, wherein the repeat expansion sequence is a heterologous repeat expansion sequence.

24. The method of claim 1, wherein the repeat expansion sequence comprises at least about 10, at least about 20, at least about 30, at least about 40, at least about 50, at least about 60, at least about 70, at least about 80, or at least about 90 copies of the repeat sequence.

25. The method of claim 1, wherein the copies of the repeat sequence are contiguous in the repeat expansion sequence.

26. The method of claim 1, wherein the repeat sequence is a trinucleotide repeat, a tetranucleotide repeat, a pentanucleotide repeat, a hexanucleotide repeat, or a dodecanucleotide repeat.

27. The method of claim 1, wherein the repeat sequence comprises any one of SEQ ID NOS: 1-12.

28. The method of claim 27, wherein:
the repeat sequence comprises SEQ ID NO: 2, and the target genomic locus is an HTT, AR, ATN1, ATXN1, ATXN2, ATXN3, CACNA1A, ATXN7, PPP2R2B, or TBP locus;
(ii) the repeat sequence comprises SEQ ID NO: 3, and the target genomic locus is an FMR1 locus;
(iii) the repeat sequence comprises SEQ ID NO: 4, and the target genomic locus is a DMPK, JPH3, ATXN8, or TCF4 locus;
(iv) the repeat sequence comprises SEQ ID NO: 5, and the target genomic locus is an FXN locus;
(v) the repeat sequence comprises SEQ ID NO: 6, and the target genomic locus is an AFF2 locus;
(vi) the repeat sequence comprises SEQ ID NO: 7, and the target genomic locus is a PABPN1 locus;
(vii) the repeat sequence comprises SEQ ID NO: 8, and the target genomic locus is a CNBP locus;
(viii) the repeat sequence comprises SEQ ID NO: 9, and the target genomic locus is an ATXN10 locus;
(ix) the repeat sequence comprises SEQ ID NO: 10, and the target genomic locus is a TK2 or BEAN1 locus;
(x) the repeat sequence comprises SEQ ID NO: 11, and the target genomic locus is a NOP56 locus;
(xi) the repeat sequence comprises SEQ ID NO: 1, and the target genomic locus is a C9ORF72 locus; or
(xii) the repeat sequence comprises SEQ ID NO: 12, and the target genomic locus is a CSTB locus.

29. The method of claim 28, wherein the repeat sequence comprises SEQ ID NO: 1, and the target genomic locus is the C9ORF72 locus.

30. The method of claim 29, wherein the nuclease agent is the Cas protein and the guide RNA, wherein the Cas protein is a Cas9 protein, and the nuclease target site comprises SEQ ID NO: 28 or 33.

31. The method of claim 1, wherein the cells are non-human animal cells.

32. The method of claim 1, wherein the cells are non-human animal embryonic stem cells, embryonic stem-cell-derived motor neurons, brain cells, cortical cells, neuronal cells, muscle cells, heart cells, or germ cells.

33. The method of claim 1, wherein the cells are non-human animal one-cell stage embryos.

34. The method of claim 1, wherein the cells are rodent cells.

35. The method of claim 34, wherein the cells are mouse cells or rat cells.

36. The method of claim 35, wherein the cells are mouse cells.

37. The method of claim 36, wherein the cells are mouse embryonic stem cells or mouse one-cell stage embryos.

38. The method of claim 1, wherein the cells are human induced pluripotent stem cells.

39. The method of claim 1, wherein the cells are in vitro.

40. The method of claim 1, wherein the cells are in vivo.

41. The method of claim 1, wherein the method comprises multiple rounds of steps (a)-(c), wherein the population of cells in step (a) in each round after the first round is a clonal population of cells expanded from the modified cell selected in step (c) of the previous round.

42. The method of claim 41, wherein the method comprises at least 3 rounds or at least 4 rounds.

43. The method of claim 41, wherein:
(I) the method is performed a first time with a first nuclease agent that makes a double-strand break or a single-strand break at a first nuclease target site within about 25 nucleotides of the 5' end of the repeat expansion sequence to produce a first modified cell, and the method is performed a second time on the first modified cell with a second nuclease agent that makes a double-strand break or a single-strand break at a second nuclease target site within about 25 nucleotides of the 3' end of the repeat expansion sequence to produce a second modified cell;
(II) the method is performed a first time with a first nuclease agent that makes a double-strand break or a single-strand break at a first nuclease target site within about 25 nucleotides of the 3' end of the repeat expansion sequence to produce a first modified cell, and the method is performed a second time on the first modified cell with a second nuclease agent that makes a double-strand break or a single-strand break at a second nuclease target site within about 25 nucleotides of the 5' end of the repeat expansion sequence to produce a second modified cell;
(III) the method is performed a first time with a first nuclease agent that makes a double-strand break or a single-strand break at a first nuclease target site within about 25 nucleotides of the 5' end of the repeat expansion sequence to produce a first modified cell, and the method is performed a second time on the first modified cell with a second nuclease agent that makes a double-strand break or a single-strand break at a second nuclease target site within about 25 nucleotides of the 5' end of the repeat expansion sequence to produce a second modified cell;
(IV) the method is performed a first time with a first nuclease agent that makes a double-strand break or a single-strand break at a first nuclease target site within about 25 nucleotides of the 3' end of the repeat expansion sequence to produce a first modified cell, and the method is performed a second time on the first modified cell with a second nuclease agent that makes a double-strand break or a single-strand break at a second nuclease target site within about 25 nucleotides of the 3' end of the repeat expansion sequence to produce a second modified cell;
(V) the method is performed a first time with a first nuclease agent that makes a double-strand break at a first nuclease target site within about 25 nucleotides of the 5' end of the repeat expansion sequence to produce a first modified cell, and the method is performed a second time on the first modified cell with a second nuclease agent that makes a double-strand break at a second nuclease target site within about 25 nucleotides of the 3' end of the repeat expansion sequence to produce a second modified cell;
(VI) the method is performed a first time with a first nuclease agent that makes a double-strand break at a first nuclease target site within about 25 nucleotides of the 3' end of the repeat expansion sequence to produce a first modified cell, and the method is performed a second time on the first modified cell with a second nuclease agent that makes a double-strand break at a second nuclease target site within about 25 nucleotides of the 5' end of the repeat expansion sequence to produce a second modified cell;
(VII) the method is performed a first time with a first nuclease agent that makes a double-strand break at a first nuclease target site within about 25 nucleotides of the 5' end of the repeat expansion sequence to produce a first modified cell, and the method is performed a second time on the first modified cell with a second nuclease agent that makes a double-strand break at a second nuclease target site within about 25 nucleotides of the 5' end of the repeat expansion sequence to produce a second modified cell;
(VIII) the method is performed a first time with a first nuclease agent that makes a double-strand break at a first nuclease target site within about 25 nucleotides of the 3' end of the repeat expansion sequence to produce a first modified cell, and the method is performed a second time on the first modified cell with a second nuclease agent that makes a double-strand break at a second nuclease target site within about 25 nucleotides of the 3' end of the repeat expansion sequence to produce a second modified cell;
(IX) the method is performed a first time with a first nuclease agent that makes a single-strand break at a first nuclease target site within about 25 nucleotides of the 5' end of the repeat expansion sequence to produce a first modified cell, and the method is performed a second time on the first modified cell with a second nuclease agent that makes a single-strand break at a second nuclease target site within about 25 nucleotides of the 3' end of the repeat expansion sequence to produce a second modified cell;
(X) the method is performed a first time with a first nuclease agent that makes a single-strand break at a first nuclease target site within about 25 nucleotides of the 3' end of the repeat expansion sequence to produce a first modified cell, and the method is performed a second time on the first modified cell with a second nuclease agent that makes a single-strand break at a second nuclease target site within about 25 nucleotides of the 5' end of the repeat expansion sequence to produce a second modified cell;
(XI) the method is performed a first time with a first nuclease agent that makes a single-strand break at a first nuclease target site within about 25 nucleotides of the 5' end of the repeat expansion sequence to produce a first modified cell, and the method is performed a second time on the first modified cell with a second nuclease agent that makes a single-strand break at a second nuclease target site within about 25 nucleotides of the 5' end of the repeat expansion sequence to produce a second modified cell; or
(XII) the method is performed a first time with a first nuclease agent that makes a single-strand break at a first nuclease target site within about 25 nucleotides of the 3' end of the repeat expansion sequence to produce a first modified cell, and the method is performed a second time on the first modified cell with a second nuclease agent that makes a single-strand break at a second nuclease target site within about 25 nucleotides of the 3' end of the repeat expansion sequence to produce a second modified cell.

44. The method of claim 43, wherein the first nuclease target site in option (III), (IV), (VII), (VIII), (XI), or (XII) is the same as the second nuclease target site.

45. The method of claim 1, wherein the nuclease target site is outside of the repeat expansion sequence, wherein the nuclease target site is within about 15 nucleotides of the 5' end or the 3' end of the repeat expansion sequence, and wherein the nuclease agent is the Cas protein and the guide RNA, wherein the Cas protein is a Cas9 protein.

46. The method of claim 45, wherein the nuclease agent is a nickase that makes the single-strand break within about 15 nucleotides of the 5' end or the 3' end of the repeat expansion sequence, wherein the nuclease target site is retained after repair of the single strand-break by the cells, and wherein repair of the single strand-break does not result in insertions or deletions outside of the repeat expansion sequence.

47. The method of claim 1, wherein the target genomic locus is an HTT, AR, ATN1, ATXN1, ATXN2, ATXN3, CACNA1A, ATXN7, PPP2R2B, TBP, FMR1, DMPK, JPH3, ATXN8, TCF4, FXN, AFF2, PABPN1, CNBP, ATXN10, TK2, BEAN1, NOP56, C9ORF72, or CSTB locus.

* * * * *

UNITED STATES PATENT AND TRADEMARK OFFICE
CERTIFICATE OF CORRECTION

| | |
|---|---|
| PATENT NO. | : 11,690,362 B2 |
| APPLICATION NO. | : 16/713834 |
| DATED | : July 4, 2023 |
| INVENTOR(S) | : Daisuke Kajimura et al. |

It is certified that error appears in the above-identified patent and that said Letters Patent is hereby corrected as shown below:

On the Title Page

Item (71) Applicant:
Delete "Regeneran" and replace it with --Regeneron--

Item (73) Assignee:
Delete "Regeneran" and replace it with --Regeneron--

In the Claims

Column 153, Claim 28, Line 20:
Insert --(i)-- before "the repeat"

Signed and Sealed this
Twelfth Day of September, 2023

Katherine Kelly Vidal
*Director of the United States Patent and Trademark Office*